(12) United States Patent
Kurtis et al.

(10) Patent No.: US 12,214,026 B2
(45) Date of Patent: Feb. 4, 2025

(54) VACCINE FOR FALCIPARUM MALARIA

(71) Applicants: Rhode Island Hospital, Providence, RI (US); Seattle Children's Hospital, Seattle, WA (US)

(72) Inventors: Jonathan Kurtis, Providence, RI (US); Christian Parcher Nixon, Little Compton, RI (US); Dipak Kumar Raj, Pawtucket, RI (US); Jennifer Frances Friedman, Providence, RI (US); Michal Fried, Rockville, MD (US); Patrick Emmet Duffy, Washington, DC (US)

(73) Assignees: RHODE ISLAND HOSPITAL, Providence, RI (US); SEATTLE CHILDREN'S HOSPITAL, Seattle, WA (US)

( * ) Notice: Subject to any disclaimer, the term of this patent is extended or adjusted under 35 U.S.C. 154(b) by 0 days.

(21) Appl. No.: 18/154,642

(22) Filed: Jan. 13, 2023

(65) Prior Publication Data

US 2023/0293654 A1    Sep. 21, 2023

Related U.S. Application Data

(60) Division of application No. 17/178,111, filed on Feb. 17, 2021, now Pat. No. 11,554,165, which is a continuation of application No. 16/283,472, filed on Feb. 22, 2019, now Pat. No. 10,960,065, which is a division of application No. 15/607,203, filed on May 26, 2017, now Pat. No. 10,213,502, which is a continuation of application No. 14/361,573, filed as application No. PCT/US2012/067404 on Nov. 30, 2012, now Pat. No. 9,662,379.

(60) Provisional application No. 61/641,445, filed on May 2, 2012, provisional application No. 61/566,365, filed on Dec. 2, 2011.

(51) Int. Cl.

| | |
|---|---|
| A61K 39/02 | (2006.01) |
| A61K 39/002 | (2006.01) |
| A61K 39/015 | (2006.01) |
| A61K 39/395 | (2006.01) |
| C07K 14/445 | (2006.01) |
| C07K 16/20 | (2006.01) |
| C07K 16/44 | (2006.01) |
| A61K 39/00 | (2006.01) |

(52) U.S. Cl.
CPC ...... *A61K 39/015* (2013.01); *A61K 39/39575* (2013.01); *C07K 14/445* (2013.01); *C07K 16/205* (2013.01); *C07K 16/44* (2013.01); *A61K 2039/505* (2013.01); *A61K 2039/522* (2013.01); *A61K 2039/54* (2013.01); *A61K 2039/55* (2013.01); *A61K 2039/575* (2013.01); *C07K 2317/34* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,722,848 | A | 2/1988 | Paoletti et al. |
| 4,837,028 | A | 6/1989 | Allen |
| 4,873,316 | A | 10/1989 | Meade et al. |
| 5,019,369 | A | 5/1991 | Presant et al. |
| 5,204,253 | A | 4/1993 | Sanford et al. |
| 5,279,833 | A | 1/1994 | Rose |
| 5,580,859 | A | 12/1996 | Felgner et al. |
| 5,589,466 | A | 12/1996 | Felgner et al. |
| 5,700,671 | A | 12/1997 | Prieto et al. |
| 5,750,176 | A | 5/1998 | Prieto et al. |
| 5,849,589 | A | 12/1998 | Tedder et al. |
| 9,662,379 | B2 | 5/2017 | Kurtis et al. |
| 10,213,502 | B2 | 2/2019 | Kurtis et al. |
| 10,272,145 | B2 | 4/2019 | Kurtis et al. |
| 2004/0137512 | A1 | 7/2004 | Horii |
| 2005/0136067 | A1 | 6/2005 | Klein et al. |
| 2010/0310602 | A1 | 12/2010 | Reed et al. |
| 2014/0341918 | A1 | 11/2014 | Kurtis et al. |
| 2017/0258884 | A1 | 9/2017 | Kurtis et al. |
| 2017/0326219 | A1 | 11/2017 | Kurtis et al. |
| 2020/0023047 | A1 | 1/2020 | Kurtis et al. |

FOREIGN PATENT DOCUMENTS

| | | |
|---|---|---|
| EP | 0264166 A1 | 4/1988 |
| WO | 8606075 A1 | 10/1986 |
| WO | 9106309 A1 | 5/1991 |
| WO | 9324640 A2 | 12/1993 |
| WO | 9618372 A2 | 6/1996 |
| WO | 2007140506 A1 | 12/2007 |
| WO | 2013082500 A2 | 6/2013 |

OTHER PUBLICATIONS

"Human Vaccines & Immunotherapeutics: News", Human Vaccines and Immunotherapeutics, vol. 16, No. 6 https://doi.org/10.1080/21645515.2020.1778422, 2020, pp. 1226-1227.
"European Search Report received for European Patent Application No. 12854476.4, mailed on Jul. 6, 2016", 11 pages.
"Extended European Search Report received for European Patent Application No. 21186416.0, mailed on Mar. 18, 2022", 9 pages.
"Final Office Action received for U.S. Appl. No. 14/361,573, mailed on Mar. 18, 2016", 18 pages.

(Continued)

*Primary Examiner* — Jennifer E Graser
(74) *Attorney, Agent, or Firm* — ADLER POLLOCK & SHEEHAN P.C.

(57) ABSTRACT

The invention provides compositions and methods for preventing or reducing the severity of malaria.

8 Claims, 19 Drawing Sheets
Specification includes a Sequence Listing.

(56) References Cited

OTHER PUBLICATIONS

"GenBank Accession No. XM_001347460", May 27, 2010.
"GenBank Accession No. XM_001347496", May 27, 2010.
"International Search Report and Written Opinion received for PCT Patent Application No. PCT/US2012/067404, mailed on Jul. 10, 2013", 15 pages.
"Non-Final Office Action received for U.S. Appl. No. 14/361,573, mailed on Jul. 9, 2015", 12 pages.
"Non-Final Office Action received for U.S. Appl. No. 16/283,472, mailed on Jun. 30, 2020", 8 pages.
"Notice of Allowance received for U.S. Appl. No. 14/361,573, mailed on Sep. 28, 2016", 7 pages.
"Notice of Allowance received for U.S. Appl. No. 16/283,472, mailed on Nov. 18, 2020", 8 pages.
"Restriction Requirement received for U.S. Appl. No. 14/361,573, mailed on Feb. 13, 2015", 11 pages.
"Restriction Requirement received for U.S. Appl. No. 16/283,472, mailed on Oct. 30, 2019", 6 pages.
"Supplemental Notice of Allowance received for U.S. Appl. No. 14/361,573, mailed on Jan. 23, 2017", 5 pages.
Allison, et al., "The Mode of Action of Immunological Adjuvants", Developments in Biological Standardization, vol. 92, 1998, pp. 3-11.
Altschul, SF, et al., "Gapped BLAST and PSI-BLAST: A New Generation of Protein Database Search Programs", Nucleic Acids Research, vol. 25, No. 17, including BLAST search for SEQ ID No. 2, Sep. 1, 1997, pp. 3389-3402.
Amann, et al., "Tightly Regulated Tac Promoter Vectors Useful for the Expression of Unfused and Fused Proteins in *Escherichia coli*", Gene, vol. 69, No. 2, Sep. 30, 1988, pp. 301-315.
Aoki, et al., "Serine Repeat Antigen (SERA5) is Predominantly Expressed; among the SERA Multigene Family of Plasmodium Falciparum and the Acquired; Antibody Titers Correlate with Serum Inhibition of the Parasite Growth", The Journal of Biological Chemistry, 277(49), Dec. 6, 2002, pp. 47533-47540.
Baldari, et al., "A Novel Leader Peptide which Allows Efficient Secretion of a Fragment of Human Interleukin 1 Beta in *Saccharomyces cerevisiae*", The EMBO Journal, vol. 6, No. 1, Jan. 1987, pp. 229-234.
Banerji, et al., ""A Lymphocyte-Specific Cellular Enhancer is Located Downstream if the Joining Region in Immunoglobulin Heavy Chain Genes"", Cell, vol. 33 No. 3, Jul. 1983, pp. 729-740.
Blackman, Michael J., "Malarial Proteases and Host Cell Egress: An 'Emerging' Cascade", Cellular Microbiology, vol. 10, No. 10, DOI: 10.111/j.1462-5822.2008.01176.x, Oct. 1, 2008, pp. 1925-1934.
Brunsvig, et al., ""Telomerase Peptide Vaccination" A Phase I/II Study in Patients with Non-Small Cell Lung Cancer", Cancer Immunology, Immunotherapy, vol. 55, No. 12, Dec. 2006, pp. 1553-1564.
Bustamante, et al., "Differential Ability of Specific Regions of Plasmodium Falciparum Sexual Stage Antigen, Pfs230, to induce malaria transmission-blocking immunity", Parasite Immunol, 22(8), Aug. 2000, pp. 373-380.
Byrne, et al., "Multiplex Gene Regulation: A Two-Tiered Approach to Transgene Regulation in Transgenic Mice", Proceedings of the National Academy of Sciences, vol. 86, No. 14, Jul. 1, 1989, pp. 5473-5477.
Calame, et al., "Transcriptional Controlling Elements in the Immunoglobulin and T Cell Receptor Loci", Advances in Immunology, vol. 43, 1988, pp. 235-275.
Camper, et al., "Postnatal Repression of the Alpha-Fetoprotein Gene is Enhancer Independent", Genes Dev., 3(4), Apr. 1989, pp. 537-546.
Cebere, et al., "Phase I Clinical Trial Safety of DNA- and Modified Virus Ankara-Vectored Human Immunodeficiency Virus Type I (HIV-1_ Vaccines Administered Alone and in a Prime-Boost Regime to Healthy HIV-1-Uninfected Volunteers", Vaccine, 24, 2006, pp. 417-425.

Cowman, et al., "The Cellular and Molecular Basis for Malaria Parasite Invasion of the Human Red Blood Cell", J. Cell Biology, 198(6), Sep. 2012, pp. 961-971.
Dorvin, "Science", Genbank Accession No. AOA5K1 K8HO, vol. 328, 2010, pp. 910-912.
Duffy, et al., "Malaria Vaccines Since 2000: Progress, Priorities, Products", npj Vaccines, vol. 5, No. 48 https://doi.org/10.1038/s41541-020-0196.3, 2020, pp. 1-9.
Dupuis, et al., "Dendritic Cells Internalize Vaccine Adjuvant after Intramuscular Injection", Cellular Immunology, vol. 186, No. 1, 1998, pp. 18-27.
Dvorin, et al., "A Plant-Like Kinase in Plasmodium Falciparum Regulates Parasite Egress from Erythrocytes", Science, 328(910), May 14, 2020, 15 pages.
Edlund, et al., "Cell-Specific Expression of the Rat Insulin Gene: Evidence for Role of Two Distinct 5' Flanking Elements", Science, vol. 230. No. 4728, Nov. 22, 1985, pp. 912-916.
Felgner, et al., "Lipofection: A Highly Efficient, Lipid-Meditated DNA-Transfection Procedure", Proceedings of the National Academy of Sciences, vol. 84, Nov. 1987, pp. 7413-7417.
Gabrilovich, et al., "IL-12 and Mutant P53 Peptide-Pulsed Dendritic Cells for the Specific Immunotherapy of Cancer", Journal of Immunotherapy with Emphasis on Tumor Immunology, vol. 19. No. 6, Nov. 1996, pp. 414-418.
Gardner, MJ, et al., "Genome Sequence of the Human Malaria Parasite Plasmodium Falciparum", Nature, vol. 419, No. 6906 DOI: 10.1038/NATURE01097, Oct. 3, 2002, pp. 498-511.
Gottesman, et al., "Gene Expression Technology", Methods in Enzymology, Academic Press, vol. 185, 1990, pp. 119-128.
Greenland, et al., "Problems Due to Small Samples and Sparse Data in Conditional Logistic Regression Analysis", American Journal of Epidemiology, vol. 151, No. 5, Mar. 1, 2000, pp. 531-539.
Hall, et al., "Sequence of Plasmodium Falciparum Chromosomes 1, 3-9 and 13", Nature 419, DOI: https://doi.org/10.1038/nature01095, Oct. 3, 2002, pp. 527-531.
Hon, et al., "Malaria According to GARP: A New Trait Towards Anti-Disease Vaccination", Cell Press Reviews, Trends in Parasitology, vol. 36, No. 8, 2020, pp. 653-655.
Horii, et al., "Evidences of Protection Against Blood-Stage Infection of Plasmodium Falciparum by the Novel Protein Vaccine SE36", Parasitol Int., 59(3), Sep. 2010, pp. 380-386.
Hurd, H, "A Promising New Malaria Vaccine Candidtae", Bugbitten, https://blogs.biomedcentral.com/bugbitten/author/hhurd, May 15, 2020, 6 pages.
Kabyemela, et al., "Decreased Susceptibility to Plasmodium Falciparum Infection in Pregnant Women with Iron Deficiency", J. Infect. Dis., 198(2), Jul. 15, 2008, pp. 163-166.
Kaslow, et al., "*Saccharomyces cerevisiae* Recombinant Pfs25 Adsorbed to Alum Elicits Antibodies that Block Transmission of Plasmodium Falciparum", Infect. Immun., 62(12), Dec. 1994, pp. 5576-5580.
Kaufman, et al., "Translational Efficiency of Polycistronic mRNAs and their Utilization to Express Heterologous Genes in Mammalian Cells", The EMBO Journal, vol. 6, No. 1, Jan. 1987, pp. 187-195.
Kessel, et al., "Murine Developmental Control Genes", Science, vol. 249, No. 4967, Jul. 27, 1990, pp. 374-379.
Kurjan, et al., "Structure of a Yeast Pheromone Gene (MFa): A Putative a-Factor Precursor Contains Four Tandem Copies of Mature a-Factor", Cell, vol. 30, No. 3, Oct. 1982, pp. 933-943.
Lee, et al., "Arresting Malaria Parasite Egress from Infected Red Blood Cells", Nature Chemical Biology, vol. 4, No. 3, DOI: 10.1038/nchembio0308-161, Mar. 1, 2008, pp. 161-162.
Luckow, et al., "High Level Expression of Nonfused Foreign Genes with Autographa Californica Nuclear Polyhedrosis Virus Expression Vectors", Virology, vol. 170, No. 1, May 1, 1989, pp. 31-39.
Mannino, et al., "Liposome Mediated Gene Transfer", Bio Techniques, vol. 6, No. 7, Jul. 1, 1988, pp. 682-690.
Zeger, et al., "Longitudinal Data Analysis for Discrete and Continuous Outcomes", Biometrics, vol. 42, No. 1, Macrh 1986, pp. 121-130.
Moorthy, et al., "Safety of DNA and Modified Vaccinia Virus Ankara Vaccines Against Liver Stage P.falciparum Malaria in Non-Immune Volunteers", Vaccine, 21, 2003, pp. 1995-2002.

(56) References Cited

OTHER PUBLICATIONS

Mutabingwa, et al., "Maternal Malaria and Gravidity Interact to Modify Infant Susceptibility to Malaria", PLoS, vol. 2, No. 12, Dec. 2005, pp. 1260-1268.

Nixon, et al., "Antibodies to Rhoptry-Associated Membrane Antigen Predict Resistance to Plasmodium falciparum", The Journal of Infectious Diseases, vol. 192, Sep. 1, 2005, pp. 861-869.

Palacpac, et al., "Plasmodium Falciparum Serine Repeat Antigen 5 (SE36) as a Malaria Vaccine Candidate", Vaccine, vol. 29, No. 35, DOI: 10.1016/J.VACCINE.2011.06.052, 2011, pp. 5837-5845.

Peterson, et al., "A Thermal Exhaust Port on the Death Star of Plasmodium Falciparum-Infected Erythrocytes", Cell Press Reviews, Trends in Pharmacological Sciences, vol. 41, No. 8, 2020, pp. 508-511.

Pinkert, et al., "An Albumin Enhancer Located 10 kb Upstream Functions along with its Promoter to Direct Efficient, Liver-Specific Expression in Transgenic Mice", Genes & Development, vol. 1, 1987, pp. 268-277.

Putrianti, et al., "The Plasmodium Serine-Type SERA Proteases Display Distinct Expression Patterns and Non-Essential in Vivo Roles During Life Cycle Progression of the Malaria Parasite", Cell Microbiology, 12(6), Jun. 2010, pp. 725-739.

Queen, et al., "Immunoglobulin Gene Transcription is Activated by Downstream Sequence Elements", Cell, vol. 33, No. 3, Jul. 1983, pp. 741-748.

Raj, et al., "Antibodies to PfSEA-1 Block Parasite Egress from RBCs and Protect Against Malaria Infection", Science, vol. 344, No. 6186, May 23, 2014, pp. 871-877.

Raj, et al., "Antibodies to Plasmodium Falciparum Glutamic Acid Rich Protein (PfGARP) Inhibit Parasite Growth by Arresting Trophozoite Development", International Journal of Infectious Diseases, vol. 45, Apr. 1, 2016, pp. 377.

Raj, et al., "Anti-PfGARP Activates Programmed Cell Death of Parasites and Reduces Severe Malaria", Nature, vol. 582, Jun. 4, 2020, 28 pages.

Sabchareon, et al., "Parasitologic and Clinical Human Response to Immunoglobulin Administration in Falciparum Malaria", Am. J. Trop. Med. Hyg., 45.3, 1991, pp. 297-308.

Sambrook, et al., "Molecular Cloning, A Laboratory Manual", Cold Spring Harbor Laboratory Press, Ed. 2, 1989, pp. 348.

Schnieke, et al., "Human Factor IX Transgenic Sheep Produced by Transfer of Nuclei from Transfected Fetal Fibroblasts", Science, vol. 278, No. 5346, Dec. 19, 1997, pp. 2130-2133.

Schultz, et al., "Expression and Secretion in Yeast of a 400-kdva Envelope Glycoprotein Derived from Epstein-Barr Virus", Gene, vol. 54, No. 1, 1987, pp. 113-123.

Seed, et al., "An LFA-3 cDNA encodes a phospholipid-linked membrane protein homologous to its Receptor CD2", Nature, vol. 329, No. 6142, Oct. 29, 1987, pp. 840-842.

Silmon, et al., "Global Identification of Multiple Substrates for Plasmodium Falciparum SUB1, an Essential Malarial Processing Protease", Infect. Immun., 79(3), Mar. 2011, pp. 1086-1097.

Singh, et al., ""Correlation of T-Cell Response, Clinical Activity and Regulatory T-Cell Levels in Renal Cell Carcinoma Patients Treated with IMA901, A Novel Multi-Peptide Vaccine"", ASCO Journal, Abstract No. 3017, Jun. 20, 2007, 2 pages.

Smith, et al., "Production of Human Beta Interferon in Insect Cells Infected with a Baculovirus Expression Vector", Molecular and Cellular Biology, Vo. 3, No. 12, Dec. 1983, pp. 2156-2165.

Smith, et al., "Single-Step Purification of Polypeptides Expressed in *Escherichia coli* as Fusions with Gluthatione S-Transferase", Gene, vol. 67, No. 1, Jul. 15, 1988, pp. 31-40.

Stover, et al., "New Use of BCG for Recombinant Vaccines", Nature, vol. 51, Jun. 6, 1991, pp. 456-460.

Studier, et al., "Gene Expression Technology", Methods in Enzymology, vol. 185, 1990, pp. 60-89.

Szoka, et al., "Comparative Properties and Methods of Preparation of Lipid Vesicles (Liposomes)", Annual Review of Biophysics and Bioengineering, vol. 9, 1980, pp. 467-508.

Taylor, HM, et al., "The Malaria Parasite Cyclic GMP-Dependent Protein Kinase Plays A Central Role in Blood-Stage Schizogony", Eukaryotic Cell, vol. 9, No. 1, DOI: 10.1128/EC.00186-09, Nov. 13, 2009, pp. 37-45.

Triglia, et al., "Structure of a Plasmodium falciparum Gene that Encodes a Glutamic Acid-Rich Protein (GARP)", Molecular and Biochemical Parasitology, vol. 31, No. 2, 1988, pp. 199-201.

Trimble, et al., "A Phase I of Trial of a Human Papillomavirus DNA Vaccine for HPV16+ Cervical Intraepithelial Neoplasia 2/3", Clinical Cancer Research, vol. 15, 2009, pp. 361-367.

Wada, et al., "Codon Usage Tabulated from the GenBank Genetic", Nucleic Acids Research, vol. 20, 1992, pp. 2111-2118.

Weintraub, et al., "Antisense RNA as a Molecular Tool for Genetic Analysis", Reviews Trends in Genetics, vol. 1, No. 1, Dec. 1985, pp. 22-25.

Winoto, et al., "A Novel, Inducible T Cell-Specific Located at the 3' End of the T Cell Receptor a Locus", The EMBO Journal, vol. 8, No. 3, 1989, pp. 729-733.

Wolff, et al., "Direct Gene Transfer into Mouse Muscle in Vivo", Science, vol. 247, No. 4949, Mar. 23, 1990, pp. 1465-1468.

Wrighton, K.H, "A Novel Vaccine Target for Malaria", Nature Reviews I Microbiology, vol. 18, No. 361, 2020, 1 page.

Yeoh, et al., "Subcellular Discharge of a Serine Protease Mediates Release of Invasive Malaria Parasites from Host Erythrocytes", Cell, vol. 131, No. 6 DOI: 10.1016/j.cell.2007.10.049, Dec. 1, 2007, pp. 1072-1083.

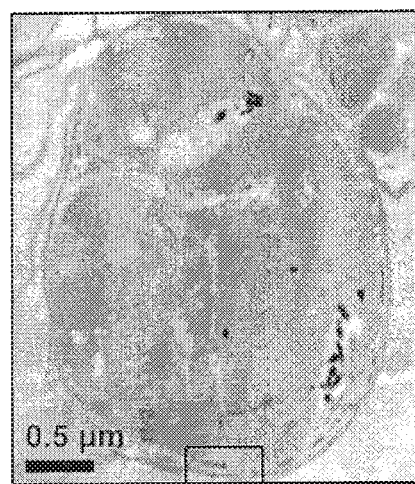
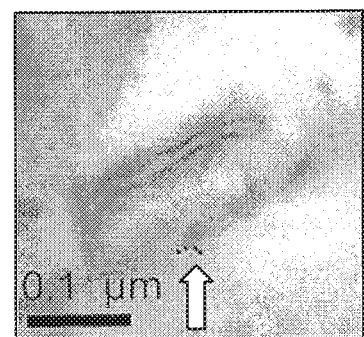
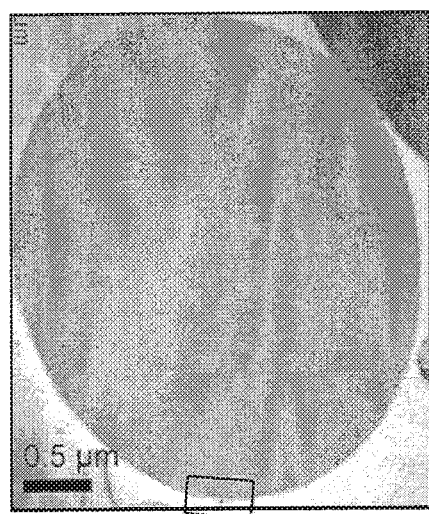
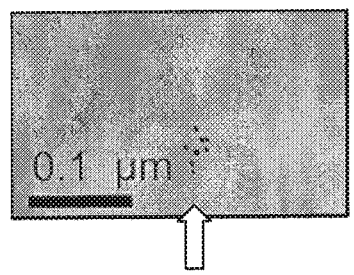
FIG. 13A                    FIG. 13B Epidemiologic characteristics of resistant and susceptible individuals used in differential screening assays

| Variable | Resistant | Susceptible | P value[a] |
|---|---|---|---|
| Number of Subjects | 12 | 11 | - |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smear from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [25.6] | 320.3 [944.1] | 0.05 |

[a] Comparisons of catagorical variables by 2 tailed Fisher's exact test.
Comparisons of continuous variables by Mann-Whitney U test

FIG. 16

Epidemiologic characteristics of resistant and susceptible individuals used in confirmatory ELISA assays

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smear from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [0] | 2106.9 [2700] | <0.001 |

[a] Comparisons of catagorical variables by 2 tailed Fisher's exact test.
Comparisons of continuous variables by Mann-Whitney U test

FIG. 17

FIG. 18A  Ring Stage
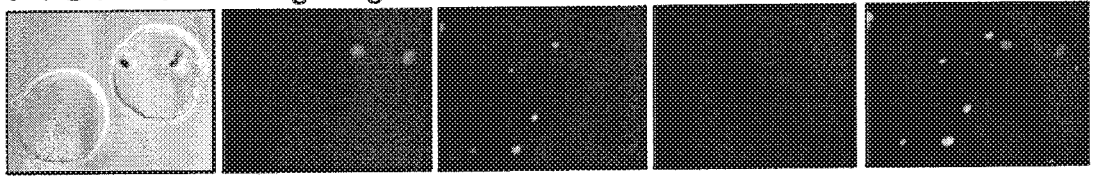
FIG. 18B  Mature Trophozoite
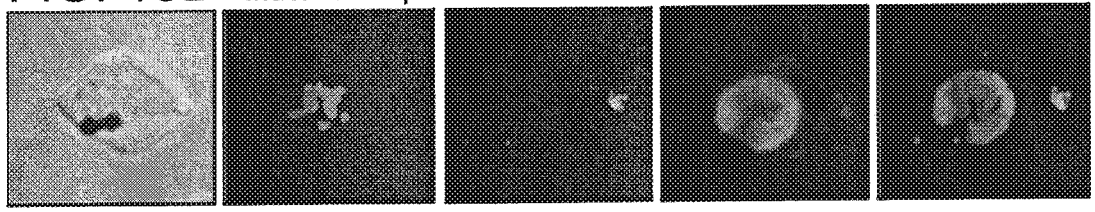
FIG. 18C  Mature Schizont
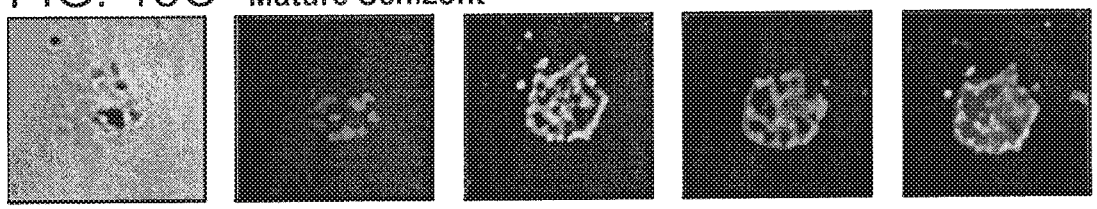
FIG. 18D  Free Merozoite
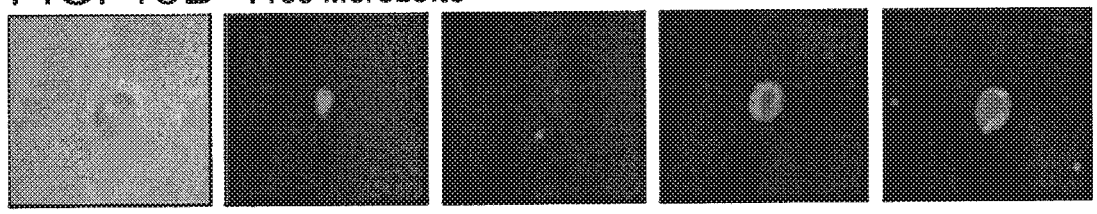
FIG. 18E  Stage I gametocyte
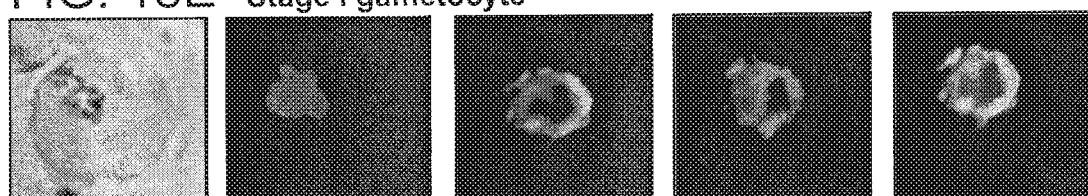
FIG. 18F  Stage III gametocyte
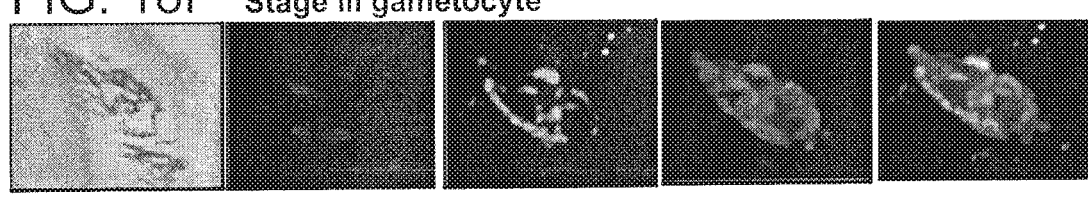
FIG. 18G  Mature Schizont
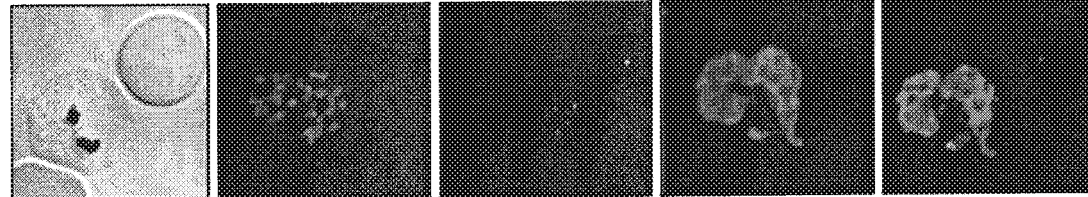

SEQUENCE LISTING

```
Sequence total quantity: 77
SEQ ID NO: 1           moltype = DNA  length = 819
FEATURE                Location/Qualifiers
misc_feature           1..819
                       note = Fragment of P. falciparum
source                 1..819
                       mol_type = other DNA
                       organism = synthetic construct
SEQUENCE: 1
aacgaggata gaggaatata cgatgaatta ttagaaaatg atatgtgtga tttatacaat   60
```

```
ttaaaaatgc atgatttgca taatttaaaa tcctatgatt ttggattatc taaagattta    120
ttaaaaaagg atatttttat atatagtaat aatttgaaaa atgatgatat ggatgatgat    180
gataataata atatgaatga tattgctata ggtgaaaatg taatatatga aaatgatata    240
catgaaaata atatagatga taatgatatg tataataatt acgtgaatgg aaatgattta    300
tatattaaca atatgcagga tgatgccatg gacgatattg tatatgatga ggaagaaatt    360
aaaagcttcc tagataaatt aaaatctgat atatcaaatc aaatgaatgt aaaaaatgga    420
aatgtcgaag ttacaggaaa tggtggtaat aagaaaatgt cttatataaa taatgatgaa    480
aatttacaag cttttgattt gttagataat ttccatatgg atgattatgg taataattat    540
aatgataatg aagaagatgg ggatggggat ggggatgacg atgaacagaa gaaaagaaaa    600
caaaaagagt tacatgttaat aaatggaaaa ttaaacttat cagatttaaa tgaattaaat    660
gtagatgata taaataataa tttttatatg tcaactcctc gaaaatctat agatgaacgt    720
aaagatacgg aatgtcaaac agattttccc ttattagatg tatcaaggaa tactaatagg    780
actcctagaa gaaaaagtgt ggaagtaata cttgtagaa                           819

SEQ ID NO: 2             moltype = AA   length = 273
FEATURE                  Location/Qualifiers
REGION                   1..273
                         note = Fragment of P. falciparum
source                   1..273
                         mol_type = protein
                         organism = synthetic construct
SEQUENCE: 2
NEDRGIYDEL LENDMCDLYN LKMHDLHNLK SYDFGLSKDL LKKDIFIYSN NLKNDDMDDD     60
DNNNMNDIAI GENVIYENDI HENNIDDNDM YNNYVNGNDL YINNMQDDAM DDIVYDEEEI    120
KSFLDKLKSD ISNQMNVKNG NVEVTGNGGN EEMSYINNDE NLQAFDLLDN FHMDDYGNNY    180
NDNEEDGDGD GDDDEQKKRK QKELHNVNGK LNLSDLNELN VDDINNNFYM STPRKSIDER    240
KDTECQTDFP LLDVSRNTNR TPRRKSVEVI LVE                                 273

SEQ ID NO: 3             moltype = AA   length = 2074
FEATURE                  Location/Qualifiers
REGION                   1..2074
                         note = Fragment of P. falciparum
source                   1..2074
                         mol_type = protein
                         organism = synthetic construct
SEQUENCE: 3
MMENKYPNEL FCYINRYNIN EIIENGEEKY VNEYDEDKNM SINHMNENDG ICEYEIPFLL     60
DYVDDSNKED SEKNSLKSYL DDGASTILSK PDELENYNKQ NENEFDENNN NKNNKIDQLK    120
EKINIIIIPN KGVINNFEEI LSMARNDKN IEKKLNDRFY QICCKSIADI NTHNLNKIKD     180
LKKKKNNKGS LNIEHIDYGD IFLTIHDTLK SNNKIKGNNK TNLLHDSSYE IKKKTRRGTN    240
IYKNPFHHRG SYLTSYENQK DIIYLNNLNN IMMDKYSNCS DSRKKEYSHF NSQEFSYDKY    300
SMKDRMFLKN LYMKQNRLRD KRGKYHKLGD YQNIENYRKT GEHSFDCNMN SDIMHSNKMS    360
HVNIMDHMIY KDNNNMSKLV DTINSREKDV KNYDDNFESY NNFFKNNNDE QHICLEYDDT    420
YNLKDTVKNI IVEEEQCGKG VACICDKNED VDDLFVSKKT NYSSNKKRED YEKVFLEDNL    480
HLKQTPSKRT KINIIPDYYD NNRSNKSYKE NEEDALFEVC GSLKNDDILY KDNKLNVINE    540
DNIKEEDDKE SVVHLNDNED KKEEMYKDVY PNVLSCEKET IRRNEKYNKS LNSTSSFEKI    600
DNPSEINVES KEDTEYFDLL IKKYEDTKIN VYDNESLLLD VSNELREEMA KGDSNKNVNK    660
VEDNDNKKEN ICHDNIMEDI CHNNNVEDMY RNNNVEDMYR NNNVEDMYRN NNVEDMYRNN    720
NVEDVCHNNN VEDVCHNNNV EDVCHNNNVE DVYHNNNVED MYHDNNIEDV CHNNNVEDVC    780
HNNNVEDHVN YDNEELNKKM DEMKEEKEER NEDRGIYDEL LENDMCDLYN LKMHDLHNLK    840
SYDFGLSKDL LKKDIFIYSN NLKNDDMDDD DNNNMNDIAI GENVIYENDI HENNIDDNDM    900
YNNYVNGNDL YINNMQDDAM DDIVYDEEEI KSFLDKLKSD ISNQMNVKNG NVEVTGNGGN    960
EEMSYINNDE NLQAFDLLDN FHMDDYGNNY NDNEEDGDGD GDDDEQKKRK QKELHNVNGK   1020
LNLSDLNELN VDDINNNFYM STPRKSIDER KDTECQTDFP LLDVSRNTNR TPRRKSVEVI   1080
LVEKKLKKKK QKCMDKYTDA NEDSNRRYPK RNRIKTLRYW IGERELTERN PYTGEIDVVG   1140
FSECKNLQDL SPHIIGPIEY KKIYLKNLNS NEHEENEDNN GDIIENNNGD VIENNNGDII   1200
EDNNANEKNH NNLESEGKGI VYDDVNNLHV HTNSDNSAHS KKIKGAPSRF SNTNNGRKKR   1260
RRRKFINVVN YIKKKKKKKL IKSMDNMEVT DNFKNDMSDE NKQSGDENKQ SGDENKQSGD   1320
ENKQSGDENK QTNNDIKQSD NDIKQSDDIY MNEDMNLFND LNDNFDNNEY FINNGDKDSH   1380
AEEEMAIENI QSKSIEKDIL NNEEQDNNNI FDIDNELIDM KDGNVDEMES DEKLKTFEKL   1440
ESLKSTTHLN NTDNCDVNLS EQTNEINYDE EKKVNKKTNH EKMKKKKKKK KKKKKKKKKE   1500
KKQIDIMYKN LSRLNLNLLL PTKKKVKKSK NSFKKEEEKQ KKKNKKVKKI KGINKGEKIK   1560
SNKKENKDNN NDSSTECVVE GEKGKDLHEF NKNGNLEDEQ MDVDISMNIS SINCESDNKN   1620
VSKEGEEEKK DIAENKEEVD KNKEEVYMDK HEMDLNNEEV YMDKNEMDLN NEEVYMDKHE   1680
MDLNNEEVYM DKHEMDLNNE EVYMDKHEMD LNKEEVYMDK HEMDLNNEEV DKENEYDENI   1740
LSDNIIYNEN NSFGNKNSF FNNTSPLKTE IINEEENSLN EMKEDINEYV EMENKLDTEK   1800
IKDSEKIGGK IEVDNKMISP INRHNFYLTI LEGMNKNFPR QWNKNNITLS KNQGQIYKGR   1860
KEKRKRSYR NDEKLLDHSI LNDINISDKM DERNELLESI KSNSTINNVL EIIKYDNRKK   1920
IKKNDTNKEI IKYDNFTSKY NNKSNDIQLN GGIYINKFKL SLDMPINKLA VSSNLGPPSS   1980
IGSTEIQPIQ KNFNDFKMNI NVYCIRMEPH EKYSSYSHKN NLVVYIDKGE KINIIINMSK   2040
TYEKGDFFYI PRFSNFQIIN DSRCDCVLYV CPLI                              2074

SEQ ID NO: 4             moltype = DNA   length = 6225
FEATURE                  Location/Qualifiers
misc_feature             1..6225
                         note = Fragment of P. falciparum
source                   1..6225
                         mol_type = other DNA
                         organism = synthetic construct
```

```
SEQUENCE: 4
atgatggaaa ataaataccc aaatgaatta ttctgttata taaatagata taatataaac    60
gaaataatag aaaatggaga agagaagtat gtaaatgaat atgatgaaga taagaatatg   120
tcaataaatc atatgaatga aaacgatggt atatgtaat  atgaaatacc attttatta    180
gactatgtgg atgatagtaa taaagaagat tcagagaata attcattaaa gagttatctc   240
gatgatggtg catccactat cctttcaaaa ccagatgaac tggaaaatta taataaacaa   300
aatgaaaatg aatttgacga aaataataat aataaaaata ataaaattga ccaattgaag   360
gaaaaaataa atattataat aataccaaat aaaggtgtta taaacaattt tgaagagata   420
ttaagcatgg caaatcgtaa tgataaaaat atagagaaaa agttgaatga tagattttat   480
caaatatgtt gtaaaagtat agctgatata aacacacaca atttaaataa aattaaagat   540
ttgaaaaaaa aaaaaaataa taaggatcc  ttaaatattg aacatataga ttatggagat   600
attttttctta ctatacatga tacattaaaa agtaataata aaataaaagg aaacaataaa   660
actaacttat tacacgattc ttcttatgaa ataaaaaaga aaacaagaag aggaacaaat   720
atatataaaa atccatttca tcatagaggt tcctatttaa cttcgtatga aaatcaaaag   780
gatatcattt accttaataa tttaaacaac attatgatgg ataaatatag taattgtagt   840
gattcacgaa aaaaggaata ttcgcatttc aattcgcagg agttttcata tgataaaatat   900
agtatgaaag acagaatgtt tctcaaaaat ttgtatatga aacaaatag  attaagagat   960
aaaaggggga aatatcacaa attgggagat tatcaaaata ttgaaaacta tcgtaaaacg  1020
ggtgaacata gttttgattg tatgaatatg tcagatatta tgcattcaaa taaaatgagc  1080
catgttaata tcatggatca tatgatatat aaagataata acaatatgag caaactagta  1140
gatacaataa attctcgtga aaaggatgta aaaaattatg acgataactt tgaaagctat  1200
aataattttt ttaagaataa taatgatgaa caacatatat gtttggagta tgacgataca  1260
tataacttaa aagatacagt taaaaatatt attgttgaag aagaacaatg tggtaagggt  1320
gttgcttgta tatgtgataa gaacgaagat gttgacgatt tgtttgtttc aaagaaaacg  1380
aattattctt ctaataaaaa aagagaagat tatgagaaag tatttcttga agataattta  1440
catttaaaac aaactccatc aaaaagaaca aaaattaata taatcccaga ttattatgat  1500
aacaatagaa gtaataagag ttataaggaa aatgaagagg atgctttgtt tgaggtatgt  1560
ggtagtttaa aaaacgatga tatattgtat aaagataata agttgaatgt cataaatgaa  1620
gataatataa aggaagagga tgacaaagaa agtgttgttc atttagataa tgatgaggat  1680
aaaaaagaag aaatgtataa agatgtatat cccaatgtat tgtcttgtga aaaagaaacg  1740
attaggagga atgaaaagta taacaaatca ttgaacagta caagtagctt tgaaaaaatt  1800
gataatccaa gtgaaattaa tgttgaaagt aaggaagata cagaatattt tgatttatta  1860
ataaaaaaat atgaggatac aaaaataaac gtatatgata atgaatctct tttattggat  1920
cttagtaatg agctacgtga agaaatggcc aaggggggat ctaataaaaa tgtaaataaa  1980
gtggaagata atgataataa aaaggaaaat atttgtcatg ataatatcat ggaagatatt  2040
tgtcataata ataacgtgga agatatgtat cgtaataata acgtggaaga tatgtatcgt  2100
aataataacg tggaagatat gtatcgtaat aataacgtgg aagatatgta tcgtaataat  2160
aacgtggaag atgtttgtca taataataac gtggaagatg tttgtcataa taataacgtg  2220
gaagatgttt gtcataataa taacgtggaa gatgtttatc ataataaca  cgtggaagat  2280
atgtatcatg ataataacat tgaagatgtt tgtcataata ataacgtgga agatgtttgt  2340
cataataata acgtggaaga ccatgttaat tatgataatg aagaattgaa taaaaaaatg  2400
gatgagatga agaagaaaa  ggaagaaaga acgaggata  gaggaatata cgatgaatta  2460
ttagaaaatg atatgtgtga tttatacaat ttaaaaatgc atgatttgca taatttaaaa  2520
tcctatgatt ttggattatc taaagattta ttaaaaaagg atattttat  atatagtaat  2580
aatttgaaaa atgatgatat ggatgatgat gataataata atatgaatga tattgctata  2640
ggtgaaaatg taatatatga aaatgatata catgaaaata atatagatga taatgatatg  2700
tataataatt acgtgaatgg aaatgattta tatattaaca atatgcagga tgatgccatg  2760
gacgatattg tatatgatga ggaagaaatt aaaagcttcc tagataaatt aaaatctgat  2820
atatcaaatc aaatgaatgt aaaaaatgga aatgtcgaag ttacaggaaa tggtggtaat  2880
gaagaaatgt cttatataaa taatgatgaa aatttacaag ctttttgatt gttagataat  2940
ttccatatgg atgattatgg taataattat aatgataatg aagaagatgg ggatggggat  3000
ggggatgacg atgaacagaa gaaaagaaaa caaaaagagt tacataatgt aaatggaaaa  3060
ttaaacttat cagatttaaa tgaattaaat gtagatgata taaataataa tttctatatg  3120
tcaactcctc gaaaatctat agatgaacgt aaagatacgg aatgtcaaac agattttcca  3180
ttattagatg tatcaaggaa tactaatagg actcctagaa gaaaaagtgt ggaagtaata  3240
cttgtagaaa aaaattaaa  aaaaaaaaaa cagaaatgta tggataaata tacagatgca  3300
aatgaggata gtaatagaag atatcccaaa gaaaatcgaa ttaaaacttt gcgttattgg  3360
ataggagaaa gagagttaac tgaaagaaac ccttacacag gagaaataga tgttgtagga  3420
tttagtgagt gtaaaaattt gcaagatttg tcacctcata ttattggtcc gattgaatat  3480
aaaaaaatat atttgaaaaa tcttaatagt aatgaacatg aggaaaatga agataataat  3540
ggagacatta ttgaaaataa taatgggac  gttattgaaa ataataatgg agacattatt  3600
gaagataata atgcaaacga aaaaaatcat aataatcttg aatctgaagg taagggtatc  3660
gtatatgatg atgtaaataa tttacatgtt cacacaaaca gtgataatag tgctcattcg  3720
aagaaaataa agggagcccc cagtaggttt agtaataaca ataatgaaag gaagaaacga  3780
agaaggagaa aattcatcaa tgtagttaat tatataaaga agaagaaaaa gaagaaactg  3840
ataaaaagta tggataatat ggaggttaca gataatttta agatgatat  gagtgatgaa  3900
aataaacaaa gtggtgatga aaataaacaa agtggtgatg aaaataaaca agtggtgat   3960
gaaaataaac aagtggtga  tgaaaataaa caaactaata atgatattaa acagagtgat  4020
aatgatatta aacagagtga tgatatttac atgaatgaag atatgaattt gttcaatgat  4080
ttaaatgata acttcgataa caatgaatat ttcataaaca atggtgataa ggattctcat  4140
gctgaagaag aaatggccat agaaaatatt caaagtaaaa gtagaaaa  ggatatttta  4200
aataatgaag agcaggataa taatacatc  tttgatattg ataatgaact tatagatatg  4260
aaggatggaa atgtagatga aatggaaagt gatgaaaaat taaaaacttt tgaaaaattg  4320
gaaagtttga aagtacaac  acatttaaac aataccgata attgtgatgt aaatttgagt  4380
gaacagacca atgaaataaa ttatgatgag gaaaaaaaag ttaataaaaa aacaaatcat  4440
gaaaaaatga gaagaagaa  gaagaaaaaa aaaaaaaaaa agaaaagaa  gaagaaagaa  4500
aaaaaacaaa tagatattat gtacaaaaat ttgtccagac ttaatttaaa tttgttactt  4560
ccaaccaaaa aaaagttaa  gaaatcgaaa aactcattta aaaagagga  agaaaacaa   4620
aagaagaaaa ataaaaagt  taaaaaatc  aaaggtatta caaggggga  aaaataaaa   4680
```

```
agtaataaga aagaaaataa ggacaataat aatgatagta gtacagaatg tgttgtagaa    4740
ggagaaaaag gaaaagattt acatgagttt aataaaaatg gaaatcttga agatgaacaa    4800
atggatgttg atatttctat gaatatttca gtataaaatt gtgaaagtga taataaaaat    4860
gtgagtaagg aaggagagga agaaaaaaaa gacatagctg aaaacaaaga agaggtggat    4920
aaaaacaaag aagaggtata tatggacaaa catgagatgg atttgaacaa tgaagaggta    4980
tatatggaca aaaatgagat ggatttgaac aatgaagagg tatatatgga caaacatgag    5040
atggatttga acaatgaaga ggtatatatg gacaaacatg aaatggattt gaacaatgaa    5100
gaggtatata tggacaaaca tgaaatggat ttgaacaaag aagaggtata tatggacaaa    5160
catgagatga tttgaacaa tgaagaggta gataaagaaa acgaatatga tgaaaatata    5220
cttagtgata acataatata taatgaaaac aattcatttg gaaacaataa gaactctttt    5280
tttaataata caagtccatt aaaaacagaa ataataaatg aagaggaaaa tagtttgaac    5340
gaaatgaaag aagacataaa tgaatacgtt gaaatgaaaa caagttgga tacggaaaaa    5400
ataaaagatt cagaaaaaat aggtggaaaa atagaggtag ataataaaat gatttctcct    5460
attaatagac ataattttta tttaacaatt cttgaaggaa tgaataagaa ttttcctagg    5520
caatggaata aaaataatat aactttatca aaaaatcaag gacaaattta taaggaagg    5580
aaagaaaaga aagaaaacg ttcctataga aatgatgaaa aattacttga tcatagtata    5640
ttaaatgata tcaatataag tgacaaaatg gatgaaagaa atgaattatt agagagtata    5700
aaatctaata gtactataaa taatgtatta gaaattataa aatatgataa taggaaaaaa    5760
ataaagaaga atgatacaaa caaggaaata atcaaatatg ataacttcac atctaaatat    5820
aataataaaa gtaatgatat tcaattgaat ggtggaatat atataaataa attcaaactt    5880
tctttagata tgcctataaa taaattagcg gtatcttcaa atcttggacc tccatcatct    5940
ataggatcaa cagaaaataca gcctattcaa aagaatttca acgatttcaa aatgaatatt    6000
aacgtgtact gtattaggat gggagccgcat gaaaaatac gctcatatag ccataaaaat    6060
aatttagttg tatatattga taagggagaa aaaaattaaca taataatcaa catgtcaaag    6120
acttatgaaa aaggtgattt ttttttacata cctagatttt ctaacttcca aataattaat    6180
gatagcgat gtgattgtgt tttatatgtt tgtcctttaa tttaa                     6225

SEQ ID NO: 5            moltype = DNA  length = 852
FEATURE                 Location/Qualifiers
misc_feature            1..852
                        note = Fragment of P. falciparum
source                  1..852
                        mol_type = other DNA
                        organism = synthetic construct
SEQUENCE: 5
attaaacaaa aaaattgaag aattacaaaa cagtaaagaa aaaaatgtac atgtattaat     60
taatggaaat tcaattattg atgaaataga aaaaaatgaa gaaaatgatg ataacgaaga    120
aaataatgat gatgacaata catatgaatt agatatgaat gatgacacat tcttaggaca    180
aaataacgat tcacattttg aaaatgttga tgatgacgca gtagaaaatg aacaagaaga    240
tgaaaacaag gaaaaatcag aatcatttcc attattccaa aatttaggat tattcggtaa    300
aaacgtatta tcaaaggtaa aggcacaaag tgaaacagat actcaatcta aaaatgaaca    360
agagatatca acacaaggac aagaagtaca aaaaccagca caaggaggag aatctgacatt    420
tcaaaaagac ctagataaga aattatataa tttaggagat gttttaatc atgtagttga    480
tatttcaaac aaaaagaaca aaataaatct cgatgaatat ggtaaaaaat atacagattt    540
caaaaaagaa tatgaagact tcgttttaaa ttctaaagaa tatgatataa tcaaaaatct    600
aataattatg tttggtcaag aagataataa gagtaaaaat ggcaaacgg atattgtaag    660
tgaagctaaa catatgactg atattttcat aaaactattt aagataagg aataccatga    720
acaatttaaa aattatattt atggtgttta tagttatgca aaacaaaata gtcacttaag    780
tgagaaaaaa ataaaaccag aagaggaata taaaaaattt ttagaatatt catttaattt    840
actaaacaca at                                                        852

SEQ ID NO: 6            moltype = AA  length = 284
FEATURE                 Location/Qualifiers
REGION                  1..284
                        note = Fragment of P. falciparum
source                  1..284
                        mol_type = protein
                        organism = synthetic construct
SEQUENCE: 6
LNKKIEELQN SKEKNVHVLI NGNSIIDEIE KNEENDDNEE NNDDDNTYEL DMNDDTFLGQ     60
NNDSHFENVD DDAVENEQED ENKEKSESFP LFQNLGLFGK NVLSKVKAQS ETDTQSKNEQ    120
EISTQGQEVQ KPAQGGESTF QKDLDKKLYN LGDVFNHVVD ISNKKNKINL DEYGKKYTDF    180
KKEYEDFVLN SKEYDIIKNL IIMFGQEDNK SKNGKTDIVS EAKHMTDIFI KLFKDKEYHE    240
QFKNIYIGVY SYAKQNSHLS EKKIKPEEEY KKFLEYSFNL LNTM                     284

SEQ ID NO: 7            moltype = AA  length = 351
FEATURE                 Location/Qualifiers
REGION                  1..351
                        note = Fragment of P. falciparum
source                  1..351
                        mol_type = protein
                        organism = synthetic construct
SEQUENCE: 7
MKSNIIFYFS FFFVYLYYVS CNQSTHSTPV NNEEDQEELY IKNKKLEKLK NIVSGDFVGN     60
YKNNEELLNK KIEELQNSKE KNVHVLINGN SIIDEIEKNE ENDDNEENND DDNTYELDMN    120
DDTFLGQNND SHFENVDDDA VENEQEDENK EKSESFPLFQ NLGLFGKNVL SKVKAQSETD    180
TQSKNEQEIS TQGQEVQKPA QGGESTFQKD LDKKLYNLGD VFNHVVDISN KKNKINLDEY    240
GKKYTDFKKE YEDFVLNSKE YDIIKNLIIM FGQEDNKSKN GKTDIVSEAK HMTEIFIKLF    300
KDKEYHEQFK NYIYGVYSYA KQNSHLSEKK IKPEEEYKKF LEYSFNLLNT M             351
```

```
SEQ ID NO: 8            moltype = DNA  length = 1056
FEATURE                 Location/Qualifiers
misc_feature            1..1056
                        note = Fragment of P. falciparum
source                  1..1056
                        mol_type = other DNA
                        organism = synthetic construct
SEQUENCE: 8
atgaagagta atatcatatt ttattttttct ttttttttttg tgtacttata ctatgtttcg    60
tgtaatcaat caactcatag tacaccagta aataatgaag aagatcaaga agaattatat    120
attaaaaata aaaaattgga aaaactaaaa aatatagtat caggagattt tgttggaaat    180
tataaaaata atgaagaatt attaaacaaa aaaattgaaa aattacaaaa cagtaaagaa    240
aaaaatgtac atgtattaat taatggaaat tcaattattg atgaaataga aaaaaatgaa    300
gaaaatgatg ataacgaaga aaataatgat gatgacaata catatgaatt agatatgaat    360
gatgacacat tcttaggaca aaataacgat tcacattttg aaaatgttga tgatgacgca    420
gtagaaaatg aacaagaaga tgaaaacaag gaaaaatcag aatcatttcc attattccaa    480
aatttaggat tattcggtaa aaacgtatta tcaaaggtaa aggcacaaag tgaaacagat    540
actcaatcta aaaatgaaca agagatatca acacaaggac aagaagtaca aaaaccagca    600
caaggaggag aatcgacatt tcaaaaagac ctagataaga aattatataa tttaggagat    660
gtttttaatc atgtagttga tatttcaaac aaaaagaaca aaataaatct cgatgaatat    720
ggtaaaaaat atacagattt caaaaaagaa tatgaagact tcgttttaaa ttctaaagaa    780
tatgatataa tcaaaaatct aataattatg tttggtcaag aagataataa gagtaaaaat    840
ggcaaaacgg atattgtaag tgaagctaaa catatgactg aaattttcat aaaactattt    900
aaagataagg aataccatga acaatttaaa aattatattt atggtgttta tagttatgca    960
aaacaaaata gtcacttaag tgagaaaaaa ataaaaccag aagaggaata taaaaaattc   1020
ttagaatatt catttaattt actaaacaca atgtaa                              1056

SEQ ID NO: 9            moltype = DNA  length = 1923
FEATURE                 Location/Qualifiers
misc_feature            1..1923
                        note = Fragment of P. falciparum
source                  1..1923
                        mol_type = other DNA
                        organism = synthetic construct
SEQUENCE: 9
gataatgtta ataataataa taataaagaa agttgtgata atattaaaca tatgagaaca    60
aaaagtttaa attttgtaag tagagaatcc tatggcgaac ataaaagtct agatgtttac   120
caggaatgtt atgtaaaaaa taataaactt attaataagg taaatgataa aaaatatgag   180
gacaataata attcctatct taatgaagat gataacgcta gtatgcaatt ttatgaagaa   240
actaatagta atccatatat tgtagaccag gaaaataata tgaaaaatta tgtcaataat   300
gttttatata acaacaatag caattattat gttgattcaa agaattatga taaatctaaa   360
gagaatgcag aaaataaatc agatgatata ttaaataagt aaaatataca taccttaaaa   420
gatcaaaaaa agaaaataca aaataataat gaattcatta gtgaacaggc tgatatagaa   480
aatataagaa attctcaaga agaagtatat gagaaagaac acgaaccttt gtgggtaata   540
aatgcatcta atgaagaaaa gaaatcatat gaagaattga tatacagcga tatgtcatct   600
aatcgtgtta cgaaaaataa atatagtgat aaagtaatgt tgaggtatt attaaatgaa   660
gataatttat taactactga aaaatacaag gtgcaattag aaaagagaaaa taaaatgatt   720
gatatgtatg aaacggtaga ggagaatata aatacaatta aaacagaaaa tacgaacgac   780
ataaatgaag aagttagaaa cgaacaaaaa agagaaagta tcaatcatat taatgataca   840
aatataaatc atataataga tgaatatccc aatgatacat ataatttcat aaaagatata   900
gaatgtgtac ataacaatga aaataacatg tacaattcta ttgaacaata tacatttat    960
catgatacac gtaataatca tttagttgat aaaaataatc aaaattttat attcgaagag  1020
gaaggtttaa atgaattgaa ctttgaagaa aaaaaggtat atatagaaaa taataccaag  1080
gatgatcaca agggagatag caaaacaagt aacttaacat ctttaaggaa taccatatgt  1140
aaaagtgaaa acgatcataa tgaaaaaaat gaaaacacat atgtggttag aaaaggcgaa  1200
aaaggaatta aacgtaaggt ttccatgaag aaaagaaatg aaaagctaaa tgaagaaaat  1260
tatattaata atatatacga taaaatggat aaccatagac aaaatgatat tacaaaaaaa  1320
gaaaatgacg aagaaaatta tattttgtac aacaacgtaa aggttaatta tgatgaatat  1380
atagaaaatg gaaataaaat aaaaataacg gaagaatcat taaatgtctt ttataaagaa  1440
aatcaaaatg aggaagattc ttctacaaaa aagttgaata gtacaagtaa aataaaacgt  1500
gcaaacaaag ggaaaacaaa aaaaaagaat gttatcacaa gggtacataa aacaaaacaa  1560
aaaattgaat atgttacaaa tagttttaat aaatcttcca aaggtgaaaa ttcagaaata  1620
ggaaaaattg gaggtaggag taaatcatta ttaacacaca gcaagaaagt tagtgaacga  1680
aataaaaata aaatagaaaa aattaatgat acaattcaa agataataaa aggaaaaag   1740
agtaatagcc aaagcaaact tgggaaggat acaaaaatta gagggaaatc aaaaactggg  1800
gaatatataa aaaataaaga tttaagaaaa aaatctaacg aaaaaaacaa aacagtgatg  1860
gataatataa atactataaa taattcttca gtatctaacc taaaaagcaa aaaacataaa  1920
ttg                                                                 1923

SEQ ID NO: 10           moltype = AA  length = 641
FEATURE                 Location/Qualifiers
REGION                  1..641
                        note = Fragment of P. falciparum
source                  1..641
                        mol_type = protein
                        organism = synthetic construct
SEQUENCE: 10
DNVNNNNNKE SCDNIKHMRT KSLNFVSRES YGEHKSLDVY QECYVKNNKL INKVNDKKYE    60
```

```
DNNNSYLNED DNASMQFYEE TNSNPYIVDQ ENNMKNYVNN VLYNNNSNYY VDSKNYDKSK  120
ENAENKSDDI LNNENIHTLK DQKKKIQNNN EFISEQADIE NIRNSQEEVY EKEHEPLWVI  180
NASNEEKKSY EELIYSDMSS NRVTKNKYSD MNNVEVLLNE DNLLTTEKYK VQLEKENKMI  240
DMYETVEENI NTIKTENTND INEEVRNEQK RESINHINDT NINHIIDEYP NDTYNFIKDI  300
ECVHNNENNM YNSIEQYTFY HDTRNNHLVD KNNQNFIFEE EGLNELNFEE KKVYIENNTK  360
DDHKGDSKTS NLTSLRNTIC KSENDHNEKN ENTYVVRKGE KGIKRKVSMK KRNEKLNEEN  420
YINNIYDKMD NHRQNDITKK ENDEENYILY NNVKVNYDEY IENGNKIKIT EESLNVFYKE  480
NQNEEDSSTK KLNSTSKIKR ANKGKTKKKN VITRVHKTKQ KIEYVTNSFN KSSKGENSEI  540
GKIGGRSKSL LTHSKKVSER NKNKIEKIND TNSKIIKGKK SNSQSKLGKD TKIRGKSKTG  600
EYIKNKDLRK KSNEKNKTVM DNINTINNSS VSNLKSKKHK L                     641

SEQ ID NO: 11          moltype = AA  length = 2227
FEATURE                Location/Qualifiers
REGION                 1..2227
                       note = Fragment of P. falciparum
source                 1..2227
                       mol_type = protein
                       organism = synthetic construct
SEQUENCE: 11
MRSKSISYFL FFKKNKKKND SCDSVIISSN KNLSIQLSKG EDDEKNEINE EKSYIKNEDV  60
YKKEKLKKKK ENKENNKKKD KNEVVYDYHD ISNDATSDYV NNYKVYEMNT CNIKKKRESF  120
FKKINILQKY KNYKIRKAAS TFHTIGHKTS FSGTDDEIEN QNKKQKKYKI KISEWKDDKS  180
HTFHKKNDIL VFDKMDKNKK FKIDNNKNNQ INIDNEERVN KNYPMATNVQ NFNIKYTSID  240
VTNDEYIIDS NKPEGSIMST DKKNNKLNYN NDTYDVDKSS DINKLGNIKK NKFDIITKTT  300
HNINNNVNNI HNYMMYTNKE NIKININHGN LNGREQNNYD EERKANVYEI FENAKKLEPN  360
NININTEEHI HISEPSIPFD MKDHKNDINE KDIILKLMYN NNGIYFDDDD ENHKNLLYKN  420
KDTHVKHLNN KFNHNFIIYN DREEGVNQKH AQKKLKKKNT ILNKNENEDI NHNSFKRPLS  480
NTNICYKDKD DKIKNGSNKY DILNNDYSNE HEKNKYNDHI TKNKRNQSAN EVKSNNNDNH  540
NNKKNNNFNI NINDSYSTNI NRNQNVMIND VNDVIKDPNM QENTQGDDEG GIIINKYLINP  600
IYNLFLRANE EIQNSNSTNN KLKMNNITKS YTNELQKTYK SMYDINDISN KRKINNKDIR  660
GTNLYNTKLC NNKLYNSNPY NMIPYNINTY NNNNNNKETC TSINIKHSEN KYPFNKSHVN  720
SYMKNTNHLP HRNAITSNNR NNEEYEKEKE KDRNITNGNN NYLVEYNNSC IPPPLKKMIP  780
IDGVRNKSIN KLNNVTNTQR TSSVSYTNKN IDENSFDMPI INGIRESKYI SNNNNINGNS  840
IGFNSSKLDN YHHQSMNVNE SYPLKNMMKN NYIEHNYDDK NIFLVKNYE DTYSNIHNGI  900
HENSMLKNYN LKKACTFHGY SRNHQKNMYT EENLNINQKK NYSHYHNNGT VLKPLVNTNN  960
VAVNEFADIN LSAQKRLHSL KSMGYEDKSM ENYRNKIYNN INNNNNNNND NNIYNDNEYC  1020
QYNNSYCFDH SDLKNMFPLN HQNSKLLTHS NNKNSFFNGI NVESKHHLAN PEIKTFAHNS  1080
YPILNQGLIN CNPLQCLGYD SNQRNKHNVV YIKKNEYLNK NIGSIINVLK REGLRKISTH  1140
NGKFESFSNM DNKNVYMEGL NIQDNVNNNN NKESCDNIKH MRTKSLNFVS RESYGEHKSL  1200
DVYQECYVKN NKLINKVNDK KYEDNNNSYL NEDDNASMQF YEETNSNPYI VDQENNMKNY  1260
VNNVLYNNNS NYYVDSKNYD KSKENAENKS DDILNNENIH TLKDQKKKIQ NNNEFISEQA  1320
DIENIRNSQE EVYEKEHEPL WVINASNEEK KSYEELIYSD MSSNRVTKNK YSDMNNVEVL  1380
LNEDNLLTTE KYKVQLEKEN KMIDMYETVE ENINTIKTEN TNDINEEVRN EQKRESINHI  1440
NDTNINHIID EYPNDTYNFI KDIECVHNNE NNMYNSIEQY TFYHDTRNNH LVDKNNQNFI  1500
FEEEGLNELN FEEKKVYIEN NTKDDHKGDS KTSNLTSLRN TICKSENDHN EKNENTYVVR  1560
KGEKGIKRKV SMKKRNEKLN EENYINNIYD KMDNHRQNDI TKKENDEENY ILYNNVKVNY  1620
DEYIENGNKI KITEESLNVF YKENQNEEDS STKKLNSTSK IKRANKGKTK KKNVITRVHK  1680
TKQKIEYVTN SFNKSSKGEN SEIGKIGGRS KSLLTHSKKV SERNKNKIEK INDTNSKIIK  1740
GKKSNSQSKL GKDTKIRGKS KTGEYIKNKD LRKKSNEKNK TVMDNINTIN NSSVSNLKSK  1800
KHKLKKKKKK NISMENINKN ITNEFCSMER KGTVLLSNMS IKKIDNANSC TLNEPLEENT  1860
LNYESNNNCS NSNLSKDKEK DRNILCNKYY SDEETNSLNK MYTSNIPEIS NYYKEIQAIN  1920
YILSNINNPN FLNSLELNDL INIEKKFINE NIYINKQIIA CNVKNEKSND EMVEKNERKV  1980
DEEKGEDEQE IKAKENNNKE ENQDNENNNK EENHDNENNN KEENQDNENN NKEENQDNEN  2040
NNKEENQDNE NNNKEENQKN ENGIIYDSRF SIIYLEHDLI YLKKNNLKVI LNVLLSNVYC  2100
FFEIKLTIIL LNFFISNNCQ WSFSLFPLSL INKLIHKFSL KINKKVPKYK LENMNINSPN  2160
IPYTYLFICD GSNYLCINDN SLNNEVYENK MKLNNIIGYY HYINLNRLTY YLEKVNANFV  2220
YNHHIYE                                                           2227

SEQ ID NO: 12          moltype = DNA  length = 6684
FEATURE                Location/Qualifiers
misc_feature           1..6684
                       note = Fragment of P. falciparum
source                 1..6684
                       mol_type = other DNA
                       organism = synthetic construct
SEQUENCE: 12
atgagatcga aatccatttc gtatttctta ttttttaaaa aaaacaaaaa gaaaaatgat  60
tcttgtgata gtgtcataat atctagcaat aagaatttat ccattcaatt atcgaaaggt  120
gaggatgatg aaaaaaatga aataaatgag gaaaaagagt atataaaaaa tgaagatgta  180
tataaaaagg aaaaattaaa aaagaagaaa gaaaacaagg aaaataataa aagaaaagat  240
aaaaatgaag tagtatatga ttatcatgac atttcaaatg atgctactag tgattatgtt  300
aataattata agtatatgaa atgaatact tgtaataaa aaagaagag agaaagttt  360
tttaaaaaaa ttaatatttt acaaaatat aaaaattaca aaattagaaa ggcagctagt  420
acctttcata ccataggaca taaaacttct ttttctggta cagatgatga aatagaaaat  480
aatcaaaaga aacaaaaaaa atataaaata aaaatttctg aatggaagga tgataaatca  540
catacttttc ataaaaaaaa tgacatattg gtatttgata gatgggataa aaataaaaaa  600
tttaaaattg ataacaacaa aaacaatcaa attaatatag ataatgaaga agagttaat  660
aaaaattatc ctatggctac taatgtacaa aattttaata taaaatatac atcaatagat  720
gtaacaaatg acgaatatat tatagattct aataaaccta aaggttctat tatgtctaca  780
```

```
gataaaaaga ataataaact taattataat aatgatacat atgatgtaga caaaagctct   840
gatataaata agttaggtaa tataaaaaag aataaatttg atattattac taaaacaaca   900
cataatatta ataataatgt aaataatata cataattata tgatgtatac aaataaagaa   960
aatataaaaa taaatataaa tcatggaaat ctaaatggaa gagaacaaaa caattatgat  1020
gaagaaagga aagcaaatgt ttatgaaata tttgaaaatg caaaaaaatt agaacctaat  1080
aatattaata tcaacacaga agaacatatt catattagtg aacccagcat accatttgat  1140
atgaaggatc ataaaaatga tataaatgaa aaagatataa tattaaaatt gatgtataac  1200
aataacggta tttattttga tgatgatgat gaaaatcaca agaatttatt atacaaaaat  1260
aaagatacac atgtaaaaca tttaaataat aaattttaacc ataattttat tatatataat  1320
gatcgcgaag aagggggtaaa tcagaaacac gcacaaaaaa aattaaaaaa aaaaaatact  1380
attcttaaca aaaacgaaaa tgaagatatt aatcataata gtttcaaaag accttttatct  1440
aatacgaata tatgttataa ggacaaagat gataaaatta aaaatggttc taataagtat  1500
gatatattaa ataatgacta ttctaatgaa cacgaaaaaa ataaatataa tgatcatata  1560
acaaaaaata aaagaaatca atcagcaaat gaagtaaaat ctaataataa tgataaccac  1620
aataataaaa aaaataataa ttttaatatt aatattaatg attcatattc tacaaatata  1680
aatagaaacc aaaatgtgat gataaatgat gtaaacgatg ttattaagga tccaaatatg  1740
caggaaaata cacaaggtga tgacgaaggt ggtattataa acaaatattt aattaaccct  1800
atttacaatt tatttctacg tgctaatgaa gaaatacaaa attcaaatag tacaaacaat  1860
aaattaaaaa tgaataatat aacaaaaagt tatacaaacg aactacaaaa gacatataaa  1920
agtatgtacg atataaatga tatatcaaat aagagaaaaa ttaataataa agatatacgt  1980
ggaactaatt tgtataacac caaattatgt aataataaat tatataattc gaatccatat  2040
aatatgattc catataatat aaacacatat aataataata aggaaacttgt  2100
accagcataa atatcaaaca ttccgaaaat aaatatccct tcaataaaatc tcatgtaaac  2160
tcatatatga aaaatacaaa tcatcttcct catagaaatg cgattacatc aaataataga  2220
aacaatgaag aatatgagaa agaaaagaa aaagatcgta acattactaa tgggaacaat  2280
aattatttgg ttgaatataa taattcttgt atacctccac cactcaaaa aatgatacca  2340
atagatggtg tgagaaataa aagtataaat aaattaaata atgtaactaa tacgcaacgt  2400
acatcaagtg tttcatatac gaataagaat attgatgaga attcgtttga tatgcctata  2460
ataaatggaa taagagaatc taaatatata agtaataata ataatattaa tggtaattcc  2520
attggtttta attcatctaa gttagataat tatcatcacc aatctatgaa tgtgaatgaa  2580
tcttatcctc taaaaaatat gatgaaaaat aattatattg aacataatta tgatgataaa  2640
aataatattt tccttgttaa aaattatgaa gatacatatt caaatattca taatggcata  2700
catgaaaata gcatgctaaa aaattataat ttaaaaaaag cgtgcacttt tcatgggtac  2760
tctagaaatc accaaaaaaa tatgtatacg gaagaaaatt taaatattaa tcaaaaaaag  2820
aattatagtc attatcataa taatggaacg gtattaaaac ctttggtaaa tactaataat  2880
gttgcagtga acgaatttgc agatattaat ttatcggctc aaaaaagatt acatagttta  2940
aaaagtatgg ggtacgagga taagagtatg gaaaattaca gaaacaaaat atacaacaac  3000
atcaataata ataataataa taatgatgat aattaataa ataatgataa tgaatattgt  3060
cagtataata atagttattg tttcgatcat agtgatttaa aaaatatgtt tccattaaat  3120
catcagaata gcaagttatt aacacatagt aataataaaa attcattttt taacggaata  3180
aatgtagaat cgaaacatca tttagcaaat cctgaaataa aaacattttgc acacaatagt  3240
tatcctatat taaatcaagg tttaataaat tgtaaccccct tacaatgctt gggttatgat  3300
tcaaatcaaa ggaataagca taatgtagta tacataaaaa aaatgaata ccttaataaa  3360
aacattggct ctattataaa tgttcttaaa agagaaggac taagaaaaat ttctacacat  3420
aatgaaaaat tcgaatcatt tagtaatatg gataataaaa atgtatatatt ggaaggacta  3480
aacatacaag ataatgttaa taataataat aataaagaaa gttgtgataa tattaaacat  3540
atgaagaacaa aaagtttaaa ttttgtaagt agagaatcct atggcgaacca taaaagtcta  3600
gatgtttacc aggaatgtta tgtaaaaaat aataaactta ttaataaggt aaatgataaa  3660
aaatatgagg acaataataa ttcctatctt aatgaagatg ataacgctag tatgcaattt  3720
tatgaagaaa ctaatagtaa tccatatatt gtagaccagg aaaataatat gaaaaattat  3780
gtcaataatg ttttatataa caacaatagc aattattaty ttgattcaaa gaattatgat  3840
aaatctaaag agaatgcaga aaataaatca gatgatatat taaataatga aaatatacat  3900
accttaaaag atcaaaaaaa gaaaatacaa aataataatg aattcattag tgaacaggct  3960
gatatagaaa atataagaaa ttctcaagaa gaagtatatg agaagaaaca cgaacctttg  4020
tgggtaataa atgcatctaa tgaagaaaag aaatcatatg aagaattgat atacagcgat  4080
atgtcatcta atcgtgttac gaaaaataaa tatagtgata tgaataatgt tgaggtatta  4140
ttaaatgaag ataatttatt aactactgaa aaatacaagg tgcaattaga aaagaaaat  4200
aaaatgattg atatgtatga aacggtagag gagaatataa atacaattaa aacagaaaat  4260
acgaacgaca taaatgaaga agttagaaac gaacaaaaaa gagaagtat caatccatatt  4320
aatgatacaa atataaatca tataatagat gaatatccca atgatacata taatttcata  4380
aaagatatag aatgtgtaca taacaatgaa aataacatgt acaattctat tgaacaaatat  4440
acattttatc atgatacacg taataatcat ttagttgata aaaataatca aaatttata  4500
ttcgaagagg aaggtttcaaa tgaattgaac tttgaagaaa aaaaggtata tatagaaaat  4560
aataccaagg atgatcacaa gggagatagc aaaaccaagt acttaacatc tttaaggaat  4620
accatatgta aaagtgaaaa cgatcataat gaaaaaatg aaaacacata tgtggttaga  4680
aaaggcgaaa aaggaattaa acgtaaggtt tccatgaaga aaagaaatga aaagctaaat  4740
gaagaaaatt atattaataa tatatacgat aaaatgata accatagaca aaatgatatt  4800
acaaaaaaag aaaatgacga agaaaattat attttgtaca acaacgtaaa ggttaattat  4860
gatgaatata tagaaaatgg aaatataata aaaataacgg aagaatcatt aaatgtctttt  4920
tataaagaaa atcaaaatga ggaagattct tctacaaaaaa agttgaatag tacaagtaaa  4980
ataaaacgtg caaacaaagg gaaaacaaaa aaaagaatgt ttatcacaag ggtacataaa  5040
acaaacaaa aaattgaata tgttacaaat agttttaata aatcttccaa aggtgaaaat  5100
tcagaaatag gaaaaattgg aggtaggagt aaatcattat taacacacag caagaaagtt  5160
agtgaacgaa ataaaaataa aatagaaaaa attaatgata caaattcaaa gataatagaa  5220
ggaaaaaaga gtaatagcca aagcaaactt gggaaggata caaaaattag agggaaatca  5280
aaaactgggg aatatataaa aaataaagat ttaagaaaaa aatctaacga aaaaaacaaa  5340
acagtgatga ataatataaa tactataaat aattcttcag tatctaacct aaaaagcaaa  5400
aaacataaat tgaaaaaaaaa aaaaaaaaaa aatatatcta tggaaaatat aaataaaaat  5460
ataacaaatg aattttgttc tatggaaaga aaaggaaccg ttctattatc taatatgagt  5520
```

```
attaagaaga ttgataatgc aaatagttgt acattaaatg aaccattaga ggaaaatacc    5580
ttaaattatg aaagtaataa taactgtagt aatagtaatt tatctaagga taaagaaaaa    5640
gatagaaata tattgtgtaa taaatattat agtgatgagg aaacaaactc tttaaacaaa    5700
atgtatacat cgaatatacc agaaataagt aattattata aggaaattca agcaattaat    5760
tacatattaa gtaatattaa taatccaaat tttttaaatt ccctcgaact gaatgattta    5820
ataaatattg aaaaaaaatt tattaacgaa aatatatata ttaataagca gataatagcc    5880
tgtaatgtaa aaaatgaaaa atcaaatgat gagatggtcg agaaaaatga acgcaaagtg    5940
gatgaagaaa aaggagaaga cgaacaagaa ataaaagcaa aggaaaataa taataaagaa    6000
gaaaaccaag ataatgaaaa taataataaa gaagaaaacc atgataatga aaataataat    6060
aaagaagaaa atcaagataa tgaaaataat aataaagaag aaaaccaaga taatgaaaat    6120
aataataaag aagaaaatca agataatgaa aataataata agaagaaaaa ccaaaaaaat    6180
gaaaatggta ttatttatga tagcaggttt agtattatct atttagaaca cgatttaata    6240
tatttaaaaa aaataattt aaaagtgata cttaatgttt tgctgtcaaa tgtgtattgc    6300
tttttgaaa ttaaattaac catatattg ttaaatttct ttatatctaa taattgtcaa    6360
tggagtttca gtttatttcc cctttcatta attaataaat taatacataa attcagttta    6420
aagataaata agaaagttcc taaatataaa ttggaaaata tgaatattaa ctcaccaaat    6480
attccatata catatctttt tatatgtgat ggaagtaact atttatgtat taatgacaat    6540
tcattaaata acgaggtata tgaaaacaag atgaaattga acaatatcat tggatattac    6600
cattatatta atttgaatag attaacatat tatttagaaa aggtaaatgc taattttgtt    6660
tataaccatc atatatatga ataa                                            6684

SEQ ID NO: 13              moltype = DNA  length = 238
FEATURE                    Location/Qualifiers
misc_feature               1..238
                           note = Fragment of P. falciparum
source                     1..238
                           mol_type = other DNA
                           organism = synthetic construct
SEQUENCE: 13
agaattctag gggaagaaaa accaaatgtg gacggagtaa gtactagtaa tactcctgga    60
ggaaatgaat cttcaagtgc ttcccccaat ttatctgacg cagcagaaaa aaaggatgaa    120
aaagaagctt ctgaacaagg agaagaaagt cataaaaaag aaaattccca agaaagcgcg    180
aatggtaagg atgatgttaa agaagaaaaa aaaactaatg aaaaaaaaga tgatggaa      238

SEQ ID NO: 14              moltype = AA  length = 79
FEATURE                    Location/Qualifiers
REGION                     1..79
                           note = Fragment of P. falciparum
source                     1..79
                           mol_type = protein
                           organism = synthetic construct
SEQUENCE: 14
RILGEEKPNV DGVSTSNTPG GNESSSASPN LSDAAEKKDE KEASEQGEES HKKENSQESA    60
NGKDDVKEEK KTNEKKDDG                                                   79

SEQ ID NO: 15              moltype = AA  length = 272
FEATURE                    Location/Qualifiers
REGION                     1..272
                           note = Fragment of P. falciparum
source                     1..272
                           mol_type = protein
                           organism = synthetic construct
SEQUENCE: 15
MWIVKFLIVV HFFIICTINF DKLYISYSYN IVPENGRMLN MRILGEEKPN VDGVSTSNTP    60
GGNESSSASP NLSDAAEKKD EKEASEQGEE SHKKENSQES ANGKDDVKEE KKTNEKKDDG    120
KTDKVQEKVL EKSPKESQMV DDKKKTEAIP KKVVQPSSSN SGGHVGEEED HNEGEGEHEE    180
EEEHEEDDDD EDDDTYNKDD LEDEDLCKHN NGGCGDDKLC EYVGNRRVKC KCKEGYKLEG    240
IECVELLSLA SSSLNLIFNS FITIFVVILL IN                                   272

SEQ ID NO: 16              moltype = DNA  length = 819
FEATURE                    Location/Qualifiers
misc_feature               1..819
                           note = Fragment of P. falciparum
source                     1..819
                           mol_type = other DNA
                           organism = synthetic construct
SEQUENCE: 16
atgtggatag ttaaattttt aatagtagtt cattttttta aatttgtac cataaacttt      60
gataaattgt atatcagtta ttcttataat atagtaccag aaaatggaag aatgttaaat    120
atgagaattc taggggaaga aaaaccaaat gtggacggag taagtactag taatactcct    180
ggaggaaatg aatcttcaag tgcttccccc aatttatctg acgcagcaga aaaaaaggat    240
gaaaagaag cttctgaaca aggagaagaa agtcataaaa agaaaattc ccaagaaagc    300
gcgaatggta aggatgatgt taagaagaa aaaaaactaa tgaaaaaaa agatgatgga    360
aaaacagaca aggttcaaga aaaggttcta gaaagtcca aaagaatcc caaatggtt    420
gatgataaaa aaaaaactga agctatccct aaaaaggtag ttcaaccaag ttcatcaaat    480
tcaggtggcc atgttggaga ggaggaagac cacaacgaag agaaggaga acatgaagag    540
gaggaagaac atgaagaaga tgacgatgac gaagatgatg atacttataa taaggacgat    600
ttggaagatg aagatttatg taaacataat aatgggggtt gtgagatga taaattgt      660
gaatatgttg gaaatagaag agtaaaatgt aaatgtaaag aaggatataa attagaaggt    720
```

```
attgaatgtg ttgaattatt atccttagca tcttcttctt taaatttaat ttttaattca   780
tttataacaa tatttgttgt tatattgtta ataaattaa                           819

SEQ ID NO: 17           moltype = DNA  length = 300
FEATURE                 Location/Qualifiers
misc_feature            1..300
                        note = Fragment of P. falciparum
source                  1..300
                        mol_type = other DNA
                        organism = synthetic construct
SEQUENCE: 17
ttctttatc ctttatttga aaaaaataaa agcattttag tacttgaact ttccttgcag     60
tgtggatttt ccatacctcc aatatatgat gaaacagata tgttagaaaa cttattaaaa   120
aatatcgaaa aatatgatca aagcttagtt atttcttcgg gatatttaaa cttcccaatg   180
aattttctta aattaattag aaatatatat atcaacgtta tgcaaaaaaa aaatggtatt   240
ttacaattaa tcacagcgtc cccatgcgct aatattttt ataaatctaa agggatatct    300

SEQ ID NO: 18           moltype = AA  length = 100
FEATURE                 Location/Qualifiers
REGION                  1..100
                        note = Fragment of P. falciparum
source                  1..100
                        mol_type = protein
                        organism = synthetic construct
SEQUENCE: 18
FFYPLFEKNK SILVLELSLQ CGFSIPPIYD ETDMLENLLK NIEKYDQSLV ISSGYLNFPM    60
NFLKLIRNIY INVMQKKNGI LQLITASPCA NSFYKSKGIS                         100

SEQ ID NO: 19           moltype = AA  length = 661
FEATURE                 Location/Qualifiers
REGION                  1..661
                        note = Fragment of P. falciparum
source                  1..661
                        mol_type = protein
                        organism = synthetic construct
SEQUENCE: 19
MALKFVIHEP KAKLLFTPKE FFNTLNDIFK NSQNRIVISC LYMGIGELEK ELIDSIKKNV    60
NIKDLKVDIL LDRQRGTRLE GKFNESSVSI LSELFKCSDN INISLFHNPL LGPILYNILP   120
PRANEAIGVM HMKIYIGDNI LMLSGANLSD SYLRNRQDRY FVIENKFLAD SIHNIINTIQ   180
GMSFTLNRDL TIKWENDLMN PLIDAYVFRE QYYRRIRFML QGIQKHISQY NKNYSYNNYY   240
KNIKNDPIND KTYIYNNQNN NKYSYTSNEF RMLNSFSTDI FDKDTYNNKN QKNNHKKENM   300
ETHTLLDTNH GTCDSTINLL NNNQNENHTN NLFTYLNEKD EFFYPLFEKN KSILVLELSL   360
QCGFSIPPIY DETDMLENLL KNIEKYDQSL VISSGYLNFP MNFLKLIRNI YINVMQKKNG   420
ILQLITASPC ANSFYKSKGI SYYIPSSYSA MANVCIEYIT KNLTNFLKKV NGQNVSEQND   480
ISNQKIYIEY YKPSWTFHSK GIWIMDNMKS MKNVSNDNDN DNDNNNNDNN NNNNINNNEF   540
HSAKKYEQNV NNSPNVKNNL NKSEYFNNEN FDKNIDEEND YYDNLPWCTV IGSSNYGYRA   600
KYRDLEMSFI IKTNDYNLRC QLKKELNIIY ESSHFVQVDE LKLRYAFWLK FLVKYIFKWL   660
L                                                                  661

SEQ ID NO: 20           moltype = DNA  length = 1986
FEATURE                 Location/Qualifiers
misc_feature            1..1986
                        note = Fragment of P. falciparum
source                  1..1986
                        mol_type = other DNA
                        organism = synthetic construct
SEQUENCE: 20
atggctctga agtttgtcat tcatgaacct aaagcaaaat tattatttac tcctaaagaa    60
tttttaata ccttaaatga catttttaag aactcacaaa atcgtattgt gattagctgt    120
ttatatatgg gaataggaga attgaaaaa gaattaatag atagtataaa aaagaatgtt    180
aatataaaag atttaaaagt tgatatatta ttagatagac aaagaggtac aagactagaa   240
gggaaattta tgaaagttc agttagtatt ttatcagaac ttttaaatg ttcagataat    300
attaataaa gctatttca taatcctta ttaggtccta tactttataa tatcttacct    360
cctagagcaa atgaagctat aggtgtaatg catatgaaaa tttatattgg ggataattt    420
ctaatgttat caggagccaa tttaagtgat agctattac gaaatagaca agatagagat   480
tttgttattg aaaataaatt cttagctgat tctattcata atattattaa taccatacaa   540
ggtatgtcat ttactctaaa tcgagattta accataaagt gggaaaatga tttaatgaac   600
ccacttatag atgcttacgt atttcgtgaa caatattata gaagaataca ttttatgtta   660
caaggaattc aaaaacatat ttcacaatat aataaaaatt attcatataa taattattat   720
aaaaatataa aaaatgatcc aataaatgat aagacatata tttataataa tcaaaataac   780
aataaatata gttatacatc aaacgaattt cgcatgttaa attctttcag tacagaatata  840
ttcgataaag atacttataa taataaaaac caaaaaaata atcataaaaa agaaaatatg   900
gaaacacata ctttattaga tactaatcat ggaacatgtg attcaacaat aatcttcta    960
aataataatc aaaatgaaaa ccatacaaat aatttattta catactctaa atgaaaaagat  1020
gaattctttt atccattatt tgaaaaaaat aaaagcattt tagtacttga acttccttg   1080
cagtgtggat tttccatacc tccaatatat gatgaaacag atatgttaga aaacttatta   1140
aaaaatatcg aaaaatatga tcaaagctta gttatttctt cgggatattt aaacttccca   1200
atgaattttc ttaaattaat tagaaatata tatatcaacg ttatgcaaaa aaaaaatggt   1260
attttacaat taatcacagc gtcaccatgc gctaatagtt tttataaatc taagggata   1320
```

```
                                             -continued
tcttattata taccaagttc atattcagct atggctaatg tgtgtattga atatattacc      1380
aaaaatttaa ccaattttct aaaaaaagta aatggacaaa atgtttctga acaaaatgat      1440
atttcaaatc aaaaaatata tattgaatat tacaaacctt catggacatt tcattcgaaa      1500
ggtatatgga taatgacaa tatgaaaagt atgaaaaatg tgagtaatga taatgataat      1560
gataatgata ataataataa tgataataat aataataaa atattaataa taatgaattt      1620
cattcagcta aaaaatatga acaaaatgtt aataactcac caaatgtaaa aaataacctg      1680
aacaagtcag aatattttaa caacgaaaat tttgataaga atattgatga agagaatgat      1740
tattatgata atttaccctg gtgtacagtg attggaagtt ctaattatgg gtatagagca      1800
aaatatagag atttggagat gagttttata ataaaaacaa atgattataa tttgaggtgt      1860
cagttaaaga aagaattaaa tataatatat gagtcatctc attttgtaca agtggatgaa      1920
ttgaaattac gatatgcttt ttggttaaaa tttttagtga aatatatatt caatggcttt      1980
ttataa                                                                1986

SEQ ID NO: 21           moltype = DNA  length = 459
FEATURE                 Location/Qualifiers
misc_feature            1..459
                        note = Fragment of P. falciparum
source                  1..459
                        mol_type = other DNA
                        organism = synthetic construct
SEQUENCE: 21
gtaaaagaag gaattaaaga aaatgatact gaaaataaag ataaagtgat aggacaagaa       60
ataataactg aagaagtaaa agaaggaatt aaagaaaatg atactgaaaa taaagataaa      120
gtgataggac aagaaataat aactgaagaa gtaaaaaaag aaattgaaaa acaagaagaa      180
aaaggaaata agaaaatat tcttgaaatt aaagatatag taattggaca agaagtaata      240
atagaaagag taaaaaaagt aattaaaaaa aagtagaaaa aaggaattaa agaaatcat      300
actgaaagta aagataaagt gataggacaa gaaataatag ttgaagaagt aaaagaagaa      360
attgaaaaac aagtagaaga aggaattaaa gaaaatgata ctgaaagtaa agataaagtg      420
ataggacaag aagtgataaa aggagatgtt aatgaagaa                             459

SEQ ID NO: 22           moltype = AA  length = 153
FEATURE                 Location/Qualifiers
REGION                  1..153
                        note = Fragment of P. falciparum
source                  1..153
                        mol_type = protein
                        organism = synthetic construct
SEQUENCE: 22
VKEGIKENDT ENKDKVIGQE IITEEVKEGI KENDTENKDK VIGQEIITEE VKKEIKQEE        60
KGNKENILEI KDIVIGQEVI IEEVKKVIKK KVEKGIKENH TESKDKVIGQ EIIVEEVKEE      120
IEKQVEEGIK ENDTESKDKV IGQEVIKGDV NEE                                   153

SEQ ID NO: 23           moltype = AA  length = 1434
FEATURE                 Location/Qualifiers
REGION                  1..1434
                        note = Fragment of P. falciparum
source                  1..1434
                        mol_type = protein
                        organism = synthetic construct
SEQUENCE: 23
MEVICRNLCY DKKNNMMENE GNKVKKVYNN SSLKKYMKFC LCTIICVFLL DIYTNCESPT        60
YSYSSIKNNN DRYVRILSET EPPMSLEEIM RTFDEDHLYS IRNYIECLRN APYIDDPLWG      120
SVVTDKRNNC LQHIKLLEMQ ESERRKQQEE ENAKDIEEIR KKEKEYLMKE LEEMDESDVE      180
KAFRELQFIK LRDRTRPRKH VNVMGESKET DESKETDESK ETGESKETGE SKETGESKET      240
GESKETGESK ETGESKETGE SKETGESKET GESKETGESK ETGESKETGE SKETGESKET      300
GESKETRIYE ETKYNKITSE FRETENVKIT EESKDREGNK VSGPYENSEN SNVTSESEET      360
KKLAEKEENE GEKLGENVND GASENSEDPK KLTEQEENGT KESSEETKDD KPEENEKKAD      420
NKKKSKKKKK SFFQMLGCNF LCNKNIETDD EEETLVVKDD AKKKHKFLRE ANTEKNDNEK      480
KDKLLGEGDK EDVKEKNDEQ KDKVLGEGDK EDVKEKNDEQ KDKVLGEGDK EDVKEKNDGK      540
KDKVIGSEKT QKEIKEKVEK RVKKKCKKKV KKGIKENDTE GNDKVKGPEI IIEEVKEEIK      600
KQVEDGIKEN DTEGNDKVKG PEIITEEVKE EIKKQVEEGI KENDTEGNDK VKGPEIITEE      660
VKEEIKKQVE EGIKENDTES KDKLIGQEII TEEVKEGIKE NDTENKDKVI GQEIITEEVK      720
EGIKENDTEN KDKVIGQEII TEEVKKEIEK QEEKGNKENI LEIKDIVIGQ EVIIEEVKKV      780
IKKKVEGIK ENHTESKDKV IGQEIIVEEV KEEIEKQVEE GIKENDTESK DKVIGQEVIK      840
GDVNEEGPEN KDKVTKQEKV KEVKKEVKKK VKKRVKKRNN KNERKDNVIG KEIMKEDVNE      900
KDTANKDKEI EQEKEKEEVK EKEEVKEKEE VKEKEEVKEK EEVKEKEEVK EKEEVKEKEE      960
VKEKDTESKD KEIEQEKEKE EVKEVKEKDT ENKDKVIGQE IIIEEIKKEV KKRVKKRNNK     1020
NENKDNVIVQ EIMNEDVNEK DTANKDKVIE QEKEKEEVKE KEEVKEKEEV KEKEEVKEKE     1080
EVKEKEEVKE KDTESKDNVI VQEIMNEDVN EKDTESKDKM IGKEVIIEEV KEEVKKRVNK     1140
EVNKRVNRRN RKNERKDVIE QEIVSEEVNE KDTKNNDKKI GKRVKKPIDD CKKEREVQEE     1200
SEEESEEESE EESEEESEEE SEEESEEESE EESEEESEEE SEEESEEESE EESEEESEEE     1260
SEEESEEESD EEKNTSGLVH RRNCKKEKKY NNGELEEYYK EKQNEEYFDE EYIIQSKEHN     1320
TLNTFPNMAL NEDFRREFHN ILSIHEDTDL MELKRILYNL FLEYNPHMNN KQKAELDKKF     1380
SEMNVVHQIL NYEERIRMYE ENAARGRLNT VILDPIITFN VIFGDDTMFK FIDE            1434

SEQ ID NO: 24           moltype = DNA  length = 4304
FEATURE                 Location/Qualifiers
misc_feature            1..4304
                        note = Fragment of P. falciparum
```

|  |  |  |
|---|---|---|
| source | 1..4304<br>mol_type = other DNA<br>organism = synthetic construct | |

SEQUENCE: 24

```
tggaggtaat ttgtagaaat ttatgctacg ataagaaaaa taatatgatg gaaaatgaag   60
ggaacaaagt gaaaaagtg tataataatt cttctttaaa gaaatatatg aagttttgtt  120
tatgcactat aatatgtgtt tttttattag atatctatac gaattgtgaa tcacccacct  180
attcatacag ttcaataaag aataataatg acagatatgt aagaatttta agtgaaactg  240
aaccaccgat gagtttagag gaaataatga gaacatttga tgaagatcat ctatattcta  300
taagaaacta tattgaatgt ttaagaaacg ctccatatat cgatgatcct ttgtggggtt  360
cggttgttac agataaacgt aataattgtc ttcagcatat taaattattg gaaatgcaag  420
aatccgaaag aagaaaacaa caagaagagg agaatgctaa ggatattgaa gaaataagaa  480
agaaagaaaa agaataccct atgaaagaat tagaagaaat ggatgaatcc gatgtagaaa  540
aggcatttag agaattacaa tttattaagt taagagatag aactagacct agaaaaacatg  600
tgaatgtaat gggagaatct aaggaaacag atgaatctaa ggaaacagat gaatctaagg  660
aaactggtga atctaaggaa actggtgaat ctaaggaaac tggtgaatct aaggaaactg  720
gtgaatctaa ggaaactggt gaatctaagg aaactggtga atctaaggaa actggtgaat  780
ctaaggaaac tggtgaatct aaggaaactg gtgaatctaa ggaaactggt gaatctaagg  840
aaactggtga atctaaggaa actggtgaat ctaaggaaac tggtgaatct aaggaaactg  900
gtgaatctaa ggaaacaaga atatatgagg aaacaaaata taacaaaata acgagtgaat  960
ttagagaaac agaaacgtg aagataacag aggaatctaa ggatagagaa ggtaacaaag 1020
tatcaggtcc atatgaaaac tcagaaaatt ccaatgtaac aagtgaatct gaagagacca 1080
aaaaattagc cgaaaagag gagaatgagg gagaaaatt aggagaaaat gttaatgatg 1140
gggcatcaga aaattcagaa gatcccaaaa aattaacaga acaagaagaa aatggtacaa 1200
aggaaagttc tgaagaaaca aaagatgata aaccggaaga aaatgagaaa aaggcagata 1260
ataaaaaaaa aagtaaaaaa aagaaaaaat cattttttca aatgttaagta tgtaatttcc 1320
tatgtaataa aaatattgaa actgatgatg aagaagaaac gttggtagta aaagatgatg 1380
ctaaaaagaa acataaattt ttaagagaag ctaaactga aaaaaatgat aatgaaaaga 1440
aagataaatt attaggagaa ggagataaag aagatgttaa agaaaagaat gatgaacaga 1500
aagataaagt attaggagaa ggagataaag aagatgttaa agaaaagaat gatgaacaga 1560
aagataaagt attaggagaa ggagataaag aagatgttaa agaaaagaat gatggaaaga 1620
aagataaagt gataggatca gaaaaaacac aaaaggaaat taagaaaaa gtagaaaaaa 1680
gagttaaaaa aaagtgtaaa aaaaaagtaa aaaaaggaat taagaaaat gatactgaag 1740
gtaacgataa agtgaaagga ccagaaataa taattgaaga agtaaaagaa gaaattaaaa 1800
aacaagtaga agatggaatt aaagaaatgt atactgaagg taacgataaa gtgaaagggc 1860
cagaaataat aactgaagaa gtaaagaag aaattaaaaa acaagtagaa gaggaattaa 1920
aagaaaatga tactgaaggt aacgataaag tgaagggcc agaaataata actgaagaag 1980
taaaagaaga aattaaaaaa caagtagaag aaggaattaa agaaaatgat actgaaagta 2040
aggataaatt gataggacaa gaaataataa ctgaagaagt aaaagaagga attaaagaaa 2100
atgtactgaa aaataaagat aaagtgatag gacaagaaat aataactgaa gaagtaaaag 2160
aaggaattaa agaaaatgat actgaaaata aagataaagt gataggacaa gaaataataa 2220
ctgaagaagt aaaaaaagaa attgaaaaac aagaagaaaa aggaaataaa gaaaatattc 2280
ttgaaattaa agatatagta attggacaag aagtaatat agaagaagta aaaaaagtaa 2340
ttaaaaaaaa agtagaaaaa ggaattaaag aaaatcatac tgaaagtaaa gataaagtga 2400
taggacaaga ataatagtt gaagaagtaa aagaagaaat tgaaaacaa gtagaagaag 2460
gaattaaaga aaatgatact gaaagtaaag ataaagtgat aggacaagaa gtgataaaag 2520
gagatgttaa tgaagaaggt cccgaaaaca aagtaaagt gacaaaacag gaaaaagtaa 2580
aagaagttaa aaaagaagta aaaaaaaag ttaaaaaag agtaaaaaaa agaaataata 2640
agaatgaaag aaagataat gtgataggaa aagaaataat gaaagaagat gttaatgaaa 2700
aagataccgc aaacaaagat aaagagatag aacaagaaaa agaaaagaa gaagttaaag 2760
aaaaagaaga agttaaagaa aaagaagta ttaaagaaaa agaagaagta aaagaaaaag 2820
aagaagtaaa agaaaagaa gaagtaaaag aaaagaaga agtaaaagaa aaagaagaag 2880
taaaagaaaa agataccgaa agcaaagata aagagataga acaagaaaaa gaaaaagaag 2940
aagtaaaaga agttaaagaa aaagatacg aaaacaaaga taagtgata ggacaagaaa 3000
taataagaga agaaatataaa aaagagtta aaaaagagt aaaaaaaga aataataaaa 3060
atgaaaacaa agataatgtg atagtacaag aaataatgaa cgaagatgtt aacgaaaaag 3120
ataccgcaaa caagataag gtgatagaac aagaaaaga aaagaagaa gttaagaaa 3180
aagaagaagt taagaaaaa gaagaagtaa agaaaaaga agaagtaaaa gaaaagaag 3240
aagtaaaaga aaaagaagaa gtaaaagaaga aagataccga aagcaaagat aatgtgatag 3300
tacaagaaat aatgaacgaa gatgttaacg aaaagatac cgaaagcaaa gataaatga 3360
taggaaaaga agtaataata gaagaagtaa aagaagaagt taaaaaaga gtaaacaaag 3420
aagttaacaa aagagtaaac agaagaaata gaaaaatga agaaaagat gtgatagaac 3480
aagaaatagt aagcgaagaa gttaacgaaa aagataccaa aaacaacgat aaaaagatag 3540
gaaaaagagt caaaaaacca atagatgatt gtaaaaaga agagaagta caagagaat 3600
ctgaagaaga gtctgaagaa gagtctgaag aagaatctga agaagagtct gaagaagaat 3660
ctgaagaaga gtctgaagaa gaatctgaag aagagtctga agaagaatct gaagaagaat 3720
ctgaagaaga gtctgaagaa gaatctgaag aagagtctga agagagtct gaagaagagt 3780
ctgaagaaga atctgaagaa gaatctgatg aagaaaaaaa tacatcaggt ttggtacata 3840
gaagaaattg taaaaaagaa aagaaatata ataatggaga attagaataa tattataaag 3900
agaaacagaa tgaagaatat tttgatgaag aatatattat tcaatcaaaa gaacataata 3960
ctttgaatac attcccaaat atggcattaa atgaagattt cagaagagaa tttcacaata 4020
tattaagtat tcatgaagat acagatttga tggaactaaa aagaatctta tataatttat 4080
ttttagaata taatccacat atgaataata aacagaaagc agaattggat aagaaattta 4140
gtgaaatgaa tgtggtacat caaatattaa attatgaaga gagaatacgc atgtatgaag 4200
aaaatgcagc acgaggaaga ctaaatacag ttattctgga tccaattatt acatttaatg 4260
taatattcgg agatgataca atgtttaagt ttattgatga ataa            4304
```

|  |  |
|---|---|
| SEQ ID NO: 25<br>FEATURE | moltype = DNA length = 792<br>Location/Qualifiers |

```
misc_feature            1..792
                        note = Fragment of P. falciparum
source                  1..792
                        mol_type = other DNA
                        organism = synthetic construct
SEQUENCE: 25
tcaaaagaac acaaatcaaa aggaaagaaa gataaaggaa agaaagataa aggaaaacat    60
aaaaaagcaa aaaaagaaaa agtaaaaaaa cacgtagtta aaaatgttat agaagatgaa   120
gacaaagatg gtgtagaaat aataaactta gaagataaag aggcatgtga agaacaacac   180
ataacagtag aaagtagacc actaagccaa ccacaatgta aactaataga tgaaccagaa   240
caattaacat taatggataa atcaaaagtt gaagaaaaaa acttatccat acaagagcaa   300
ttaataggta ccataggacg tgttaatgta gtacccagaa gagataatca taagaaaaaa   360
atggcgaaga tagaggaagc tgaacttcaa aaacagaaac atgttgataa ggaagaagac   420
aaaaaagaag aatccaaaga agtagaagaa gaatctaaag aggtacaaga agatgaagaa   480
gaagtagaag aagatgaaga agaagaagaa gaagaagagg aagaagaaga agaagaagaa   540
gaagaagagg aagaagaaga agatgaagta gaagaagatg aagatgatgc tgaagaagat   600
gaagatgatg ctgaagaaga tgaagatgat gctgaagaag atgatgatga tgctgaagaa   660
gatgaagatg atgctgaaga agatgatgat gaagatgaag atgaagaagaa gaagaagaa   720
gaagatgaag aagaagaaga agaatcagaa aaaaaaataa aagaaatttt gagaaaaaat   780
gccaaaattt aa                                                      792

SEQ ID NO: 26           moltype = AA  length = 263
FEATURE                 Location/Qualifiers
REGION                  1..263
                        note = Fragment of P. falciparum
source                  1..263
                        mol_type = protein
                        organism = synthetic construct
SEQUENCE: 26
SKEHKSKGKK DKGKKDKGKH KKAKKEKVKK HVVKNVIEDE DKDGVEIINL EDKEACEEQH    60
ITVESRPLSQ PQCKLIDEPE QLTLMDKSKV EEKNLSIQEQ LIGTIGRVNV VPRRDNHKKK   120
MAKIEEAELQ KQKHVDKEED KKEESKEVEE ESKEVQEDEE EVEEDEEEEE EEEEEEEEEE   180
EEEEEEEEDV EEDEDDAEED EDDAEEDEDD AEEDDDDAEE DDDDAEEDDD EDEDEDEEEE   240
EDEEEEEESE KKIKRNLRKN AKI                                          263

SEQ ID NO: 27           moltype = AA  length = 673
FEATURE                 Location/Qualifiers
REGION                  1..673
                        note = Fragment of P. falciparum
source                  1..673
                        mol_type = protein
                        organism = synthetic construct
SEQUENCE: 27
MNVLFLSYNI CILFFVVCTL NFSTKCFSNG LLKNQNILNK SFDSITGRLL NETELEKNKD    60
DNSKSETLLK EEKDEKDDVP TTSNDNLKNA HNNNEISSST DPTNIINVND KDNENSVDKK   120
KDKKEKHHKK DKKEKKEKKD KKEKKDKKEK HKKEKHHKK DKKEENSEV MSLYKTGQHK    180
PKNATEHGEE NLYEEMVSEI NNNAQGGLLL SSPYQYREQG GCGIISSVHE TSNDTKDNDK   240
ENISEDKKED HQQEEMLKTL DKKERKQKEK EMKEQEKIEK KKKQEEKEK KKQEKERKKQ    300
EKKERKQKEK EMKKQKKIEK ERKKEEKEK KKKHDKENE ETMQQPDQTS EETNNEIMVP    360
LPSPLTDVTT PEEHKEGEHK EEEHKEGEHK EGEHKEEEHK EEEHKKEEHK SKEHKSKGKK   420
DKGKKDKGKH KKAKKEKVKK HVVKNVIEDE DKDGVEIINL EDKEACEEQH ITVESRPLSQ   480
PQCKLIDEPE QLTLMDKSKV EEKNLSIQEQ LIGTIGRVNV VPRRDNHKKK MAKIEEAELQ   540
KQKHVDKEED KKEESKEVEE ESKEVQEDEE EVEEDEEEEE EEEEEEEEEE EEEEEEEDV   600
EEDEDDAEED EDDAEEDEDD AEEDDDDAEE DDDDAEEDDD EDEDEDEEEE EDEEEEEESE   660
KKIKRNLRKN AKI                                                     673

SEQ ID NO: 28           moltype = DNA  length = 2022
FEATURE                 Location/Qualifiers
misc_feature            1..2022
                        note = Fragment of P. falciparum
source                  1..2022
                        mol_type = other DNA
                        organism = synthetic construct
SEQUENCE: 28
atgaatgtgc tatttctttc gtataatatt tgtattcttt tttttgttgt atgcacatta    60
aattttctcta ctaagtgctt ttccaatggg ttattgaaga atcaaaatat cctaaacaaa   120
agttttgatt ccataacggg aagattatta acgaaaccg aattagaaaa aaataaagat   180
gataattcaa aatctgaaac gttgttaaaa gaggaaaaga atgaaaagga tgatgtacct   240
acaacgagta atgacaacct taagaatgct cataataata atgaaatttc aagttcaact   300
gatccaacga atattattaa tgttaatgat aaagataatg aaaactctgt agataaaaaa   360
aaagataaaa aagaaaaaaa gcataaaaaa gataaaaag aaaaaaaaga aaaaaaagat   420
aaaaaagaaa aaaagataaa aaagaaaaa aaacataaaa agaaaaaaaa acataaaaaa   480
gataaaaaaa aagaagaaaa cagtgaagtg atgtctttat ataaaacggg tcaacataaa   540
ccaaaaaacg caacagaaca tggtgaagaa aatttatatg aagaaatggt aagtgaaata   600
aataataatg cacaaggtgg actccttta tcaagcccat atcaatatag gaacaaggaa   660
ggatgtggaa tcatatctag tgttcatgag acgtctaatg atacaaaaga taatgataaa   720
gaaaatatat ccgaagacaa aaaggaggac catcaacaag aagaaatgtt gaaaacactt   780
gataaaaaag aacgtaaaca aaaagaaaaa gaaatgaaag aacaagaaaa aatcgaaaaa   840
aaaaaaaaa agcaagaaga aaaggaaaag aaaaaacaag aaaaagaaag aaaaaaacaa   900
```

```
gaaaagaaag aacgtaaaca aaaagaaaaa gaaatgaaaa aacaaaaaaa aatagaaaaa   960
gaaagaaaaa agaaagaaga aaaggaaaag aaaaagaaaa aacatgataa ggaaaatgaa  1020
gaaacaatgc aacaaccaga tcaaacaagt gaagaaacca acaatgaaat tatggtacca  1080
ttaccaagtc cattgacaga cgtaactaca ccagaagaac acaagaagg agaacacaaa  1140
gaagaagaac acaagaagg agaacacaaa gaaggagaac acaagaagaa agaacacaaa  1200
gaagaagaac acaaaaaaga agaacacaaa tcaaaagaac acaaatcaaa aggaaagaaa  1260
gataaaggaa agaaagataa aggaaaacat aaaaaagcaa aaaaagaaaa agtaaaaaaa  1320
cacgtagtta aaaatgttat agaagatgaa gacaaagatg gtgtagaaat aataaactta  1380
gaagataaag aggcatgtga agaacaacac ataacagtag aaagtagacc actaagccaa  1440
ccacaatgta aactaataga tgaaccagaa caattaacat taatgggataa atcaaaagtt  1500
gaagaaaaaa acttatccat acaagagcaa ttaataggta ccataggacg tgttaatgta  1560
gtacccagaa gagataatca taagaaaaaa atggcgaaga tagaggaagc tgaacttcaa  1620
aaacagaaac atgttgataa ggaagaagac aaaaaagaag aatccaaaga agtagaagaa  1680
gaatctaaag aggtacaaga agatgaagaa gaagtagaaa gaagtgaaga agaagaaaa   1740
gaagaagagg aagaagaaga aagaagaaga aagaagaagg aagaagaaga agatgaagta  1800
gaagaagatg aagatgatgc tgaagaagat gaagatgatg ctgaagaaga tgaagatgat  1860
gctgaagaag atgatgatga tgctgaagaa gatgatgatg atgctgaaga agatgatgat  1920
gaagatgaag atgaagatga agaagaagaa gaagtgaaga agaagaaga agaatcagaa  1980
aaaaaaataa aaagaaattt gagaaaaaat gccaaaattt aa                    2022

SEQ ID NO: 29           moltype = DNA    length = 303
FEATURE                 Location/Qualifiers
misc_feature            1..303
                        note = Fragment of P. falciparum
source                  1..303
                        mol_type = other DNA
                        organism = synthetic construct
SEQUENCE: 29
gaacatggtg aaatgctaaa tcaaaaaaga aaacttaaac aacatgaact tgatagaaga   60
gcacaaaggg aaaaaatgtt agaagaacat agtagaggaa tatttgctaa aggatatttg  120
ggagaagtag aatcagaaac tataaaaaag aaaacggaac accatgaaaa tgtaaatgaa  180
gataatgtag aaaaaccaaa attgcaacaa cataaagttc aaccaccaaa agtccaacaa  240
caaaagttc aaccaccaaa atcacaacaa caaaagttc aaccaccaaa atcacaacaa  300
caa                                                               303

SEQ ID NO: 30           moltype = AA    length = 101
FEATURE                 Location/Qualifiers
REGION                  1..101
                        note = Fragment of P. falciparum
source                  1..101
                        mol_type = protein
                        organism = synthetic construct
SEQUENCE: 30
EHGEMLNQKR KLKQHELDRR AQREKMLEEH SRGIFAKGYL GEVESETIKK KTEHHENVNE   60
DNVEKPKLQQ HKVQPPKVQQ QKVQPPKSQQ QKVQPPKSQQ Q                      101

SEQ ID NO: 31           moltype = AA    length = 383
FEATURE                 Location/Qualifiers
REGION                  1..383
                        note = Fragment of P. falciparum
source                  1..383
                        mol_type = protein
                        organism = synthetic construct
SEQUENCE: 31
MAVSTYNNTR RNGLRYVLKR RTILSVFAVI CMLSLNLSIF ENNNNNYGFH CNKRHFKSLA   60
EASPEEHNNL RSHSTSDPKK NEEKSLSDEI NKCDMKKYTA EEINEMINSS NEFINRNDMN  120
IIFSYVHESE REKFKKVEEN IFKFIQSIVE TYKIPDEYKM RKFKFAHFEM QGYALKQEKF  180
LLEYAFLSLN GKLCERKKFK EVLEYVKREW IEFRKSMFDV WKEKLASEFR EHGEMLNQKR  240
KLKQHELDRR AQREKMLEEH SRGIFAKGYL GEVESETIKK KTEHHENVNE DNVEKPKLQQ  300
HKVQPPKVQQ QKVQPPKSQQ QKVQPPKVQQ QKVQPPKVQK PKLQNQKGQK             360
QVSPKAKGNN QAKPTKGNKL KKN                                         383

SEQ ID NO: 32           moltype = DNA    length = 1152
FEATURE                 Location/Qualifiers
misc_feature            1..1152
                        note = Fragment of P. falciparum
source                  1..1152
                        mol_type = other DNA
                        organism = synthetic construct
SEQUENCE: 32
atggctgtta gtacatataa taatactcga aggaatggtc taagatatgt ccttaaaaga   60
cgtaccattc tatctgtttt tgctgtcatt tgtatgttat cattgaattt atcaatattt  120
gaaataata ataataatta tggattccat tgcaataaaa gacattttaa agtttagct   180
gaagcaagtc cagaagaaca taacaattta agaagtcatt caacaagtga tccaaagaag  240
aatgaagaga aatcattaag tgacgaaata aataaatgtg atatgaaaaa atacactgct  300
gaagaaataa atgaaatgat taacagttct aatgaattta aaatagaaa tgatatgaat  360
ataatatta gttatgtaca tgaatctgag agagaaaaat ttaaaaaggt agaagaaaat  420
atatttaaat ttattcaaag tatagtgaaa acatataaaa taccagatga atataaaatg  480
agaaaattca aatttgcaca ctttgaaatg caaggatatg cattaaaaca agaaaagttc  540
```

```
cttttagaat atgctttttct ttccttaaat ggtaaattat gtgaacgtaa aaaatttaaa    600
gaagttttag aatatgtaaa aagggaatgg attgagttta gaaaatcaat gtttgacgta    660
tggaaggaaa aattagcttc tgaattcaga gaacatggtg aaatgctaaa tcaaaaaaga    720
aaacttaaac aacatgaact tgatagaaga gcacaaaggg aaaaaatgtt agaagaacat    780
agtagaggaa tatttgctaa aggatatttg ggagaagtaa aatcagaaac tataaaaaag    840
aaaacggaac accatgaaaa tgtaaatgaa gataatgtag aaaaaccaaa attgcaacaa    900
cataaagttc aaccaccaaa agtccaacaa caaaaagttc aaccaccaaa atcacaacaa    960
caaaaagttc aaccaccaaa atcacaacaa caaaaagttc aaccaccaaa agtacaacaa   1020
caaaaagttc aaccaccaaa agtgcaaaaa ccaaaacttc aaaatcaaaa aggacaaaag   1080
caagtatctc ccaaagcaaa gggtaataat caagcgaaac caaccaaagg aaacaagtta   1140
aagaaaaatt aa                                                       1152

SEQ ID NO: 33              moltype = DNA   length = 242
FEATURE                    Location/Qualifiers
misc_feature               1..242
                           note = Fragment of P. falciparum
source                     1..242
                           mol_type = other DNA
                           organism = synthetic construct
SEQUENCE: 33
gttaaagaaa agggagaaaa gcataatgga aaaaaaccat gcagcaaaaa aactaacgaa     60
gaaaataaaa ataagaaaaa aaccaataat tcaaaatcaa atggatcaaa agctcatgaa    120
aaaaaagaaa atgaaacaaa aaacaccgct ggagaaaata aaaaagtaga ttctacttca    180
gctgataata aatcaacaaa tgctgctaca ccaggcgcaa agataaaac  tcaaggagga    240
aa                                                                   242

SEQ ID NO: 34              moltype = AA    length = 80
FEATURE                    Location/Qualifiers
REGION                     1..80
                           note = Fragment of P. falciparum
source                     1..80
                           mol_type = protein
                           organism = synthetic construct
SEQUENCE: 34
VKEKGEKHNG KKPCSKKTNE ENKNKEKTNN SKSDGSKAHE KKENETKNTA GENKKVDSTS     60
ADNKSTNAAT PGAKDKTQGG                                                 80

SEQ ID NO: 35              moltype = AA    length = 654
FEATURE                    Location/Qualifiers
REGION                     1..654
                           note = Fragment of P. falciparum
source                     1..654
                           mol_type = protein
                           organism = synthetic construct
SEQUENCE: 35
MKSFKNKNTL RRKKAFPVFT KILLVSFLVW VLKCSNNCNN GNGSGDSFDF RNKRTLAQKQ     60
HEHHHHHHHQ HQHQHQAPHQ AHHHHHHGEV NHQAPQVHQQ VHGQDQAHHH HHHHHQLQP    120
QQPQGTVANP PSNEPVVKTQ VFREARPGGG FKAYEEKYES KHYKLKENVV DGKKDCDEKY    180
EAANYAFSEE CPYTVNDYSQ ENGPNIFALR KRFPLGMNDE DEEGKEALAI KDKLPGGLDE    240
YQNQLYGICN ETCTTCGPAA IDYVPADAPN GYAYGGSAHD GSHGNLRGHD NKGSEGYGYE    300
APYNPGFNGA PGSNGMQNYV PPHGAGYSAP YGVPHGAAHG SRYSSFSSVN KYGKHGDEKH    360
HSSKKHEGND GEGEKKKKSK KHKDHDGEKK KSKKHKDNED AESVKSKKHH SHDCEKKKSK    420
KHKDNEDAES VKSKKSVKEK GEKHNGKKPC SKKTNEENKN KEKTNNSKSD GSKAHEKKEN    480
ETKNTAGENK KVDSTSADNK STNAATPGAK DKTQGGKTDK TGASTNAATN KGQCAAEGAT    540
KGATKEASTS KEATKEASTS KEATKEASTS KEATKEASTS KGATKEASTT KEATKEASTT    600
AGSTTGATTG ANAVQSKDET ADKNAANNGE QVMSRGQAQL QEAGKKKKKR GCCG           654

SEQ ID NO: 36              moltype = DNA   length = 1965
FEATURE                    Location/Qualifiers
misc_feature               1..1965
                           note = Fragment of P. falciparum
source                     1..1965
                           mol_type = other DNA
                           organism = synthetic construct
SEQUENCE: 36
atgaaaagtt ttaagaacaa aaatactttg aggagaaaga aggctttccc tgttttact      60
aaaattcttt tagtctcttt tttagtatgg gttttgaagt gctctaataa ctgcaataat    120
ggaaacggat ccggtgactc cttcgatttc agaaataaga aactttagc acaaaagcaa    180
catgaacacc atcaccacca tcaccatcaa catcaaccaa caccaccacc accacaccaa    240
gcacaccacc atcatcatca tggagaagta aatcaccaag caccacaggt tcaccaacaa    300
gtacatggtc aagaccaagc acaccatcac catcatcacc accatcatca attcaaacct    360
caacaacccc agggaacagt tgctaatcct cctagtaatg aaccagttgt aaaaccaa      420
gtattcaggg aagcaagacc aggtggaggt tcaaagcat atgaagaaaa atacgaatca    480
aaacactata aattaaagga aaatgttgtc gatggtaaaa aagattgta tgaaaaatac    540
gaagctgcca attatgcttt ctccgaagag tgcccataca ccgtaaacga ttatagccaa    600
gaaaatggtc caaatatatt tgccttaaga aaaagattcc ctcttggaat gaatgatgaa    660
gatgaagaag gtaagaagc attagcaata aaagataaat taccaggtgg tttagatgaa    720
taccaaaacc aattatatgg aatatgtaat gagacatgta ccacatgtgg acctgccgct    780
atagattatg ttccagcaga tgcaccaaat ggctatgctt atggaggaag tgcacacgat    840
```

```
ggttctcacg gtaatttaag aggacacgat aataaaggtt cagaaggtta tggatatgaa    900
gctccatata acccaggatt taatggtgct cctggaagta atggtatgca aaattatgtc    960
ccacccatg tgtgcaggcta ttcagctcca tacggagttc cacatggtgc agcccatggt   1020
tcaagatata gttcattcag ttccgtaaat aaatatggaa acacggtga tgaaaaacac    1080
cattcctcta aaaagcatga aggaaatgac ggtgaaggaa aaaaaagaa aaaatcaaaa    1140
aaacacaaag accacgatgg agaaaagaaa aaatcaaaaa aacacaaaga caatgaagat   1200
gcagaaagcg taaaatcaaa aaaacacaaa agccacgatt gtgaaagaa aaaatcaaaa    1260
aaacacaaag acaatgaaga tgcagaaagc gtaaaatcaa aaaaagtgt taagaaaag    1320
ggagaaaagc ataatggaaa aaaaccatgc agcaaaaaaa ctaacgaaga aaataaaaat   1380
aagaaaaaaa ccaataattc aaaatcagat ggatcaaaag ctcatgaaa aaaagaaat    1440
gaaacaaaaa acaccgctgg agaaaataaa aaagtagatt ctacttcagc tgataataaa   1500
tcaacaaatg ctgctacacc aggcgcaaaa gataaaactc aaggaggaaa aactgacaaa   1560
acaggagcaa gtactaatgc cgcaacaaat aaaggacaat gtgctgctga aggagcaact   1620
aagggagcaa ctaaagaagc aagtacttct aaagaagcaa caaagaagc aagtacttct    1680
aaagaagcaa caaagaagc aagtacttct aaagaagcaa caaagaagc aagtacttct    1740
aaaggagcaa ctaaagaagc aagtactact gaaggagcaa ctaaaggagc aagtactact   1800
gcaggttcaa ctacaggagc aactacagga gctaatgcag tacaatctaa agatgaaact   1860
gccgataaaa atgctgcaaa taatggtgaa caagtaatgt caagaggaca agcacaatta   1920
caagaagcag gaaagaaaaa gaagaaaaga ggatgctgtg gttaa                   1965

SEQ ID NO: 37          moltype = DNA  length = 432
FEATURE                Location/Qualifiers
misc_feature           1..432
                       note = Fragment of P. falciparum
source                 1..432
                       mol_type = other DNA
                       organism = synthetic construct
SEQUENCE: 37
gaagaatcca aaaatgaaga atttaaaaat gaagaattca aaaatgtaga taaagaaaat     60
tatgatgata aaaatatttt ctatggttat agtgataatg atgatgaaag cttttttagaa   120
actgattctt atgaagaata tgaagacgaa gataaagatg ttgaagatga gtatgaagaa    180
agtttcttac aaaatgatga gaaaaaaatg gtcttttatg atttataaa gccagaagaa    240
aatgaatctt attatgaaaa gaaacaaaag aagaagaaa agaagagaa agaagagaaa     300
gaacaaagtt tgaacaaaca aaacgatatg gaagaccaag aagataatga gaatataaaa    360
tttgaagaag aaaataaaga agaccttcta gatgtccaac aagatgaaga attaccaagt    420
gaaggaaaac aa                                                       432

SEQ ID NO: 38          moltype = AA  length = 144
FEATURE                Location/Qualifiers
REGION                 1..144
                       note = Fragment of P. falciparum
source                 1..144
                       mol_type = protein
                       organism = synthetic construct
SEQUENCE: 38
EESKNEEFKN EEFKNVDKEN YDDKNIFYGY SDNDDESFLE TDSYEEYEDE DKDVEDEYEE     60
SFLQNDEKKM VFYDLYKPEE NESYYEKKQK KEEKEEKEEK EQSLNKQNDM EDQEDNEEYK    120
FEEENKEDLL DVQQDEELPS EGKQ                                          144

SEQ ID NO: 39          moltype = AA  length = 704
FEATURE                Location/Qualifiers
REGION                 1..704
                       note = Fragment of P. falciparum
source                 1..704
                       mol_type = protein
                       organism = synthetic construct
SEQUENCE: 39
ISFSDYERSI KNFSISSHAE NNYDNIINEY KKIKDINNNI NILSSVHRKG RILYDSFLEI     60
NKLENDKKEK HEKEDEYEDN DESFLETEEY EDNEDKEYNK DEDDYAESFI ETDEYEDNED    120
DKYNKDEDDY SESFIETDEY DDNEEEQYNK DEDDYADSFI ETDHYENNDD KNEEEEEYND    180
QDNDYGYNFL ETDEYDDSEE YDYDDKEYGE SFLEKEEGEE MKDEEMKDEE MKDVEMKDEE    240
MKDEEIKYDE MKNEEMKYDE MKDEVMKDEE MKDEVMKDEE MKDEQMKYEE FKNEESKNEE    300
SKNEESKNEE SKNEEFKNEE SKNEEFKNEE FKNVDKENYD DKNIFYGYSD NDDESFLETD    360
SYEEYEDEDK DVEDEYEESF LQNDEKKMVF YDLYKPEENE SYYEKKQKKE EKEEKEEKEQ    420
SLNKQNDMED QEDNEEYKFE EENKEDLLDV QQDEELPSEG KQKVKGKSFD NEHLNEIQNV    480
SDVHAFIQKD MKYLDDLIDE EQTIKDAVKK SAYKGNKKLG NNKKSQMILE EEPEENFEED    540
ADEELNKLME QEKNIVDKEI KNSKANKSNK KLQFNNTNKQ NKMYMKNEYN NKTKNNKNNK    600
FEQQNYDESY MDDDYEQNEE FNDNNQSEDM KETNELDKIN DELLTDQGPN EDTLLENNNK    660
IFDNKFVAHK KREKSISPHS YQKVSTKVQN KEDMENKEEK QLIS                    704

SEQ ID NO: 40          moltype = DNA  length = 2114
FEATURE                Location/Qualifiers
misc_feature           1..2114
                       note = Fragment of P. falciparum
source                 1..2114
                       mol_type = other DNA
                       organism = synthetic construct
SEQUENCE: 40
attagctttt ctgattatga gagatcaata aaaaactttt ctatttcttc tcatgcagaa     60
```

-continued

```
aataattatg ataatataat aaatgaatat aaaaaaataa aagatattaa caacaatata  120
aacatattat catcagtaca tagaaaagga agaatattgt acgacagctt tttagaaata  180
aataagttgg aaaatgacaa aaaagagaaa catgaaaaag aagatgaata tgaagataat  240
gatgaaagct tttagaaac tgaagaatat aagataatg aagatgaaaa atataacaaa   300
gatgaagatg attatgcaga aagttttatt gagactgatg aatatgaaga taatgaagat  360
gataaatata ataaagatga agatgattat tcagaaagct ttattgagac tgatgaatat  420
gatgataatg aagaagaaca atataataaa gatgaagatg attatgcaga tagtttatt   480
gagacagacc attatgaaaa taacgatgat aaaaatgaag aagaagaaga atataatgat  540
caagataatg attatggata taactttta gaaactgacg aatacgatga tagcgaagaa   600
tatgattacg acgataagga atacggagag agtttcctcg aaaaagaaga aggtgaagaa  660
atgaaagatg aagagatgaa agatgaagag atgaaagatg tagaaatgaa agatgaagag  720
atgaaagatg aagagataaa atatgacgag atgaaaatg aagagatgaa atatgacgag   780
atgaaagatg aagtgatgaa agatgaagag atgaaagatg aagtgatgaa agatgaagag  840
atgaaagacg aacaaatgaa atatgaagaa ttcaaaaatg aagaatccaa aaatgaagaa  900
tccaaaaatg aagaatccaa aaatgaagaa tccaaaaatg aagaattcaa aaatgaagaa  960
tccaaaaatg aagaatttaa aaatgaagaa ttcaaaaatg tagataaaga aaattatgat 1020
gataaaaata ttttctatgg ttatagtgat aatgatgatg aaagcttttt agaaactgat 1080
tcttatgaag aatatgaaga cgaagataaa gatgttgaaa gatgagtatga agaaagtttc 1140
ttacaaaatg atgagaaaaa aatggtcttt tatgattat acaagccaga agaaaatgaa   1200
tcttatatg aaaagaaaca aaagaaagaa gaaaagaaag agaaagaaga gaaagaacaa  1260
agtttgaaca aacaaaacga tatggaagac caagaagata tgaagaata taaatttgaa   1320
gaagaaaata aagaagacct tctagatgtc caacaagata aagaattacc aagtgaagga  1380
aaacaaaaag taaaggaaa atcattcgat aatgaacatt tgaatgaaat acaaaatgtt  1440
agcgacgtac atgcatttat acaaaaagat atgaaatatt tagatgatct catagatgaa  1500
gagcaaacta ttaaagatgc cgtcaaaaaa agtgcttata aggaaataa gaattagga    1560
aataataaaa aatcacaaat gatactggaa gaagaaccag aagaaaattt tgaagaagat  1620
gctgatgaag aattaaataa actaatggaa caagaaaaaa atattgtaga taagaaaatc  1680
aaaaatagta aagcaaataa aagcaacaaa aaattacaat tcaataacac taataaacaa  1740
aacaaaatgt atatgaaaaa cgaatataat aataagacaa aaaataataa aaacaataaa  1800
tttgaacaac aaaaattatga tgaatcatat atggatgatg attatgaaca aatgaagaa   1860
tttaatgata ataatcaaag cgaagatatg aaagaaacaa atgaactcga taaaattaat  1920
gatgaactat taactgatca aggaccaaac gaagatacat tattagaaaa taataataaa  1980
atttttcgata ataatttgt agcacataaa aaaagagaaa aagtatatc cccacacagt   2040
taccaaaagg tatctaccaa agtacaaaat aaggaagaca tggaaaataa ggaagagaaa  2100
caattgataa gtaa                                                    2114
```

SEQ ID NO: 41  moltype = DNA  length = 650
FEATURE        Location/Qualifiers
misc_feature   1..650
               note = Fragment of P. falciparum
source         1..650
               mol_type = other DNA
               organism = synthetic construct
SEQUENCE: 41

```
tcaccaaata aaacagaatt aaaaaaagga gaagaaggaa aagtacaaac atgttataca    60
acaataccta ttgaaacatt attagctcaa ggatcttata gttctaaaga tatattcaat  120
tttagtgaac aggaaattaa tatgcaacat agtgatatat tagaaggaga acgattaaaa  180
catcttaatg aactagaaac tattatatat gaaagtagaa gtagacttaa tggtatatat  240
aaaaattttg ttatgggatga tgaaagagat cgtatttac tttccttaga tgattatgaa   300
aattggttat atgataatat agaagaaat aaaaatatgt ttattaaaaa aaagaagaa    360
attagagatc ttataaaaaa tattgtacaa aaatttgata tataattc aaaacaacaa    420
aatctaggaa atataattaa tcatcttaat aatatcataa cacaatgttc aaataaacca  480
tcggatgaaa gtcaaaatat aattaataga acaacgaaat tcttaaataa tattaattct  540
ttacaagaac aagaaaaaaa taaaccacta tacgaaccac ctgtatatac acttaacgat  600
attgaagcag aatttaatga agtcacacaa ctcgctcaaa aattcttttc             650
```

SEQ ID NO: 42  moltype = AA  length = 216
FEATURE        Location/Qualifiers
REGION         1..216
               note = Fragment of P. falciparum
source         1..216
               mol_type = protein
               organism = synthetic construct
SEQUENCE: 42

```
SPNKTELKKG EEGKVQTCYT TIPIETLLAQ GSYSSKDIFN FSEQEINMQH SDILEGERLK    60
HLNELETIIY ESRSRLNGIY KNFVMDDERD RILLSLDDYE NWLYDNIEEN KNMFIKKKEE   120
IRDLIKNIVQ KFDVYNSKQQ NLGNIINHLN NIITQCSNKP SDESQNIINR TTKFLNNINS   180
LQEQEKNKPL YEPPVYTLND IEAEFNEVTQ LAQKFF                              216
```

SEQ ID NO: 43  moltype = AA  length = 873
FEATURE        Location/Qualifiers
REGION         1..873
               note = Fragment of P. falciparum
source         1..873
               mol_type = protein
               organism = synthetic construct
SEQUENCE: 43

```
MSVLGIDIGN DNSVVATINK GAINVVRNDI SERLTPTLVG FTEKERLIGD SALSKLKSNY    60
KNTCRNIKNL IGKIGTDVKD DIEIHEAYGD LIPCEYNYLG YEVEYKNEKV VFSAVRVLSA   120
```

```
LLSHLIKMAE KYIGKECKEI VLSYPPTFTN CQKECLLAAT KIINANVLRI ISDNTAVALD   180
YGMYRMKEFK EDNGSLLVFV NIGYANTCVC VARFFSNKCE ILCDIADSNL GGRNLDNELI   240
KYITNIFVNN YKMNPLYKNN TPELCPMGTG RLNKFLVTST ASDQQNGINN KVRIKLQEVA   300
IKTKKVLSAN NEASIHVECL YEDLDCQGSI NRETFEELCS NFFLTKLKHL LDTALCISKV   360
NIQDIHSIEV LGGSTRVPFI QNFLQQYFQK PLSKTLIADE SIARGCVLSA AMVSKHYKVK   420
EYECVEKVTH PINVEWHNIN DASKSNVEKL YTRDSLKKKV KKIVIPEKGH IKLTAYYENT   480
PDLPSNCIKE LGSCIVKINE KNDKIVESHV MTTFSNYDTF TFLGAQTVTK SVIKSKDEKK   540
KADDDKTEDKG EKKDAKDQEQ NDDKDQTNDN NMNEKDTNDK KEKNNETNSP NKTELKKGEE   600
GKVQTCYTTI PIETLLAQGS YSSKDIFNFS EQEINMQHSD ILEGERLKHL NELETIIYES   660
RSRLNGIYKN FVMDDERDRI LLSLDDYENW LYDNIEENKN MFIKKKEEIR DLIKNIVQKF   720
DVYNSKQQNL GNIINHLNNI ITQCSNKPSD ESQNIINRTT KFLNNINSLQ EQEKNKPLYE   780
PPVYTLNDIE AEFNEVTQLA QKFFSKLEVE ELAKQKAKQE KEKEKEKEKE KEKEKEKNEE   840
TNLDANEEQN NEAKNNEEKE NSTKNENSAN PEE                                873

SEQ ID NO: 44           moltype = DNA  length = 2622
FEATURE                 Location/Qualifiers
misc_feature            1..2622
                        note = Fragment of P. falciparum
source                  1..2622
                        mol_type = other DNA
                        organism = synthetic construct
SEQUENCE: 44
atgtcggttt taggtataga tataggaaat gacaattctg ttgtagctac tattaataaa     60
ggtgctataa atgttgtgag gaatgacata tccgaaaggt taaccccgac attagttggt    120
ttcaccgaaa agaaagatt aataggtgat agtgctttat ctaaattgaa atctaattat    180
aagaatacat gtaggaatat aaagaatttg ataggtaaa taggtaccga tgtaaaagat    240
gatatagaaa tacatgaagc atatgggat ttaataccat gtgaataaa ttatttaggt    300
tatgaagttg aatataaaaa tgaaaaagtt gtatttagtg ctgttcgtgt tttatcagcc    360
ttattatcac atttgattaa aatggctgaa aaatatattg gaaggaatg taagaaatt    420
gtcttatcat atcctccaac attttacaaat tgtcaaaaag aatgttttatt agctgcaact    480
aaaattatta atgctaatgc tttgagaatt attagtgata atacagctgt tgctctagat    540
tatggaatgt acagaatgaa agaattcaaa gaagataatg gatccttact agttttgtt    600
aacattggtt atgcaaatac ttgtgtatgt gttgcgcgtt ttttttctaa taatgtgaa    660
atcttatgtg atattgctga ttcaaattta ggtggtagaa atttagataa tgaacttatt    720
aaatatatta caaatatatt tgttaataat tgtaaaatga atccattata taaaaacaat    780
actccggaat tatgccccat gggtactggt agattaaata gtttttagt aacatctaca    840
gcatctgatc aacaaaatgg tattaataat aaagtacgta ttaaattaca agaagttgct    900
ataaaaacaa agaaagtact ttcagcaaat aatgaagcgt ccatacatgt tgaatgttta    960
tatgaagatt tagattgtca aggttccatt aatagagaaa cctttgaaga attgtgttca   1020
aacttcttct taacaaaatt aaaacatctt ctagatactg ctctatgtat tagtaaagta   1080
aacatacaag atatacattc tattgaagtt ttgggtggat ccacaagagt tccatttatt   1140
caaaattttt tacaacaata ttttcagaaa ccattatcta agaccttat agcagatgaa   1200
tctatagcaa gaggttgtgt actatcagct gctatgatta gtaaaccatt taaagtaaaa   1260
gaatatgaat gtagaaaaa agttacacat ccaattaatg ttgaatggca taatattaat   1320
gacgcatcta aaagtaatgt agaaaaatta tatacaagag attccttaaa aagaaagtt   1380
aagaaattg ttatcccaga aaaggacac attaaactta cagcttatta tgaaaataca   1440
ccagatttac catccaattg tataaaagaa ttgggatcta gtgttgttaa aataatgaa   1500
aagaatgata aaattgttga atcccacgtt atgaccacct tttcaaatta tgatacatttt   1560
acatttttag gtgcacagac agtaaccaag tctgttatta agtccaagga tgaaaaaaaa   1620
aaagcagatg acaaaacgga ggataaggga gaaaaaaaag atgcaaaaga tcaagaacaa   1680
aatgatgata aagatcaaac aaatgataat aacatgaatg agaaagatac taatgataaa   1740
aaagaaaaaa ataatgaaac aaactcacca aataaaacag aattaaaaaa aggagaagaa   1800
ggaaaagtac aacatgttta taacaatat cctattgaaa cattattagc tcaaggatct   1860
tatagttcta agatatatt caattttagt gaacaggaaa ttaatatgca acatagtgat   1920
atattagaag gagaacgatt aaaacatctt aatgaactag aaactattat atatgaaagt   1980
agaagtagac ttaatgggtat atataaaaat tttgttatgg atgatgaaag gatcgtatt   2040
ttactttcct tagatgatta tgaaaattgg ttatatgata atatagaaga aataaaaat   2100
atgtttatta aaaaaaaga agaaattaga gatcttataa aaatattgt acaaaaattt   2160
gatgtatata attcaaaaca acaaaatcta ggaaatataa ttaatcatct taataatatc   2220
ataacacaat gttcaaataa accatcggat gaaagtcaaa atataattaa tagaacaacg   2280
aaattcttaa ataatattaa ttctttacaa gaacaagaaa aaaataaacc actatacgaa   2340
ccacctgtat atacacttaa cgatattgaa gcagaattta tgaagtcac acaactcgct   2400
caaaaattc tttcaaagct tgaagtagaa gaactagcca acaaaaaagc aaagcaagaa   2460
aaggaaaagg aaaaggaaaa agaaaaagag aagaaaaag aaaaaaagag   2520
acaaacttgg atgcaaatga ggaacaaaat aatgaagcaa aaaataatga agaaaggag   2580
aactcaacaa aaaatgaaaa ttcagctaat ccagaggaat aa                      2622

SEQ ID NO: 45           moltype = DNA  length = 255
FEATURE                 Location/Qualifiers
misc_feature            1..255
                        note = Fragment of P. falciparum
source                  1..255
                        mol_type = other DNA
                        organism = synthetic construct
SEQUENCE: 45
ttcttagcag cttgtttaga tcatagtata tttcaacaag atgttatctg tagaaatgct     60
ttcaatgttt tgatttaga tggtgatggt gttataacaa aggatgaatt atttaaaatt    120
ctatccttta gtgctgtaca agtatccttt agtaaagaaa ttattgaaaa tcttattaaa    180
gaagtcgatt ctaataatga tggatttata gattatgatg aattttataa gatgatgacg    240
```

```
ggagttaaag aatga                                                      255

SEQ ID NO: 46           moltype = AA  length = 84
FEATURE                 Location/Qualifiers
REGION                  1..84
                        note = Fragment of P. falciparum
source                  1..84
                        mol_type = protein
                        organism = synthetic construct
SEQUENCE: 46
FLAACLDHSI FQQDVICRNA FNVFDLDGDG VITKDELFKI LSFSAVQVSF SKEIIENLIK   60
EVDSNNDGFI DYDEFYKMMT GVKE                                          84

SEQ ID NO: 47           moltype = AA  length = 568
FEATURE                 Location/Qualifiers
REGION                  1..568
                        note = Pf-CDPK5
source                  1..568
                        mol_type = protein
                        organism = synthetic construct
SEQUENCE: 47
MKETEVEDMD TNRKDGKIKK KEKIVNMKNE EVKSTTKSTL ADSDEDYSII TLCTKCLSKK    60
LEDNKNRIIL DSKAFKDNRL KGRCSVSSNE DPLDNKLNLS PYFDRSQIIQ EIILMNNDEL   120
SDVYEIDRYK LGKGSYGNVV KAVSKRTGQQ RAIKIIEKKK IHNIERLKRE ILIMKQMDHP   180
NIIKLYEVYE DNEKLYLVLE LCDGGELFDK IVKYGSFSEY EAYKIMKQIF SALYYCHSKN   240
IMHRDLKPEN ILYVDNTEDS PIQIIDWGFA SKCMNNHNLK SVVGTPYYIA PEILRGKYDK   300
RCDIWSSGVI MYILLCGYPP FNGKNNDEIL KKVEKGEFVF DSNYWARVSD DAKDLICQCL   360
NYNYKERIDV EQVLKHRWFK KFKSNNLIIN KTLNKTLIEK PKEFHKLCKI KKLAVTCIAY   420
QLNEKDIGKL KKTFEAFDHN GDGVLTISEI FQCLKVNDNE FDRELYFLLK QLDTDGNGLI   480
DYTEFLAACL DHSIFQQDVI CRNAFNVFDL DGDGVITKDE LFKILSFSAV QVSFSKEIIE   540
NLIKEVDSNN DGFIDYDEFY KMMTGVKE                                     568

SEQ ID NO: 48           moltype = DNA  length = 1707
FEATURE                 Location/Qualifiers
misc_feature            1..1707
                        note = Pf-CDPK5
source                  1..1707
                        mol_type = other DNA
                        organism = synthetic construct
SEQUENCE: 48
atgaaagaga cggaggtcga agatatggat acgaatagaa aagatggtaa aattaaaaag    60
aaagaaaaaa tagtaaatat gaaaaatgaa gaagtgaaaa gtacgacaaa gagtacgtta   120
gccgatagtg atgaagacta ttcgattata actttatgta cgaaatgttt atctaaaaaa   180
cttgaagata ataagaatcg aataattctt gatagtaaag cttttaaaga taatagatta   240
aaaggtagat gtagtgttag ttccaatgaa gatcctttag ataacaaatt aaatttatca   300
ccatattttg atagatccca ataattcaa gaaataattt tgatgaataa tgatgaatta   360
agtgatgtat atgaaataga tagatacaag ttaggcaaag gatcttatgg aaatgttgtt   420
aaagccgtaa gtaaaagaac tggtcaacag agagctataa aaattataga aaaaagaaa    480
attcataata ttgaaagatt aaaaagagaa atattaataa tgaaacagat ggatcatcct   540
aatattataa aattatatga agtttatgaa gacaatgaaa aattatattt agtattgaa    600
ttatgtgacg gtgagaatt atttgataaa atttgtaaaat atggtagctt ctctgaatat   660
gaagcatata aaattatgaa acaaatattt tcagctttat attattgtca tagtaaaaat   720
attatgcata gagatttaaa accagaaaat atttttatg tagataatac agaagattct   780
cctatacaaa taattgattg gggattcgct agtaaatgta tgaataatca atttgaaa    840
tcagttgttg ggacaccta ttatatagca cccgaaatat taagggtaa atatgacaaa    900
agatgtgata tatggagtag tggtgtaatt atgtatattt tattatgtgg atatccacca   960
tttaatggaa aaaataatga tgaaatctta aaaaaagtgg aaaaaggaga atttgttttc  1020
gattccaatt attgggcaag agttagtgat gatgctaaag atttaatttg tcaatgttta  1080
aattataatt ataaagaaag aatagatgtt gagcaagttc taaaacatag atggttcaaa  1140
aaatttaaat caaataatct tattataaat aaaacattaa ataaaacttt aatcgaaaaa  1200
tttaaagaat tccataaatt atgtaaatt aaaaaagctag ctgtaacatg tatagcatac  1260
caattaaatg aaaagatat agggaaatta aaaaaaacat tgaagctttt tgatcataat  1320
ggagatggag tattaaccat atcagaaatt tttcaatgtt taaagttaa tgacaatgaa  1380
tttgatagag aattatactt tttattaaaa caacttgata cagatggaaa tgggttaata  1440
gattatactg aattcttagc agcttgttta gatcatagta tatttcaaca agatgttatc  1500
tgtagaaatg ctttcaatgt ttttgattta gatggtgatg gtgttataac aaaggatgaa  1560
ttatttaaaa ttctatcctt tagtgctgta caagtatcct ttagtaaaga aattattgaa  1620
aatcttatta agaagtcga ttctaataat gatggattta gattatgat gaattttat     1680
aagatgatga cggagttaa agaatga                                       1707

SEQ ID NO: 49           moltype = DNA  length = 34
FEATURE                 Location/Qualifiers
misc_feature            1..34
                        note = Primer
source                  1..34
                        mol_type = other DNA
                        organism = synthetic construct
SEQUENCE: 49
gaagatgttt gtcataataa taacgtggaa gacc                               34
```

```
SEQ ID NO: 50           moltype = DNA   length = 30
FEATURE                 Location/Qualifiers
misc_feature            1..30
                        note = Primer
source                  1..30
                        mol_type = other DNA
                        organism = synthetic construct
SEQUENCE: 50
tcctacaaca tctatttctc ctgtgtaagg                                            30

SEQ ID NO: 51           moltype = DNA   length = 26
FEATURE                 Location/Qualifiers
misc_feature            1..26
                        note = Primer
source                  1..26
                        mol_type = other DNA
                        organism = synthetic construct
SEQUENCE: 51
gaataaaaaa atggatgaga tgaaag                                                26

SEQ ID NO: 52           moltype = DNA   length = 36
FEATURE                 Location/Qualifiers
misc_feature            1..36
                        note = Primer
source                  1..36
                        mol_type = other DNA
                        organism = synthetic construct
SEQUENCE: 52
ctattactat cctcatttgc atctgtatat ttatcc                                     36

SEQ ID NO: 53           moltype = DNA   length = 29
FEATURE                 Location/Qualifiers
misc_feature            1..29
                        note = Primer
source                  1..29
                        mol_type = other DNA
                        organism = synthetic construct
SEQUENCE: 53
gcactgcaga gcactgaata aatgaaatg                                             29

SEQ ID NO: 54           moltype = DNA   length = 31
FEATURE                 Location/Qualifiers
misc_feature            1..31
                        note = Primer
source                  1..31
                        mol_type = other DNA
                        organism = synthetic construct
SEQUENCE: 54
gcagcggccg cgtggatgca ccatcatcga g                                          31

SEQ ID NO: 55           moltype = DNA   length = 29
FEATURE                 Location/Qualifiers
misc_feature            1..29
                        note = Primer
source                  1..29
                        mol_type = other DNA
                        organism = synthetic construct
SEQUENCE: 55
gcactgcagg agttatctcg atgatggtg                                             29

SEQ ID NO: 56           moltype = DNA   length = 34
FEATURE                 Location/Qualifiers
misc_feature            1..34
                        note = Primer
source                  1..34
                        mol_type = other DNA
                        organism = synthetic construct
SEQUENCE: 56
gcagcggccg cgatccatga tattaacatg gctc                                       34

SEQ ID NO: 57           moltype = DNA   length = 26
FEATURE                 Location/Qualifiers
misc_feature            1..26
                        note = Primer
source                  1..26
                        mol_type = other DNA
                        organism = synthetic construct
SEQUENCE: 57
```

```
catgttttgt aatttatggg atagcg                                              26

SEQ ID NO: 58          moltype = DNA   length = 25
FEATURE                Location/Qualifiers
misc_feature           1..25
                       note = Primer
source                 1..25
                       mol_type = other DNA
                       organism = synthetic construct
SEQUENCE: 58
cgccaagctc gaaattaacc ctcac                                               25

SEQ ID NO: 59          moltype = DNA   length = 25
FEATURE                Location/Qualifiers
misc_feature           1..25
                       note = Primer
source                 1..25
                       mol_type = other DNA
                       organism = synthetic construct
SEQUENCE: 59
gccacatata attcttgtac ttgtc                                               25

SEQ ID NO: 60          moltype = DNA   length = 22
FEATURE                Location/Qualifiers
misc_feature           1..22
                       note = Primer
source                 1..22
                       mol_type = other DNA
                       organism = synthetic construct
SEQUENCE: 60
cgaaattaac cctcactaaa gg                                                  22

SEQ ID NO: 61          moltype = DNA   length = 25
FEATURE                Location/Qualifiers
misc_feature           1..25
                       note = Primer
source                 1..25
                       mol_type = other DNA
                       organism = synthetic construct
SEQUENCE: 61
gacaagtaca agaattatat gtggc                                               25

SEQ ID NO: 62          moltype = DNA   length = 27
FEATURE                Location/Qualifiers
misc_feature           1..27
                       note = Primer
source                 1..27
                       mol_type = other DNA
                       organism = synthetic construct
SEQUENCE: 62
gtatgatgga aaataaatac ccaaatg                                             27

SEQ ID NO: 63          moltype = DNA   length = 22
FEATURE                Location/Qualifiers
misc_feature           1..22
                       note = Primer
source                 1..22
                       mol_type = other DNA
                       organism = synthetic construct
SEQUENCE: 63
cgaaattaac cctcactaaa gg                                                  22

SEQ ID NO: 64          moltype = DNA   length = 25
FEATURE                Location/Qualifiers
misc_feature           1..25
                       note = Primer
source                 1..25
                       mol_type = other DNA
                       organism = synthetic construct
SEQUENCE: 64
gacaagtaca agaattatat gtggc                                               25

SEQ ID NO: 65          moltype = DNA   length = 828
FEATURE                Location/Qualifiers
misc_feature           1..828
                       note = PbSEP-1A
source                 1..828
                       mol_type = other DNA
                       organism = synthetic construct
```

```
SEQUENCE: 65
ttaaaagata gtgatggata tgagaaatta ttaaaaaatg acatgtacga tttatataat    60
attaagatgc atgatttaaa taacttaaaa tcatatgatt ttgaattttc aaaaaattta   120
ttaaaaaacg agatttttt ttgtggtgat aatataaaaa gtgatgaaat aaatttaaat   180
gataatgaca taaatgaaaa gattgattca ctaatgaaca attacaatat tatgaaaaac   240
aaacgtgaca aatttaatga agaagaaaac gaaattcaaa acttttagc agaattaaaa   300
gctgatgtaa ctaatcaact caatctaaat aacggggaag atgaacaggc ttttgatttg   360
cttaattcgt ttgatataaa caataacttt gacgattttg ttggcaactt tgatgataca   420
aatgataaca tagctcaaaa taaatcagac atagacaata taaagagt cgaacacgaa   480
aatgatataa atcatgatta taacgattgt ggtacatata tggatgatat atataataac   540
aataatggtg atgatattc gagaaaggga tcacgtctga aattgtctga tttaaatgac   600
gaaaagaatt tatttccaga tgtcaactcc tcttttaata ctcctataaa atcttctgaa   660
ctaaagagag attcagaatg ccaaacaaat tcaccactta tatttctag aagtaataga   720
actcctagga aaaaagtgt agaagtaata ttagtaaaga aaaaattaaa aaaaagaaaa   780
gaaaaagaat caaatatatc atttgaaaat acaacacatg atgattat                828

SEQ ID NO: 66             moltype = AA   length = 276
FEATURE                   Location/Qualifiers
REGION                    1..276
                          note = PbSEP-1A
source                    1..276
                          mol_type = protein
                          organism = synthetic construct
SEQUENCE: 66
LKDSDGYEKL LKNDMYDLYN IKMHDLNNLK SYDFEFSKNL LKNEIFFCGD NIKSDEINLN    60
DNDINEKIDS LMNNYNIMKN KRDKFNEEEN EIQNFLAELK ADVTNQLNLN NGEDEQAFDL   120
LNSFDINNNF DDFVGNFDDT NDNIAQNKSD IDNNKEFEHE NDINHDYNDC GTYMDDIYNN   180
NNGDDISRKG SRLKLSDLND EKNLFPDVNS SFNTPIKSSE LKRDSECQTN SPLIFSRSNR   240
TPRKKSVEVI LVKKKLKKRK EKESNISFEN TTHDDY                             276

SEQ ID NO: 67             moltype = AA   length = 1810
FEATURE                   Location/Qualifiers
REGION                    1..1810
                          note = PBANKA_050600
source                    1..1810
                          mol_type = protein
                          organism = synthetic construct
SEQUENCE: 67
MTDNEDQNKE DLIYYINRYS VNDILGNLEE NDKLTNYDEN SGICEYEIPF LLENVDNNNN    60
NNTKEHSDRN SVSSYFDDGT CSIISKNDEK HYIDKCEKDK MPKEKINIIF IQNKGEMNSF   120
EDILSMNNAS SENLENKLND RFYQLCCKSI ADVNTHNLNK TKNIVKDKKG TLNIEHIDYG   180
DIFLTIRHRL RGREEKTNNM LNNNNNNDNN NNHLYSDMAD SVISNWREIK NHENFIKYEN   240
YKEHEKEFIR RKLKKKCVNS LNGDKYFMAN RKVFDYYRNN LDSYMTNGNE KDICKQENMS   300
LHFLPKKRKS MNNSSLYNSQ IIGQNEYILK NRTFLKKFYI KKNFKQQEHI HNDDYYCDDN   360
HSENLYNDDI YNYNKNLSNR QGNLPSNDFI YSCEIQNKKN SIPHNICVDR NVITPRNSTW   420
NNENEIHEED MVYYHSQNKG KNSHYVEAEN EIQSNHYCED KNTNSFNEYV NEIDKLDENY   480
NMFNKVEEDD NNNNKENFNI YDGDEIDNNE AFDIKIEEND DYETYNNELE LEVEVDDGIG   540
NNIPFNNNDN FVNSNKNEDL DNINNCEHVS NSNHTKYGEE DNEQKAPSIT SKDDKDYFDL   600
LIKKYEQTRM SINESSTASL SESIYLSKEG TKEPSLNAHE MLKIASNTKN DVNNKIECLN   660
ENLIDLKNNK EIINEGECFS NGFSIEKNDI EKENDNIVKL GSVYNNDKTE GERGNIGNKN   720
EKVDLKDSDG YEKLLKNDMY DLYNIKMHDL NNLKSYDFEF SKNLLKNEIF FCGDNIKSDE   780
INLNDNDINE KIDSLMNNYN IMKNKRDKFN EEENEIQNFL AELKADVTNQ LNLNNGEDEQ   840
AFDLLNSFDI NNNFDDFVGN FDDTNDNIAQ NKSDIDNNKE FEHENDINHD YNDCGTYMDD   900
IYNNNNGDDI SRKGSRLKLS DLNDEKNLFP DVNSSFNTPI KSSELKRDSE CQTNSPLIFS   960
RSNRTPRKKS VEVILVKKKL KKRKEKESNI SFENTTHDDY TVGTTTATSS INSKRRYPKR  1020
NRIKTLRYWI GERELTRRNP ETGEIDVVGF SECKNLEELS PHIIGPVYYK KMYLRDVNNL  1080
HGKGNEDANN NIDRNDNTDE ENEITIEINN GMYENEVYNK IQNKENSVNK NDNVSNILKK  1140
SINGSIHNRS DNDAITRNGK KKRKKFINVV NYIKKKTKKK LVKVIDKEVE QENENVDNRN  1200
TFSNNDNIIN DITNVNHSQ NNLDQNFIAI SNDPFIENDDN IFFDAISLGD NAHINDIPEK  1260
SEEIIEAPGV DAIETTKVNG NEKEINLEKE INLEKEINLE KNKDVHVKKK LLDKKKKKKK  1320
KKNKGKEKEI DEMYKQLSFL NFNSPYSKGN EDKSKIEILK KTSTKKKGSK IDKEKVDEEN  1380
DKHNKNSGKE AKELITKKKK AKNMKKNKKR NMQNKEMKNY YEYTNNEIEK FYNNPNDRIE  1440
NEYNMGVDLE ASIKTEEEKT EKIGELPILN SYTNEQYEHI TNTNDITNSK SENFELHKNE  1500
DEEVEKLQTS TRRKKKKKSE SLIHDTNELN KKRRKTDGNN SGELISINEN DEIKNVDADK  1560
KINDKEGKYI KKVDKDTIMG SNGNNIDELN KDFEDNDQIK NIKKDEKKKE TNTDGSNNMR  1620
NINLLEEIDA NEKNSTLCLV THNKKNNTNS QSFIIDKLKS YFNIKELINV KKQKTNNVIL  1680
NTFENKQIIN NNPIRISLSY PSSVELSVEN RCNQTRNGQF PLIQKNLSNF KVDINLFCVQ  1740
IFPNKAHSSN SYDKILIGYI YQGKKVKIYF KNQERYFEKD EFFYIPKYSP FKIVNISRDN  1800
CILYVYPINK                                                         1810

SEQ ID NO: 68             moltype = DNA   length = 5434
FEATURE                   Location/Qualifiers
misc_feature              1..5434
                          note = PBANKA_050600
source                    1..5434
                          mol_type = other DNA
                          organism = synthetic construct
SEQUENCE: 68
atgacagaca acgaggatca aaataaagaa gatctgatat attacataaa tagatacagt    60
```

```
gtcaatgata tattgggaaa tttagaagaa aatgataagt taacaaatta tgatgaaaat    120
agcggaatat gtgaatatga aattccattt cttttggaaa atgtcgaata taataataat    180
aataatacta aagaacattc cgatagaaat tctgtatcta gttatttcga tgatggaaca    240
tgttcgatta tttctaaaaa tgatgaaaaa cattatatag acaaatgtga aaagacaaa     300
atgccaaagg aaaaaataaa tattatattt attcagaata aaggtgaaat gaatagcttt    360
gaagatattt tatccatgaa taatgcaagc agtgaaaatt tagaaaacaa gttaaatgat    420
agattttatc aactatgttg taaaagtatt gctgatgtga acacccacaa tttaaataaa    480
actaaaaata ttgtaaaaga taaaaaaggg acattgaata ttgagcatat agattatggt    540
gatatatttt taaccattcg tcatcgtcta agagggcgtg aagaaaaaac gaataacatg    600
ctaaataata ataataataa tgataataat aataatcatt tatatagtga catggctgat    660
agtgttatta gtaattggag ggaaataaaa aatcatgaaa attttataaa atatgaaaac    720
tataaagagc atgaaaagga gtttataagg aggaaattga aaagaaatg cgtcaatagt     780
ttaaatggag ataaatattt tatggccaat agaaaagtat ttgattatta tcgtaataat    840
ttagatagtt acatgactaa tgggaatgaa aaagatatt gcaagcaaga aaatatgtct      900
ctacattttt taccaaaaaa gagaaaatca atgaataata gttctttata caattctcaa    960
ataattggac aaaatgaata tattttaaag aatagaacat tttaaaaaa attttatata    1020
aaaaaaaatt ttaagcaaca agaacatatc cataatgatg attattattg tgatgataat   1080
catagtgaaa atttatataa tgatagtata tataattata ataaaaactt gagtaataga   1140
caaggtaatc tacccagcaa tgattttatt tattcatgtg aaattcaaaa taagaaaaat   1200
tcaataccac ataatatatg tgtcgataga aatgtaataa ccccacgaaa cagtacatgg   1260
aataatgaaa acgaaattca cgaagaggat atggtttatt atcattctca aaataaggga   1320
aaaaattcac attatgtaga agcagaaaat gaaatacaat caaatcatta ttgtgaagat   1380
aaaaatacaa acagttttaa cgaatatgtt aatgaaattg ataaactcga tgaaaattat   1440
aatatgttta acaagttgaa agaggacgat aataaattga acaagaaaa ttttaacatt    1500
tatgatggtg atgaaataga taataacgaa gcatttgata tcaaaatcga agaaaatgat   1560
gattatgaaa catataacga cgaattagaa ttagaggtag aggtagatta ggtgaataggt   1620
aataatattc catttaataa taatgataat tttgtaaatt caaataagaa tgaagatttg   1680
gataatataa ataattgtga acatgtttca aattcaaatc atacaaaata tggggaagaa   1740
gacaatgagc aaaaagctcc atcaataacc agtaaagatg ataagatta ttttgattta    1800
ctaataaaaa aatatgaaca aactagaatg tcaattaatg aatctagtac agcctcactt   1860
agtgaaagta tttatttatc aaaagaagga acaaaagaac cttctttaaa tgctcacgaa   1920
atgttaaaaa tcgcatctaa cacaaagaat gatgtaaata ataaaattga atgtttgaat   1980
gaaacttaa tagatttaaa aaataacaag gaaattatta tgaagggga atgttttagt     2040
aatggttttt ctatcgaaaa aaatgacata gaaaaggaaa atgataaata agtaaaatta   2100
ggaagtgtat ataataatga caaaacagag ggggaaagag ggaatattgg aaacaaaaat   2160
gaaaaagtag acctttaaaag atagtgatgg atatgagaaa ttattaaaaa atgacatgta   2220
cgatttatat aatattaaga tgcatgattt aaataactta aaatcatatg atttgaatt    2280
ttcaaaaaat ttattaaaaa acgagatttt tttttgtggt gataatataa aagtgatga    2340
aataaattta aatgataatg acaaatatga aaagattgat tcactaatga acaattacaa   2400
tattatgaaa aacaaacgtg acaaatttaa tgaagaagaa aacgaaattc aaaactttttt   2460
agcagaatta aaagctgatg taactaatca actcaatcta aataacgggg aagatgaaca   2520
ggcttttgat ttgcttaatt cgtttgatat aaacaataac tttgacgatt tgttggcaa    2580
ctttgatgat acaaatgata gacatagctca aaataaatc agcatagaca ataataaaga   2640
gttcgaacac gaaaatgata taaatcatga ttataacgat tgtggtacat atatggatga   2700
tatatataat aacaataatg gtgatgatat ttcgagaaag ggatcacgtc tgaaattgtc   2760
tgatttaaat gacgaaaaga atttattttcc agatgtcaac tcctctttta atactccat   2820
aaaatcttct gaactaaaga gagattcaga atgccaaaca aattcaccac ttatattttc   2880
tagaagtaat agaactccta ggaaaaaaag tgtagaagta atattagtaa agaaaaaatt   2940
aaaaaaaaga aaagaaaaag aatcaaatat atcatttgaa aatacaacac atgatgatta   3000
tactgttggt acaactactg ctactagtag catcaattcg aaaagaagat atcctaaaag   3060
aataagaata aaaacgttgc gatactggat aggtgaaagg gaacttacta gaagaaatcc   3120
tgaaacaggc gaaatagatg ttgtaggttt tagtgaatgc aaaaatttag aagaattatc   3180
tcctcatatt attggtccag tttattataa aaaaatgtat ttacgagatg tgaataattt   3240
acatggaaaa ggaaacgaag atgctaacaa caatatagat agaaatgata atactgatga   3300
agaaatgaa ataacgatag aaatcaataa tggaatgtat tgaaatgaag tgtataataa    3360
aattcagaat aaagagaatt ctgtgaataa aaatgataat gttagtaaca tattgaaaaa   3420
aagtatatat ggtagcattc ataatagaag tgataatgat gcaataacta gaaatgggaa   3480
aaagaaaaga aaaagttta ttaatgttgt taattatatt aaaaaaaaaa caaaaaaaaa    3540
attagtcaaa gttatagata aagaagtaga gcaggaaaat gaaaatgtag ataatcgtaa   3600
cactttttca aataatgata atataattaa tgacataaca aatgtcaatc acaattctca   3660
aataaatttg gatcaaaatt ttattgcaat tagtaatgat tttattgaaa atgatgacaa   3720
tatttttttc gatgcgatta gtcttggcga taatgctcac ataaatgata ttccagaaaa   3780
aagcgaagaa attattgaag caccaggagt agatgcaatt gaaacgacta agttaatgg    3840
aaacgaaaag gaaatcaatt tagaaaagga aatcaattta gaaaaggaa tcaatttaga    3900
aaagaataaa gatgtacatg tgaaaaagaa attattagat aaaagaaaa agaaaaaaa    3960
aaagaaaaac aagggaaaag aaaggaaat agacgaaatg tacaagcaat tatcatttt    4020
gaattttaat tcgttttatt ctaaaggaaa tgaagataaa tcaaaatag aaattttgaa    4080
aaaacaagt accaaaaaaa aagggagtaa aattgataaa gaaaaggtag atgaggaaa     4140
tgataaacat aataaaaatt cgggaaagga agccaaagaa ttaattacaa aaaaaagaa    4200
agccaagaat atgaagaaaa ataaaaagag aaatatgcag aataaagaaa tgaaaatta    4260
ttatgaatat acaaataatg aaatcgaaaa gttctacaac aatccaaatg atagaataga   4320
gaatgaatac aatatgggag tcgatttaga agcatcaata aaaactgaag aagaaaaac    4380
agaaaaatt ggagagttgc ccattttaaa ttcatatact aatgagcaat atgagcacat    4440
aacgaataca aatgatataa caaattcgaa aagtgaactc acaaaaagtga              4500
agacgaagaa gtggaaaagc tacaaacttc tacacgtcga aaaaagaaaa aaaaagtga    4560
aagtttaatt catgatacaa atgaattgaa taaaagcga agaaaacag atggaaataa     4620
ttcagggaaa ttaatttcta ttaatgaaaa tgatgagata aaaatgtag atgctgataa     4680
aaaatatat gacaaagaag gtaaatatat aagaaagtt gacaaggata caattatggg     4740
atcaaatgga aataatattg atgaattaaa taaggatttt gaagataatg atcaaattaa    4800
```

-continued

```
aaatataaaa aaagatgaaa aaaaaaaaga gacaaataca gatggttcta ataatatgag   4860
aaatataaat ttattagaag aaatagatgc aaatgaaaaa aatagtacat tatgtttggt   4920
aactcacaat aaaaaaaata atacgaatag tcaaagtttt attatagata aattaaaatc   4980
gtatttcaat ataaaagagt taataaatgt caaaaaacaa aaaacaaata atgtaatatt   5040
aaatacttt  gaaaataaac aaataataaa taataatcct atacgtattt ctctttccta   5100
tccttctagt gtagaattat cagttgaaaa tagatgcaac caaacaagaa atggacaatt   5160
tccacttata caaaagaact taagcaactt caaggtagac ataaatttat tttgtgttca   5220
aatttttccca aacaaagcac atagctcgaa tagttatgat aaaattttga ttgggtatat   5280
atatcaggga aaaaaggtaa agatttattt taagaaccaa gaaagatatt ttgaaaagga   5340
tgagtttttt tacataccca aatactctcc tttcaaaatt gtcaacataa gcagggacaa   5400
ttgtatttta tatgtttatc caataaataa ataa                              5434

SEQ ID NO: 69             moltype = DNA  length = 2994
FEATURE                   Location/Qualifiers
misc_feature              1..2994
                          note = SERA5
source                    1..2994
                          mol_type = other DNA
                          organism = synthetic construct
SEQUENCE: 69
atgaagtcat atatttcctt gttttttcata ttgtgtgtta tatttaacaa aaatgttata   60
aaatgtacag gagaaagtca aacaggtaat acaggaggag gtcaagcagg taatacagga   120
ggagatcaag caggtagtac aggaggaagt ccacaaggta gtacgggagc aagtccacaa   180
ggtagtacgg gagcaagtcc acaaggtagt acgggagcaa gtcaaccggg aagttccgaa   240
ccaagcaatc ctgtaagttc cggacattct gtaagtactg tatcagtatc acaaacttca   300
acttcttcag aaaaacagga tacaattcaa gtaaaatcaa ctttattaaa agattatatg   360
ggtttaaaag ttactggtcc atgtaacgaa aatttcataa tgttcttagt tcctcatata   420
tatattgatg ttgatacaga agatactaat atcgaattaa gaacaacatt gaaaaaaaca   480
aataatgcaa tatcatttga atcaaacagt ggttcattag aaaaaaaaaa atatgtaaaa   540
ctaccatcaa atggtacaac tggtgaacaa ggttcaagta cgggaacagt tagaggagat   600
acagaaccaa tttcagattc aagctcaagt tcaagttcaa gctctagttc aagttcaagt   660
tcaagttcaa gttctagttc aagttctagt tcaagttcag aaagtcttcc tgctaatgga   720
cctgattccc ctactgttaa accgccaaga aatttacaaa atatatgtga aactggaaaa   780
aacttcaagt tggtagtata tattaaggag aatacattaa tacttaaatg gaaagtatac   840
ggagaaacaa aagatactac tgaaaataac aaagttgatg taagaaagta tttgataaat   900
gaaaaggaaa ccccatttac taatatacta atacatgcgt ataaagaaca aatgggaaca   960
aacttaatag aaagtaaaaa ctacgcaata ggatcagaca ttccagaaaa atgtgatacc   1020
ttagcttcca attgcttttt aagtggtaat tttaacattg aaaaatgctt tcaatgtgct   1080
cttttagtag aaaaagaaaa taaaaatgac gtatgttaca aataccctac tgaagatatt   1140
gtaagtaaat tcaaagaaat aaaagctgag acagaagatg atgatgaaga tgattatact   1200
gaatataaat taacagaatc tattgataat atattagtaa aaatgtttaa aacaaatgaa   1260
aataatgata aatcagaatt aataaaatta gaagaagtag atgatagttt gaattagaaa   1320
ttaatgaatt actgtagttt acttaaagac gtagatacaa caggtacctt agataattat   1380
gggatgggaa atgaaatgga tatatttaat aacttaaaga gattattaat ttatcattca   1440
gaagaaaata ttaatacttt aaaaaataaa ttccgtaatg cagctgtatg tcttaaaaat   1500
gttgatgatt ggattgtaaa taagagaggt ttagtattac ctgaattaaa tttatgattta   1560
gaatatttca atgaacattt atataatgat aaaaattctc cagaagataa agataataaa   1620
ggaaaaggtg tcgtacatgt tgatacaact ttagaaaaag aagatacttt atcatatgat   1680
aactcagata atatgttttg taataaagaa tattgtaaca gattaaaaga tgaaaataat   1740
tgtatatcta atcttcaagt tgaagatcaa ggtaattgtg atacttcatg gatttttgct   1800
tcaaaatatc atttagaaac tattagatgt atgaaaggat atgaacctac caaaattttct   1860
gctctttatg tagctaattg ttataaaggt gaacataaag atagatgtga tgaaggttct   1920
agtccaatgg aattcttaca aattattgaa gattatggat tcttaccagc agaatcaaat   1980
tatccatata actatgtgaa agttggagaa caatgtccaa aggtagaaga tcactggatg   2040
aatctatggg ataatggaaa aatcttacat aacaaaaatg aacctaatag tttagatgtt   2100
aagggatata ctgcatatga aagtgaaaga tttcatgata atatggatgc atttgttaaa   2160
attattaaaa ctgaagtaat gaataaaggt tcagttattg catatattaa agctgaaaat   2220
gttatgggat atgaatttag tggaagaaaa gtacagaact tatgtggtga tgatacagct   2280
gatcatgcag ttaatattgt tggttatggt aattatgtga gatgcgaagg agaaaaaaaa   2340
tcctattgga ttgtaagaaa cagttgggggt ccatattggg gagatgaagg ttattttaaa   2400
gtagatatgt atggaccaac tcattgtcat tttaacttta ttcacagtgt tgttatattc   2460
aatgttgatt tacctatgaa taataaaaca actaaaaaag aatcaaaaat atatgattat   2520
tatttaaagg cctctccaga atttttatcat aaccttttact ttaagaattt taatgttggt   2580
aagaaaaatt tattctctga aaaggaagat aatgaaaaca aaaaaatt ggtaacaac   2640
tatattatat tcggtcaaga tacggcagga tcaggacaaa gtggaaagga aagcaatact   2700
gcattagaat ctgcaggaac ttcaatgaa gtctcagaac gtgttcatgt ttatcacata   2760
ttaaaacata taaaggatgg caaaataaga atgggtatgc gtaaatatat agatacaaa   2820
gatgtaaata agaaacattc ttgtacaaga tcctatgcat ttaatccaga gaattatgaa   2880
aaatgtgtaa atttatgtaa tgtgaactgg aaaacatgcg aggaaaaaac atcaccagga   2940
cttttgttat ccaaattgga tacaaataac gaatgttatt tctgttatgt ataa         2994

SEQ ID NO: 70             moltype = AA  length = 997
FEATURE                   Location/Qualifiers
REGION                    1..997
                          note = SERA5
source                    1..997
                          mol_type = protein
                          organism = synthetic construct
SEQUENCE: 70
```

```
MKSYISLFFI LCVIFNKNVI KCTGESQTGN TGGGQAGNTG GDQAGSTGGS PQGSTGASPQ    60
GSTGASPQGS TGASQPGSSE PSNPVSSGHS VSTVSVSQTS TSSEKQDTIQ VKSALLKDYM   120
GLKVTGPCNE NFIMFLVPHI YIDVDTEDTN IELRTTLKKT NNAISFESNS GSLEKKKYVK   180
LPSNGTTGEQ GSSTGTVRGD TEPISDSSSS SSSSSSSSSS SSSSSSSSSS SSSESLPANG   240
PDSPTVKPPR NLQNICETGK NFKLVVYIKE NTLILKWKVY GETKDTTENN KVDVRKYLIN   300
EKETPFTNIL IHAYKEHNGT NLIESKNYAI GSDIPEKCDT LASNCFLSGN FNIEKCFQCA   360
LLVEKENKND VCYKYLSEDI VSKFKEIKAE TEDDDEDDYT EYKLTESIDN ILVKMPKTNE   420
NNDKSELIKL EEVDDSLKLE LMNYCSLLKD VDTTGTLDNY GMGNEMDIFN NLKRLLIYHS   480
EENINTLKNK FRNAAVCLKN VDDWIVNKRG LVLPELNYDL EYFNEHLYND KNSPEDKDNK   540
GKGVVHVDTT LEKEDTLSYD NSDNMFCNKE YCNRLKDENN CISNLQVEDQ GNCDTSWIFA   600
SKYHLETIRC MKGYEPTKIS ALYVANCYKG EHKDRCDEGS SPMEFLQIIE DYGFLPAESN   660
YPYNYVKVGE QCPKVEDHWM NLWDNGKILH NKNEPNSLDG KGYTAYESER FHDNMDAFVK   720
IIKTEVMNKG SVIAYIKAEN VMGYEFSGKK VQNLCGDDTA DHAVNIVGYG NYVNSEGEKK   780
SYWIVRNSWG PYWGDEGYFK VDMYGPTHCH FNFIHSVVIF NVDLPMNNKT TKKESKIYDY   840
YLKASPEFYH NLYFKNFNVG KKNLFSEKED NENNKKLGNN YIIFGQDTAG SGQSGKESNT   900
ALESAGTSNE VSERVHVYHI LKHIKDGKIR MGMRKYIDTQ DVNKKHSCTR SYAFNPENYE   960
KCVNLCNVNW KTCEEKTSPG LCLSKLDTNN ECYFCYV                            997

SEQ ID NO: 71            moltype = DNA   length = 561
FEATURE                  Location/Qualifiers
misc_feature             1..561
                         note = Y2H Clone name: 1 7-1
source                   1..561
                         mol_type = other DNA
                         organism = synthetic construct
SEQUENCE: 71
aacttattc acagtgttgt tatattcaat gttgatttac ctatgaataa taaaacaact    60
aaaaaagaat caaaaatata tgattattat ttaaaggcct ctccagaatt ttatcataac   120
ctttacttta agaattttaa tgttggtaag aaaaattat tctctgaaaa ggaagataat    180
gaaacaaca aaaaattagg taacaactat attatattcg gtcaagatac ggcaggatca   240
ggacaaagtg gaaggaaagg caatactgca ttagaatctc caggaacttc aaatgaagtc   300
tcagaacgtg ttcatgttta tcacatatta aaacatataa aggatggcaa ataagaatg    360
ggtatgcgta atatataga tacacaagat gtaaataaga acattcttg tacaagatcc    420
tatgcattta atccagagaa tttatgaaaaa tgtgtaaatt tatgtaatgt gaactggaaa   480
acatgcgagg aaaaaacatc accaggactt tgtttatcca aattggatac aaataacgaa   540
tgttatttct gttatgtata a                                             561

SEQ ID NO: 72            moltype = AA   length = 186
FEATURE                  Location/Qualifiers
REGION                   1..186
                         note = Y2H Clone name: 1 7-1
source                   1..186
                         mol_type = protein
                         organism = synthetic construct
SEQUENCE: 72
NFIHSVVIFN VDLPMNNKTT KKESKIYDYY LKASPEFYHN LYFKNFNVGK KNLFSEKEDN    60
ENNKKLGNNY IIFGQDTAGS GQSGKESNTA LESAGTSNEV SERVHVYHIL KHIKDGKIRM   120
GMRKYIDTQD VNKKHSCTRS YAFNPENYEK CVNLCNVNWK TCEEKTSPGL CLSKLDTNNE   180
CYFCYV                                                              186

SEQ ID NO: 73            moltype = DNA   length = 2067
FEATURE                  Location/Qualifiers
misc_feature             1..2067
                         note = SUB1
source                   1..2067
                         mol_type = other DNA
                         organism = synthetic construct
SEQUENCE: 73
atgatgctca ataaaaaagt tgttgctttg tgcacactta ccttacatct ttttttgtata    60
tttctatgtc taggaaagga agtaaggtct gaagaaaatg ggaaaataca agatgatgct   120
aaaaagattg ttagcgaatt acgattccta gaaaaagtag aagatgttat tgaaaagagt   180
aacataggag ggaatgaggt agatgccgat gaaaaattcat ttaatccgga tactgaggtt   240
cccatagaag agatagaaga aataaaaatg agggaactga agatgtaaa ggaagaaaaa   300
aataaaaatg acaaccataa taataataat aataatatta gtagtagtag tagtagtagt    360
agtaatactt ttggtgaaga aaagaagaa gtatctaaga aaaaaaaaa gttaagactt    420
atagttagcg agaatcatgc aactacccc tcgttttcc aagaatccct tttagaacct    480
gatgttttat cctttttaga aagtaaaggg aatttgtcca acttgaaaaa tatcaattct   540
atgattatag aactaaagga agataacaacg gatgtgaat taatatctta tattaaaatt    600
cttgaggaga agggagcttt gattgaatca gataaaattag tgagtgcaga taatattgat   660
ataagtggta taaagatgc tataagaaga ggtgaagaaa atattgatgt taatgattat   720
aaaagtatgt tagaagtcga aaatgatgct gaagattatg ataaaatgtt tggtatgttt   780
aatgaatcac atgctgcaac atcaaaagg aaacgccatt caacaaatga gcgtggatat   840
gatacatttt catcaccttc ataagaca tattcaaaaa gtgattattt atatgatgat   900
gataaaata ttattatagt ttattatagt catagtagt catagtagt  960
cgtaatagta gtagtagtcg tagtagacca ggtaaaatatc atttcaatga tgaatttcgt   1020
aatttgcaat gggggtttaga tttatccaga ttagatgaaa cacaagaatt aattaacgaa   1080
catcaagtga tgagtactcg tatatgtgtt atagatagtg gtattgatta atcatccc    1140
gatttaaaag ataatattga attaaattta aaagaattac atggaaggaa aggttttgat   1200
gatgataata atggtatagt tgatgatata tatggtgcta attttgtaaa taattcagga   1260
```

```
aacccgatgg atgataatta tcatggtact catgtatcag gaattatatc tgccatagga  1320
aataataata taggtgttgt aggtgttgat gtaaattcaa aattaattat ttgtaaagca  1380
ttagatgaac ataaattagg aagattagga gatatgttca aatgtttaga ttattgtata  1440
agtagaaatg cacatatgat aaatggaagc ttttcatttg atgaatatag tggtattttt  1500
aattcttctg tagaatattt acaaagaaaa ggtatcctct ttttttgtatc tgcaagtaat  1560
tgtagtcatc ctaaatcgtc aacaccagat attagaaaat gtgatttatc cataaatgca  1620
aaatatcccc ctatcttatc tactgtttat gataatgtta tatctgttgc taatttaaaa  1680
aaaaatgata ataataatca ttattcatta tccattaatt cttttatag caataaatat  1740
tgtcaactag ctgcaccagg aactaatata tattctactg ctccacataa ttcatatcga  1800
aaattaaatg gtacatctat ggctgctcca catgtagctg caatagcatc actcatattt  1860
tctattaatc ctgacttatc atataaaaaa gttatacaaa tattaaaaga ttctattgta  1920
tatctcccctt cctaaaaaaa tatggttgca tgggcaggat atgcagatat aaataaggca  1980
gtcaatttag ccataaaatc aaaaaaaaaca tatatcaatt ctaatatatc taacaagtgg  2040
aaaaaaaaaa gtagatattt gcattaa                                       2067

SEQ ID NO: 74          moltype = AA   length = 688
FEATURE                Location/Qualifiers
REGION                 1..688
                       note = SUB1
source                 1..688
                       mol_type = protein
                       organism = synthetic construct
SEQUENCE: 74
MMLNKKVVAL CTLTLHLFCI FLCLGKEVRS EENGKIQDDA KKIVSELRFL EKVEDVIEKS   60
NIGGNEVDAD ENSFNPDTEV PIEEIEEIKM RELKDVKEEK NKNDNHNNNN NNISSSSSSS  120
SNTFGEEKEE VSKKKKKLRL IVSENHATTP SFFQESLLEP DVLSFLESKG NLSNLKNINS  180
MIIELKEDTT DDELISYIKI LEEKGALIES DKLVSADNID ISGIKDAIRR GEENIDVNDY  240
KSMLEVENDA EDYDKMFGMF NESHAATSKR KRHSTNERGY DTFSSPSYKT YSKSDYLYDD  300
DNNNNNYYYS HSSNGHNSSS RNSSSSRSRP GKYHFNDEFR NLQWGLDLSR LDETQELINE  360
HQVMSTRICV IDSGIDYNHP DLKDNIELNL KELHGRKGPD DDNNGIVDDI YGANFVNNSG  420
NPMDDNYHGT HVSGIISAIG NNNIGVVGVD VNSKLIICKA LDEHKLGRLG DMFKCLDYCI  480
SRNAHMINGS FSFDEYSGIF NSSVEYLQRK GILFFVSASN CSHPKSSTPD IRKCDLSINA  540
KYPPILSTVY DNVISVANLK KNDNNNHYSL SINSFYSNKY CQLAAPGTNI YSTAPHNSYR  600
KLNGTSMAAP HVAAIASLIF SINPDLSYKK VIQILKDSIV YLPSLKNMVA WAGYADINKA  660
VNLAIKSKKT YINSNISNKW KKKSRYLH                                     688

SEQ ID NO: 75          moltype = DNA   length = 2562
FEATURE                Location/Qualifiers
misc_feature           1..2562
                       note = PKG (cGMP-dependent protein kinase)
source                 1..2562
                       mol_type = other DNA
                       organism = synthetic construct
SEQUENCE: 75
atggaagaag atgataatct aaaaaaaggg aatgaaagaa ataaaagaa ggctatattt    60
tcaaatgatg attttacagg agaagatagt ttaatggagg atcatttaga acttcgggaa  120
aagctttcag aagatattga tatgataaag acttccttaa aaaataatct agtttgtagt  180
acattaaacg ataatgaaat attgactctg tctaattata tgcaattctt tgttttttaaa 240
agtggaaatt tagtaataaa acaaggggaa aaagggtcat acttttttcat tattaatagt  300
ggcaaatttg acgtttatgt aaatgataaa aaagtaaaga ctatgggaaa aggtagttct  360
ttcggtgaag ctgctttaat tcataatacc caaagaagtg caactattat tgcagaaact  420
gatgaaactc tatggggagt tcaaagaagt acatttagag ctaccctaaa acaattatct  480
aatagaaatt ttaacgaaaa cagaacattt atcgattccg tttcagtttt tgatatgtta  540
actgaagcac aaaaaaacat gattactaat gcttgtgtaa tacaaaactt taaatctggt  600
gaaaccattg ttaaacaagg agattatgga gatgtcttat acttttgaa agaaggaaag  660
gctacagtat atattaacga tgaagagata agggttttaa agaaaggttc ctattttggg  720
gaaagagctc tactgtatga tgaaccaaga agtgcaacaa tcattgcaaa agaaccaacc  780
gcttgtgcat ccatttgtag gaaattatta atatattgttc taggaaactt acaagtagtt  840
ttatttcgta atattatgac tgaagcttta caacagagtg aaattttttaa acaatttagt  900
ggggatcaat taaacgattt agcagatacc gccattgttc tgagattatcc agctaattat 960
aatatattac ataaggataa ggtaaaatcc gttaaatata ttattgtatt ggaaggtaaa 1020
gtagaattat ttcttgatga tacttctatt ggtatattat ccagaggaat gtcttttgga 1080
gatcaatatg tattaaatca gaaacaacca tttaagcata ctattaaatc attagaagtt 1140
tgtaaaatcg cattaataac ggaaacttgt ttagctgatt gtctaggaaa ttaataatt  1200
gatgcatcta ttgattataa taataaaaaa agtattataa agaaaatgta tatctttaga 1260
tacttaactg ataaacaatg taatttatta attgaagctt ttagaaccac aagatatgaa 1320
gaaggtgatt atataataca agaaggagaa gtaggatcta gatttatat aataaaaaat 1380
ggagaagtag aaaatagtaaa aaataaaaaa aggttacgta ccttaggaaa gaatgattac 1440
tttggtgaaa gagctttatt atatgatgaa ccaagaacag cttctgttat aagtaaagta 1500
aataatgttg aatgttggtt tgttgataaa agtgtgtttt tacaaattat acaaggacct 1560
atgttagcac atttggaaga aagaataaaa atgcaagata ctaaagtaga aatggatgaa 1620
ctagaaacag aacgaattat tggaagaggt acttcggaa cagttaaatt agttcatcat 1680
aaaccaacaa aaataagata tgcttttaaa tgtgttagta aagaagtat tattaattta 1740
aatcaacaaa acaatataaa attagaaaga gaaataacag cagaaaatga tcatccattt 1800
attataaagat tagtaagaac atttaaagat tctaaatatt tctattttct aacagaatta 1860
gtaacaggtg gagaattata tgatgctatt agaaaattag gttattatc taaatcacaa 1920
gctcaatttt atttaggttc tatcatttta gctattgaat atttacatga agaaatatt  1980
gtatatagag atttaaaacc agaaaacatt ttattagata acaaggtta tgtaaaacta 2040
atcgattttg gttgtgccaa aaaggtacaa ggtagagctt atacattagt aggtacacct 2100
```

-continued

```
cattatatgg cacctgaggt tattttagga aaaggttatg gatgtactgt tgacatatgg  2160
gcattgggaa tatgcctata tgaatttata tgtggtccat taccatttgg taatgatgaa  2220
gaagatcaat tagaaatttt ccgtgatata ttaaccggcc aacttacatt tccagattat  2280
gtaacagaca cagatagcat aaatttgatg aaaagacttc tatgtagatt acctcaagga  2340
agaattggtt gttcaataaa tggcttcaaa gacataaagg atcacccatt tttctcaaac  2400
tttaattggg ataaattggc tggtcgtttg cttgatccgc ctttagtatc aaaaagtgaa  2460
acttatgcag aagatattga tattaaacaa atagaggagg aggatgctga ggatgatgag  2520
gaaccattga acgatgaaga caactgggac atagattttt aa                    2562

SEQ ID NO: 76          moltype = AA  length = 853
FEATURE                Location/Qualifiers
REGION                 1..853
                       note = PKG (cGMP-dependent protein kinase)
source                 1..853
                       mol_type = protein
                       organism = synthetic construct
SEQUENCE: 76
MEEDDNLKKG NERNKKKAIF SNDDFTGEDS LMEDHLELRE KLSEDIDMIK TSLKNNLVCS   60
TLNDNEILTL SNYMQFFVFK SGNLVIKQGE KGSYFFIINS GKFDVYVNDK KVKTMGKGSS  120
FGEAALIHNT QRSATIIAET DGTLWGVQRS TFRATLKQLS NRNFNENRTF IDSVSVFDML  180
TEAQKNMITN ACVIQNFKSG ETIVKQGDYG DVLYILKEGK ATVYINDEEI RVLEKGSYFG  240
ERALLYDEPR SATIIAKEPT ACASICRKLL NIVLGNLQVV LFRNIMTEAL QQSEIFKQFS  300
GDQLNDLADT AIVRDYPANY NILHKDKVKS VKYIIVLEGK VELFLDDTSI GILSRGMSFG  360
DQYVLNQKQP FKHTIKSLEV CKIALITETC LADCLGNNNI DASIDYNNKK SIIKKMYIFR  420
YLTDKQCNLL IEAFRTTRYE EGDYIIQEGE VGSRFYIIKN GEVEIVKNKK RLRTLGKNDY  480
FGERALLYDE PRTASVISKV NNVECWFVDK SVFLQIIQGP MLAHLEERIK MQDTKVEMDE  540
LETERIIGRG TFGTVKLVHH KPTKIRYALK CVSKRSIINL NQQNNIKLER EITAENDHPF  600
IIRLVRTFKD SKYFYPLTEL VTGGELYDAI RKLGLLSKSQ AQPYLGSIIL AIEYLHERNI  660
VYRDLKPENI LLDKQGYVKL IDFGCAKKVQ GRAYTLVGTP HYMAPEVILG KGYGCTVDIW  720
ALGICLYEFI CGPLPFGNDE EDQLEIFRDI LTGQLTFPDY VTDTDSINLM KRLLCRLPQG  780
RIGCSINGFK DIKDHPFFSN FNWDKLAGRL LDPPLVSKSE TYAEDIDIKQ IEEEDAEDDE  840
EPLNDEDNWD IDF                                                    853

SEQ ID NO: 77          moltype = AA  length = 88
FEATURE                Location/Qualifiers
REGION                 1..88
                       note = peptide fragment
source                 1..88
                       mol_type = protein
                       organism = synthetic construct
SEQUENCE: 77
DYTEFLAACL DHSIFQQDVI CRNAFNVFDL DGDGVITKDE LFKILSFSAV QVSFSKEIIE   60
NLIKEVDSNN DGFIDYDEFY KMMTGVKE                                     88
```

VACCINE FOR FALCIPARUM MALARIA

REFERENCE TO RELATED APPLICATIONS

This application is a divisional of U.S. application Ser. No. 17/178,111, filed on Feb. 17, 2021, now U.S. Pat. No. 11,554,165, which is a continuation of U.S. application Ser. No. 16/283,472, filed on Feb. 22, 2019, now U.S. Pat. No. 10,960,065, which is a divisional application of U.S. application Ser. No. 15/607,203 filed on May 26, 2017, now U.S. Pat. No. 10,213,502, which is a continuation application of U.S. application Ser. No. 14/361,573 filed on May 29, 2014, now U.S. Pat. No. 9,662,379, which is a national stage application, filed under 35 U.S.C. § 371, of international Application No. PCT/US2012/067404 filed on Nov. 30, 2012, published as WO 2013/082500, which claims priority to U.S. Provisional Application No. 61/641,445, filed May 2, 2012, and U.S. Provisional Application No. 61/566,365, filed Dec. 2, 2011, the contents of each are hereby incorporated by reference in their entireties.

STATEMENT AS TO FEDERALLY SPONSORED RESEARCH

This invention was made with government support under Grant No. AI076353 awarded by the National Institutes of Health. The Government has certain rights in the invention.

INCORPORATION OF SEQUENCE LISTING

The contents of the XML file named "405002-607C03US_SL.xml", which was created on May 16, 2023 and is 169,722 bytes in size, are hereby incorporated by reference in their entireties.

FIELD OF THE INVENTION

The invention relates generally to the field of malaria vaccines.

BACKGROUND OF THE INVENTION

Malaria is a mosquito-borne infectious disease caused by a parasite. At least four species of malaria parasites can infect humans under natural conditions: *Plasmodium falciparum*: (*P. falciparum*), *P. vivax*, *P. ovale* and *P. malariae*. The first two species cause the most infections worldwide. *P. vivax* and *P. ovale* have dormant liver stage parasites (hypnozoites) that can reactivate (or "relapse") and cause malaria several months or years after the infecting mosquito bite; consequently, these species can be difficult to detect in infected individuals. Severe disease is largely caused by *P. falciparum* while the disease caused by *P. vivax*, *P. ovale*, and *P. malariae* is generally a milder disease that is rarely fatal.

In humans, the parasites grow and multiply first in the liver cells and then in the red blood cells. In the blood, successive broods of parasites grow inside the red cells and destroy them, releasing daughter parasites (merozoites) that continue the cycle by invading other red cells. The blood stage parasites cause the symptoms of malaria. When certain forms of blood stage parasites, gametocytes, are picked up by a female *Anopheles* mosquito during a blood meal, they start another, different cycle of growth and multiplication in the mosquito. After 10-18 days, the parasites are found as sporozoites in the mosquito's salivary glands. When the *Anopheles* mosquito takes a blood meal from another human, the sporozoites are injected with the mosquito's saliva and start another human infection when they parasitize the liver cells.

Infection with malaria parasites can result in a wide variety of symptoms, typically including fever and headache, in severe cases progressing to coma or death. There were an estimated 225 million cases of malaria worldwide in 2009. An estimated 781,000 people died from malaria in 2009 according to the World Health Organization's 2010 World Malaria Report, accounting for 2.23% of deaths worldwide. Ninety percent of malaria-related deaths occur in sub-Saharan Africa, with the majority of deaths being young children. *Plasmodium falciparum*, the most severe form of malaria, is responsible for the vast majority of deaths associated with the disease. Children suffer the greatest morbidity and mortality from malaria, yet this age group has not been targeted at the identification stage of vaccine development. Of the 100 vaccine candidates currently under investigation, more than 60% are based on only four parasite antigens—a fact that has caused considerable concern. New antigen candidates are urgently needed.

SUMMARY OF THE INVENTION

The vaccine of the invention successfully and surprisingly elicits an immune response that blocks the Schizont rupture of RBCs (parasite egress from RBCs), therefore protecting vaccinated individuals from severe malaria. The vaccines elicit a strong antibody response to the vaccine antigen, such as PfSEP1 or PfSEP-1A. Due to the permeability of parasitized red blood cells (RBCs) at the later stages of schizogony, antibodies gain access into the infected RBCs. Antibodies to the vaccine antigen, e.g., a Schizont Egress Protein (SEP) such as PfSEP-1A (SEQ ID NO:2, and other antigenic fragments of the whole protein PfSEP-1 (SEQ ID NO:3)) decrease parasite replication by at least 10% (e.g., 20, 40, 60%, 70% or more) by arresting schizont rupture.

Accordingly, the invention features a vaccine for preventing or reducing the severity of malaria comprising a composition that leads to inhibition of parasite egress from red blood cells or inhibits parasite egress. For example, the composition comprises a purified polypeptide comprising the amino acid sequence of SEQ ID NO:2 or a purified nucleic acid encoding a gene product that comprises the amino acid sequence of SEQ ID NO:2. The vaccine contains one or more compositions of a class of proteins that are involved in schizont egress such as PfSEP-1/1A (SEQ ID NO:3, 2, respectively), PbSEP-1/1A (SEQ ID NO:67, 68, respectively), PfCDPK5 (SEQ ID NO:47), SERA5 (SEQ ID NO:70, 72), PfSUB1 (SEQ ID NO:74), or PfPKG (SEQ ID NO:76). An immune response elicited by immunization with these vaccine antigens inhibits schizont egress. For example, the composition comprises a purified antigen that elicits an anti-PfSEP-1 antibody response. Alternatively, a passive immunization approach is used. In the latter case, the composition comprises a purified antibody that specifically binds to one or more of the vaccine antigens that are involved in schizont egress (listed above). For example, the composition comprises an anti-PfSEP-1 antibody or antigen binding fragment thereof. Thus, a method for preventing or reducing the severity of malaria is carried out by administering to a subject a composition that inhibits parasite egress from red blood cells.

The invention also includes a vaccine for preventing or reducing the severity of malaria comprising a polypeptide composition, wherein the polypeptide comprising an amino acid sequence selected from the group consisting of SEQ ID NO: 2, 10, 14, 18, 22, 26, 30, 34, 38, 42, and 46, 66 and 72 (antigenic polypeptides or protein fragments). A vaccine for preventing or reducing the severity of malaria comprising a polypeptide composition comprising whole protein antigens such as proteins comprising the following amino acid sequences: SEQ ID NO: 3, 8, 11, 15, 19, 22, 27, 31, 35, 39, 43, 47, 67, 70, 74, and/or 76.

In a preferred embodiment, the invention features an isolated peptide comprising a peptide having at least 90%, 95% or 99% identity with the sequence of SEQ ID NO: 2; a peptide encoded by a nucleic acid sequence having at least 90%, 95% or 99% identity with the sequence of SEQ ID NO: 1, or a fragment thereof in a vaccine composition for treatment or prevention of *P. falciparum* malaria. Alternatively, the isolated peptide of the present invention can be a peptide of SEQ ID NO: 3, a peptide encoded by a nucleic acid of SEQ ID NO: 4, or a fragment thereof.

The present invention also features an isolated nucleic acid sequence comprising a nucleic acid sequence having at least 90%, 95% or 99% identity with the sequence of SEQ ID NO: 1 or SEQ ID NO: 4, or any fragment thereof in a vaccine composition for treatment or prevention of *P. falciparum* malaria.

Antigens for use in a malaria vaccine include one or more of the following polypeptides (or fragments thereof) that elicit a clinically relevant decrease in the severity of the disease or that reduce/prevent infection or spread of parasites, reduce or inhibit parasite egress from a red blood cell (RBC), reduce or inhibit gametocyte egress (thereby reducing/inhibiting human→mosquito transmission), elicit a parasite-specific antibody or cellular immune response or nucleotides encoding such polypeptides/fragments: SEQ ID NO: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76. For example, the vaccine composition comprises polypeptides (or nucleic acids encoding them) comprising the following sequences: SEQ ID NO: 2, 10, 14, 18, 22, 26, 30, 34, 38, 42, 46, 47, 66, 67, 70, 72, 74, and/or 76.

Also provided herein is a vector or a host cell expressing one or more isolated peptides or one or more isolated nucleic acid sequences described herewith.

Another aspect of the present invention relates to a vaccine composition. The vaccine composition contains one or more isolated peptides or one or more isolated nucleic acid sequences described herewith. The peptide vaccine may also contain an adjuvant. Exemplary adjuvants include aluminum salts, such as aluminum phosphate and aluminum hydroxide. Another exemplary adjuvant is an oil adjuvant such as the Montanide ISA series, e.g., ISA 50 V2 or ISA 720 VG. The DNA vaccine contains a eukaryotic vector to direct/control expression of the antigen in the subject to be treated.

The vaccine of the present invention provides a new regimen in treating or preventing *P. falciparum* malaria in a subject. Accordingly, the present invention further provides a method of treating or preventing *P. falciparum* malaria in a subject in need by administering the vaccine to the subject. Preferably, the subject is a child under 5 years of age. More preferably, the subject is at least about 6-8 weeks of age. The vaccine is also suitable for administration to older children or adults. The vaccine can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the vaccine is administered intramuscularly. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, or more times alone or in combination with 1, 2, 3, 4, or more additional vaccines in a subject, preferably a human subject. One exemplary additional vaccine contains an inhibitor of parasite liver invasion, such as RTS,S (Mosquirix). Another exemplary additional vaccine contains an inhibitor of parasite red blood cell invasion, such as MSP-1. The vaccine can be made by any known method in the art.

Also provided herein are an antibody that specifically binds to an antigen comprising the isolated peptide of the present invention and a method of treating *P. falciparum* malaria in a subject in need of by administering a therapeutically effective amount of such antibody to the subject. The *P. falciparum* malaria can be acute *P. falciparum* malaria.

Also provided herein is a method of treating *P. falciparum* malaria in a subject in need of by administering a therapeutically effective amount of an antibody described herewith to the subject. Preferably, the antibody is a purified monoclonal antibody, e.g., one that has been raised to and is specific for the protein of SEQ ID NO:2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute *P. falciparum* malaria but has not responded to treatment with anti-malarial drugs. In this passive immunity approach, the purified humanized monoclonal antibody that binds specifically to the protein of SEQ ID NO:2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of *P. falciparum* malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

The present invention further provides a kit for determining the presence of antibody to *P. falciparum* in a sample obtained from a subject. A "sample" is any bodily fluid or tissue sample obtained from a subject, including, but not limited to, blood, blood serum, urine, and saliva. The kit contains an antigen or an antibody of the present invention and optionally one or more reagents for detection.

The kit may also contain a sample collection means, storage means for storing the collected sample, and for shipment. The kit further comprises instructions for use or a CD, or CD-ROM with instructions on how to collect sample, ship sample, and means to interpret test results. The kit may also contain an instruction for use to diagnose malaria or a receptacle for receiving subject derived bodily fluid or tissue.

The kit may also contain a control sample either positive or negative or a standard and/or an algorithmic device for assessing the results and additional reagents and components. The kit may further comprise one or more additional compounds to generate a detectable product.

A "vaccine" is to be understood as meaning a composition for generating immunity for the prophylaxis and/or treatment of diseases. Accordingly, vaccines are medicaments which comprise antigens and are intended to be used in humans or animals for generating specific defense and protective substance by vaccination.

A "subject" in the context of the present invention is preferably a mammal. The mammal can be a human, non-human primate, mouse, rat, dog, cat, horse, or cow, but are not limited to these examples. A subject can be male or female. A subject can be a child or an adult. A subject can be one who has been previously diagnosed or identified as having malaria, and optionally has already undergone, or is undergoing, a therapeutic intervention for the malaria.

Alternatively, a subject can also be one who has not been previously diagnosed as having malaria, but who is at risk of developing such condition, e.g. due to infection or due to travel within a region in which malaria is prevalent. For example, a subject can be one who exhibits one or more symptoms for malaria.

A subject "at risk of developing malaria" in the context of the present invention refers to a subject who is living in an area where malaria is prevalent, such as the tropics and subtropics areas, or a subject who is traveling in such an area. Alternatively, a subject at risk of developing malaria can also refer to a subject who lives with or lives close by a subject diagnosed or identified as having malaria.

As used herein, an "isolated" or "purified" nucleotide or polypeptide is substantially free of other nucleotides and polypeptides. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides is one that is at least 90%, 91%, 92%, 93%, 94%, 95%, 98%, 99%, or 100% (w/w) of the desired nucleic acid or polypeptide by weight.

Purity is measured by any appropriate standard method, for example, by column chromatography, thin layer chromatography, or high-performance liquid chromatography (HPLC) analysis. The nucleotides and polypeptides are purified and used in a number of products for consumption by humans as well as animals, such as companion animals (dogs, cats) as well as livestock (bovine, equine, ovine, caprine, or porcine animals, as well as poultry). A purified or isolated polynucleotide (ribonucleic acid (RNA) or deoxyribonucleic acid (DNA)) is free of the genes or sequences that flank it in its naturally-occurring state. For example, the DNA is a cDNA. "Purified" also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By the terms "effective amount" and "therapeutically effective amount" of a formulation or formulation component is meant a sufficient amount of the formulation or component to provide the desired effect. For example, "an effective amount" of a vaccine is an amount of a compound required to blocking red blood cells (RBCs) rupture, block egress of parasites from RBCs, block gametocyte egress, or elicit an antibody or cellular immune response to the vaccine antigen(s). Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps and permits those that do not materially affect the basic and the characteristic(s) of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIGS. 4A-C show that vaccination with rPbSEP-1A (recombinant SEP-1A antigenic polypeptide from P. berghei) protects mice from challenge with the infectious agent, e.g., P. berghei ANKA. A) rPbSEP-1A was expressed and purified from induced, clarified E. coli soluble lysates. Recombinant protein containing fractions were resolved on an 8-15% SDS PAGE-gel and stained with Gel-Code Blue. Lane 1) nickel chelate chromatography of soluble E. coli lysate, lane 2) hydrophobic interaction chromatography of lane 1, lane 3) anion exchange chromatography of lane 2. B) Antibody response of mice vaccinated with rPbSEP-1A. Following vaccination, mice generated high-titer anti-rPbSEP-1A IgG responses. C) Mice vaccinated with rPbSEP-1A had markedly reduced parasitemia (4.5 fold reduction on day 7 post challenge, P<0.002) and parasite growth rate compared to control mice. All control mice were euthanized on day 7 due to high parasitemia and associated illness.

FIGS. 13A-B are photomicrographs showing that PfSEP-1 is not detected in trophozoite infected RBCs or non-infected RBCs. Non-permeabilized, non-fixed trophozoite infected RBCs (A) or uninfected RBCs (B) were probed with mouse anti-PfSEP-1 (5 nm gold particles) and rabbit anti-glycophorin A (10 nm gold particles) and counterstained with uranyl acetate to enhance membrane contrast. PfSEP-1 was not detected in trophozoite infected RBC or uninfected RBCs, while glycophorin A was confined to the outer leaflet of the RBC membrane (white arrow).

FIG. 16 is a table showing epidemiological characteristics of resistant and susceptible individuals used in differential screening assays.

FIG. 17 is a table showing epidemiological characteristics of resistant and susceptible individuals used in confirmatory ELISA assays.

FIGS. 18A-G are photomicrographs showing the results of an immunofluorescence analysis on methanol fixed infected red blood cells (iRBCs) using mouse anti-PfSEP-1 sera.

FIG. 21 B illustrates the role of PfSEP in and protein-protein interactions involved in schizont egress.

DETAILED DESCRIPTION

Figure 1A:
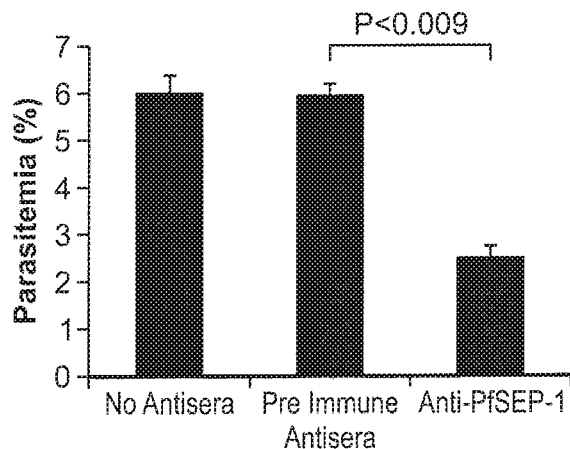
FIGS. 1A-C are bar graphs showing that anti-PfSEP-1 antibodies generated by DNA vaccination inhibit parasite growth/invasion by 58¬65% across 3 parasite strains in vitro. Ring stage 3D7 (A), W2 (B) and D10 (C) parasites were synchronized three times using sorbitol, plated at 0.3-0.4% parasitemia, and cultured to obtain mature trophozoites. Mature trophozoites were cultured in the presence of anti-PfSEP-1 mouse sera (1:10 dilution). Negative controls included no mouse sera and pre-immune mouse sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P<0.009 for comparison between pre and post immune mouse sera by non-parametric Mann-Whitney U test.
Figure 1B:
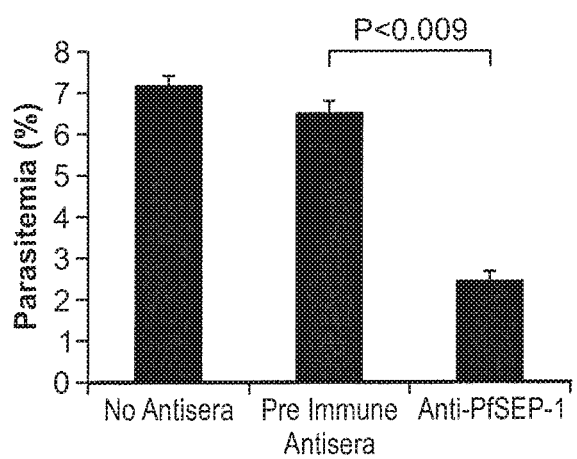
Figure 1C:
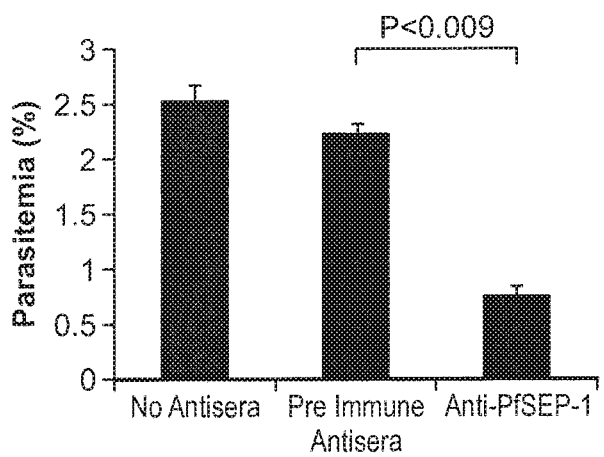

The invention represents a significant breakthrough in the treatment or prevention of malaria, for example, such as *P. falciparum* malaria. Prior to the present invention, an effective vaccine was not yet available for malaria, although several vaccines are under development. The vaccine, SPf66, was tested extensively in endemic areas in the 1990s, but clinical trials showed it to be insufficiently effective. Other vaccine candidates, targeting the blood-stage of the parasite's life cycle, such as anti-red blood cell (RBC) invasion (*P. falciparum* merozoite specific protein 1 (MSP-1) antigen and *P. falciparum* merozoites Apical Membrane Antigen 1 (AMA-1) antigen), have also been insufficient on their own. Several potential vaccines, for example, RTS,S (also called Mosquirix) targeting the pre-erythrocytic stage are being developed. One major challenge in the field is short acting time for a vaccine due to the quick infection/life cycle of the parasite. A vaccine, such as RTS,S, functioning at pre-liver stage has only 5 minutes to act before sporazoite enters hepatocytes. Anti-RBC invasion vaccines have only 15 seconds before merozoite enters RBCs.

*P. falciparum* remains a leading cause of morbidity and mortality in developing countries and vaccines for this parasite are urgently needed. Human residents of endemic areas develop protective immunity that limits parasitemia and disease. The subject invention relates to nucleic acid and polypeptide sequences designed from *P. falciparum* in a vaccine composition. The vaccine antigens were identified using a differential screening strategy using sera from resistant individuals and from susceptible ones. Antigens were identified by binding to antisera from resistant individuals were further characterized. Such nucleic acid sequences and polypeptides were found to be useful for therapeutic as well as diagnostic purposes.

Polynucleotide Sequence and Encoded Polypeptides

The invention is directed in part to *P. falciparum* polynucleotides and polypeptides that are useful, for example, for antigens for vaccines against *P. falciparum* malaria.

Human residents of endemic areas develop protective immunity that limits parasitemia and disease, and naturally acquired human immunity provides an attractive model for vaccine antigen identification. Plasma samples and parasitologic data collected during a longitudinal birth cohort study in Muheza, Tanzania (TZN) were used to identify previously unknown *P. falciparum* antigens associated with resistance during early life. The antigens were then validated as targets of antibodies associated with resistance to parasitemia in a large cohort of young children.

Using plasma obtained from maximally resistant and susceptible members of the Muheza cohort, parasite antigens recognized by host antibodies that mediate resistance to parasitemia were identified.

750,000 phage from a 3D7 based blood stage *P. falciparum* library were differentially screened using pooled plasma from the resistant and susceptible individuals. Three clones that are uniquely recognized by antibodies in the plasma of resistant but not susceptible pools were identified. These clones encode MSP-7 (MSP-7 nts 200-1,052), a unique hypothetical gene on Ch10 (Chromosome #10 bp 901175 to 900359), and a unique hypothetical gene on Ch11 (Chromosome #11 nts. 1333936 to 1335849). The gene on Ch11 has the gene ID of PF10_0212a.

```
Clone #2: Plasmodb.org designation: Gene
PF10_0212a (Version 9.2)
Nucleic acid sequence of Clone #2, 819bp
(Sequence 2,431-3,249 of gene PF10_0212a)
                                                          (SEQ ID NO: 1)
AACGAGGATAGAGGAATATACGATGAATTATTAGAAAATGATATGTGTGATTTATACAATTTAAAAAT

GCATGATTTGCATAATTTAAAATCCTATGATTTTGGATTATCTAAAGATTTATTAAAAAAGGATATTTT

TATATATAGTAATAATTTGAAAAATGATGATATGGATGATGATGATAATAATAATATGAATGATATTG

CTATAGGTGAAAATGTAATATATGAAAATGATATACATGAAAATAATATAGATGATAATGATATGTAT

AATAATTACGTGAATGGAAATGATTTATATATTAACAATATGCAGGATGATGCCATGGACGATATTGT

ATATGATGAGGAAGAAATTAAAAGCTTCCTAGATAAATTAAAATCTGATATATCAAATCAAATGAATG

TAAAAAATGGAAATGTCGAAGTTACAGGAAATGGTGGTAATGAAGAAATGTCTTATATAAATAATGA

TGAAAATTTACAAGCTTTTGATTTGTTAGATAATTTCCATATGGATGATTATGGTAATAATTATAATGA

TAATGAAGAAGATGGGGATGGGGATGGGGATGACGATGAACAGAAGAAAAGAAAACAAAAAGAGTT

ACATAATGTAAATGGAAAATTAAACTTATCAGATTTAAATGAATTAAATGTAGATGATATAAATAATA

ATTTTTATATGTCAACTCCTCGAAAATCTATAGATGAACGTAAAGATACGGAATGTCAAACAGATTTT

CCCTTATTAGATGTATCAAGGAATACTAATAGGACTCCTAGAAGAAAAAGTGTGGAAGTAATACTTGT

AGAA Sequence Length: 819

Amino acid sequence of Clone # 2 (a.k.a., PfSEP-1A)
                                                          (SEQ ID NO: 2)
NEDRGIYDELLENDMCDLYNLKMHDLHNLKSYDFGLSKDLLKKDIFIYSNNLKNDDMDDDNNNMNDIA

IGENVIYENDIHENNIDDNDMYNNYVNGNDLYINNMQDDAMDDIVYDEEEIKSFLDKLKSDISNQMNVKN

GNVEVTGNGGNEEMSYINNDENLQAFDLLDNFHMDDYGNNYNDNEEDGDGDGDDDEQKKRKQKELHN

VNGKLNLSDLNELNVDDINNNFYMSTPRKSIDERKDTECQTDFPLLDVSRNTNRTPRRKSVEVILVE

Sequence Length: 273

Amino acid sequence of PF10_0212a(PfSEP-1)
                                                          (SEQ ID NO: 3)
MMENKYPNELFCYINRYNINEIIENGEEKYVNEYDEDKNMSINHMNENDGICEYEIPFLL

DYVDDSNKEDSEKNSLKSYLDDGASTILSKPDELENYNKQNENEFDENNNNKNNKIDQLK

EKINIIIIPNKGVINNFEEILSMANRNDKNIEKKLNDRFYQICCKSIADINTHNLNKIKD

LKKKKNNKGSLNIEHIDYGDIFLTIHDTLKSNNKIKGNNKTNLLHDSSYEIKKKTRRGTN

IYKNPFHHRGSYLTSYENQKDIIYLNNLNNIMMDKYSNCSDSRKKEYSHFNSQEFSYDKY

SMKDRMFLKNLYMKQNRLRDKRGKYHKLGDYQNIENYRKTGEHSFDCMNMSDIMHSNKMS

HVNIMDHMIYKDNNNMSKLVDTINSREKDVKNYDDNFESYNNFFKNNNDEQHICLEYDDT

YNLKDTVKNIIVEEEQCGKGVACICDKNEDVDDLFVSKKTNYSSNKKREDYEKVFLEDNL

HLKQTPSKRTKINIIPDYYDNNRSNKSYKENEEDALFEVCGSLKNDDILYKDNKLNVINE
```

-continued

DNIKEEDDKESVVHLDNDEDKKEEMYKDVYPNVLSCEKETIRRNEKYNKSLNSTSSFEKI

DNPSEINVESKEDTEYFDLLIKKYEDTKINVYDNESLLLDLSNELREEMAKGDSNKNVNK

VEDNDNKKENICHDNIMEDICHNNNVEDMYRNNNVEDMYRNNNVEDMYRNNNVEDMYRNN

NVEDVCHNNNVEDVCHNNNVEDVCHNNNVEDVYHNNNVEDMYHDNNIEDVCHNNNVEDVC

HNNNVEDHVNYDNEELNKKMDEMKEEKEERNEDRGIYDELLENDMCDLYNLKMHDLHNLK

SYDFGLSKDLLKKDIFIYSNNLKNDDMDDDDNNNMNDIAIGENVIYENDIHENNIDDNDM

YNNYVNGNDLYINNMQDDAMDDIVYDEEEIKSFLDKLKSDISNQMNVKNGNVEVTGNGGN

EEMSYINNDENLQAFDLLDNFHMDDYGNNYNDNEEDGDGDGDDDEQKKRKQKELHNVNGK

LNLSDLNELNVDDINNNFYMSTPRKSIDERKDTECQTDFPLLDVSRNTNRTPRRKSVEVI

LVEKKLKKKKQKCMDKYTDANEDSNRRYPKRNRIKTLRYWIGERELTERNPYTGEIDVVG

FSECKNLQDLSPHIIGPIEYKKIYLKNLNSNEHEENEDNNGDIIENNNGDVIENNNGDII

EDNNANEKNHNNLESEGKGIVYDDVNNLHVHTNSDNSAHSKKIKGAPSRFSNTNNGRKKR

RRRKFINVVNYIKKKKKKKLIKSMDNMEVTDNFKNDMSDENKQSGDENKQSGDENKQSGD

ENKQSGDENKQTNNDIKQSDNDIKQSDDIYMNEDMNLFNDLNDNFDNNEYFINNGDKDSH

AEEEMAIENIQSKSIEKDILNNEEQDNNNIFDIDNELIDMKDGNVDEMESDEKLKTFEKL

ESLKSTTHLNNTDNCDVNLSEQTNEINYDEEKKVNKKTNHEKMKKKKKKKKKKKKKKE

KKQIDIMYKNLSRLNLNLLLPTKKKVKKSKNSFKKEEEKQKKKNKKVKKIKGINKGEKIK

SNKKENKDNNNDSSTECVVEGEKGKDLHEFNKNGNLEDEQMDVDISMNISSINCESDNKN

VSKEGEEEKKDIAENKEEVDKNKEEVYMDKHEMDLNNEEVYMDKNEMDLNNEEVYMDKHE

MDLNNEEVYMDKHEMDLNNEEVYMDKHEMDLNKEEVYMDKHEMDLNNEEVDKENEYDENI

LSDNIIYNENNSFGNNKNSFFNNTSPLKTEIINEEENSLNEMKEDINEYVEMENKLDTEK

IKDSEKIGGKIEVDNKMISPINRHNFYLTILEGMNKNFPRQWNKNNITLSKNQGQIYKGR

KEKKRKRSYRNDEKLLDHSILNDINISDKMDERNELLESIKSNSTINNVLEIIKYDNRKK

IKKNDTNKEIIKYDNFTSKYNNKSNDIQLNGGIYINKFKLSLDMPINKLAVSSNLGPPSS

IGSTEIQPIQKNFNDFKMNINVYCIRMEPHEKYSSYSHKNNLVVYIDKGEKINIIINMSK

TYEKGDFFYIPRFSNFQIINDSRCDCVLYVCPLI Sequence Length:

2074 aa; underlined sequence corresponds to PfSEP-1A antigenic fragment.

Coding Nucleotide sequence of PF10_0212a(PfSEP-1)

(SEQ ID NO: 4)

ATGATGGAAAATAAATACCCAAATGAATTATTCTGTTATATAAATAGATATAATATAAAC

GAAATAATAGAAAATGGAGAAGAGAAGTATGTAAATGAATATGATGAAGATAAGAATATG

TCAATAAATCATATGAATGAAAACGATGGTATATGTGAATATGAAATACCATTTTTATTA

GACTATGTGGATGATAGTAATAAAGAAGATTCAGAGAAAAATTCATTAAAGAGTTATCTC

GATGATGGTGCATCCACTATCCTTTCAAAACCAGATGAACTGGAAAATTATAATAAACAA

AATGAAAATGAATTTGACGAAAATAATAATAATAAAAATAATAAAATTGACCAATTGAAG

GAAAAAATAAATATTATAATAATACCAAATAAAGGTGTTATAAACAATTTTGAAGAGATA

TTAAGCATGGCAAATCGTAATGATAAAAATATAGAGAAAAAGTTGAATGATAGATTTTAT

CAAATATGTTGTAAAAGTATAGCTGATATAAACACACACAATTTAAATAAAATTAAAGAT

TTGAAAAAAAAAAAAAATAATAAAGGATCCTTAAATATTGAACATATAGATTATGGAGAT

ATTTTTCTTACTATACATGATACATTAAAAAGTAATAATAAAATAAAAGGAAACAATAAA

ACTAACTTATTACACGATTCTTCTTATGAAATAAAAAAGAAAACAAGAAGAGGAACAAAT

-continued

```
ATATATAAAAATCCATTTCATCATAGAGGTTCCTATTTAACTTCGTATGAAAATCAAAAG

GATATCATTTACCTTAATAATTTAAACAACATTATGATGGATAAATATAGTAATTGTAGT

GATTCACGAAAAAAGGAATATTCGCATTTCAATTCGCAGGAGTTTTCATATGATAAATAT

AGTATGAAAGACAGAATGTTTCTCAAAAATTTGTATATGAAACAAAATAGATTAAGAGAT

AAAAGGGGGAAATATCACAAATTGGGAGATTATCAAAATATTGAAAACTATCGTAAAACG

GGTGAACATAGTTTTGATTGTATGAATATGTCAGATATTATGCATTCAAATAAAATGAGC

CATGTTAATATCATGGATCATATGATATATAAAGATAATAACAATATGAGCAAACTAGTA

GATACAATAAATTCTCGTGAAAAGGATGTAAAAAATTATGACGATAACTTTGAAAGCTAT

AATAATTTTTTAAGAATAATAATGATGAACAACATATATGTTTGGAGTATGACGATACA

TATAACTTAAAAGATACAGTTAAAAATATTATTGTTGAAGAAGAACAATGTGGTAAGGGT

GTTGCTTGTATATGTGATAAGAACGAAGATGTTGACGATTTGTTTGTTTCAAAGAAAACG

AATTATTCTTCTAATAAAAAAAGAGAAGATTATGAGAAAGTATTTCTTGAAGATAATTTA

CATTTAAAACAAACTCCATCAAAAAGAACAAAAATTAATATAATCCCAGATTATTATGAT

AACAATAGAAGTAATAAGAGTTATAAGGAAAATGAAGAGGATGCTTTGTTTGAGGTATGT

GGTAGTTTAAAAAACGATGATATATTGTATAAAGATAATAAGTTGAATGTCATAAATGAA

GATAATATAAAGGAAGAGGATGACAAAGAAAGTGTTGTTCATTTAGATAATGATGAGGAT

AAAAAAGAAGAAATGTATAAAGATGTATATCCCAATGTATTGTCTTGTGAAAAAGAAACG

ATTAGGAGGAATGAAAAGTATAACAAATCATTGAACAGTACAAGTAGCTTTGAAAAAATT

GATAATCCAAGTGAAATTAATGTTGAAAGTAAGGAAGATACAGAATATTTTGATTTATTA

ATAAAAAAATATGAGGATACAAAAATAAACGTATATGATAATGAATCTCTTTTATTGGAT

CTTAGTAATGAGCTACGTGAAGAAATGGCCAAGGGGGATTCTAATAAAAATGTAAATAAA

GTGGAAGATAATGATAATAAAAAGGAAAATATTTGTCATGATAATATCATGGAAGATATT

TGTCATAATAATAACGTGGAAGATATGTATCGTAATAATAACGTGGAAGATATGTATCGT

AATAATAACGTGGAAGATATGTATCGTAATAATAACGTGGAAGATATGTATCGTAATAAT

AACGTGGAAGATGTTTGTCATAATAATAACGTGGAAGATGTTTGTCATAATAATAACGTG

GAAGATGTTTGTCATAATAATAACGTGGAAGATGTTTATCATAATAATAACGTGGAAGAT

ATGTATCATGATAATAACATTGAAGATGTTTGTCATAATAATAACGTGGAAGATGTTTGT

CATAATAATAACGTGGAAGACCATGTTAATTATGATAATGAAGAATTGAATAAAAAAATG

GATGAGATGAAAGAAGAAAGGAAGAAAGAAACGAGGATAGAGGAATATACGATGAATTA

TTAGAAAATGATATGTGTGATTTATACAATTTAAAAATGCATGATTTGCATAATTTAAAA

TCCTATGATTTTGGATTATCTAAAGATTTATTAAAAAAGGATATTTTTATATATAGTAAT

AATTTGAAAAATGATGATATGGATGATGATGATAATAATAATATGAATGATATTGCTATA

GGTGAAAATGTAATATATGAAAATGATATACATGAAAATAATATAGATGATAATGATATG

TATAATAATTACGTGAATGGAAATGATTTATATATTAACAATATGCAGGATGATGCCATG

GACGATATTGTATATGATGAGGAAGAAATTAAAAGCTTCCTAGATAAATTAAAATCTGAT

ATATCAAATCAAATGAATGTAAAAAATGGAAATGTCGAAGTTACAGGAAATGGTGGTAAT

GAAGAAATGTCTTATATAAATAATGATGAAAATTTACAAGCTTTTGATTGTTAGATAAT

TTCCATATGGATGATTATGGTAATAATTATAATGATAATGAAGATGGGGATGGGGAT

GGGGATGACGATGAACAGAAGAAAAGAAAACAAAAAGAGTTACATAATGTAAATGGAAAA

TTAAACTTATCAGATTTAAATGAATTAAATGTAGATGATATAAATAATTTCTATATG

TCAACTCCTCGAAAATCTATAGATGAACGTAAAGATACGGAATGTCAAACAGATTTTCCA
```

-continued

TTATTAGATGTATCAAGGAATACTAATAGGACTCCTAGAAGAAAAAGTGTGGAAGTAATA

CTTGTAGAAAAAAAATTAAAAAAAAAAAAACAGAAATGTATGGATAAATATACAGATGCA

AATGAGGATAGTAATAGAAGATATCCCAAAAGAAATCGAATTAAAACTTTGCGTTATTGG

ATAGGAGAAAGAGAGTTAACTGAAAGAAACCCTTACACAGGAGAAATAGATGTTGTAGGA

TTTAGTGAGTGTAAAAATTTGCAAGATTTGTCACCTCATATTATTGGTCCGATTGAATAT

AAAAAAATATATTTGAAAAATCTTAATAGTAATGAACATGAGGAAAATGAAGATAATAAT

GGAGACATTATTGAAAATAATAATGGGGACGTTATTGAAAATAATAATGGAGACATTATT

GAAGATAATAATGCAAACGAAAAAAATCATAATAATCTTGAATCTGAAGGTAAGGGTATC

GTATATGATGATGTAAATAATTTACATGTTCACACAAACAGTGATAATAGTGCTCATTCG

AAGAAAATAAAGGGAGCCCCCAGTAGGTTTAGTAATACAAATAATGGAAGGAAGAAACGA

AGAAGGAGAAAATTCATCAATGTAGTTAATTATATAAAGAAGAAGAAAAGAAGAAACTG

ATAAAAAGTATGGATAATATGGAGGTTACAGATAATTTTAAGAATGATATGAGTGATGAA

AATAAACAAAGTGGTGATGAAAATAAACAAAGTGGTGATGAAAATAAACAAAGTGGTGAT

GAAAATAAACAAAGTGGTGATGAAAATAAACAAACTAATAATGATATTAAACAGAGTGAT

AATGATATTAAACAGAGTGATGATATTTACATGAATGAAGATATGAATTTGTTCAATGAT

TTAAATGATAACTTCGATAACAATGAATATTTCATAAACAATGGTGATAAGGATTCTCAT

GCTGAAGAAGAAATGGCCATAGAAAATATTCAAAGTAAAAGTATAGAAAAGGATATTTTA

AATAATGAAGAGCAGGATAATAATAACATCTTTGATATTGATAATGAACTTATAGATATG

AAGGATGGAAATGTAGATGAAATGGAAAGTGATGAAAAATTAAAAACTTTTGAAAAATTG

GAAAGTTTGAAAAGTACAACACATTTAAACAATACCGATAATTGTGATGTAAATTTGAGT

GAACAGACCAATGAAATAAATTATGATGAGGAAAAAAAAGTTAATAAAAAAACAAATCAT

GAAAAAATGAAGAAGAAGAAGAAAAAAAAAAAAAAAGAAAAAGAAGAAGAAAGAA

AAAAAACAAATAGATATTATGTACAAAAATTTGTCCAGACTTAATTTAAATTTGTTACTT

CCAACCAAAAAAAAAGTTAAGAAATCGAAAAACTCATTTAAAAAAGAGGAAGAAAAACAA

AAGAAGAAAAATAAAAAAGTTAAAAAAATCAAAGGTATTAACAAGGGGGAAAAAATAAAA

AGTAATAAGAAAGAAAATAAGGACAATAATAATGATAGTAGTACAGAATGTGTTGTAGAA

GGAGAAAAAGGAAAAGATTTACATGAGTTTAATAAAAATGGAAATCTTGAAGATGAACAA

ATGGATGTTGATATTTCTATGAATATTTCAAGTATAAATTGTGAAAGTGATAATAAAAAT

GTGAGTAAGGAAGGAGAGGAAGAAAAAAAAGACATAGCTGAAAACAAAGAAGAGGTGGAT

AAAAACAAGAAGAGGTATATATGGACAAACATGAGATGGATTTGAACAATGAAGAGGTA

TATATGGACAAAATGAGATGGATTTGAACAATGAAGAGGTATATATGGACAAACATGAG

ATGGATTTGAACAATGAAGAGGTATATATGGACAAACATGAAATGGATTTGAACAATGAA

GAGGTATATATGGACAAACATGAAATGGATTTGAACAAGAAGAGGTATATATGGACAAA

CATGAGATGGATTTGAACAATGAAGAGGTAGATAAAGAAACGAATATGATGAAAATATA

CTTAGTGATAACATAATATATAATGAAAACAATTCATTTGGAAACAATAAGAACTCTTTT

TTTAATAATACAAGTCCATTAAAAACAGAAATAATAAATGAAGAGGAAAATAGTTTGAAC

GAAATGAAGAAGACATAAATGAATACGTTGAAATGGAAAACAAGTTGGATACGGAAAAA

ATAAAAGATTCAGAAAAAATAGGTGGAAAAATAGAGGTAGATAATAAAATGATTTCTCCT

ATTAATAGACATAATTTTTATTTAACAATTCTTGAAGGAATGAATAAGAATTTTCCTAGG

CAATGGAATAAAAATAATATAACTTTATCAAAAAATCAAGGACAAATTTATAAAGGAAGG

-continued

```
AAAGAAAAGAAAAGAAAACGTTCCTATAGAAATGATGAAAAATTACTTGATCATAGTATA

TTAAATGATATCAATATAAGTGACAAAATGGATGAAAGAAATGAATTATTAGAGAGTATA

AAATCTAATAGTACTATAAATAATGTATTAGAAATTATAAAATATGATAATAGGAAAAA

ATAAAGAAGAATGATACAAACAAGGAAATAATCAAATATGATAACTTCACATCTAAATAT

AATAATAAAAGTAATGATATTCAATTGAATGGTGGAATATATATAAATAAATTCAAACTT

TCTTTAGATATGCCTATAAATAAATTAGCGGTATCTTCAAATCTTGGACCTCCATCATCT

ATAGGATCAACAGAAATACAGCCTATTCAAAAGAATTTCAACGATTTCAAAATGAATATT

AACGTGTACTGTATTAGGATGGAGCCGCATGAAAAATACAGCTCATATAGCCATAAAAT

AATTTAGTTGTATATATTGATAAGGGAGAAAAAATTAACATAATAATCAACATGTCAAAG

ACTTATGAAAAAGGTGATTTTTTTACATACCTAGATTTTCTAACTTCCAAATAATTAAT

GATAGCAGATGTGATTGTGTTTTATATGTTTGTCCTTTAATTTAA
```

Sequence Length: 6225 bp; underlined sequence corresponds
to nucleotide sequence encoding;
PfSEP-1A antigenic fragment.

The invention is also directed in part to polynucleotides and polypeptides shown in the Table below that are useful, for example, for antigens for vaccines against *P. falciparum* malaria.

| Serial Number | Clone Name | Plasmodb.org GENE ID | Gene Name/Function | Length of peptide in aa | Length of Protein aa | Clone size in bp | Gene size in bp |
|---|---|---|---|---|---|---|---|
| 1 | Clone#2 | PF10_0212a Version 9.2 | PfSEP-1/Schizont egress | 273 | 2074 | 819 (2431-3249) | 6225 |
| 2 | Clone#5 | PF13_0197 | MSP-7/Merozoite surface protein/RBC invasion | 284 | 351 | 852 (201-1052) | 1056 |
| 3 | Clone#10 | PF11_0354 | Schizont egress | 641 | 2227 | 1923 (3490-5412) | 6684 |
| 4 | Clone#T108 | PFB0310c | MSP-4/Merozoite surface protein/RBC invasion | 79 | 272 | 238 (124-361) | 819 |
| 5 | Clone#T32 | MAL8P1.58 | Pf-PGPS/phosphatidyl glycerophosphate synthase | 100 | 661 | 300 (1023-1322) | 1986 |
| 6 | Clone#T9 | PFE0040c | MESA/Mature Erythrocyte Surface Antigen | 153 | 1434 | 459 (2080-2538) | 4305 |
| 7 | Clone#TL22 | PFA0620c | Pf-GARP/glutamic acid rich protein | 263 | 673 | 792 (1231-2022) | 2022 |
| 8 | Clone#TL27 | PFI1780w | Plasmodium exported protein | 101 | 383 | 303 (691-993 | 1152 |
| 9 | Clone#TL5 | PFB0100c | Pf-KAHRP/Pathogenicity, Adhesion/Knob Associated Histidine Rich Protein | 80 | 654 | 242 (1309-1550) | 1965 |
| 10 | Clone#TL16 | MAL7P1.208 | RAMA/Rhoptry Associated membrane antigen/RBC invasion/DNA | 144 | 873 | 432 (953-1384 | 2114 |

| | | | | | | | |
|---|---|---|---|---|---|---|---|
| 11 | Clone#TL45 | PF07_0033 | Cg4 protein/parasite heat shock protein 70/protein transport mismatch repair protein | 216 | 873 | 650 (1764-2413) | 2622 |
| 12 | PF3D7 | PF13_0211 | Ca$^{++}$ dep. Protein kinase | 84 | 568 | 255 | 1707 |

```
Clone #5: MSP-7 (PF13_0197)
Nucleic acid sequence of Clone #5, 852 bp
(Sequence 201-1,052 of gene PF13_0197)
ATTAAACAAAAAATTGAAGAATTACAAAACAGTAAAGAAAAAAATGTACATGTAT
TAATTAATGGAAATTCAATTATTGATGAAATAGAAAAAAATGAAGAAAATGATGAT
AACGAAGAAAATAATGATGATGACAATACATATGAATTAGATATGAATGATGACAC
ATTCTTAGGACAAAATAACGATTCACATTTTGAAAATGTTGATGATGACGCAGTAGA
AAATGAACAAGAAGATGAAAACAAGGAAAAATCAGAATCATTTCCATTATTCCAAA
ATTTAGGATTATTCGGTAAAAACGTATTATCAAAGGTAAAGGCACAAAGTGAAACA
GATACTCAATCTAAAAATGAACAAGAGATATCAACACAAGGACAAGAAGTACAAA
AACCAGCACAAGGAGGAGAATCGACATTTCAAAAAGACCTAGATAAGAAATTATAT
AATTTAGGAGATGTTTTTAATCATGTAGTTGATATTTCAAACAAAAAGAACAAAATA
AATCTCGATGAATATGGTAAAAAATATACAGATTTCAAAAAAGAATATGAAGACTT
CGTTTTAAATTCTAAAGAATATGATATAATCAAAAATCTAATAATTATGTTTGGTCA
AGAAGATAATAAGAGTAAAAATGGCAAAACGGATATTGTAAGTGAAGCTAAACATA
TGACTGATATTTTCATAAAACTATTTAAAGATAAGGAATACCATGAACAATTTAAAA
ATTATATTTATGGTGTTTATAGTTATGCAAAACAAAATAGTCACTTAAGTGAGAAAA
AAATAAAACCAGAAGAGGAATATAAAAAATTTTTAGAATATTCATTTAATTTACTAA
ACACAAT Sequence Lenght: 852 bp (SEQ ID NO: 5)

Amino acid sequence of Clone #5
LNKKIEELQNSKEKNVHVLINGNSIIDEIEKNEENDDNEENNDDDNTYELDMNDDTFLG
QNNDSHFENVDDDAVENEQEDENKEKSESFPLFQNLGLFGKNVLSKVKAQSETDTQSK
NEQEISTQGQEVQKPAQGGESTFQKDLDKKLYNLGDVFNHVVDISNKKNKINLDEYGK
KYTDFKKEYEDFVLNSKEYDIIKNLIIMFGQEDNKSKNGKTDIVSEAKHMTDIFIKLFKD
KEYHEQFKNYIYGVYSYAKQNSHLSEKKIKPEEEYKKFLEYSFNLLNTM Sequence
Length: 284 aa (SEQ ID NO: 6)

Amino acid sequence of MSP7 gene (PF13_0197)
MKSNIIFYFSFFFVYLYYVSCNQSTHSTPVNNEEDQEELYIKNKKLEKLKNIVSGDFVGN
YKNNEELLNKKIEELQNSKEKNVHVLINGNSIIDEIEKNEENDDNEENNDDDNTYELDMN
DDTFLGQNNDSHFENVDDDAVENEQEDENKEKSESFPLFQNLGLFGKNVLSKVKAQSETD
TQSKNEQEISTQGQEVQKPAQGGESTFQKDLDKKLYNLGDVFNHVVDISNKKNKINLDEY
GKKYTDFKKEYEDFVLNSKEYDIIKNLIIMFGQEDNKSKNGKTDIVSEAKHMTEIFIKLF
KDKEYHEQFKNYIYGVYSYAKQNSHLSEKKIKPEEEYKKFLEYSFNLLNTM
Sequence Length: 351 aa (SEQ ID NO: 7)

Nucleic acid sequence of MSP7 gene (PF13_0197)
ATGAAGAGTAATATCATATTTTATTTTCTTTTTTTTTGTGTACTTATACTATGTTTC
GTGTAATCAATCAACTCATAGTACACCAGTAAATAATGAAGAAGATCAAGAAGAAT
TATATATTAAAAATAAAAAATTGGAAAAACTAAAAAATATAGTATCAGGAGATTTT
GTTGGAAATTATAAAAATAATGAAGAATTATTAAACAAAAAAATTGAAGAATTACAAAAC
AGTAAAGAAAAAAATGTACATGTATTAATTAATGGAAATTCAATTATTGATGAAATAGAAAAA
AATGAAGAAAATGATGATAACGAAGAAAATAATGATGATGACAATACATATGAATTAGATAT
GAATGATGACACATTCTTAGGACAAAATAACGATTCACATTTTGAAAATGTTGATGATGACG
CAGTAGAAAATGAACAAGAAGATGAAAACAAGGAAAAATCAGAATCATTTCCATTATTCCAA
AATTTAGGATTATTCGGTAAAAACGTATTATCAAAGGTAAAGGCACAAAGTGAAACAGATAC
TCAATCTAAAAATGAACAAGAGATATCAACACAAGGACAAGAAGTACAAAAACCAGCACAA
GGAGGAGAATCGACATTTCAAAAAGACCTAGATAAGAAATTATATAATTTAGGAGATGTTTT
TAATCATGTAGTTGATATTTCAAACAAAAAGAACAAAATAAATCTCGATGAATATGGTAAAA
ATATACAGATTTCAAAAAGAATATGAAGACTTCGTTTTAAATTCTAAAGAATATGATATAAT
CAAAAATCTAATAATTATGTTTGGTCAAGAAGATAATAAGAGTAAAAATGGCAAAACGGATA
TTGTAAGTGAAGCTAAACATATGACTGAAATTTTCATAAAACTATTTAAAGATAAGGAATACC
ATGAACAATTTAAAAATTATATTTATGGTGTTTATAGTTATGCAAAACAAAATAGTCACTTAA
GTGAGAAAAAAATAAAACCAGAAGAGGAATATAAAAAATTCTTAGAATATTCATTTAATTTAC
TAAACACAATGTAA Sequence Length: 1056 bp (SEQ ID NO: 8)

Clone #10 (PF11_0354)
Nucleic acid sequence of Clone #10, 1923 bp (Sequence
3490-5412 of gene PF11_0354
GATAATGTTAATAATAATAATAATAAAGAAAGTTGTGATAATATTAAACATATGAG
AACAAAAAGTTTAAATTTTGTAAGTAGAGAATCCTATGGCGAACATAAAAGTCTAG
ATGTTTACCAGGAATGTTATGTAAAAAATAATAAACTTATTAATAAGGTAAATGATA
AAAAATATGAGGACAATAATAATTCCTATCTTAATGAAGATGATAACGCTAGTATG
CAATTTTATGAAGAAACTAATAGTAATCCATATATTGTAGACCAGGAAAATAATAT
GAAAAATTATGTCAATAATGTTTTATATAACAACAATAGCAATTATTATGTTGATTC
AAAGAATTATGATAAATCTAAAGAGAATGCAGAAAATAAATCAGATGATATATTAA
ATAATGAAAATATACATACCTTAAAAGATCAAAAAAAGAAAATACAAATAATAAT
GAATTCATTAGTGAACAGGCTGATATAGAAAATATAAGAAATTCTCAAGAAGAAGT
```

```
ATATGAGAAAGAACACGAACCTTTGTGGGTAATAAATGCATCTAATGAAGAAAAGA
AATCATATGAAGAATTGATATACAGCGATATGTCATCTAATCGTGTTACGAAAAATA
AATATAGTGATATGAATAATGTTGAGGTATTATTAAATGAAGATAATTTATTAACTA
CTGAAAAATACAAGGTGCAATTAGAAAAGAAAATAAAATGATTGATATGTATGAA
ACGGTAGAGGAGAATATAAATACAATTAAAACAGAAAATACGAACGACATAAATG
AAGAAGTTAGAAACGAACAAAAAAGAGAAAGTATCAATCATATTAATGATACAAA
TATAAATCTATAATAGATGAATATCCCAATGATACATATAATTTCATAAAAGATAT
AGAATGTGTACATAACAATGAAAATAACATGTACAATTCTATTGAACAATATACATT
TTATCATGATACACGTAATAATCATTTAGTTGATAAAAATAATCAAAATTTTATATT
CGAAGAGGAAGGTTTAAATGAATTGAACTTTGAAGAAAAAAAGGTATATATAGAAA
ATAATACCAAGGATGATCACAAGGGAGATAGCAAACAAGTAACTTAACATCTTTA
AGGAATACCATATGTAAAAGTGAAAACGATCATAATGAAAAAATGAAAACACAT
ATGTGGTTAGAAAAGGCGAAAAGGAATTAAACGTAAGGTTTCCATGAAGAAAAG
AAATGAAAAGCTAAATGAAGAAATTATATTAATAATATATACGATAAAATGGATA
ACCATAGACAAAATGATATTACAAAAAAAGAAAATGACGAAGAAAATTATATTTTG
TACAACAACGTAAAGGTTAATTATGATGAATATATAGAAAATGGAAATAAAATAAA
AATAACGGAAGAATCATTAAATGTCTTTTATAAAGAAAATCAAAATGAGGAAGATT
CTTCTACAAAAAAGTTGAATAGTACAAGTAAAATAAAACGTGCAAACAAAGGGAA
AACAAAAAAAAAGAATGTTATCACAAGGGTACATAAAACAAAACAAAAAATTGAA
TATGTTACAAATAGTTTTAATAAATCTTCCAAAGGTGAAAATTCAGAAATAGGAAA
AATTGGAGGTAGGAGTAAATCATTATTAACACACAGCAAGAAAGTTAGTGAACGAA
ATAAAAATAAAATAGAAAAAATTAATGATACAAATTCAAAGATAATAAAAGGAAA
AAAGAGTAATAGCCAAAGCAAACTTGGGAAGGATACAAAAATTAGAGGGAAATCA
AAAACTGGGGAATATATAAAAAATAAAGATTTAAGAAAAAAATCTAACGAAAAAA
ACAAAACAGTGATGGATAATATAAATACTATAAATAATTCTTCAGTATCTAACCTAA
AAAGCAAAAAACATAAATTG Sequence Length: 1923 (SEQ ID NO: 9)

Amino acid sequence of Clone #10, (PF11_0354)
DNVNNNNNKESCDNIKHMRTKSLNFVSRESYGEHKSLDVYQECYVKNNKLINKVNDK
KYEDNNNSYLNEDDNASMQFYEETNSNPYIVDQENNMKNYVNNVLYNNNSNYYVDS
KNYDKSKENAENKSDDILNNENIHTLKDQKKKIQNNNEFISEQADIENIRNSQEEVYEKE
HEPLWVINASNEEKKSYEELIYSDMSSNRVTKNKYSDMNNVEVLLNEDNLLTTEKYKV
QLEKENKMIDMYETVEENINTIKTENTNDINEEVRNEQKRESINHINDTNINHIIDEYPND
TYNFIKDIECVHNNENNMYNSIEQYTFYHDTRNNHLVDKNNQNFIFEEEGLNELNFEEK
KVYIENNTKDDHKGDSKTSNLTSLRNTICKSENDHNEKNENTYVVRKGEKGIKRKVSM
KKRNEKLNEENYINNIYDKMDNHRQNDITKKENDEENYILYNNVKVNYDEYIENGNKI
KITEESLNVFYKENQNEEDSSTKKLNSTSKIKRANKGKTKKKNVITRVHKTKQKIEYVT
NSFNKSSKGENSEIGKIGGRSKSLLTHSKKVSERNKNKIEKINDTNSKIIKGKKSNSQSKL
GKDTKIRGKSKTGEYIKNKDLRKKSNEKNKTVMDNINTINNSSVSNLKSKKHKL,
Sequence Length: 641 (SEQ ID NO: 10)

Amino acid sequence of PF11_0354
MRSKSISYFLFFKKNKKKNDSCDSVIISSNKNLSIQLSKGEDDEKNEINEEKSYIKNEDVY
KKEKLKKKKENKENNKKKDKNEVVYDYHDISNDATSDYVNNYKVYEMNTCNIKKKR
ESFFKKINILQKYKNYKIRKAASTFHTIGHKTSFSGTDDEIENNQKKQKKYKIKISEWKD
DKSHTFHKKNDILVFDKMDKNKKFKIDNNKNNQINIDNEERVNKNYPMATNVQNFNIK
YTSIDVTNDEYIIDSNKPEGSIMSTDKKNNKLNYNNDTYDVDKSSDINKLGNIKKNKFDII
TKTTHNINNNVNNIHNYMMYTNKENIKININHGNLNGREQNNYDEERKANVYEIFENA
KKLEPNNININTEEHIHISEPSIPFDMKDHKNDINEKDIILKLMYNNNGIYFDDDDENHKN
LLYKNKDTHVKHLNNKFNHNFIIYNDREEGVNQKHAQKKLKKKNTILNKNENEDINHN
SFKRPLSNTNICYKDKDDKIKNGSNKYDILNNDYSNEHEKNKYNDHITKNKRNQSANE
VKSNNNDNHNNKKNNNFNININDSYSTNINRNQNVMINDVNDVIKDPNMQENTQGDD
EGGIINKYLINPIYNLFLRANEEIQNSNSTNNKLKMNNITKSYTNELQKTYKSMYDINDIS
NKRKINNKDIRGTNLYNTKLCNNKLYNSNPYNMIPYNINTYNNNNNNKETCTSINIKHS
ENKYPFNKSHVNSYMKNTNHLPHRNAITSNNRNNEEYEKEKEKDRNITNGNNNYLVEY
NNSCIPPPLKKMIPIDGVRNKSINKLNNVTNTQRTSSVSYTNKNIDENSFDMPIINGIRESK
YISNNNNINGNSIGFNSSKLDNYHHQSMNVNESYPLKNMMKNNYIEHNYDDKNNIFLV
KNYEDTYSNIHNGIHENSMLKNYNLKKACTFHGYSRNHQKNMYTEENLNINQKKNYS
HYHNNGTVLKPLVNTNNVAVNEFADINLSAQKRLHSLKSMGYEDKSMENYRNKIYNNI
NNNNNNNNDNNIYNDNEYCQYNNSYCFDHSDLKNMFPLNHQNSKLLTHSNNKNSFFN
GINVESKHHLANPEIKTFAHNSYPILNQGLINCNPLQCLGYDSNQRNKHNVVYIKKNEY
LNKNIGSIINVLKREGLRKISTHNGKFESFSNMDNKNVYMEGLNIQ*DNVNNNNNKESCDN
IKHMRTKSLNFVSRESYGEHKSLDVYQECYVKNNKLINKVNDKKYEDNNNSYLNEDDNASMQ
FYEETNSNPYIVDQENNMKNYVNNVLYNNNSNYYVDSKNYDKSKENAENKSDDILNNENIHTL
KDQKKKIQNNNEFISEQADIENIRNSQEEVYEKEHEPLWVINASNEEKKSYEELIYSDMSSNRV
TKNKYSDMNNVEVLLNEDNLLTTEKYKVQLEKENKMIDMYETVEENINTIKTENTNDINEEV
NEQKRESINHINDTNINHIIDEYPNDTYNFIKDIECVHNNENNMYNSIEQYTFYHDTRNNHLVD
KNNQNFIFEEEGLNELNFEEKKVYIENNTKDDHKGDSKTSNLTSLRNTICKSENDHNEKNEN
TYVVRKGEKGIKRKVSMKKRNEKLNEENYINNIYDKMDNHRQNDITKKENDEENYILYNNVK
VNYDEYIENGNKIKITEESLNVFYKENQNEEDSSTKKLNSTSKIKRANKGKTKKKNVITRVHKT
KQKIEYVTNSFNKSSKGENSEIGKIGGRSKSLLTHSKKVSERNKNKIEKINDTNSKIIKGKKSNS
QSKLGKDTKIRGKSKTGEYIKNKDLRKKSNEKNKTVMDNINTINNSSVSNLKSKKHKL*KKKK
KKNISMENINKNITNEFCSMERKGTVLLSNMSIKKIDNANSCTLNEPLEENTLNYESNNN
CSNSNLSKDKEKDRNILCNKYYSDEETNSLNKMYTSNIPEISNYYKEIQAINYILSNINNP
NFLNSLELNDLINIEKKFINENIYINKQIIACNVKNEKSNDEMVEKNERKVDEEKGEDEQ
EIKAKENNNKEENQDNENNNKEENHDNENNNKEENQDNENNNKEENQDNENNNKEE
NQDNENNNKEENQKNENGIIYDSRFSIIYLEHDLIYLKKNNLKVILNVLLSNVYCFFEIKL
```

TIILLNFFISNNCQWSFSLFPLSLINKLIHKFSLKINKKVPKYKLENMNINSPNIPYTYLFIC
DGSNYLCINDNSLNNEVYENKMKLNNIIGYYHYINLNRLTYYLEKVNANFVYNHHIYE,
Sequence Length: 2227 (SEQ ID NO: 11)

Coding Nucleic acid sequence gene PF11_0354
ATGAGATCGAAATCCATTTCGTATTTCTTATTTTTTAAAAAAAACAAAAAGAAAAAT
GATTCTTGTGATAGTGTCATAATATCTAGCAATAAGAATTTATCCATTCAATTATCG
AAAGGTGAGGATGATGAAAAAAATGAAATAAATGAGGAAAAGAGTTATATAAAAA
ATGAAGATGTATATAAAAAGGAAAAATTAAAAAAGAAGAAAGAAAACAAGGAAAA
TAATAAAAAGAAAGATAAAAATGAAGTAGTATATGATTATCATGACATTTCAAATG
ATGCTACTAGTGATTATGTTAATAATTATAAAGTATATGAAATGAATACTTGTAATA
TAAAAAAGAAGAGAGAAAGTTTTTTTAAAAAAATTAATATTTTACAAAAATATAAA
AATTACAAAATTAGAAAGGCAGCTAGTACCTTTCATACCATAGGACATAAAACATC
TTTTTCTGGTACAGATGATGAAATAGAAATAATCAAAAGAAACAAAAAAAATATA
AATATAAAAATTTCTGAATGGAAGGATGATAAATCACATACTTTTCATAAAAAAAT
GACATATTGGTATTTGATAAGATGGATAAAAATAAAAAATTTAAAATTGATAACAA
CAAAAACAATCAATTAATATAGATAATGAAGAAAGAGTTAATAAAAATTATCCTA
TGGCTACTAATGTACAAAATTTTAATATAAAATATACATCAATAGATGTAACAAATG
ACGAATATATTATAGATTCTAATAAACCTGAAGGTTCTATTATGTCTACAGATAAAA
AGAATAATAAACTTAATTATAATAATGATACATATGATGTAGACAAAAGCTCTGAT
ATAAATAAGTTAGGTAATATAAAAAAGAATAAATTTGATATTATTACTAAAACAAC
ACATAATATTAATAATAATGTAAATAATATACATAATTATATGATGTATACAAATAA
AGAAAATATAAAAATAAATATAAATCATGGAAATCTAAATGGAAGAGAACAAAAC
AATTATGATGAAGAAAGGAAAGCAAATGTTTATGAAATATTTGAAATGCAAAAAA
ATTAGAACCTAATAATATTAATATCAACACAGAAGAACATATTCATATTAGTGAACC
CAGCATACCATTTGATATGAAGGATCATAAAAATGATATAAATGAAAAAGATATAA
TATTAAAATTGATGTATAACAATAACGGTATTTATTTTGATGATGATGATGAAAATC
ACAAGAATTTATTATACAAAATAAAGATACACATGTAAAACATTTAAATAATAAA
TTTAACCATAATTTTATTATATATAATGATCGCGAAGAAGGGGTAAATCAGAAACAC
GCACAAAAAAATTAAAAAAAAAAAAATACTATTCTTAACAAAAACGAAAATGAAG
ATATTAATCATAATAGTTTCAAAAGACCTTTATCTAATACGAATATATGTTATAAGG
ACAAAGATGATAAAATTAAAAATGGTTCTAATAAGTATGATATATTAAATAATGAC
TATTCTAATGAACACGAAAAAAATAAATATAATGATCATATAACAAAAAATAAAG
AAATCAATCAGCAAATGAAGTAAAATCTAATAATAATGATAACCACAATAATAAA
AAAATAATAATTTTAATATTAATATTAATGATTCATATTCTACAAATATAAATAGAA
ACCAAAATGTGATGATAAATGATGTAAACGATGTTATTAAGGATCCAAATATGCAG
GAAAATACACAAGGTGATGACGAAGGTGGTATTATAAACAAATATTTAATTAACCC
TATTTACAATTTATTTCTACGTGCTAATGAAGAAATACAAAATTCAAATAGTACAAA
CAATAAAATTAAAAATGAATAATATAACAAAAAGTTATACAAACGAACTACAAAAGA
CATATAAAAGTATGTACGATATAAATGATATATCAAATAAGAGAAAAATTAATAAT
AAAGATATACGTGGAACTAATTTGTATAACACCAAATTATGTAATAATAAATTATAT
AATTCGAATCCATATAATATGATTCCATATAATATAAACACATATAATAATAATAAT
AATAATAAGGAAACTTGTACCAGCATAAATATCAAACATTCCGAAAATAAATATCC
CTTCAATAAATCTCATGTAAACTCATATATGAAAAATACAAATCATCTTCCTCATAG
AAATGCGATTACATCAAATAATAGAAACAATGAAGAATATGAGAAAGAAAAAGAA
AAAGATCGTAACATTACTAATGGGAACAATAATTATTTGGTTGAATATAATAATTCT
TGTATACCTCCACCACTCAAAAAAATGATACCAATAGATGGTGAGAAATAAAAG
TATAAATAAATTAAATAATGTAACTAATACGCAACGTACATCAAGTGTTTCATATAC
GAATAAGAATATTGATGAGAATTCGTTTGATATGCCTATAATAAATGGAATAAGAG
AATCTAAATATATAAGTAATAATAATAATATTAATGGTAATTCCATTGGTTTTAATT
CATCTAAGTTAGATAATTATCATCACCAATCTATGAATGTGAATGAATCTTATCCTC
TAAAAAAATATGATGAAAATAATTATATTGAACATAATTATGATGATAAAAATAAT
ATTTTCCTTGTTAAAAATTATGAAGATACATATTCAAATATTCATAATGGCATACAT
GAAAATAGCATGCTAAAAAATTATAATTTAAAAAAGCGTGCACTTTTCATGGGTA
CTCTAGAAATCACCAAAAAAATATGTATACGGAAGAAAATTTAAATATTAATCAA
AAAAGAATTATAGTCATTATCATAATAATGGAACGGTATTAAAACCTTTGGTAAATA
CTAATAATGTTGCAGTGAACGAATTTGCAGATATTAATTTATCGGCTCAAAAAGAT
TACATAGTTTAAAAAGTATGGGGTACGAGGATAAGAGTATGGAAAATTACAGAAAC
AAAATATACAACAACATCAATAATAATAATAATAATAATAATGATAATAATATATA
TAATGATAATGAATATTGTCAGTATAATAATAGTTATTGTTTCGATCATAGTGATTT
AAAAAAATGTTTCCATTAAATCATCAGAATAGCAAGTTATTAACACATAGTAATAA
TAAAAATTCATTTTTTAACGGAATAAATGTAGAATCGAAACATCATTTAGCAAATCC
TGAAATAAAAACATTTGCACACAATAGTTATCCTATATTAAATCAAGGTTTAATAAA
TTGTAACCCCTTACAATGCTTGGGTTATGATTCAAATCAAAGGAATAAGCATAATGT
AGTATACATAAAAAAAAATGAATACCTTAATAAAAACATTGGCTCTATTATAAATG
TTCTTAAAGAGAAGGACTAAGAAAAATTCTACACATAATGGAAAATTCGAATCA
TTTAGTAATATGGATAATAAAAATGTATATATGGAAGGACTAAACATACAA<u>GATAAT
GTTAATAATAATAATAATAAAGAAAGTTGTGATAATATTAAACATATGAGAACAAAAAGTTTA
AATTTTGTAAGTAGAGAATCCTATGGCGAACATAAAAGTCTAGATGTTTACCAGGAATGTTA
TGTAAAAAATAAATAAACTTATTAATAAGGTAAATGATAAAAAATATGAGGACAATAATAATTC
CTATCTTAATGAAGATGATAACGCTAGTATGCAATTTTATGAAGAAACTAATAGTAATCCATA
TATTGTAGACCAGGAAAATAATATGAAAAATTATGTCAATAATGTTTTATATAACAACAATAG
CAATTATTATGTTGATTCAAAGAATTATGATAAATCTAAAGAAGATGCAGAAGAATACAGA
TGATATATTAAATAATGAAAATATACATACCTTAAAAGATCAAAAAAAGAAAATACAAAATAA
TAATGAATTCATTAGTGAACAGGCTGATATAGAAAATATAAGAAATTCTCAAGAAGAAGTAT
ATGAGAAGAACACGAACCTTTGTGGGTAATAAATGCATCTAATGAAGAAAAGAAATCATAT
GAAGAATTGATATACAGCGATATGTCATCTAATCGTGTTACGAAAAATAAATATAGTGATAT
GAATAATGTTGAGGTATTATTAAATGAAGATAATTTATTAACTACTGAAAAATACAAGGTGCA
ATTAGAAAAAGAAAATAAAATGATTGATATGTATGAAACGGTAGAGGAGAATATAAATACAA</u>

TTAAAACAGAAAATACGAACGACATAAATGAAGAAGTTAGAAACGAACAAAAAAGAGAAAG
TATCAATCATATTAATGATACAAATATAAATCATATAATAGATGAATATCCCAATGATACATAT
AATTTCATAAAAGATATAGAATGTGTACATAACAATGAAAATAACATGTACAATTCTATTGAA
CAATATACATTTTATCATGATACACGTAATAATCATTTAGTTGATAAAAATAATCAAAATTTTA
TATTCGAAGAGGAAGGTTTAAATGAATTGAACTTTGAAGAAAAAAAGGTATATATAGAAAAT
AATACCAAGGATGATCACAAGGGAGATAGCAAAACAAGTAACTTAACATCTTTAAGGAATA
CCATATGTAAAAGTGAAAACGATCATAATGAAAAAAATGAAAACACATATGTGGTTAGAAAA
GGCGAAAAAGGAATTAAACGTAAGGTTTCCATGAAGAAAAGAAATGAAAAGCTAAATGAAG
AAAATTATATTAATAATATATACGATAAAATGGATAACCATAACAAATGATATTACAAAAA
AAGAAAATGACGAAGAAAATTATATTTTGTACAACAACGTAAAGGTTAATTATGATGAATATA
TAGAAAATGGAAATAAAATAAAAATAACGGAAGAATCATTAAATGTCTTTTATAAAGAAAATC
AAAATGAGGAAGATTCTTCTACAAAAAAGTTGAATAGTACAAGTAAAATAAAACGTGCAAAC
AAAGGGAAAACAAAAAAAAAGAATGTTATCACAAGGGTACATAAAACAAAACAAAAAATTGA
ATATGTTACAAATAGTTTTAATAAATCTTCCAAAGGTGAAAATTCAGAAATAGGAAAAATTGG
AGGTAGGAGTAAATCATTATTAACACACAGCAAGAAAGTTAGTGAACGAAATAAAAATAAAA
TAGAAAAAATTAATGATACAAATTCAAAGATAATAAAAGGAAAAAAGAGTAATAGCCAAAGC
AAACTTGGGAAGGATACAAAAATTAGAGGGAAATCAAAAACTGGGGAATATATAAAAAATA
AAGATTTAAGAAAAAAATCTAACGAAAAAAACAAAACAGTGATGGTAATATAAATACTATAA
ATAATTCTTCAGTATCTAACCTAAAAAGCAAAAAACATAAATTGAAAAAAAAAAAAAAAA
AAAATATATCTATGGAAAATATAAATAAAAATATAACAAATGAATTTTGTTCTATGG
AAAGAAAAGGAACCGTTCTATTATCTAATATGAGTATTAAGAAGATTGATAATGCA
AATAGTTGTACATTAAATGAACCATTAGAGGAAAATACCTTAAATTATGAAAGTAA
TAATAACTGTAGTAATAGTAATTTATCTAAGGATAAAGAAAAAGATAGAAATATAT
TGTGTAATAAATATTATAGTGATGAGGAAACAAACTCTTTAAACAAAATGTATACAT
CGAATATACCAGAAATAAGTAATTATTATAAGGAAATTCAAGCAATTAATTACATA
TTAAGTAATATTAATAATCCAAATTTTTTAAATTCCCTCGAACTGAATGATTTAATA
AATATTGAAAAAAAATTTATTAACGAAAATATATATATTAATAAGCAGATAATAGC
CTGTAATGTAAAAAATGAAAATCAAATGATGAGATGGTCGAGAAAAATGAACGC
AAAGTGGATGAAGAAAAAGGAGAAGACGAACAAGAAATAAAAGCAAAGGAAAAT
AATAATAAAGAAGAAAACCAAGATAATGAAAATAATAATAAAGAAGAAAACCATG
ATAATGAAAATAATAATAAAGAAGAAAATCAAGATAATGAAAATAATAATAAAGA
AGAAAACCAAGATAATGAAAATAATAATAAAGAAGAAAATCAAGATAATGAAAAT
AATAATAAAGAAGAAAACCAAAAAAATGAAAATGGTATTATTTATGATAGCAGGTT
TAGTATTATCTATTTAGAACACGATTTAATATATTTAAAAAAAAATAATTTAAAAGT
GATACTTAATGTTTTGCTGTCAAATGTGTATTGCTTTTTTGAAATTAAATTAACCATA
ATATTGTTAAATTTCTTTATATCTAATAATTGTCAATGGAGTTTCAGTTTATTTCCCC
TTTCATTAATTAATAAATTAATACATAAATTCAGTTTAAAGATAAATAAGAAAGTTC
CTAAATATAAATTGGAAATATGAATATTAACTCACCAAATATTCCATATACATATC
TTTTTATATGTGATGGAAGTAACTATTTATGTATTAATGACAATTCATTAAATAACG
AGGTATATGAAAACAAGATGAAATTGAACAATATCATTGGATATTACCATTATATTA
ATTTGAATAGATTAACATATTATTTAGAAAAGGTAAATGCTAATTTTGTTTATAACC
ATCATATATATGAATAA, Sequence Length: 6684 bp (SEQ ID NO: 12)

Clone #T108: MSP-4(PFB0310c)
Nucleic acid sequence of Clone #T108, 238 bp
(Sequence 124-361 of gene PFB0310c 1-819)
AGAATTCTAGGGGAAGAAAAACCAAATGTGGACGGAGTAAGTACTAGTAATACTCC
TGGAGGAAATGAATCTTCAAGTGCTTCCCCCAATTTATCTGACGCAGCAGAAAAAA
AGGATGAAAAGAAGCTTCTGAACAAGGAGAAGAAAGTCATAAAAAAGAAAATTC
CCAAGAAAGCGCGAATGGTAAGGATGATGTTAAAGAAGAAAAAAAAACTAATGAA
AAAAAAGATGATGGAA Sequence Length: 238 bp (SEQ ID NO: 13)

Amino acid sequence of Clone #T108
RILGEEKPNVDGVSTSNTPGGNESSSASPNLSDAAEKKDEKEASEQGEESHKKENSQESA
NGKDDVKEEKKTNEKKDDG Sequence Length: 79 aa (SEQ ID NO: 14)

Amino acid sequence of PFB0310c (MSP-4)
MWIVKFLIVVHFFIICTINFDKLYISYSYNIVPENGRMLNM*RILGEEKPNVDGVSTSNTPGG
NESSSASPNLSDAAEKKDEKEASEQGEESHKKENSQESANGKDDVKEEKKTNEKKDDG*KTD
KVQEKVLEKSPKESQMVDDKKKTEAIPKKVVQPSSSNSGGHVGEEEDHNEGEGEHEEE
EEHEEDDDDEDDDTYNKDDLEDEDLCKHNNGGCGDDKLCEYVGNRRVKCKCKEGYK
LEGIECVELLSLASSSLNLIFNSFITIFVVILLIN, Sequence Length: 272 aa
(SEQ ID NO: 15)

Coding Nucleotide Sequence of PFB0310c (MSP-4)
ATGTGGATAGTTAAATTTTTAATAGTAGTTCATTTTTTTATAATTTGTACCATAAACT
TTGATAAATTGTATATCAGTTATTCTTATAATATAGTACCAGAAAATGGAAGAATGT
TAAATATGAGAATTCTAGGGGAAGAAAAACCAAATGTGGACGGAGTAAGTACTAGTAATA
CTCCTGGAGGAAATGAATCTTCAAGTGCTTCCCCCAATTTATCTGACGCAGCAGAAAAAAA
GGATGAAAAGAAGCTTCTGAACAAGGAGAAGAAAGTCATAAAAAAGAAAATTCCCAAGAA
AGCGCGAATGGTAAGGATGATGTTAAAGAAGAAAAAAAAACTAATGAAAAAAAAGATGATG
GAAAAACAGACAAGGTTCAAGAAAAGGTTCTAGAAAAGTCTCCAAAAGAATCCCAA
ATGGTTGATGATAAAAAAAAAACTGAAGCTATCCCTAAAAAGGTAGTTCAACCAAG
TTCATCAAATTCAGGTGGCCATGTTGGAGAGGAGGAAGACCACAACGAAGGAGAA
GGAGAACATGAAGAGGAGGAAGAACATGAAGAAGATGACGATGACGAAGATGATG
ATACTTATAATAAGGACGATTTGGAAGATGAAGATTTATGTAAACATAATAATGGG
GGTTGTGGAGATGATAAATTATGTGAATATGTTGGGAATAGAAGAGTAAAATGTAA ATGTAAAGAAGGATATAAATTAGAAGGTATTGAATGTGTTGAATTATTATCCTTAGC
ATCTTCTTCTTTAAATTTAATTTTTAATTCATTTATAACAATATTTGTTGTTATATTGT
TAATAAATTAA, Sequence Length: 819 bp (SEQ ID NO: 16)

Clone #T32: Pf-PGPS(MAL8P1.58)
Nucleic acid sequence of Clone #T32, 300 bp (Sequence
1,023-1,3,22 of gene MAL8P1.58 (Pf-PGPS) 1-1986
TTCTTTTATCCTTTATTTGAAAAAATAAAAGCATTTTAGTACTTGAACTTTCCTTGC
AGTGTGGATTTTCCATACCTCCAATATATGATGAAACAGATATGTTAGAAAACTTAT
TAAAAAATATCGAAAAATATGATCAAAGCTTAGTTATTTCTTCGGGATATTTAAACT
TCCCAATGAATTTTCTTAAATTAATTAGAAATATATATATCAACGTTATGCAAAAAA
AAAATGGTATTTTACAATTAATCACAGCGTCCCCATGCGCTAATATTTTTTATAAATC
TAAAGGGATATCT Sequence Length: 300 bp (SEQ ID NO: 17)

Amino acid sequence of Clone #T32
FFYPLFEKNKSILVLELSLQCGFSIPPIYDETDMLENLLKNIEKYDQSLVISSGYLNFPMNF
LKLIRNIYINVMQKKNGILQLITASPCANSFYKSKGIS, Sequence Length: 100
(SEQ ID NO: 18)

Amino acid sequence of MAL8P1.58 (PfPGPS)
MALKFVIHEPKAKLLFTPKEFFNTLNDIFKNSQNRIVISCLYMGIGELEKELIDSIKKNVNI
KDLKVDILLDRQRGTRLEGKFNESSVSILSELFKCSDNINISLFHNPLLGPILYNILPPRAN
EAIGVMHMKIYIGDNILMLSGANLSDSYLRNRQDRYFVIENKFLADSIHNIINTIQGMSFT
LNRDLTIKWENDLMNPLIDAYVFREQYYRRIRFMLQGIQKHISQYNKNYSYNNYYKNIK
NDPINDKTYIYNNQNNNKYSYTSNEFRMLNSFSTDIFDKDTYNNKNQKNNHKKENMET
HTLLDTNHGTCDSTINLLNNNQNENHTNNLFTYLNEKD*EFFYPLFEKNKSILVLELSLQCG*
*FSIPPIYDETDMLENLLKNIEKYDQSLVISSGYLNFPMNFLKLIRNIYINVMQKKNGILQLITASP*
*CANSFYKSKGIS*YYIPSSYSAMANVCIEYITKNLTNPLKKVNGQNVSEQNDISNQKIYIEY
YKPSWTFHSKGIWIMDNMKSMKNVSNDNDNDNDNNNNDNNNNNNINNNEFHSAKKY
EQNVNNSPNVKNNLNKSEYFNNENFDKNIDEENDYYDNLPWCTVIGSSNYGYRAKYR
DLEMSFIIKTNDYNLRCQLKKELNIIYESSHFVQVDELKLRYAFWLKFLVKYIFKWLL,
Sequence Length: 661 (SEQ ID NO: 19)

Coding Nucleic acid sequence of gene MAL8P1.58
(PfPGPS) 1-1986
ATGGCTCTGAAGTTTGTCATTCATGAACCTAAAGCAAAATTATTATTTACTCCTAAA
GAATTTTTTAATACCTTAAATGACATTTTTAAGAACTCACAAATCGTATTGTGATTA
GCTGTTTATATATGGGAATAGGAGAATTAGAAAAAGAATTAATAGATAGTATAAAA
AAGAATGTGAATATAAAAGATTTAAAAGTTGATATATTATTAGATAGACAAAGAGG
TACAAGACTAGAAGGGAAATTTAATGAAAGTTCAGTTAGTATTTTATCAGAACTTTT
TAAATGTTCAGATAATATTAATATAAGCTTATTTCATAATCCTTTATTAGGTCCTATA
CTTTATAATATCTTACCTCCTAGAGCAAATGAAGCTATAGGTGTAATGCATATGAAA
ATTTATATTGGGGATAATATTCTAATGTTATCAGGAGCCAATTTAAGTGATAGCTAT
TTACGAAATAGACAAGATAGATATTTTGTTATTGAAAATAAATTCTTAGCTGATTCT
ATTCATAATATTATTAATACCATACAAGGTATGTCATTTACTCTAAATCGAGATTTA
ACCATAAAGTGGGAAATGATTTAATGAACCCACTTATAGATGCTTACGTATTTCGT
GAACAATATTATAGAAGAATACGTTTTATGTTACAAGGAATTCAAAAACATATTTCA
CAATATAATAAAAATTATTCATATAATAATTATTATAAAAATATAAAAAATGATCCA
ATAAATGATAAGACATATATTTATAATAATCAAAATAACAATAAATATAGTTATACA
TCAAACGAATTTCGCATGTTAAATTCTTTCAGTACAGATATATTCGATAAAGATACT
TATAATAATAAAAACCAAAAAATAATCATAAAAAAGAAAATATGGAAACACATA
CTTTATTAGATACTAATCATGGAACATGTGATTCAACAATTAATCTTCTAAATAATA
ATCAAATGAAAACCATACAAATAATTTATTTACATATCTAAATGAAAAGATGAA
*TTCTTTTATCCATTATTTGAAAAAATAAAAGCATTTTAGTACTTGAACTTTCCTTGCAGTGT*
*GGATTTTCCATACCTCCAATATATGATGAAACAGATATGTTAGAAAACTTATTAAAAAATATC*
*GAAAAATATGATCAAAGCTTAGTTATTTCTTCGGGATATTTAAACTTCCCAATGAATTTTCTT*
*AAATTAATTAGAAATATATATATCAACGTTATGCAAAAAAAAATGGTATTTTACAATTAATCA*
*CAGCGTCACCATGCGCTAATAGTTTTTATAAATCTAAAGGGATATCT*TATTATATACCAAG
TTCATATATTCAGCTATGGCTAATGTGTGTATTGAATATATTACCAAAAATTTAACCAA
TTTTCTAAAAAAAGTAAATGGACAAAATGTTTCTGAACAAAATGATATTTCAAATCA
AAAAATATATATTGAATATTACAAACCTTCATGGACATTTCATTCGAAAGGTATATG
GATAATGGACAATATGAAAAGTATGAAAAATGTGAGTAATGATAATGATAATGATA
ATGATAATAATAATAATGATAATAATAATAATAATATTAATAATAATGAATTTC
ATTCAGCTAAAAAATATGAACAAAATGTTAATAACTCACCAAATGTAAAAAATAAC
CTGAACAAGTCAGAATATTTTAACAACGAAAATTTTGATAAGAATATTGATGAAGA
GAATGATTATTATGATAATTTACCCTGGTGTACAGTGATTGGAAGTTCTAATTATGG
GTATAGAGCAAAATATAGAGATTTGGAGATGAGTTTTATAATAAAAACAAATGATT
ATAATTTGAGGTGTCAGTTAAAGAAAGAATTAAATATAATATATGAGTCATCTCATT
TTGTACAAGTGGATGAATTGAAATTACGATATGCTTTTTGGTTAAAATTTTTAGTGA
AATATATATTCAAATGGCTTTTATAA Sequence Length: 1986 bp
(SEQ ID NO: 20)

Clone #T9: Mature parasite-infected erythrocyte
surface antigen, erythrocyte membrane protein 2 (MESA)
Nucleic acid sequence of Clone #T9, 459 bp (Sequence
2,080-2,538 of PFE0040c (MESA)
GTAAAAGAAGGAATTAAAGAAAATGATACTGAAAATAAAGATAAAGTGATAGGAC
AAGAAATAATAACTGAAGAAGTAAAAGAAGGAATTAAAGAAAATGATACTGAAAA
TAAAGATAAAGTGATAGGACAAGAAATAATAACTGAAGAAGTAAAAAAAGAAATT

```
GAAAAACAAGAAGAAAAAGGAAATAAAGAAAATATTCTTGAAATTAAAGATATAG
TAATTGGACAAGAAGTAATAATAGAAGAAGTAAAAAAAGTAATTAAAAAAAAAGT
AGAAAAAGGAATTAAAGAAAATCATACTGAAAGTAAAGATAAAGTGATAGGACAA
GAAATAATAGTTGAAGAAGTAAAAGAAGAAATTGAAAAACAAGTAGAAGAAGGAA
TTAAAGAAAATGATACTGAAAGTAAAGATAAAGTGATAGGACAAGAAGTGATAAA
AGGAGATGTTAATGAAGAA Sequence Length: 459 bp
(SEQ ID NO: 21)

Amino acid sequence of Clone #T9
VKEGIKENDTENKDKVIGQEIITEEVKEGIKENDTENKDKVIGQEIITEEVKKEIEKQEEK
GNKENILEIKDIVIGQEVIIEEVKKVIKKKVEKGIKENHTESKDKVIGQEIIVEEVKEEIEKQ
VEEGIKENDTESKDKVIGQEVIKGDVNEE Sequence Length 153 aa
(SEQ ID NO: 22)

Amino acid sequence of PFE0040c (MESA)
MEVICRNLCYDKKNNMMENEGNKVKKVYNNSSLKKYMKFCLCTIICVFLLDIYTNCES
PTYSYSSIKNNNDRYVRILSETEPPMSLEEIMRTFDEDHLYSIRNYIECLRNAPYIDDPLW
GSVVTDKRNNCLQHIKLLEMQESERRKQQEEENAKDIEEIRKKEKEYLMKELEEMDESD
VEKAFRELQFIKLRDRTRPRKHVNVMGESKETDESKETDESKETGESKETGESKETGES
KETGESKETGESKETGESKETGESKETGESKETGESKETGESKETGESKETGESKETGES
KETGESKETRIYEETKYNKITSEFRETENVKITEEESKDREGNKVSGPYENSENSNVTSESE
ETKKLAEKEENEGEKLGENVNDGASENSEDPKKLTEQEENGTKESSEETKDDKPEENEK
KADNKKKSKKKKKSFFQMLGCNFLCNKNIETDDEEETLVVKDDAKKKHKFLREANTE
KNDNEKKDKLLGEGDKEDVKEKNDEQKDKVLGEGDKEDVKEKNDEQKDKVLGEGDK
EDVKEKNDGKKDKVIGSEKTQKEIKEKVEKRVKKKCKKKVKKGIKENDTEGNDKVKG
PEIIIEEVKEEIKKQVEDGIKENDTEGNDKVKGPEIITEEVKEEIKKQVEEGIKENDTEGND
KVKGPELITEEVKEEIKKQVEEGIKENDTESKDKLIGQEIITEEVKEGIKENDTENKDKVIG
QEIITEEVKEGIKENDTENKDKVIGQEIITEEVKKEIEKQEEKGNKENILEIKDIVIGQEVIIE
EVKKVIKKKVEKGIKENHTESKDKVIGQEIIVEEVKEEIEKQVEEGIKENDTESKDKVIGQ
EVIKGDVNEEGPENKDKVTKQEKVKEVKKEVKKKVKKRVKKRNNKNERKDNVIGKEI
MKEDVNEKDTANKDKEIEQEKEKEEVKEKEEVKEKEEVKEKEEVKEKEEVKEKEEVKE
KEEVKEKEEVKEKDTESKDKEIEQEKEKEEVKEVKEKDTENKDKVIGQEIIIEEIKKEVK
KRVKKRNNKNENKDNVIVQEIMNEDVNEKDTANKDKVIEQEKEKEEVKEKEEVKEKE
EVKEKEKEEVKEKEEVKEKDTESKDNVIVQEIMNEDVNEKDTESKDKMIGKEVII
EEVKEEVKKRVNKEVNKRVNRRNRKNERKDVIEQEIVSEEVNEKDTKNNDKKIGKRVK
KPIDDCKKEREVQEESEEESEEESEEESEEESEEESEEESEEESEEESEEESEEESEEESEEE
SEEESEEESEEESEEESEEESDEEKNTSGLVHRRNCKKEKKYNNGELEEYYKEKQNEEYF
DEEYIIQSKEHNTLNTFPNMALNEDFRREFHNILSIHEDTDLMELKRILYNLFLEYNPHM
NNKQKAELDKKFSEMNVVHQILNYEERIRMYEENAARGRLNTVILDPIITFNVIFGDDT
MFKFIDE Sequence Length: 1434 aa (SEQ ID NO: 23)

Coding Nucleotide sequence of PFE0040c (MESA)
TGGAGGTAATTTGTAGAAATTTATGCTACGATAAGAAAATAATATGATGGAAAAT
GAAGGGAACAAAGTGAAAAAAGTGTATAATAATTCTTCTTTAAAGAAATATATGAA
GTTTTGTTTATGCACTATAATATGTGTTTTTTATTAGATATCTATACGAATTGTGAA
TCACCCACCTATTCATACAGTTCAATAAAGAATAATAATGACAGATATGTAAGAATT
TTAAGTGAAACTGAACCACCGATGAGTTTAGAGGAAATAATGAGAACATTTGATGA
AGATCATCTATATTCTATAAGAAACTATATTGAATGTTTAAGAAACGCTCCATATAT
CGATGATCCTTTGTGGGGTTCGGTTGTTACAGATAAACGTAATAATTGTCTTCAGCA
TATTAAATTATTGGAAATGCAAGAATCCGAAAGAAGAAAACAACAAGAAGAGGAG
AATGCTAAGGATATTGAAGAAATAAGAAAGAAAGAAAAAGAATACCTTATGAAAG
AATTAGAAGAAATGGATGAATCCGATGTAGAAAAGGCATTTAGAGAATTACAATTT
ATTAAGTTAAGAGATAGAACTAGACCTAGAAAACATGTGAATGTAATGGGAGAATC
TAAGGAAACAGATGAATCTAAGGAAACAGATGAATCTAAGGAAACTGGTGAATCTA
AGGAAACTGGTGAATCTAAGGAAACTGGTGAATCTAAGGAAACTGGTGAATCTAAG
GAAACTGGTGAATCTAAGGAAACTGGTGAATCTAAGGAAACTGGTGAATCTAAGGA
AACTGGTGAATCTAAGGAAACTGGTGAATCTAAGGAAACTGGTGAATCTAAGGA
CTGGTGAATCTAAGGAAACTGGTGAATCTAAGGAAACTGGTGAATCTAAGGAAACT
GGTGAATCTAAGGAAACAAGAATATATGAGGAAACAAAATATAACAAAATAACGA
GTGAATTTAGAGAAACAGAAAACGTGAAGATAACAGAGGAATCTAAGGATAGAGA
AGGTAACAAAGTATCAGGTCCATATGAAAACTCAGAAAATTCCAATGTAACAAGTG
AATCTGAAGAGACCAAAAAATTAGCCGAAAAAGAGGAGAATGAGGGAGAAAAATT
AGGAGAAAATGTTAATGATGGGGCATCAGAAAATTCAGAAGATCCCAAAAAATTAA
CAGAACAAGAAGAAAATGGTACAAAGGAAAGTTCTGAAGAAACAAAAGATGATAA
ACCGGAAGAAAATGAGAAAAAGGCAGATAATAAAAAAAAAAGTAAAAAAAAGAA
AAAATCATTTTTTCAAATGTTAGGATGTAATTTCCTATGTAATAAAAATATTGAAAC
TGATGATGAAGAAGAAACGTTGGTAGTAAAAGATGATGCTAAAAAGAAACATAAAT
TTTTAAGAGAAGCTAATACTGAAAAAAATGATAATGAAAAGAAAGATAAATTATTA
GGAGAAGGAGATAAAGAAGATGTTAAAGAAAAGAATGATGAACAGAAAGATAAAG
TATTAGGAGAAGGAGATAAAGAAGATGTTAAAGAAAAGAATGATGAACAGAAAGA
TAAAGTATTAGGAGAAGGAGATAAAGAAGATGTTAAAGAAAAGAATGATGGAAAG
AAAGATAAAGTGATAGGATCAGAAAAAACACAAAAGGAAATTAAAGAAAAGTAG
AAAAAGAGTTAAAAAAAGTGTAAAAAAAAGTAAAAAAGGAATTAAAGAAA
TGATACTGAAGGTAACGATAAAGTGAAAGGACCAGAAATAATAATTGAAGAAGTA
AAAGAAGAAATTAAAAAACAAGTAGAAGATGGAATTAAAGAAATGATACTGAAG
GTAACGATAAAGTGAAAGGGCCAGAAATAATAACTGAAGAAGTAAAGAAGAAAT
TAAAAAACAAGTAGAAGAAGGAATTAAAGAAATGATACTGAAGGTAACGATAAA
GTGAAAGGGCCAGAAATAATAACTGAAGAAGTAAAGAAGAAATTAAAAAACAAG
TAGAAGAAGGAATTAAAGAAAATGATACTGAAAGTAAGGATAAATTGATAGGACA
```

```
AGAAATAATAACTGAAGAAGTAAAAGAAGGAATTAAAGAAAATGATACTGAAAATAAAGA
TAAAGTGATAGGACAAGAAATAATAACTGAAGAAGTAAAAGAAGGAATTAAAGAAAATGATA
CTGAAAATAAAGATAAAGTGATAGGACAAGAAATAATAACTGAAGAAGTAAAAAAGAAATT
GAAAAACAAGAAGAAAAAGGAAATAAAGAAAATATTCTTGAAATTAAAGATATAGTAATTGG
ACAAGAAGTAATAATAGAAGAAGTAAAAAAAGTAATTAAAAAAAAAGTAGAAAAAGGAATTA
AAGAAAATCATACTGAAAGTAAAGATAAAGTGATAGGACAAGAAATAATAGTTGAAGAAGTA
AAAGAAGAAATTGAAAAACAAGTAGAAGAAGGAATTAAAGAAAATGATACTGAAAGTAAAGA
TAAAGTGATAGGACAAGAAGTGATAAAAGGAGATGTTAATGAAGAAGGTCCCGAAAACAA
AGATAAAGTGACAAACAGGAAAAAGTAAAAGAAGTTAAAAAAGAAGTAAAAAAA
AAAGTTAAAAAAGAGTAAAAAAAAGAAATAATAAGAATGAAAGAAAAGATAATG
TGATAGGAAAAGAAATAATGAAAGAAGATGTTAATGAAAAAGATACCGCAAACAA
AGATAAAGAGATAGAACAAGAAAAAGAAAAAGAAGAAGTTAAAGAAAAAGAAGA
AGTTAAAGAAAAAGAAGAAGTTAAAGAAAAAGAAGAAGTAAAAGAAAAAGAAGA
AGTAAAAGAAAAAGAAGAAGTAAAAGAAAAAGAAGAAGTAAAAGAAAAAGAAGA
AGTAAAAGAAAAAGATACCGAAAGCAAAGATAAAGAGATAGAACAAGAAAAAGA
AAAAGAAGAAGTAAAAGAAGTTAAAGAAAAAGATACCGAAAACAAAGATAAAGTG
ATAGGACAAGAAATAATAATAGAAGAAATAAAAAAAGAAGTTAAAAAAAAGAGTAA
AAAAAAGAAATAATAAAAATGAAAACAAAGATAATGTGATAGTACAAGAAATAAT
GAACGAAGATGTTAACGAAAAAGATACCGCAAACAAAGATAAGGTGATAGAACAA
GAAAAAGAAAAAGAAGAAGTTAAAGAAAAAGAAGAAGTTAAAGAAAAAGAAGAA
GTAAAAGAAAAAGAAGAAGTAAAAGAAAAAGAAGAAGTAAAAGAAAAAGAAGAA
GTAAAAGAAAAAGATACCGAAAGCAAAGATAATGTGATAGTACAAGAAATAATGA
ACGAAGATGTTAACGAAAAAGATACCGAAAGCAAAGATAAAATGATAGGAAAAGA
AGTAATAATAGAAGAAGTAAAAGAAGAAGTTAAAAAAAGAGTAAACAAAGAAGTT
AACAAAAGAGTAAACAGAAGAAATAGAAAAAATGAAAGAAAAGATGTGATAGAAC
AAGAAAATAGTAAGCGAAGAAGTTAACGAAAAAGATACCAAAAACAACGATAAAA
GATAGGAAAAGAGTCAAAAAACCAATAGATGATTGTAAAAAAGAAAGAGAAGTA
CAAGAAGAATCTGAAGAAGAGTCTGAAGAAGAGTCTGAAGAAGAATCTGAAGAAG
AGTCTGAAGAAGAATCTGAAGAAGAGTCTGAAGAAGAATCTGAAGAAGAGTCTGA
AGAAGAATCTGAAGAAGAATCTGAAGAAGAGTCTGAAGAAGAATCTGAAGAGAG
TCTGAAGAAGAGTCTGAAGAAGAGTCTGAAGAAGAATCTGAAGAAGAATCTGATGA
AGAAAAAATACATCAGGTTTGGTACATAGAAGAAATTGTAAAAAGAAAAGAAA
TATAATAATGGAGAATTAGAAGAATATTATAAAGAGAAACAGAATGAAGAATATTT
TGATGAAGAATATATTATTCAATCAAAAGAACATAATACTTTGAATACATTCCCAAA
TATGGCATTAAATGAAGATTTCAGAAGAGAATTTCACAATATATTAAGTATTCATGA
AGATACAGATTTGATGGAACTAAAAAGAATCTTATATAATTTATTTTTAGAATATAA
TCCACATATGAATAATAAACAGAAAGCAGAATTGGATAAGAAATTTAGTGAAATGA
ATGTGGTACATCAAATATTAAATTATGAAGAGAATACGCATGTATGAAGAAAAT
GCAGCACGAGGAAGACTAAATACAGTTATTCTGGATCCAATTATTACATTTAATGTA
ATATTCGGAGATGATACAATGTTTAAGTTTATTGATGAATAA Sequence
Length: 4305 bp (SEQ ID NO: 24)

Clone #TL22: Plasmodium falciparum glutamic acid-
rich protein (Pf-GARP)
Nucleic acid sequence of Clone #TL22, 792 bp
(Sequence 1,231-2,022 of gene PFA_0620c)
TCAAAAGAACACAAATCAAAAGGAAAGAAAGATAAAGGAAAGAAAGATAAAGGA
AAACATAAAAAAGCAAAAAAAGAAAAAGTAAAAAAACACGTAGTTAAAAATGTTA
TAGAAGATGAAGACAAAGATGGTGTAGAAATAATAAACTTAGAAGATAAAGAGGC
ATGTGAAGAACAACACATAACAGTAGAAAGTAGACCACTAAGCCAACCACAATGTA
AACTAATAGATGAACCAGAACAATTAACATTAATGGATAAATCAAAAGTTGAAGAA
AAAAACTTATCCATACAAGAGCAATTAATAGGTACCATAGGACGTGTTAATGTAGT
ACCCAGAAGAGATAATCATAAGAAAAAATGGCGAAGATAGAGGAAGCTGAACTT
CAAAAACAGAAACATGTTGATAAGGAAGAAGACAAAAAAGAAGAATCCAAAGAAG
TAGAAGAAGAATCTAAAGAGGTACAAGAAGATGAAGAAGAAGTAGAAGAAGATGA
AGAAGAAGAAGAAGAAGAGGAAGAAGAAGAAGAAGAAGAAGAAGAAGAGG
AAGAAGAAGAAGATGAAGTAGAAGAAGATGAAGATGATGCTGAAGAAGATGAAGA
TGATGCTGAAGAAGATGAAGATGATGCTGAAGAAGATGATGATGATGCTGAAGAAG
ATGATGATGATGCTGAAGAAGATGATGATGAAGATGAAGATGAAGATGAAGAGAGA
AGAAGAAGATGAAGAAGAAGAAGAAGAATCAGAAAAAAAAATAAAAAGAAATTT
GAGAAAAAATGCCAAAATTTAA Sequence Length: 792
(SEQ ID NO: 25)

Amino acid sequence of Clone #TL22
SKEHKSKGKKDKGKKDKGKHKKAKKEKVKKHVVKNVIEDEDKDGVEIINLEDKEACE
EQHITVESRPLSQPQCKLIDEPEQLTLMDKSKVEEKNLSIQEQLIGTIGRVNVVPRRDNHK
KKMAKIEEAELQKQKHVDKEEDKKEESKEVEEESKEVQEDEEEVEEDEEEEEEEEEEE
EEEEEEEEEEDEVEEDEDDAEEDEDDAEEDEDDAEEDDDDAEEDDDDAEEDDDEDEDE
DEEEEEDEEEEEESEKKIKRNLRKNAKI Sequence Length: 263
(SEQ ID NO: 26)

Amino acid sequence of Pf-GARP (PFA_0620c)
MNVLFLSYNICILFFVVCTLNFSTKCFSNGLLKNQNILNKSFDSITGRLLNETELEKNKDD
NSKSETLLKEEKDEKDDVPTTSNDNLKNAHNNNEISSSTDPTNIINVNDKDNENSVDKK
KDKKEKKHKKDKKEKKEKKDKKEKKDKKEKKHKKEKKHKKDKKKEENSEVMSLYK
TGQHKPKNATEHGEENLYEEMVSEINNNAQGGLLLSSPYQYREQGGCGIISSVHETSND
TKDNDKENISEDKKEDHQQEEMLKTLDKKERKQKEKEMKEQEKIEKKKKKQEEKEKK
KQEKERKKQEKKERKQKEKEMKKQKKIEKERKKKEEKEKKKKKHDKENEETMQQPD
QTSEETNNEIMVPLPSPLTDVTTPEEHKEGEHKEEEHKEGEHKEGEHKEEEHKEEEHKK
```

EEHK*SKEHKSKGKKDKGKKDKGKHKKAKKEKVKKHVVKNVIEDEDKDGVEIINLEDKEAC*
*EEQHITVESRPLSQPQCKLIDEPEQLTLMDKSKVEEKNLSIQEQLIGTIGRVNVVPRRDNHKK*
*KMAKIEEAELQKQKHVDKEEDKKEESKEVEEESKEVQEDEEEVEEDEEEEEEEEEEEEEEE*
*EEEEEEDEVEEDEDDAEEDEDDAEEDEDDAEEDDDDAEEDDDDAEEDDDEDEDEDEEEE*
*EDEEEEEESEKKIKRNLRKNAKI* Sequence Length: 673 aa
(SEQ ID NO: 27)

Coding Nucleic acid sequence gene Pf-GARP (PFA_0620c)
ATGAATGTGCTATTTCTTTCGTATAATATTTGTATTCTTTTTTTTGTTGTATGCACATT
AAATTTTTCTACTAAGTGCTTTTCCAATGGTTTATTGAAGAATCAAAATATCCTAAAC
AAAAGTTTTGATTCCATAACGGGAAGATTATTAAACGAAACCGAATTAGAAAAAA
TAAAGATGATAATTCAAATCTGAAACGTTGTTAAAAGAGGAAAAAGATGAAAAGG
ATGATGTACCTACAACGAGTAATGACAACCTTAAGAATGCTCATAATAATAATGAA
ATTTCAAGTTCAACTGATCCAACGAATATTATTAATGTTAATGATAAAGATAATGAA
AACTCTGTAGATAAAAAAAAAGATAAAAAAGAAAAAAAGCATAAAAAAGATAAAA
AAGAAAAAAAAGAAAAAAAAGATAAAAAAGAAAAAAAAGATAAAAAAGAAAAAA
AACATAAAAAGAAAAAAAACATAAAAAGATAAAAAAAAAGAAGAAAACAGTG
AAGTGATGTCTTTATATAAAACGGGTCAACATAAACCAAAAAACGCAACAGAACAT
GGTGAAGAAATTTATATGAAGAAATGGTAAGTGAAATAAATAATAATGCACAAGG
TGGACTCCTTTTATCAAGCCCATATCAATATAGAGAACAAGGAGGATGTGGAATCA
TATCTAGTGTTCATGAGACGTCTAATGATACAAAAGATAATGATAAAGAAAATATA
TCCGAAGACAAAAAGGAGGACCATCAACAAGAAGAAATGTTGAAAACACTTGATA
AAAAAGAACGTAAACAAAAAGAAAAAGAAATGAAAGAACAAGAAAAATCGAAA
AAAAAAAAAAAAAGCAAGAAGAAAAGGAAAAGAAAAAACAAGAAAAAGAAAGAA
AAAAACAAGAAAAGAAAGAACGTAAACAAAAAGAAAAAGAAATGAAAAAACAAA
AAAAAATAGAAAAAGAAAGAAAAAGAAAGAAGAAAAGGAAAAGAAAAAGAAAA
AACATGATAAGGAAAATGAAGAAACAATGCAACAACCAGATCAAACAAGTGAAGA
AACCAACAATGAATTATGGTACCATTACCAAGTCCATTGACAGACGTAACTACAC
CAGAAGAACACAAAGAAGGAGAACACAAAGAAGAAGAACACAAAGAAGGAGAAC
ACAAAGAAGGAGAACACAAAGAAGAAGAACACAAAGAAGAACACAAAAAG
AAGAACACAAA*TCAAAAGAACACAAATCAAAAGGAAAGAAAGATAAAGGAAAGAAAGATA*
*AAGGAAAACATAAAAAAGCAAAAAAAGAAAAAGTAAAAAAAACACGTAGTTAAAAATGTTATA*
*GAAGATGAAGACAAAGATGGTGTAGAAATAATAAACTTAGAAGATAAAGAGGCATGTGAAG*
*AACAACACATAACAGTAGAAAGTAGACCACTAAGCCAACCACAATGTAAACTAATAGATGA*
*ACCAGAACAATTAACATTAATGGATAAATCAAAAGTTGAAGAAAAAAACTTATCCATACAAG*
*AGCAATTAATAGGTACCATAGGACGTGTTAATGTAGTACCCAGAAGAGATAATCATAAGAA*
*AAAAATGGCGAAGATAGAGGAAGCTGAACTTCAAAAACAGAAACATGTTGATAAGGAAGAA*
*GACAAAAAAGAAGAATCCAAAGAAGTAGAAGAAGAATCTAAAGAGGTACAAGAAGATGAAG*
*AAGAAGTAGAAGAAGATGAAGAAGAAGAAGAAGAAGAAGAGGAAGAAGAAGAAGAAG*
*AAGAAGAAGAGGAAGAAGAAGAAGATGAAGTAGAAGAAGATGAAGATGATGCTGAAGAAG*
*ATGAAGATGATGCTGAAGAAGATGAAGATGATGCTGAAGAAGATGATGATGATGCTGAAG*
*AAGATGATGATGATGCTGAAGAAGATGATGATGAAGATGAAGATGAAGATGAAGAAGAAG*
*AAGAAGATGAAGAAGAAGAAGAATCAGAAAAAAAAATAAAAAGAAATTTGAGAAAAAAT*
*GCCAAAATTTAA* Sequence Length: 2022 bp (SEQ ID NO: 28)

Clone #TL27: *Plasmodium falciparum* 3D7 Plasmodium
exported protein (PHISTc), unknown function (PFI1780w)
mRNA, complete cds
Nucleic acid sequence of Clone #TL27, 303 bp
(Sequence 691-998 of gene (PFI1780w)
GAACATGGTGAAATGCTAAATCAAAAAGAAAACTTAAACAACATGAACTTGATAG
AAGAGCACAAAGGGAAAAAATGTTAGAAGAACATAGTAGAGGAATATTTGCTAAA
GGATATTTGGGAGAAGTAGAATCAGAAACTATAAAAAAGAAAACGGAACACCATG
AAAATGTAAATGAAGATAATGTAGAAAAACCAAAATTGCAACAACATAAAGTTCAA
CCACCAAAAGTCCAACAACAAAAAGTTCAACCACCAAAATCACAACAACAAAAAG
TTCAACCACCAAAATCACAACAACAA Sequence Length: 303
(SEQ ID NO: 29)

Amino acid sequence of Clone #TL27
EHGEMLNQKRKLKQHELDRRAQREKMLEEHSRGIFAKGYLGEVESETIKKKTEHHENV
NEDNVEKPKLQQHKVQPPKVQQQKVQPPKSQQQKVQPPKSQQQ Sequence
Length: 101 (SEQ ID NO: 30)

Amino acid sequence of PFI1780w
MAVSTYNNTRRNGLRYVLKRRTILSVFAVICMLSLNLSIFENNNNNYGFHCNKRHFKSL
AEASPEEHNNLRSHSTSDPKKNEEKSLSDEINKCDMKKYTAEEINEMINSSNEFINRNDM
NIIFSYVHESEREKFKKVEENIFKFIQSIVETYKIPDEYKMRKFKFAHFEMQGYALKQEKF
LLEYAFLSLNGKLCERKKFKEVLEYVKREWIEFRKSMFDVWKEKLASE*FREHGEMLNQ*
*KRKLKQHELDRRAQREKMLEEHSRGIFAKGYLGEVESETIKKKTEHHENVNEDNVEKP*
*KLQQHKVQPPKVQQQKVQPPKSQQQKVQPPKSQQQKVQPPKVQQQKVQPPKVQKPKL*
QNQKGQKQVSPKAKGNNQAKPTKGNKLKKN Sequence Length: 383 aa
(SEQ ID NO: 31)

Coding Nucleic acid sequence gene PFI1780w
ATGGCTGTTAGTACATATAATAATACTCGAAGGAATGGTCTAAGATATGTCCTTAAA
AGACGTACCATTCTATCTGTTTTTGCTGTCATTTGTATGTTATCATTGAATTTATCAA
TATTTGAAAATAATAATAATAATTATGGATTCCATTGCAATAAAAGACATTTTAAAA
GTTTAGCTGAAGCAAGTCCAGAAGAACATAACAATTTAAGAGTCATTCAACAAGT
GATCCAAAGAAGAATGAAGAGAAATCATTAAGTGACGAAATAAATAAATGTGATAT -continued

```
GAAAAAATACACTGCTGAAGAAATAAATGAAATGATTAACAGTTCTAATGAATTTA
TAAATAGAAATGATATGAATATAATATTTAGTTATGTACATGAATCTGAGAGAGAA
AAATTTAAAAAGGTAGAAGAAAATATATTTAAATTTATTCAAAGTATAGTAGAAAC
ATATAAAATACCAGATGAATATAAAATGAGAAAATTCAAATTTGCACACTTTGAAA
TGCAAGGATATGCATTAAAACAAGAAAAGTTCCTTTTAGAATATGCTTTTCTTTCCTT
AAATGGTAAATTATGTGAACGTAAAAAATTTAAAGAAGTTTTAGAATATGTAAAAA
GGGAATGGATTGAGTTTAGAAAATCAATGTTTGACGTATGGAAGGAAAAATTAGCT
TCTGAATTCAGAGAACATGGTGAAATGCTAAATCAAAAAAGAAAACTTAAACAACA
TGAACTTGATAGAAGAGCACAAAGGGAAAAAATGTTAGAAGAACATAGTAGAGGA
ATATTTGCTAAAGGATATTTGGGAGAAGTAGAATCAGAAACTATAAAAAAGAAAAC
GGAACACCATGAAAATGTAAATGAAGATAATGTAGAAAAACCAAAATTGCAACAA
CATAAAGTTCAACCACCAAAAGTCCAACAACAAAAAGTTCAACCACCAAAATCACA
ACAACAAAAAGTTCAACCACCAAATCACAACAACAAAAAGTTCAACCACCAAAA
GTACAACAACAAAAAGTTCAACCACCAAAAGTGCAAAAACCAAAACTTCAAAATCA
AAAAGGACAAAAGCAAGTATCTCCCAAAGCAAAGGGTAATAATCAAGCGAAACCA
ACCAAAGGAAACAAGTTAAAGAAAAATTAA
Sequence Length: 1152 bp (SEQ ID NO: 32)

Clone #TL5: Plasmodium falciparum 3D7 knob-
associated histidine-rich protein (PFB0100c)
Nucleic acid sequence of Clone #TL5, 242 bp
(Sequence 1309-1550 of gene (PFB0100c)
GTTAAAGAAAAGGGAGAAAAGCATAATGGAAAAAAACCATGCAGCAAAAAAACTA
ACGAAGAAAATAAAAATAAAGAAAAAACCAATAATTCAAAATCAGATGGATCAAA
AGCTCATGAAAAAAAGAAAATGAAACAAAAAACACCGCTGGAGAAAATAAAAAA
GTAGATTCTACTTCAGCTGATAATAAATCAACAAATGCTGCTACACCAGGCGCAAA
AGATAAAACTCAAGGAGGAAA Sequence Length: 242 bp
(SEQ ID NO: 33)

Amino acid sequence of Clone #TL5
VKEKGEKHNGKKPCSKKTNEENKNKEKTNNSKSDGSKAHEKKENETKNTAGENKKVD
STSADNKSTNAATPGAKDKTQGG Sequence Length: 80 aa
(SEQ ID NO: 34)

Amino acid sequence of PFB0100c
MKSFKNKNTLRRKKAFPVFTKILLVSFLVWVLKCSNNCNNGNGSGDSFDFRNKRTLAQ
KQHEHHHHHHQHQHQAPHQAHHHHHHGEVNHQAPQVHQQVHGQDQAHHHHH
HHHHQLQPQQPQGTVANPPSNEPVVKTQVFREARPGGGFKAYEEKYESKHYKLKENV
VDGKKDCDEKYEAANYAFSEECPYTVNDYSQENGPNIFALRKRFPLGMNDEDEEGKEA
LAIKDKLPGGLDEYQNQLYGICNETCTTCGPAAIDYVPADAPNGYAYGGSAHDGSHGN
LRGHDNKGSEGYGYEAPYNPGFNGAPGSNGMQNYVPPHGAGYSAPYGVPHGAAHGSR
YSSFSSVNKYGKHGDEKHHSSKKHEGNDGEGEKKKKSKKHKDHDGEKKKSKKHKDN
EDAESVKSKKHKSHDCEKKKSKKHKDNEDAESVKSKKS VKEKGEKHNGKKPCSKKTNE
ENKNKEKTNNSKSDGSKAHEKKENETKNTAGENKKVDSTSADNKSTNAATPGAKDKTQGGK
TDKTGASTNAATNKGQCAAEGATKGATKEASTSKEATKEASTSKEATKEASTSKEATK
EASTSKGATKEASTTEGATKGASTTAGSTTGATTGANAVQSKDETADKNAANNGEQV
MSRGQAQLQEAGKKKKKRGCCG Sequence Length: 654 aa
(SEQ ID NO: 35)

Coding Nucleic acid sequence gene PFB0100c
ATGAAAAGTTTTAAGAACAAAAATACTTTGAGGAGAAAGAAGGCTTTCCCTGTTTTT
ACTAAAATTCTTTTAGTCTCTTTTTTTAGTATGGGTTTTGAAGTGCTCTAATAACTGCA
ATAATGGAAACGGATCCGGTGACTCCTTCGATTTCAGAAATAAGAGAACTTTAGCA
CAAAAGCAACATGAACACCATCACCACCATCACCATCAACATCAACACCAACACCA
AGCTCCACACCAAGCACACCACCATCATCATCATGGAGAAGTAAATCACCAAGCAC
CACAGGTTCACCAACAAGTACATGGTCAAGACCAAGCACACCATCACCATCATCAC
CACCATCATCAATTACAACCTCAACAACCCCAGGGAACAGTTGCTAATCCTCCTAGT
AATGAACCAGTTGTAAAAACCCAAGTATTCAGGGAAGCAAGACCAGGTGGAGGTTT
CAAAGCATATGAAGAAAATACGAATCAAAACACTATAAATTAAAGGAAAATGTTG
TCGATGGTAAAAAAGATTGTGATGAAAAATACGAAGCTGCCAATTATGCTTTCTCCG
AAGAGTGCCCATACACCGTAAACGATTATAGCCAAGAAATGGTCCAAATATATTT
GCCTTAAGAAAAGATTCCCTCTTGGAATGAATGATGAAGATGAAGAAGGTAAAGA
AGCATTAGCAATAAAAGATAAATTACCAGGTGGTTTAGATGAATACCAAAACCAAT
TATATGGAATATGTAATGAGACATGTACCACATGTGGACCTGCCGCTATAGATTATG
TTCCAGCAGATGCACCAAATGGCTATGCTTATGGAGGAAGTGCACACGATGGTTCTC
ACGGTAATTTAAGAGGACACGATAATAAAGGTTCAGAAGGTTATGGATATGAAGCT
CCATATAACCCAGGATTTAATGGTGCTCCTGGAAGTAATGGTATGCAAAATTATGTC
CCACCCCATGGTGCAGGCTATTCAGCTCCATACGGAGTTCCACATGGTGCAGCCCAT
GGTTCAAGATATAGTTCATTCAGTTCCGTAAATAAATATGGAAAACACGGTGATGA
AAAACACCATTCCTCTAAAAAGCATGAAGGAAATGACGGTGAAGGAGAAAAAAAG
AAAAAATCAAAAAAACACAAAGACCACGATGGAGAAAAGAAAAAATCAAAAAAA
CACAAAGACAATGAAGATGCAGAAAGCGTAAAATCAAAAAAACACAAAAGCCACG
ATTGTGAAAAGAAAAAATCAAAAAAACACAAAGCAATGAAGATGCAGAAGAGCGT
AAAATCAAAAAAAAGTGTTAAAGAAAAGGGAGAAAAGCATAATGGAAAAAAACCATGCA
GCAAAAAAACTAACGAAGAAAATAAAAATAAAGAAAAAACCAATAATTCAAAATCAGATGGA
TCAAAAGCTCATGAAAAAAAGAAAATGAAACAAAAAACACCGCTGGAGAAAATAAAAAAGT
AGATTCTACTTCAGCTGATAATAAATCAACAAATGCTGCTACACCAGGCGCAAAAGATAAA
CTCAAGGAGGAAAACTGACAAAACAGGAGCAAGTACTAATGCCGCAACAAATAAA
GGACAATGTGCTGCTGAAGGAGCAACTAAGGGAGCAACTAAAGAAGCAAGTACTTC
```

-continued

```
TAAAGAAGCAACAAAAGAAGCAAGTACTTCTAAAGAAGCAACAAAAGAAGCAAGT
ACTTCTAAAGAAGCAACAAAAGAAGCAAGTACTTCTAAAGGAGCAACTAAAGAAG
CAAGTACTACTGAAGGAGCAACTAAAGGAGCAAGTACTACTGCAGGTTCAACTACA
GGAGCAACTACAGGAGCTAATGCAGTACAATCTAAAGATGAAACTGCCGATAAAA
TGCTGCAAATAATGGTGAACAAGTAATGTCAAGAGGACAAGCACAATTACAAGAAG
CAGGAAAGAAAAAGAAGAAAAGAGGATGCTGTGGTTAA
Sequence Length: 1965 bp (SEQ ID NO: 36)

Clone #TL16: Plasmodium falciparum isolate 822 rhoptry
associated membrane antigen gene (MAL7P1.208)
Nucleic acid sequence of Clone #TL16, 432 bp
(Sequence 953-,1384 of gene MAL7P1.208)
GAAGAATCCAAAAATGAAGAATTTAAAAATGAAGAATTCAAAAATGTAGATAAAG
AAAATTATGATGATAAAAATATTTTCTATGGTTATAGTGATAATGATGATGAAAGCT
TTTTAGAAACTGATTCTTATGAAGAATATGAAGACGAAGATAAAGATGTTGAAGAT
GAGTATGAAGAAAGTTTCTTACAAAATGATGAGAAAAAAATGGTCTTTTATGATTTA
TACAAGCCAGAAGAAATGAATCTTATTATGAAAAGAAACAAAAGAAAGAAGAAA
AAGAAGAGAAAGAAGAGAAAGAACAAAGTTTGAACAAACAAAACGATATGGAAG
ACCAAGAAGATAATGAAGAATATAAATTTGAAGAAGAAATAAAGAAGACCTTCTA
GATGTCCAACAAGATGAAGAATTACCAAGTGAAGGAAAACAA Sequence
Length: 432 (SEQ ID NO: 37)

Amino acid sequence of Clone #TL16
EESKNEEFKNEEFKNVDKENYDDKNIFYGYSDNDDESFLETDSYEEYEDEDKDVEDEYE
ESFLQNDEKKMVFYDLYKPEENESYYEKKQKKEEKEEKEEKEQSLNKQNDMEDQEDN
EEYKFEEENKEDLLDVQQDEELPSEGKQ Sequence Length: 144
(SEQ ID NO: 38)

Amino acid sequence of MAL7P1.208
ISFSDYERSIKNFSISSSHAENNYDNIINEYKKIKDINNNINILSSVHRKGRILYDSFLEINKLE
NDKKEKHEKEDEYEDNDESFLETEEYEDNEDEKYNKDEDDYAESFIETDEYEDNEDDK
YNKDEDDYSESFIETDEYDDNEEEQYNKDEDDYADSFIETDHYENNDDKNEEEEEYND
QDNDYGYNFLETDEYDDSEEYDYDDKEYGESFLEKEEGEEMKDEEMKDEEMKDVEM
KDEEMKDEEIKYDEMKNEEMKYDEMKDEVMKDEEMKDEVMKDEEMKDEQMKYEEF
KNEESKNEESKNEESKNEESKNEEFKNEESKNEEFKNEEFKNVDKENYDDKNIFYGYSDND
DESFLETDSYEEYEDEDKDVEDEYEESFLQNDEKKMVFYDLYKPEENESYYEKKQKKEEKEE
KEEKEQSLNKQNDMEDQEDNEEYKFEEENKEDLLDVQQDEELPSEGKQKVKGKSFDNEH
LNEIQNVSDVHAFIQKDMKYLDDLIDEEQTIKDAVKKSAYKGNKKLGNNKKSQMILEE
EPEENFEEDADEELNKLMEQEKNIVDKEIKNSKANKSNKKLQFNNTNKQNKMYMKNE
YNNKTKNNKNNKFEQQNYDESYMDDDYEQNEEFNDNNQSEDMKETNELDKINDELLT
DQGPNEDTLLENNNKIFDNKFVAHKKREKSISPHSYQKVSTKVQNKEDMENKEEKQLIS
Sequence Length: 704 (SEQ ID NO: 39)

Coding Nucleic acid sequence gene MAL7P1.208
ATTAGCTTTTCTGATTATGAGAGATCAATAAAAAACTTTTCTATTTCTTCTCATGCAG
AAAATAATTATGATAATATAATAAATGAATATAAAAAAATAAAGATATTAACAAC
AATATAAACATATTATCATCAGTACATAGAAAAGGAAGAATATTGTACGACAGCTT
TTTTAGAAATAAATAAGTTGGAAAATGACAAAAAAGAGAAACATGAAAAAGAAGAT
GAATATGAAGATAATGATGAAAGCTTTTTAGAAACTGAAGAATATGAAGATAATGA
AGATGAAAAATATAACAAAGATGAAGATGATTATGCAGAAAGTTTTATTGAGACTG
ATGAATATGAAGATAATGAAGATGATAAATATAAAGATGAAGATGATTATTCA
GAAAGCTTTATTGAGACTGATGAATATGATGATAATGAAGAAGAACAATATAATAA
AGATGAAGATGATTATGCAGATAGTTTTATTGAGACAGACCATTATGAAAATAACG
ATGATAAAAATGAAGAAGAAGAAGAATATAATGATCAAGATAATGATTATGGATAT
AACTTTTTAGAAACTGACGAATACGATGATAGCGAAGAATATGATTACGACGATAA
GGAATACGGAGAGAGTTTCCTCGAAAAAGAAGAAGGTGAAGAAATGAAAGATGAA
GAGATGAAAGATGAAGAAATGAAAGATGTAGAAATGAAAGATGAAGAGATGAAAG
ATGAAGAGATAAATATGACGAGATGAAAAATGAAGAGATGAAATATGACGAGAT
GAAAGATGAAGTGATGAAAGATGAAGAGATGAAAGATGAAGTGATGAAAGATGAA
GAGATGAAAGACGAACAAATGAAATATGAAGAATTCAAAAATGAAGAATCCAAAAAT
GAAGAATCCAAAAATGAAGAATCCAAAAATGAAGAATCCAAAAATGAAGAATTCAAAAATGA
AGAATCCAAAAATGAAGAATTTAAAAATGAAGAATTCAAAAATGTAGATAAAGAAAATTATGA
TGATAAAAATATTTTCTATGGTTATAGTGATAATGATGATGAAAGCTTTTTAGAAACTGATTC
TTATGAAGAATATGAAGACGAAGATAAAGATGTTGAAGATGAGTATGAAGAAAGTTTCTT
AAAATGATGAGAAAAAAATGGTCTTTTATGATTTATACAAGCCAGAAGAAATGAATCTTATT
ATGAAAAGAAACAAAAGAAAGAAGAAAAAGAAGAGAAAGAAGAGAAAGAACAAAGTTTGAA
CAAACAAAACGATATGGAAGACCAAGAAGATAATGAAGAATATAAATTTGAAGAAGAAATA
AAGAAGACCTTCTAGATGTCCAACAAGATGAAGAATTACCAAGTGAAGGAAAACAAAAAGT
AAAAGGAAAATCATTCGATAATGAACATTTGAATGAAATACAAAATGTTAGCGACGTACATG
CATTTATACAAAAAGATATGAAATATTTAGATGATCTCATAGATGAAGAGCAAACTATTAAAG
ATGCCGTCAAAAAAAGTGCTTATAAAGGAAATAAGAATTAGGAAATAATAAAAAATCACAA
ATGATACTGGAAGAAGAACCAGAAGAAAATTTTGAAGAAGATGCTGATGAAGAATTAAATA
AACTAATGGAACAAGAAAAAAATATTGTAGATAAAGAAATCAAAAATAGTAAAGCAAATAA
AGCAACAAAAAATTACAATTCAATAACACTAATAAACAAAACAAAATGTATATGAAAAACGAA
TATAATAATAAGACAAAAAATAATAAAAACAATAAATTTGAACAACAAAATTATGATGAA
TCATATATGGATGATGATTATGAACAAAATGAAGAATTTAATGATAATAATCAAAG
CGAAGATATGAAAGAAACAAATGAACTCGATAAAATTAATGATGAACTATTAACTG
ATCAAGGACCAAACGAAGATACATTATTAGAAAATAATAATAAAATTTTCGATAAT
AAATTTGTAGCACATAAAAAAAGAGAAAAAAGTATATCCCCACACAGTTACCAAAA
```

GGTATCTACCAAAGTACAAAATAAGGAAGACATGGAAAATAAGGAAGAGAAACAA
TTGATAAGTAA Sequence Length: 2114 (SEQ ID NO: 40)

Clone #TL45: *Plasmodium falciparum* 3D7 Cg4 protein
(PF07_0033)
Nucleic acid sequence of Clone #TL45, 650 bp
(Sequence 1,764-2413 of gene PF07_0033)
TCACCAAATAAAACAGAATTAAAAAAAGGAGAAGAAGGAAAAGTACAAACATGTT
ATACAACAATACCTATTGAAACATTATTAGCTCAAGGATCTTATAGTTCTAAAGATA
TATTCAATTTTAGTGAACAGGAAATTAATATGCAACATAGTGATATATTAGAAGGAG
AACGATTAAAACATCTTAATGAACTAGAAACTATTATATATGAAAGTAGAAGTAGA
CTTAATGGTATATATAAAAATTTTGTTATGGATGATGAAAGAGATCGTATTTTACTTT
CCTTAGATGATTATGAAAATTGGTTATATGATAATATAGAAGAAAATAAAAATATGT
TTATTAAAAAAAAGAAGAAATTAGAGATCTTATAAAAAATATTGTACAAAAATTT
GATGTATATAATTCAAACAACAAATCTAGGAAATATAATTAATCATCTTAATAAT
ATCATAACACAATGTTCAAATAAACCATCGGATGAAAGTCAAATATAATTAATAG
AACAACGAAATTCTTAAATAATATTAATTCTTTACAAGAACAAGAAAAAAATAAAC
CACTATACGAACCACCTGTATATACACTTAACGATATTGAAGCAGAATTTAATGAAG
TCACACAACTCGCTCAAAAATTCTTTTC Sequence Length: 650 bp
(SEQ ID NO: 41)

Amino acid sequence of Clone #TL45
SPNKTELKKGEEGKVQTCYTTIPIETLLAQGSYSSKDIFNFSEQEINMQHSDILEGERLKH
LNELETIIYESRSRLNGIYKNFVMDDERDRILLSLDDYENWLYDNIEENKNMFIKKKEEIR
DLIKNIVQKFDVYNSKQQNLGNIINHLNNIITQCSNKPSDESQNIINRTTKFLNNINSLQEQ
EKNKPLYEPPVYTLNDIEAEFNEVTQLAQKFF Sequence Length: 216 aa
(SEQ ID NO: 42)

Amino acid sequence of gene PF07_0033
MSVLGIDIGNDNSVVATINKGAINVVRNDISERLTPTLVGFTEKERLIGDSALSKLKSNYK
NTCRNIKNLIGKIGTDVKDDIEIHEAYGDLIPCEYNYLGYEVEYKNEKVVFSAVRVLSALL
SHLIKMAEKYIGKECKEIVLSYPPTFTNCQKECLLAATKIINANVLRIISDNTAVALDYGM
YRMKEFKEDNGSLLVFVNIGYANTCVCVARFFSNKCEILCDIADSNLGGRNLDNELIKYI
TNIFVNNYKMNPLYKNNTPELCPMGTGRLNKFLVTSTASDQQNGINNKVRIKLQEVAIK
TKKVLSANNEASIHVECLYEDLDCQGSINRETFEELCSNFFLTKLKHLLDTALCISKVNIQ
DIHSIEVLGGSTRVPFIQNFLQQYFQKPLSKTLIADESIARGCVLSAAMVSKHYKVKEYEC
VEKVTHPINVEWHNINDASKSNVEKLYTRDSLKKKVKKIVIPEKGHIKLTAYYENTPDLP
SNCIKELGSCIVKINEKNDKIVESHVMTTFSNYDTFTFLGAQTVTKSVIKSKDEKKKADD
KTEDKGEKKDAKDQEQNDDKDQTNDNNMNEKDTNDKKEKNNETNSPNKTELKKGEE
GKVQTCYTTIPIETLLAQGSYSSKDIFNFSEQEINMQHSDILEGERLKHLNELETIIYESRSR
LNGIYKNFVMDDERDRILLSLDDYENWLYDNIEENKNMFIKKKEEIRDLIKNIVQKFDVY
NSKQQNLGNIINHLNNIITQCSNKPSDESQNIINRTTKFLNNINSLQEQEKNKPLYEPPVYT
LNDIEAEFNEVTQLAQKFFSKLEVEELAKQKAKQEKEKEKEKEKEKEKEKNEETNLD
ANEEQNNEAKNNEEKENSTKNENSANPEE Sequence Length: 873 aa
(SEQ ID NO: 43)

Coding Nucleic acid sequence gene PF07_0033
ATGTCGGTTTTAGGTATAGATATAGGAAATGACAATTCTGTTGTAGCTACTATTAAT
AAAGGTGCTATAAATGTTGTGAGGAATGACATATCCGAAAGGTTAACCCCGACATT
AGTTGGTTTCACCGAAAAAGAAAGATTAATAGGTGATAGTGCTTTATCTAAATTGAA
ATCTAATTATAAGAATACATGTAGGAATATAAAGAATTTGATAGGTAAAATAGGTA
CCGATGTAAAAGATGATATAGAAATACATGAAGCATATGGGGATTTAATACCATGT
GAATATAATTATTTAGGTTATGAAGTTGAATATAAAAATGAAAAGTTGTATTTAGT
GCTGTTCGTGTTTTATCAGCCTTATTATCACATTTGATTAAAATGGCTGAAAAATATA
TTGGAAAGGAATGTAAAGAAATTGTCTTATCATATCCTCCAACATTTACAAATTGTC
AAAAAAGAATGTTTATTAGCTGCAACTAAAATTATTAATGCTAATGTTTTGAGAATTA
TTAGTGATAATACAGCTGTTGCTCTAGATTATGGAATGTACAGAATGAAAGAATTCA
AAGAAGATAATGGATCCTTACTAGTTTTTGTTAACATTGGTTATGCAAATACTTGTG
TATGTGTTGCGCGTTTTTTTCTAATAAATGTGAAATCTTATGTGATATTGCTGATTC
AAATTTAGGTGGTAGAAATTTAGATAATGAACTTATTAAATATATTACAAATATATT
TGTTAATAATTATAAAATGAATCCATTATATAAAACAATACTCCGGAATTATGCCC
CATGGGTACTGGTAGATTAAATAAGTTTTTAGTAACATCTACAGCATCTGATCAACA
AAATGGTATTAATAATAAAGTACGTATTAAATTACAAGAAGTTGCTATAAAAACAA
AGAAAGTACTTTCAGCAAATAATGAAGCGTCCATACATGTTGAATGTTTATATGAAG
ATTTAGATTGTCAAGGTTCCATTAATAGAGAAACCTTTGAAGAATTGTGTTCAAACT
TCTTCTTAACAAAATTAAAACATCTTCTAGATACTGCTCTATGTATTAGTAAAGTAA
ACATACAAGATATACATTCTATTGAAGTTTTGGGTGGATCCACAAGAGTTCCATTTA
TTCAAAATTTTTTACAACAATATTTTCAGAAACCATTATCTAAGACCCTTATAGCAG
ATGAATCTATAGCAAGAGGTTGTGTACTATCAGCTGCTATGGTTAGTAAACATTATA
AAGTAAAAGAATATGAATGTGTAGAAAAAGTTACACATCCAATTAATGTTGAATGG
CATAATATTAATGACGCATCTAAAAGTAATGTAGAAAAATTATATACAAGAGATTC
CTTAAAAAAGAAAGTTAAGAAAATTGTTATCCCAGAAAAAGGACACATTAAACTTA
CAGCTTATTATGAAAATACACCAGATTTACCATCCAATTGTATAAAAGAATTGGGAT
CATGTATTGTTAAAATAAATGAAAAGAATGATAAAATTGTTGAATCCCACGTTATGA
CCACCTTTTCAAATTATGATACATTTACATTTTTAGGTGCACAGACAGTAACCAAGT
CTGTTATTAAGTCCAAGGATGAAAAAAAAAAGCAGATGACAAAACGGAGGATAA
GGGAGAAAAAAAGATGCAAAAGATCAAGAACAAAATGATGATAAAGATCAAACA
AATGATAATAACATGAATGAGAAAGATACTAATGATAAAAAGAAAAAAATAATG
AAACAAACTCACCAAATAAAACAGAATTAAAAAAAGGAGAAGAAGGAAAAGTACA

```
AACATGTTATACAACAATACCTATTGAAACATTATTAGCTCAAGGATCTTATAGTTC
TAAAGATATATTCAATTTTAGTGAACAGGAAATTAATATGCAACATAGTGATATATT
AGAAGGAGAACGATTAAAACATCTTAATGAACTAGAAACTATTATATATGAAGTA
GAAGTAGACTTAATGGTATATATAAAAATTTTGTTATGGATGATGAAAGAGATCGTA
TTTTACTTTCCTTAGATGATTATGAAAATTGGTTATATGATAATATAGAAGAAAATA
AAAATATGTTTATTAAAAAAAAAGAAGAAATTAGAGATCTTATAAAAAATATTGTA
CAAAAATTTGATGTATATAATTCAAAACAACAAAATCTAGGAAATATAATTAATCAT
CTTAATAATATCATAACACAATGTTCAAATAAACCATCGGATGAAAGTCAAAATAT
AATTAATAGAACAACGAAATTCTTAAATAATATTAATTCTTTACAAGAACAAGAAA
AAAATAAACCACTATACGAACCACCTGTATATACACTTAACGATATTGAAGCAGAA
TTTAATGAAGTCACACAACTCGCTCAAAAATTCTTTTCAAAGCTTGAAGTAGAAGAA
CTAGCCAAACAAAAGCAAAGCAAGAAAAGGAAAAGGAAAAGGAAAAAGAAAAA
GAGAAAGAAAAAGAAAGGAAAAAAATGAAGAGACAAACTTGGATGCAAATGAG
GAACAAAATAATGAAGCAAAAAATAATGAAGAAAAGGAGAACTCAACAAAAAATG
AAAATTCAGCTAATCCAGAGGAATAA Sequence Length: 2622 bp
(SEQ ID NO: 44)

*Plasmodium falciparum* calcium-dependent protein kinase
(PF-CDPK5), putative Gene PF3D7_1337800 (fragment C)
Nucleic acid sequence 255 bp (Sequence 1452-1706(255)
of gene PF3D7_1337800
TTCTTAGCAGCTTGTTTAGATCATAGTATATTTCAACAAGATGTTATCTGTAGAAATGCTTTCA
ATGTTTTTGATTTAGATGGTGATGGTGTTATAACAAAGGATGAATTATTTAAAATTCTATCCTT
TAGTGCTGTACAAGTATCCTTTAGTAAAGAAATTATTGAAAATCTTATTAAAGAAGTCGATTCT
AATAATGATGGATTTATAGATTATGATGAATTTTATAAGATGATGACGGGAGTTAAAGAATGA
Sequence Length: 255 (SEQ ID NO: 45)

Amino acid sequence of Fragment C (Pf-CDPK5)
FLAACLDHSIFQQDVICRNAFNVFDLDGDGVITKDELFKILSFSAVQVSFSKEIIENLIKEVDS
NNDGFIDYDEFYKMMTGVKE
Sequence Length: 84 (SEQ ID NO: 46)

Amino acid sequence of PF3D7_1337800(Pf-CDPK5)
MKETEVEDMDTNRKDGKIKKKEKIVNMKNEEVKSTTKSTLADSDEDYSIITLCTKCLSKK
LEDNKNRIILDSKAFKDNRLKGRCSVSSNEDPLDNKLNLSPYFDRSQIIQEIILMNNDEL
SDVYEIDRYKLGKGSYGNVVKAVSKRTGQQRAIKIIEKKKIHNIERLKREILIMKQMDHP
IMHRDLKPENILYVDNTEDSPIQIIDWGFASKCMNNHNLKSVVGTPYYIAPEILRGKYDK
RCDIWSSGVIMYILLCGYPPFNGKNNDEILKKVEKGEFVFDSNYWARVSDDAKDLICQCL
NYNYKERIDVEQVLKHRWFKKFKSNNLIINKTLNKTLIEKFKEFHKLCKIKKLAVTCIAY
QLNEKDIGKLKKTFEAFDHNGDGVLTISEIFQCLKVNDNEFDRELYFLLKQLDTDGNGLI
DYTEFLAACLDHSIFQQDVICRNAFNVFDLDGDGVITKDELFKILSFSAVQVSFSKEIIE
NLIKEVDSNNDGFIDYDEFYKMMTGVKE
Sequence Length: 568 aa (SEQ ID NO: 47)

Coding Nucleotide sequence of PF3D7_1337800 (Pf-CDPK5)
ATGAAAGAGACGGAGGTCGAAGATATGGATACGAATAGAAAAGATGGTAAAATTAAAAAG
AAAGAAAAAATAGTAAATATGAAAAATGAAGAAGTGAAAAGTACGACAAAGAGTACGTTA
GCCGATAGTGATGAAGACTATTCGATTATAACTTTATGTACGAAATGTTTATCTAAAAAA
CTTGAAGATAATAAGATCGAATAATTCTTGATAGTAAAGCTTTTAAAGATAATAGATTA
AAAGGTAGATGTAGTGTTAGTTCCAATGAAGATCCTTTAGATAACAAATTAAATTTATCA
CCATATTTTGATAGATCCCAAATAATTCAAGAAATAATTTTGATGAATAATGATGAATTA
AGTGATGTATATGAAATAGATAGATACAAGTTAGGCAAAGGATCTTATGGAAATGTTGTT
AAAGCCGTAAGTAAAAGAACTGGTCAACAGAGAGCTATAAAAATTATAGAGAAAAGAAA
ATTCATAATATTGAAAGATTAAAAAGAGAAATATTAATAATGAAACAGATGGATCATCCT
AATATTATAAAATTATATGAAGTTTATGAAGACAATGAAAAATTATATTTAGTATTAGAA
TTATGTGACGGTGGAGAATTATTTGATAAAATTGTAAAATATGGTAGCTTCTCTGAATAT
GAAGCATATAAAATTATGAAACAAATATTTTCAGCTTTATATTATTGTCATAGTAAAAAT
ATTATGCATAGAGATTTAAAACCAGAAAATATTTTATATGTAGATAATACAGAAGATTCT
CCTATACAAATAATTGATTGGGGATTCGCTAGTAAATGTATGAATAATCATAATTTGAA
TCAGTTGTTGGGACACCTTATTATATAGCACCCGAAATATTAAGAGGTAAATATGACAAA
AGATGTGATATATGGAGTAGTGGTGTAATTATGTATATTTTATTATGTGGATATCCACCA
TTTAATGGAAAAAATAATGATGAAATCTTAAAAAAAGTGGAAAAAGGAGAATTTGTTTTC
GATTCCAATTATTGGGCAAGAGTTAGTGATGATGCTAAAGATTTAATTTGTCAATGTTTA
AATTATAATTATAAAGAAAGAATAGATGTTGAGCAAGTTCTAAAACATAGATGGTTCAAA
AAATTTAAATCAAATAATCTTATTATAAATAAAACATTAAATAAAACTTTAATCGAAAAA
TTTAAAGAATTCCATAAATTATGTAAAATTAAAAAGCTAGCTGTAACATGTATAGCATAC
CAATTAAATGAAAAAGATATAGGGAAATTAAAAAAAACATTTGAAGCTTTTGATCATAAT
GGAGATGGAGTATTAACCATATCAGAAATTTTTCAATGTTTAAAAGTTAATGACAATGAA
TTTGATAGAGAATTATACTTTTTATTAAAACAACTTGATACAGATGGAAATGGATTAATT
GATTATACTGAATTCTTAGCAGCTTGTTTAGATCATAGTATATTTCAACAAGATGTTATC
TGTAGAAATGCTTTCAATGTTTTTGATTTAGATGGTGATGGTGTTATAACAAGGATGAA
TTATTTAAAATTCTATCCTTTAGTGCTGTACAAGTATCCTTTAGTAAAGAAATTATTGAA
AATCTTATTAAAGAAGTCGATTCTAATAATGATGGATTTATAGATTATGATGAATTTTAT
AAGATGATGACGGGAGTTAAAGAATGA
Sequence Length: 1707 bp (SEQ ID NO: 48)

PbSEP-1; Gene PBANKA_050600 (PbSEP-1A)
Nucleic acid sequence of PB Clone #2 828 bp (Sequence
2172-2991 of gene PBANKA_050600)
```

```
TTAAAAGATAGTGATGGATATGAGAAATTATTAAAAAATGACATGTACGATTTATATAATATTA
AGATGCATGATTTAAATAACTTAAAATCATATGATTTTGAATTTTCAAAAAATTTATTAAAAAA
CGAGATTTTTTTTGTGGTGATAATATAAAAAGTGATGAAATAAATTTAAATGATAATGACATA
AATGAAAAGATTGATTCACTAATGAACAATTACAATATTATGAAAAACAAACGTGACAAATTA
ATGAAGAAGAAAACGAAATTCAAACTTTTTAGCAGAATTAAAAGCTGATGTAACTAATCAAT
CAATCTAAATAACGGGGAAGATGAACAGGCTTTTGATTTGCTTAATTCGTTTGATATAAACAAT
AACTTTGACGATTTTGTTGGCAACTTTGATGATACAAATGATAACATAGCTCAAATAAATCAG
ACATAGACAATAATAAAGAGTTCGAACACGAAATGATATAAATCATGATTATAACGATTGTGG
TACATATATGGATGATATATAATAACAATAATGGTGATGATATTTCGAGAAAGGGATCACGT
CTGAAATTGTCTGATTTAAATGACGAAAAGAATTTATTTCCAGATGTCAACTCCTCTTTTAATA
CTCCTATAAAATCTTCTGAACTAAAGAGAGATTCAGAATGCCAAACAAATTCACCACTTATATT
TTCTAGAAGTAATAGAACTCCTAGGAAAAAAAGTGTAGAAGTAATATTAGTAAAGAAAAAATTA
AAAAAAGAAAGAAAAAGAATCAAATATATCATTTGAAAATACAACACATGATGATTAT
Sequence Length: 828 bp (SEQ ID NO: 65)

PBANKA_050600 (PbSEP-1A aa 724-997)
LKDSDGYEKLLKNDMYDLYNIKMHDLNNLKSYDFEFSKNLLKNEIFFCGDNIKSDEINLNDNDI
NEKIDSLMNNYNIMKNKRDKFNEEENEIQNFLAELKADVTNQLNLNNGEDEQAFDLLNSFDINN
NFDDFVGNFDDTNDNIAQNKSDIDNNKEFEHENDINHDYNDCGTYMDDIYNNNNGDDISRKGSR
LKLSDLNDEKNLFPDVNSSFNTPIKSSELKRDSECQTNSPLIFSRSNRTPRKKSVEVILVKKKL
KKRKEKESNISFENTTHDDY Sequence Length: 276 aa (SEQ ID NO: 66)

Amino acid sequence of Gene PBANKA_050600
MTDNEDQNKEDLIYYINRYSVNDILGNLEENDKLTNYDENSGICEYEIPFLLENVDNNNN
NNTKEHSDRNSVSSYFDDGTCSIISKNDEKHYIDKCEKDKMPKEKINIIFIQNKGEMNSF
EDILSMNNASSENLENKLNDRFYQLCCKSIADVNTHNLNKTKNIVDKKGTLNIEHIDYG
DIFLTIRHRLRGREEKTNNMLNNNNNNDNNNNHLYSDMADSVISNWREIKNHENFIKYEN
YKEHEKEFIRRKLKKKCVNSLNGDKYFMANRKVFDYYRNNLDSYMTNGNEKDICKQENMS
LHFLPKKRKSMNNSSLYNSQIIGQNEYILKNRTFLKKFYIKKNFKQQEHIHNDDYYCDDN
HSENLYNDDIYNYNKNLSNRQGNLPSNDFIYSCEIQNKKNSIPHNICVDRNVITPRNSTW
NNENEIHEEDMVYYHSQNKGKNSHYVEAENEIQSNHYCEDKNTNSFNEYVNEIDKLDENY
NMFNKVEEDDNNNNKENFNIYDGDEIDNNEAPDIKIEENDDYETYNNELELEVEVDDGIG
NNIPFNNNDNFVNSNKNEDLDNINNCEHVSNSNHTKYGEEDNEQKAPSITSKDDKDYFDL
LIKKYEQTRMSINESSTASLSESIYLSKEGTKEPSLNAHEMLKIASNTKNDVNNKIECLN
ENLIDLKNNKEIINEGECFSNGFSIEKNDIEKENDNIVKLGSVYNNDKTEGERGNIGNKN
EKVDLKDSDGYEKLLKNDMYDLYNIKMHDLNNLKSYDFEFSKNLLKNEIFFCGDNIKSDE
INLNDNDINEKIDSLMNNYNIMKNKRDKFNEEENEIQNFLAELKADVTNQLNLNNGEDEQ
AFDLLNSFDINNNFDDFVGNFDDTNDNIAQNKSDIDNNKEFEHENDINHDYNDCGTYMDD
IYNNNNGDDISRKGSRLKLSDLNDEKNLFPDVNSSFNTPIKSSELKRDSECQTNSPLIFS
RSNRTPRKKSVEVILVKKKLKRKEKESNISFENTTHDDYTVGTTTATSSINSKRRYPKR
NRIKTLRYWIGERELTRENPETGEIDVVGFSECKNLEELSPHIIGPVYYKKMYLRDVNNL
HGKGNEDANNNIDRNDNTDEENEITIEINNGMYENEVYNKIQNKENSVNKNDNVSNILKK
SINGSIHNRSDNDAITRNGKKRKKFINVVNYIKKKTKKKLVKVIDKEVEQENENVDNRN
TFSNNDNIINDITNVNHNSQNNLDQNFIAISNDFIENDDNIFFDAISLGDNAHINDIPEK
SEEIIEAPGVDAIETTKVNGNEKEINLEKEINLEKEINLEKNKDVHVKKKLLDKKKKKKK
KKNKGKEKEIDEMYKQLSFLNFNSFYSKGNEDKSKIEILKKTSTKKKGSKIDKEKVDEEN
DKHNKNSGKEAKELITKKKKAKNMKKNKKRNMQNKEMKNYYEYTNNEIEKFYNNPNDRIE
NEYNMGVDLEASIKTEEEKTEKIGELPILNSYTNEQYEHITNTNDITNSKSENFELHKNE
DEEVEKLQTSTRRKKKKKSESLIHDTNELNKKRRKTDGNNSGELISINENDEIKNVDADK
KINDKEGKYIKKVDKDTIMGSNGNNIDELNKDFEDNDQIKNIKKDEKKKETNTDGSNNMR
NINLLEEIDANEKNSTLCLVTHNKKNNTNSQSFIIDKLKSYFNIKELINVKKQKTNNVIL
NTFENKQIINNNPIRISLSYPSSVELSVENRCNQTRNGQFPLIQKNLSNFKVDINLFCVQ
IFPNKAHSSNSYDKILIGYIYQGKKVKIYFKNQERYFEKDEFFYIPKYSPFKIVNISRDN
CILYVYPINK Sequence Length: 1810 aa (SEQ ID NO: 67)

Coding Nucleotide sequence of PBANKA_050600
ATGACAGACAACGAGGATCAAAATAAAGAAGATCTGATATATTACATAAATAGATACAGT
GTCAATGATATATTGGGAAATTTAGAAGAAAATGATAAGTTAACAAATTATGATGAAAAT
AGCGGAATATGTGAATATGAAATTCCATTTCTTTTGGAAAATGTCATAATAATAATAAT
AATAATACTAAAGAACATTCCGATAGAAATTCTGTATCTAGTTATTTCGATGATGGAACA
TGTTCGATTATTTCTAAAAATGATGAAAAACATTATATAGACAAATGTGAAAAAGACAAA
ATGCCAAAGGAAAAAATAAATATTATATTTATTCAGAATAAAGGTGAAATGAATAGCTTT
GAAGATATTTTATCCATGAATAATGCAAGCAGTGAAAATTTAGAAAACAAGTTAAATGAT
AGATTTTATCAACTATGTTGTAAAAGTATTGCTGATGTGAACACCCACAATTTAAATAAA
ACTAAAAATATTGTAAAAGATAAAAAAGGGACATTGAATATTGAGCATATAGATTATGGT
GATATATTTTTAACCATTCGTCATCGTCTAAGAGGCGTGAAGAAAAACGAATAACATG
CTAAATAATAATAATAATAATGATAATAATAATAATCATTTATATAGTGACATGGCTGAT
AGTGTTATTAGTAATTGGAGGGAAATAAAAAATCATGAAAATTTTATAAAATATGAAAAC
TATAAAGAGCATGAAAAGGAGTTTATAAGGAGGAAATTGAAAAGAAATGCGTCAATAGT
TTAAATGGAGATAAATATTTTATGGCCAATAGAAAGTATTTGATTATTATCGTAATAAT
TTAGATAGTTACATGACTAATGGGAATGAAAAAGATATATGCAAGCAAGAAAATATGTCT
CTACATTTTTTACCAAAAAAGAGAAAATCAATGAATAATAGTTCTTTATACAATTCTCAA
ATAATTGGACAAATGAATATATTTTAAAGAATAGAACATTTTTAAAAAAATTTTATATA
AAAAAAAATTTTAAGCAACAAGAACATATCCATAATGATGATTATTATTGTGATGATAAT
CATAGTGAAAATTTATATAATGATGATATATATAATTATAATAAAAACTTGAGTAATAGA
CAAGGTAATCTACCCAGCAATGATTTTATTTATTCATGTGAAATTCAAAATAAGAAAAAT
TCAATACCACATAATATATGTGTCGATAGAAATGTAATAACCCCACGGAACAGTACATGG
AATAATGAAAACGAAATTCACGAAGAGGATATGGTTTATTATCATTCTCAAAATAAGGGA
AAAAAATTCACATTATGTAGAAGCAGAAAATGAAATACAATCAAATCATTATTGTGAAGAT
```

-continued

```
AAAAATACAAACAGTTTTAACGAATATGTTAATGAAATTGATAAACTCGATGAAAATTAT
AATATGTTTAACAAAGTTGAAGAGGACGATAATAATAATAACAAAGAAAATTTTAACATT
TATGATGGTGATGAAATAGATAATAACGAAGCATTTGATATCAAAATCGAAGAAAATGAT
GATTATGAAACATATAACAACGAATTAGAATTAGAGGTAGAGGTAGATGATGGAATAGGT
AATAATATTCCATTTAATAATAATGATAATTTTGTAAATTCAAATAAGAATGAAGATTTG
GATAATATAAATAATTGTGAACATGTTTCAAATTCAAATCATACAAAATATGGGGAAGAA
GACAATGAGCAAAAAGCTCCATCAATAACCAGTAAAGATGATAAAGATTATTTTGATTTA
CTAATAAAAAAATATGAACAAACTAGAATGTCAATTAATGAATCTAGTACAGCCTCACTT
AGTGAAAGTATTTATTTATCAAAAGAAGGAACAAAAGAACCTTCTTTAAATGCTCACGAA
ATGTTAAAAATCGCATCTAACACAAAGAATGATGTAAATAATAAAATTGAATGTTTGAAT
GAAAACTTAATAGATTTAAAAAATAACAAGGAAATTATTAATGAAGGGGAATGTTTTAGT
AATGGTTTTCTATCGAAAAAATGACATAGAAAGGAAAATGATAATATAGTAAAATTA
GGAAGTGTATATAATAATGACAAAACAGAGGGGGAAAGGGGAATATTGGAAACAAAAAT
GAAAAGTAGACCTTAAAAGATAGTGATGGATATGAGAAATTATTAAAAAATGACATGTAC
GATTTATATAATATTAAGATGCATGATTTAAATAACTTAAAATCATATGATTTTGAATTT
TCAAAAAATTTATTAAAAAACGAGATTTTTTTTTGTGGTGATAATATAAAAAGTGATGAA
ATAAATTTAAATGATAATGACATAAATGAAAAGATTGATTCACTAATGAACAATTACAAT
ATTATGAAAAACAAACGTGACAAATTTAATGAAGAAGAAAACGAAATTCAAAACTTTTTA
GCAGAATTAAAAGCTGATGTAACTAATCAACTCAATCTAAATAACGGGGAAGATGAACAG
GCTTTTGATTTGCTTAATTCGTTTGATATAAACAATAACTTTGACGATTTTGTTGGCAAC
TTTGATGATACAAATGATAACATAGCTCAAATAAATCAGACATAGACAATAATAAAGAG
TTCGAACACGAAAATGATATAAATCATGATTATAACGATTGTGGTACATATATGGATGAT
ATATATAATAACAATAATGGTGATGATATTTCGAGAAAGGGATCACGTCTGAAATTGTCT
GATTTAAATGACGAAAGAATTTATTTCCAGATGTCAACTCCTCTTTTAATACTCCTATA
AAATCTTCTGAACTAAAGAGAGATTCAGAATGCCAAACAAATTCACCCACTTATATTTTCT
AGAAGTAATAGAACTCCTAGGAAAAAAGTGTAGAAGTAATATTAGTAAAGAAAAATTA
AAAAAAAGAAAAGAAAAAGAATCAAATATATCATTTGAAAATACAACACATGATGATTAT
ACTGTTGGTACAACTACTGCTACTAGTAGCATCAATTCGAAAAGAAGATATCCTAAAAGA
AATAGAATAAAAACGTTGCGATACTGGATAGGTGAAAGGGAACTTACTAGAAGAAATCCT
GAAACAGGCGAAATAGATGTTGTAGGTTTTAGTGAATGCAAAAATTTAGAAGAATTATCT
CCTCATATTATTGGTCCAGTTTATTATAAAAAAATGTATTTACGAGATGTGAATAATTTA
CATGGAAAAGGAAACGAAGATGCTAACAACAATATAGATAGAAATGATAATACTGATGAA
GAAAATGAAATAACGATAGAAATCAATAATGGAATGTATGAAAATGAAGTGTATAATAAA
ATTCAGAATAAAGAGAATTCTGTGAATAAAAATGATAATGTTAGTAACATATTGAAAAAA
AGTATAAATGGTAGCATTCATAATAGAAGTGATAATGATGCAATAACTAGAAATGGGAAA
AAGAAAAGAAAAAGTTTATTAATGTTGTTAATTATATTAAAAAAAAAAACAAAAAAAAA
TTAGTCAAAGTTATAGATAAAGAAGTAGAGCAGGAAAATGAAAATGTAGATAATCGTAAC
ACTTTTTCAAATAATGATAATATAATTAATGACATAACAAATGTCAATCACAATTCTCAA
AATAATTTGGATCAAAATTTTATTGCAATTAGTAATGATTTTATTGAAAATGATGACAAT
ATTTTTTTCGATGCGATTAGTCTTGGCGATAATGCTCACATAAATGATATTCCAGAAAAA
AGCGAAGAAATTATTGAAGCACCAGGAGTAGATGCAATTGAAACGACTAAAGTTAATGGA
AACGAAAAGGAAATCAATTTAGAAAAAGGAAATCAATTTAGAAAAAGGAAATCAATTTAGAA
AAGAATAAAGATGTACATGTGAAAAAGAAATTATTAGATAAAAAGAAAAAGAAAAAATA
AAGAAAAACAAGGGAAAAGAAAAGGAAATAGACGAAATGTACAAGCAATTATCATTTTTG
AATTTTAATTCGTTTTATTCTAAAGGAAATGAAGATAAATCAAAAATAGAAATTTTGAAA
AAAACAAGTACCAAAAAAAAAGGGAGTAAAATTGATAAAGAAAAGGTAGATGAGGAAAAT
GATAAACATAATAAAAATTCGGGAAAGGAAGCCAAAGAATTAATTACAAAAAAAAAGAAA
GCCAAGAATATGAAGAAAATAAAAAGAGAAATATGCAGAATAAAGAAATGAAAAATTAT
TATGAATATACAAATAATGAAATCGAAAAGTTCTACAACAATCCAAATGATAGAATAGAG
AATGAATACAATATGGGAGTCGATTTAGAAGCATCAATAAAAACTGAAGAAGAAAAAACA
GAAAAAATTGGAGAGTTGCCCCATTTTAAATTCATATACTAATGAGCAATATGAGCACATA
ACGAATACAAATGTATATAACAAATTCGAAAAGTGAAAATTTTGAACTCCACAAAAATGAA
GACGAAGAAGTGGAAAAGCTACAAACTTCTACACGTCGAAAAAAGAAAAAAAAAGTGAA
AGTTTAATTCATGATACAAATGAATTGAATAAAAAGCGAAGAAAAACAGATGGAAATAAT
TCAGGGGAATTAATTTCTATTAATGAAAATGATGAGATAAAAAATGTAGATGCTGATAAA
AAAATAAATGACAAAGAAGGTAAATATATAAAGAAAGTTGACAAGGATACAATTATGGGA
TCAAATGGAAATAATATTGATGAATTAAATAAGGATTTTGAAGTAATGATCAAATTAAA
AATATAAAAAAGATGAAAAAAAAAAGAGACAAATACAGATGGTTCTAATAATATGAGA
AATATAAATTTATTAGAAGAAATAGATGCAAATGAAAAAAATAGTACATTATGTTTGGTA
ACTCACAATAAAAAAATAATACGAATAGTCAAAGTTTTATTATAGATAAATTAAAATCG
TATTTCAATATAAAAGAGTTAATAAATGTCAAAAAACAAAAACAAATAATGTAATATTA
AATACTTTTGAAATAAACAAATAATAAATAATAATCCTATACGTATTTCTCTTTCCTAT
CCTTCTAGTGTAGAATTATCAGTTGAAAATGATGCAACCAAACAAGAAATGGACAATTT
CCACTTATACAAAAGAACTTAAGCAACTTCAAGGTAGACATAAATTTATTTTGTGTTCAA
ATTTTCCCAAACAAAGCACATAGCTCGAATAGTTATGATAAAATTTTGATTGGGTATATA
TATCAGGGAAAAAGGTAAAGATTTATTTTAAGAACCAAGAAAGATATTTTGAAAAGGAT
GAGTTTTTTTACATACCCAAATACTCTCCTTTCAAAATTGTCAACATAAGCAGGGACAAT
TGTATTTTATATGTTTATCCAATAAATAAATAA Sequence Length: 5434 bp
(SEQ ID NO: 68)

SERA5 (serine repeat antigen 5)
PlasmoDB ID: PF3D7_0207600
Chromosome 2; position 303,593-307,027

Full Sequence: base pairs 1-2994 (excluding introns)
ATGAAGTCATATATTTCCTTGTTTTTCATATTGTGTGTTATATTTAACAAAAATGTTATAAAAT
GTACAGGAGAAAGTCAAACAGGTAATACAGGAGGAGGTCAAGCAGGTAATACAGGAGGAGATCA
AGCAGGTAGTACAGGAGGAAGTCCACAAGGTAGTACGGGAGCAAGTCCACAAGGTAGTACGGGA
GCAAGTCCACAAGGTAGTACGGGAGCAAGTCAACCCGGAAGTTCCGAACCAAGCAATCCTGTAA
```

```
GTTCCGGACATTCTGTAAGTACTGTATCAGTATCACAAACTTCAACTTCTTCAGAAAAACAGGA
TACAATTCAAGTAAAATCAGCTTTATTAAAAGATTATATGGGTTTAAAAGTTACTGGTCCATGT
AACGAAAATTTCATAATGTTCTTAGTTCCTCATATATATATTGATGTTGATACAGAAGATACTA
ATATCGAATTAAGAACAACATTGAAAAAAACAAATAATGCAATATCATTTGAATCAAACAGTGG
TTCATTAGAAAAAAAAAAATATGTAAAACTACCATCAAATGGTACAACTGGTGAACAAGGTTCA
AGTACGGGAACAGTTAGAGGAGATACAGAACCAATTTCAGATTCAAGCTCAAGTTCAAGTTCAA
GCTCTAGTTCAAGTTCAAGTTCAAGTTCAAGTTCTAGTTCAAGTTCTAGTTCAAGTTCAGAAAG
TCTTCCTGCTAATGGACCTGATTCCCCTACTGTTAAACCGCCAAGAAATTTACAAAATATATGT
GAAACTGGAAAAAACTTCAAGTTGGTAGTATATATTAAGGAGAATACATTAATACTTAAATGGA
AAGTATACGGAGAAACAAAAGATACTACTGAAAATAACAAAGTTGATGTAAGAAAGTATTTGAT
AAATGAAAAGGAAACCCCATTTACTAATATACTAATACATGCGTATAAAGACATAATGGAACA
AACTTAATAGAAAGTAAAAACTACGCAATAGGATCAGACATTCCAGAAAATGTGATACCTTAG
CTTCCAATTGCTTTTTAAGTGGTAATTTTAACATTGAAAATGCTTTCAATGTGCTCTTTTAGT
AGAAAAAGAAAATAAAAATGACGTATGTTACAAATACCTATCTGAAGATATTGTAAGTAAATTC
AAAGAAATAAAAGCTGAGACAGAAGATGATGATGAAGATGATTATACTGAATATAAATTAACAG
AATCTATTGATAATATATTAGTAAAAATGTTTAAAACAAATGAAAATAATGATAAATCAGAATT
AATAAAATTAGAAGAAGTAGATGATAGTTTGAAATTAGAATTAATGAATTACTGTAGTTTACTT
AAAGACGTAGATACAACAGGTACCTTAGATAATTATGGGATGGGAAATGAAATGGATATATTTA
ATAACTTAAAGAGATTATTAATTTATCATTCAGAAGAAAATATTAATACTTTAAAAAATAAATT
CCGTAATGCAGCTGTATGTCTTAAAAATGTTGATGATTGGATTGTAAATAAGAGAGGTTTAGTA
TTACCTGAATTAAATTATGATTTAGAATATTTCAATGAACATTTATATAATGATAAAAATTCTC
CAGAAGATAAAGATAATAAAGGAAAAGGTGTCGTACATGTTGATCAACTTTAGAAAAAGAAGA
TACTTTATCATATGATAACTCAGATAATATGTTTTGTAATAAAGAATATTGTAACAGATTAAAA
GATGAAAATAATTGTATATCTAATCTTCAAGTTGAAGATCAAGGTAATTGTGATACTTCATGGA
TTTTTGCTTCAAAATATCATTTAGAAACTATTAGATGTATGAAAGGATATGAACCTACCAAAAT
TTCTGCTCTTTATGTAGCTAATTGTTATAAAGGTGAACATAAAGATAGATGTGATGAAGGTTCT
AGTCCAATGGAATTCTTACAAATTATTGAAGATTATGGATTCTTACCAGCAGAATCAAATTATC
CATATAACTATGTGAAAGTTGGAGAACAATGTCCAAAGGTAGAAGATCACTGGATGAATCTATG
GGATAATGGAAAAATCTTACATAACAAAAATGAACCTAATAGTTTAGATGGTAAGGGATATACT
GCATATGAAAGTGAAAGATTTCATGATAATATGGATGCATTTGTTAAAATTATTAAAACTGAAG
TAATGAATAAAGGTTCAGTTATTGCATATATTAAAGCTGAAAATGTTATGGGATATGAATTTAG
TGGAAAGAAAGTACAGAACTTATGTGGTGATGATACAGCTGATCATGCAGTTAATATTGTTGGT
TATGGTAATTATGTGAATAGCGAAGGAGAAAAAAAATCCTATTGGATTGTAAGAAACAGTTGGG
GTCCATATTGGGGAGATGAAGGTTATTTTAAAGTAGATATGTATGGACCAACTCATTGTCATTT
TAACTTTATTCACAGTGTTGTTATATTCAATGTTGATTTACCTATGAATAATAAAACAACTAAA
AAAGAATCAAAAATATATGATTATTATTTAAAGGCCTCTCCAGAATTTTATCATAACCTTTACT
TTAAGAATTTTAATGTTGGTAAGAAAAATTTATTCTCTGAAAAGGAAGATAATGAAAACAACAA
AAAATTAGGTAACAACTATATTATATTCGGTCAAGATACGGCAGGATCAGGACAAAGTGGAAAG
GAAAGCAATACTGCATTAGAATCTGCAGGAACTTCAAATGAAGTCTCAGAACGTGTTCATGTTT
ATCACATATTAAAACATATAAAGGATGGCAAAATAAGAATGGGTATGCGTAAATATATAGATAC
ACAAGATGTAAATAAGAAACATTCTTGTACAAGATCCTATGCATTTAATCCAGAGAATTATGAA
AAATGTGTAAATTTATGTAATGTGAACTGGAAAACATGCGAGGAAAAAACATCACCAGGACTTT
GTTTATCCAAATTGGATACAAATAACGAATGTTATTTCTGTTATGTATAA (SEQ ID
NO: 69)

Full Sequence: 1-997 amino acids
MKSYISLFFILCVIFNKNVIKCTGESQTGNTGGGQAGNTGGDQAGSTGGSPQGSTGASPQGSTG
ASPQGSTGASQPGSSEPSNPVSSGHSVSTVSVSQTSTSSEKQDTIQVKSALLKDYMGLKVTGPC
NENFIMFLVPHIYIDVDTEDTNIELRTTLKKTNNAISFESNSGSLEKKKYVKLPSNGTTGEQGS
STGTVRGDTEPISDSSSSSSSSSSSSSSSSSSSSSSSSSSSESLPANGPDSPTVKPPRNLQNIC
ETGKNFKLVVYIKENTLILKWKVYGETKDTTENNKVDVRKYLINEKETPFTNILIHAYKEHNGT
NLIESKNYAIGSDIPEKCDTLASNCFLSGNFNIEKCFQCALLVEKENKNDVCYKYLSEDIVSKF
KEIKAETEDDDEDDYTEYKLTESIDNILVKMFKTNENNDKSELIKLEEVDDSLKLELMNYCSLL
KDVDTTGTLDNYGMGNEMDIFNNLKRLLIYHSEENINTLKNKFRNAAVCLKNVDDWIVNKRGLV
LPELNYDLEYFNEHLYNDKNSPEDKDNKGKGVVHVDTTLEKEDTLSYDNSDNMFCNKEYCNRLK
DENNCISNLQVEDQGNCDTSWIFASKYHLETIRCMKGYEPTKISALYVANCYKGEHKDRCDEGS
SPMEFLQIIEDYGFLPAESNYPYNYVKVGEQCPKVEDHWMNLWDNGKILHNKNEPNSLDGKGYT
AYESERFHDNMDAFVKIIKTEVMNKGSVIAYIKAENVMGYEFSGKKVQNLCGDDTADHAVNIVG
YGNYVNSEGEKKSYWIVRNSWGPYWGDEGYFKVDMYGPTHCHFNFIHSVVIFNVDLPMNNKTTK
KESKIYDYYLKASPEFYHNLYFKNFNVGKKNLFSEKEDNENNKKLGNNYIIFGQDTAGSGQSGK
ESNTALESAGTSNEVSERVHVYHILKHIKDGKIRMGMRKYIDTQDVNKKHSCTRSYAFNPENYE
KCVNLCNVNWKTCEEKTSPGLCLSKLDTNNECYFCYV (SEQ ID NO: 70)

Y2H Clone name: 1 7-1 (nucleotides 2433-2994; amino acids
561 base pairs
AACTTTATTCACAGTGTTGTTATATTCAATGTTGATTTACCTATGAATAATAAAACAAC
TAAAAAAGAATCAAAAATATATGATTATTATTTAAAGGCCTCTCCAGAATTTTATCATAACCTT
TACTTTAAGAATTTTAATGTTGGTAAGAAAAATTTATTCTCTGAAAAGGAAGATAATGAAAACA
ACAAAAAATTAGGTAACAACTATATTATATTCGGTCAAGATACGGCAGGATCAGGACAAAGTGG
AAAGGAAAGCAATACTGCATTAGAATCTGCAGGAACTTCAAATGAAGTCTCAGAACGTGTTCAT
GTTTATCACATATTAAAACATATAAAGGATGGCAAAATAAGAATGGGTATGCGTAAATATATAG
ATACACAAGATGTAAATAAGAAACATTCTTGTACAAGATCCTATGCATTTAATCCAGAGAATTA
TGAAAAATGTGTAAATTTATGTAATGTGAACTGGAAAACATGCGAGGAAAAAACATCACCAGGA
CTTTGTTTATCCAAATTGGATACAAATAACGAATGTTATTTCTGTTATGTATAA (SEQ ID
NO: 71)

186 amino acids
NFIHSVVIFNVDLPMNNKTTKKESKIYDYYLKASPEFYHNLYFKNFNVGKKNLFSEKEDNENNK
KLGNNYIIFGQDTAGSGQSGKESNTALESAGTSNEVSERVHVYHILKHIKDGKIRMGMRKYIDT
```

QDVNKKHSCTRSYAFNPENYEKCVNLCNVNWKTCEEKTSPGLCLSKLDTNNECYFCYV (SEQ
ID NO: 72)

SUB1 (subtilisin-like protease 1)
PlasmoDB ID: PF3D7_0507500
Chromosome 5; position 307,490-309,556

Full Sequence: base pairs 1-2067 (excluding introns)
ATGATGCTCAATAAAAAAGTTGTTGCTTTGTGCACACTTACCTTACATCTTTTTTGTATATTTC
TATGTCTAGGAAAGGAAGTAAGGTCTGAAGAAAATGGGAAAATACAAGATGATGCTAAAAAGAT
TGTTAGCGAATTACGATTCCTAGAAAAAGTAGAAGATGTTATTGAAAAGAGTAACATAGGAGGG
AATGAGGTAGATGCCGATGAAAATTCATTTAATCCGGATACTGAGGTTCCCATAGAAGAGATAG
AAGAAATAAAAATGAGGGAACTGAAAGATGTAAAGGAAGAAAAATAAAAATGACAACCATAA
TAATAATAATAATAATATTAGTAGTAGTAGTAGTAGTAGTAGTAATACTTTTGGTGAAGAAAAA
GAAGAAGTATCTAAGAAAAAAAAAAGTTAAGACTTATAGTTAGCGAGAATCATGCAACTACCC
CCTCGTTTTCCAAGAATCCCTTTTAGAACCTGATGTTTTATCCTTTTTAGAAAGTAAAGGGAA
TTTGTCCAACTTGAAAAATATCAATTCTATGATTATAGAACTAAAGGAAGATACAACGGATGAT
GAATTAATATCTTATATTAAAATTCTTGAGGAGAAGGGAGCTTTGATTGAATCAGATAAATTAG
TGAGTCAGATAATATTGATATAAGTGGTATAAAAGATGCTATAAGAAGAGGTGAAGAAAATAT
TGATGTTAATGATTATAAAAGTATGTTAGAAGTCGAAATGATGCTGAAGATTATGATAAAATG
TTTGGTATGTTTAATGAATCACATGCTGCAACATCTAAAAGGAAACGCCATTCAACAAATGAGC
GTGGATATGATACATTTTCATCACCTTCATATAAGACATATTCAAAAAGTGATTATTTATATGA
TGATGATAATAATAATAATAATTATTATTATAGTCATAGTAGTAATGGTCATAATAGTAGTAGT
CGTAATAGTAGTAGTAGTCGTAGTAGACCAGGTAAATATCATTTCAATGATGAATTTCGTAATT
TGCAATGGGGTTTAGATTTATCCAGATTAGATGAAACACAAGAATTAATTAACGAACATCAAGT
GATGAGTACTCGTATATGTGTTATAGATAGTGGTATTGATTATAATCATCCCGATTTAAAAGAT
AATATTGAATTAAATTTAAAAGAATTACATGAAGGAAAGGTTTTGATGATGATAATAATGGTA
TAGTTGATGATATATATGGTGCTAATTTTGTAAATAATTCAGGAAACCCGATGGATGATAATTA
TCATGGTACTCATGTATCAGGAATTATATCTGCCATAGGAAATAATAATATAGGTGTTGTAGGT
GTTGATGTAAATTCAAAATTAATTATTTGTAAAGCATTAGATGAACATAAATTAGGAAGATTAG
GAGATATGTTCAAATGTTTAGATTATTGTATAAGTAGAAATGCACATATGATAAATGGAAGCTT
TTCATTTGATGAATATAGTGGTATTTTTAATTCTTCTGTAGAATATTTACAAAGAAAAGGTATC
CTCTTTTTTGTATCTGCAAGTAATTGTAGTCATCCTAAATCGTCAACACCAGATATTAGAAAAT
GTGATTTATCCATAAATGCAAAATATCCCCCTATCTTATCTACTGTTTATGATAATGTTATATC
TGTTGCTAATTTAAAAAAAAATGATAATAATAATCATTATTCATTATCCATTAATTCTTTTTAT
AGCAATAAATATTGTCAACTAGCTGCACCAGGAACTAATATATATTCTACTGCTCCACATAATT
CATATCGAAAATTAAATGGTACATCTATGGCTGCTCCACATGTAGCTGCAATAGCATCACTCAT
ATTTTCTATTAATCCTGACTTATCATATAAAAAAGTTATACAAATATTAAAAGATTCTATTGTA
TATCTCCCTTCCTTAAAAAATATGGTTGCATGGGCAGGATATGCAGATATAAATAAGGCAGTCA
ATTTAGCCATAAAATCAAAAAAAACATATATCAATTCTAATATATCTAACAAGTGGAAAAAAAA
AAGTAGATATTTGCATTAA (SEQ ID NO: 73)

Full Sequence: 1-688 amino acids
MMLNKKVVALCTLTLHLFCIFLCLGKEVRSEENGKIQDDAKKIVSELRFLEKVEDVIEKSNIGG
NEVDADENSFNPDTEVPIEEIEEIKMRELKDVKEEKNKNDNHNNNNNISSSSSSSSSNTFGEEK
EEVSKKKKKLRLIVSENHATTPSFFQESLLEPDVLSFLESKGNLSNLKNINSMIIELKEDTTDD
ELISYIKILEEKGALIESDKLVSADNIDISGIKDAIRRGEENIDVNDYKSMLEVENDAEDYDKM
FGMFNESHAATSKRKRHSTNERGYDTFSSPSYKTYSKSDYLYDDDNNNNNYYYSHSSNGHNSSS
RNSSSSSRSRPGKYHFNDEFRNLQWGLDLSRLDETQELINEHQVMSTRICVIDSGIDYNHPDLKD
NIELNLKELHGRKGFDDDNNGIVDDIYGANFVNNSGNPMDDNYHGTHVSGIISAIGNNNIGVVG
VDVNSKLIICKALDEHKLGRLGDMFKCLDYCISRNAHMINGSFSFDEYSGIFNSSVEYLQRKGI
LFFVSASNCSHPKSSTPDIRKCDLSINAKYPPILSTVYDNVISVANLKKNDNNNHYSLSINSFY
SNKYCQLAAPGTNIYSTAPHNSYRKLNGTSMAAPHVAAIASLIFSINPDLSYKKVIQILKDSIV
YLPSLKNMVAWAGYADINKAVNLAIKSKKTYINSNISNKWKKKSRYLH (SEQ ID NO: 74)

PKG (cGMP-dependent protein kinase)
PlasmoDB ID: PF3D7_1436600
Chromosome 14; position 1,490,654-1,494,214
Full Sequence: base pairs 1-2562 (excluding introns)
ATGGAAGAAGATGATAATCTAAAAAAAGGGAATGAAAGAAATAAAAAGAAGGCTATATTTTCAAATGATG
ATTTTACAGGAGAAGATAGTTTAATGGAGGATCATTTAGAACTTCGGGAAAAGCTTTCAGAAGATATTGA
TATGATAAAGACTTCCTTAAAAAATAATCTAGTTTGTAGTACATTAAACGATAATGAAATATTGACTCTG
TCTAATTATATGCAATTCTTTGTTTTTAAAAGTGGAAATTTAGTAATAAAACAAGGGGAAAAAGGGTCAT
ACTTTTTCATTATTAATAGTGGCAAATTTGACGTTTATGTAAATGATAAAAAAGTAAAGACTATGGGAAA
AGGTAGTTCTTTCGGTGAAGCTGCTTTAATTCATAATACCCAAAGAAGTGCAACTATTATTGCAGAAACT
GATGGAACTCTATGGGGAGTTCAAAGAAGTACATTTAGAGCTACCCTAAAACAATTATCTAATAGAAATT
TTAACGAAAACAGAACATTTATCGATTCCGTTTCAGTTTTTGATATGTTAACTGAAGCACAAAAAAACAT
GATTACTAATGCTTGTGTAATACAAAACTTTAAATCTGGTGAACATGTTAAACAAGGAGATTATGGA
GATGTCTTATACATTTTGAAAGAAGGAAAGGCTACAGTATATATTAACGATGAAGAGATAAGGGTTTTAG
AGAAAGGTTCCTATTTTGGGGAAAGAGCTCTACTGTATGATGAACCAAGAAGTGCAACAATCATTGCAAA
AGAACCAACCGCTTGTGCATCCATTTGTAGGAAATTATTAAATATTGTTCTAGGAAACTTACAAGTAGTT
TTATTTCGTAATATTATGACTGAAGCTTTACAACAGAGTGAAATTTTAAACAATTTAGTGGGGATCAAT
TAAACGATTTAGCAGATACCGCCATTGTTCGAGATTATCCAGCTAATTATAATATATTACATAAGGATAA
GGTAAAATCCGTTAAATATATTATTGTATTGGAAGGTAAAGTAGAATTATTCTTGATGATACTTCTATT
GGTATATTATCCAGAGGAATGTCTTTGGAGATCAATATGTATTAAATCAGAAACAACCATTTAAGCATA
CTATTAAATCATTAGAAGTTTGTAAAATCGCATTAATAACGGAAACTTGTTTAGCTGATTGTCTAGGAAA
TAATAATATTGATGCATCTATTGATTATAATAATAAAAAAGTATTATAAAGAAAATGTATATCTTTAGA
TACTTAACTGATAAACAATGTAATTTATTAATTGAAGCTTTTAGAACCACAAGATATGAAGAAGGTGATT
ATATAATACAAGAAGGAGAAGTAGGATCTAGATTTTATATAATAAAAAATGGAGAAGTAGAAATAGTAAA -continued

```
AAATAAAAAAAGGTTACGTACCTTAGGAAAGAATGATTACTTTGGTGAAAGAGCTTTATTATATGATGAA
CCAAGAACAGCTTCTGTTATAAGTAAAGTAAATAATGTTGAATGTTGGTTTGTTGATAAAAGTGTGTTTT
TACAAATTATACAAGGACCTATGTTAGCACATTTGGAAGAAAGAATAAAAATGCAAGATACTAAAGTAGA
AATGGATGAACTAGAAACAGAACGAATTATTGGAAGAGGTACTTTCGGAACAGTTAAATTAGTTCATCAT
AAACCAACAAAAATAAGATATGCTTTAAAATGTGTTAGTAAAAGAAGTATTATTAATTTAAATCAACAAA
ACAATATAAAATTAGAAAGAGAAATAACAGCAGAAAATGATCATCCATTTATTATAAGATTAGTAAGAAC
ATTTAAAGATTCTAAATATTTCTATTTTCTAACAGAATTAGTAACAGGTGGAGAATTATATGATGCTATT
AGAAAATTAGGTTTATTATCTAAATCACAAGCTCAATTTTATTTAGGTTCTATCATTTTAGCTATTGAAT
ATTTACATGAAAGAAATATTGTATATAGAGATTTAAAACCAGAAAACATTTTATTAGATAAACAAGGTTA
TGTAAAACTAATCGATTTTGGTTGTGCCAAAAAGGTACAAGGTAGAGCTTATACATTAGTAGGTACACCT
CATTATATGGCACCTGAGGTTATTTTAGGAAAAGGTTATGGATGTACTGTTGACATATGGGCATTGGGAA
TATGCCTATATGAATTTATATGTGGTCCATTACCATTTGGTAATGATGAAGAAGATCAATTAGAAATTTT
CCGTGATATATTAACCGGCCAACTTACATTTCCAGATTATGTAACAGACACAGATAGCATAAATTTGATG
AAAAGACTTCTATGTAGATTACCTCAAGGAAGAATTGGTTGTTCAATAAATGGCTTCAAAGACATAAAGG
ATCACCCATTTTTCTCAAACTTTTAATTGGGATAAATTGGCTGGTCGTTTGCTTGATCCGCCTTTAGTATC
AAAAAGTGAAACTTATGCAGAAGATATTGATATTAAACAAATAGAGGAGGAGGATGCTGAGGATGATGAG
GAACCATTGAACGATGAAGACAACTGGGACATAGATTTTTAA (SEQ ID NO: 75)

Full Sequence: 1-853 amino acids
MEEDDNLKKGNERNKKKAIFSNDDFTGEDSLMEDHLELREKLSEDIDMIKTSLKNNLVCSTLNDNEILTL
SNYMQFFVFKSGNLVIKQGEKGSYFFIINSGKFDVYVNDKKVKTMGKGSSFGEAALIHNTQRSATIIAET
DGTLWGVQRSTFRATLKQLSNRNFNENRTFIDSVSVFDMLTEAQKNMITNACVIQNFKSGETIVKQGDYG
DVLYILKEGKATVYINDEEIRVLEKGSYFGERALLYDEPRSATIIAKEPTACASICRKLLNIVLGNLQVV
LFRNIMTEALQQSEIFKQFSGDQLNDLADTAIVRDYPANYNILHKDKVKSVKYIIVLEGKVELFLDDTSI
GILSRGMSFGDQYVLNQKQPFKHTIKSLEVCKIALITETCLADCLGNNNIDASIDYNNKKSIIKKMYIFR
YLTDKQCNLLIEAFRTTRYEEGDYIIQEGEVGSRFYIIKNGEVEIVKNKKRLRTLGKNDYFGERALLYDE
PRTASVISKVNNVECWFVDKSVFLQIIQGPMLAHLEERIKMQDTKVEMDELETERIIGRGTFGTVKLVHH
KPTKIRYALKCVSKRSIINLNQQNNIKLEREITAENDHPFIIRLVRTFKDSKYFYFLTELVTGGELYDAI
RKLGLLSKSQAQFYLGSIILAIEYLHERNIVYRDLKPENILLDKQGYVKLIDFGCAKKVQGRAYTLVGTP
HYMAPEVILGKGYGCTVDIWALGICLYEFICGPLPFGNDEEDQLEIFRDILTGQLTFPDYVTDTDSINLM
KRLLCRLPQGRIGCSINGFKDIKDHPFFSNFNWDKLAGRLLDPPLVSKSETYAEDIDIKQIEEEDAEDDE
EPLNDEDNWDIDF (SEQ ID NO: 76)
```

Underlined amino acid sequences and cDNA nucleic acid sequences correspond to immunorelevant regions of the gene products and nucleic acids encoding them. The antigenic fragments (polypeptides) were identified by virtue of binding of antibodies from patients that are resistant to malaria.

The invention encompasses "fragments" and "peptides" of SEQ ID NOs: 2, 3, 6, 7, 10, 11, 14, 15, 18, 19, 22, 23, 26, 27, 30, 31, 34, 35, 38, 39, 42, or 43, 47, 67, 70, 74, or 76 preferably, the clone 2 polypeptide or the PF10_0212a polypeptide (a.k.a., PfSEP-1A; SEQ ID NO:2) described herein. Such peptides represent portions of the polypeptide that have, for example, specific immunogenic or binding properties. A fragment can be between 3-10 amino acids, 10-20 amino acids, 20-40 amino acids, 40-56 amino acids in length or even longer. Amino acid sequences having at least 70% amino acid identity, preferably at least 80% amino acid identity, more preferably at least 90% identity, and most preferably 95% identity to the fragments described herein are also included within the scope of the present invention.

Furthermore, the present invention encompasses fragments and derivatives of the nucleic acid sequences of the present invention, as well as fragments and portions of the amino acid sequences of the present invention.

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleobases, sugars and covalent internucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1. Variants do not encompass the native nucleotide sequence. Other variant polynucleotides include those that differ from SEQ ID NO: 1, but because of the redundancy of the genetic code, encode a polypeptide of SEQ ID No: 2, or amino acids 2-50 of SEQ ID No: 2, fragments of variants thereof.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

In general, a polypeptide variant preserves antigenic function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. comprising "A polypeptide variant" means a polypeptide having at least about 70% amino acid sequence identity with an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2 or SEQ ID NO:3. For example, polypeptide variants include those wherein one or more amino acid residues are added or deleted at the N- or C-terminus of the full-length native amino acid sequence. A polypeptide variant will have at least about 71%-75% amino acid sequence identity; at least about 76%-79% amino acid sequence identity; at least about 80% amino acid sequence identity, at least about 81% amino acid sequence identity, at least about 82%, 83%, 84%, 85%, 86%, 87%, 88%, 89%, 90%, 91%, 92%, 93%, 94%, 95%, 96%, 97%, 98% amino acid sequence identity and at least about 99% amino acid sequence identity with a full-length sequence. Ordinarily, variant polypeptides are at least about 10 amino acids in length, often at least about 20 amino acids in length, more often at least about 30, 40, 50, 60, 70, 80, 90, 100, 150, 200, or 300 amino acids in length, or more.

Useful conservative substitutions are shown in Table 2 below. Conservative substitutions whereby an amino acid of one class is replaced with another amino acid of the same type fall within the scope of the subject invention so long as the substitution does not materially alter the biological activity of the compound.

TABLE 2

Exemplary substitutions

| Original residue | Exemplary substitutions | Preferred substitutions |
|---|---|---|
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp W) | Tyr, Phe | Tyr |
| Tyr (Y) | Trp, Phe, Thr, Ser | Phe |
| Val (V) | Ile, Leu, Met, Phe, Ala, Norleucine | Leu |

The polypeptides of the invention can be either synthesized in vitro or expressed recombinantly from the polynucleotide sequences. Because of redundancy in the genetic code, the sequences need not be identical to practice the invention. Polynucleotide and polypeptide sequence identities can be from 70%-100%, such as 70%, 75%, 80%, 81%, 82%, 83%, 84%, 85%, 86%, 87%, 88%, 89%, 90%, 91%, 92%, 93%, 94%, 95%, 96%, 97%, 98%, 99% and of course, 100%.

The polypeptides of the invention can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

The side chains of many amino acids contain chemically reactive groups, such as amines, alcohols, or thiols. These side chains must be additionally protected to prevent undesired side-reactions during the coupling step. Side chain protecting groups that are base-stable, more preferably, both base-stabile and acid-labile are most useful.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nts long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

Vaccine Compositions

The present invention is further directed to an immunogenic composition, e.g., a vaccine composition capable of blocking *P. falciparum* infection, for example a peptide vaccine or a DNA vaccine capable of blocking Schizont rupture at blood stage infection. The vaccine composition comprises one or more of the polypeptides, the nucleic acid sequences, or antigens thereof, as described herein.

A person skilled in the art will be able to select preferred peptides, polypeptides, nucleic acid sequences or combination of thereof by testing, e.g., the blocking of the Schizont rupture or parasite egress from RBCs in vitro. Peptide(s) with the desired activity are then combined as a vaccine. A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides. Alternatively, a suitable vaccine will preferably contain between 1 and 20 nucleic acid sequences, more preferably 2, 3, 4, 5, 6, 7, 8, 9, 10, 11, 12, 13, 14, 15, 16, 17, 18, 19, or 20 different nucleic acid sequences, further preferred 6, 7, 8, 9, 10 11, 12, 13, or 14 different nucleic acid sequences, and most preferably 12, 13 or 14 different nucleic acid sequences.

Such a vaccine is used for active immunization of a mammal, for example, a human who risks being exposed to one or more *Plasmodium* antigens (for example, due to travel within a region in which malaria is prevalent). For example, the vaccine can contain at least one antigen selected from the group consisting of: 1) a *P. falciparum* antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 2) a *P. falciparum* antigen comprising a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3, or fragment thereof; 3) a *P. falciparum* antigen comprising a polypeptide consisting essentially of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 4) a *P. falciparum* antigen consisting of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 5) a nucleic acid sequence having at least 70% sequence identity with a nucleic acid sequence encoding any one of the peptides listed above, preferably SEQ ID NO: 1 or SEQ ID NO: 4; 6) a nucleic acid sequence having at least 70% to 99%, such as 80%, 85%, 90%, 91%, 92%, 93%, 94%, 95%, 96%, 97%, 98% and 99% sequence identity to a nucleic acid sequence encoding the listed polypeptides, preferably SEQ ID NO: 1 or SEQ ID NO: 4; 7) a nucleic acid sequence consisting essentially of the nucleic acid sequence sequences described above. and 8) a nucleic acid sequence described above, preferably SEQ ID NO: 1 or SEQ ID NO: 4. A fragment of these polypeptides can be approximately 8-56 amino acid residues, such as 8, 9, 10, 20, 30, 40, 50, 51, 52, 53, 54, 55, and 56 residues. A fragment of these nucleic acid sequences can be approximately 10-300 nucleotides, such as 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides.

Alternatively, if passive immunization is desired, one can administer one or more antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47 preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, and amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

The vaccine composition can further comprise an adjuvant and/or a carrier. Examples of useful adjuvants and carriers are given herein below. The peptides and/or polypeptides in the composition can be associated with a carrier such as e.g. a protein or an antigen-presenting cell such as e.g. a dendritic cell (DC) capable of presenting the peptide to a T-cell.

Adjuvants are any substance whose admixture into the vaccine composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to aluminium salts, Montanide ISA 206, Montanide ISA 50V, Montanide ISA 50, Montanide ISA-51, Montanide ISA-720, 1018 ISS, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Other examples of useful immunostimulatory agents include, but are not limited to, Toll-like Receptor (TLR) agonists such as chemically modified CpGs (e.g. CpR, Idera), Poly(I:C)(e.g. polyi:CI2U), non-CpG bacterial DNA or RNA as well as immunoactive small molecules, such as cyclophosphamide, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim). The vaccine may also contain a blocker of PD-L1 (CD274) binding to its receptor (PD-1) or to CD80 to prevent/inhibit the development of T regulatory cells (Treg) and thereby reducing the development of tolerance to the vaccine antigen. And exemplary PD-1 inhibitor is Bristol Meyers Squibb's BMS-936558 (also known as MDX-1106 and ONO-4538).

A vaccine composition according to the present invention may comprise more than one different adjuvants. Furthermore, the invention encompasses a therapeutic composition comprising any adjuvant substance including any of the above or combinations thereof. It is also contemplated that the peptide or polypeptide, and the adjuvant can be administered separately in any appropriate sequence.

A carrier may be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine composition according to the present invention additionally contains at least one antigen presenting cell.

In the case of a DNA vaccine, a nucleic acid comprising the sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1 or SEQ ID NO: 4 formulated in a eukaryotic vector for use as a vaccine that is administered to human subjects. The nucleotides encoding the antigen are operably linked promoter and other regulatory sequences in the vector. Such eukaryotic, e.g., mammalian vectors, are known in the art [e.g., pcDNA™ (Invitrogen) and vectors available from Vical Inc. (San Diego, CA)]. Other exemplary vectors, e.g., pNGVL4a, and derivatives thereof, are described in Moorty et al., 2003, Vaccine 21:1995-2002; Cebere et al., 2006, Vaccine 24:41-425; or Trimble et al., 2009, Clin. Cancer Res. 15:364-367; hereby incorporated by reference).

Recombinant Expression Vectors and Host Cells

The antigen of the present invention can be made by any recombinant method that provides the epitope of interest. Accordingly, another aspect of the invention pertains to vectors, preferably expression vectors, containing a nucleic acid encoding any clones of Table 1, such as a PF10_0212a or clone 2 protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PF10_0212a or clone 2 proteins, mutant forms of PF10_0212a or clone 2 (e.g., PfSEP-1A, SEQ ID NO:2), fusion proteins, etc.).

The recombinant expression vectors of the invention can be designed for expression of any of the polypeptides or polynucleotide sequences of the present invention in prokaryotic or eukaryotic cells. For example, any of the polypeptides or polynucleotide sequences of the present invention can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31 40), pMAL (New England Biolabs, Beverly, Mass.) and pRIT5 (Pharmacia, Piscataway, N.J.) that fuse glutathione S transferase (GST), maltose E binding protein, or protein A, respectively, to the target recombinant protein. Examples of suitable inducible non fusion *E. coli* expression vectors include pTrc (Amrann et al., (1988) Gene 69:301 315) and pET11d (Studier et al., GENE EXPRESSION TECHNOLOGY: METHODS IN ENZYMOLOGY 185, Academic Press, San Diego, Calif. (1990) 60 89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119 128. Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111 2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari, et al., (1987) EMBO J 6:229 234), pMFa (Kurjan and Herskowitz, (1982) Cell 30:933 943), pJRY88 (Schultz et al., (1987) Gene 54:113 123), pYES2 (Invitrogen Corporation, San Diego, Calif.), and picZ (InVitrogen Corp, San Diego, Calif.).

Alternatively, any of the polypeptides or polynucleotide sequences of the present invention can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156 2165) and the pVL series (Lucklow and Summers (1989) Virology 170:31 39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187 195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue specific regulatory elements are used to express the nucleic acid). Tissue specific regulatory elements are known in the art. Non limiting examples of suitable tissue specific promoters include the albumin promoter (liver specific; Pinkert et al. (1987) Genes Dev 1:268 277), lymphoid specific promoters (Calame and Eaton (1988) Adv Immunol 43:235 275), in particular promoters of T cell receptors (Winoto and Baltimore (1989) EMBO J 8:729 733) and immunoglobulins (Banerji et al. (1983) Cell 33:729 740; Queen and Baltimore (1983) Cell 33:741 748), neuron specific promoters (e.g., the neurofilament promoter; Byrne and Ruddle (1989) PNAS 86:5473 5477), pancreas specific promoters (Edlund et al. (1985) Science 230:912 916), and mammary gland specific promoters (e.g., milk whey promoter; U.S. Pat. No. 4,873,316 and European Application Publication No. 264,166). Developmentally regulated promoters are also encompassed, e.g., the murine hox promoters (Kessel and Gruss (1990) Science 249:374 379) and the α-fetoprotein promoter (Campes and Tilghman (1989) Genes Dev 3:537 546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to mRNA of any of the polynucleotide sequences of the present invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, any of the polypeptides or polynucleotide sequences of the present invention can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art recognized techniques for introducing foreign nucleic acid (e.g., DNA) into a host cell, including calcium phosphate or calcium chloride co precipitation, DEAE dextran mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. Transfection may be "stable" (i.e. integration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding any of the polypeptides or polynucleotide sequences of the present invention can be introduced on a separate vector. Cells stably transfected with the introduced nucleic acid can be identified by drug selection (e.g., cells that have incorporated the selectable marker gene will survive, while the other cells die). In a specific embodiment, the promoter is the insulin promoter driving the expression of green fluorescent protein (GFP).

In one embodiment nucleic acid of any of the polypeptides or polynucleotide sequences of the present invention is present in a viral vector. In another embodiment the nucleic acid is encapsulated in a virus. In some embodiments the virus preferably infects pluripotent cells of various tissue types, e.g. hematopoietic stem, cells, neuronal stem cells, hepatic stem cells or embryonic stem cells, preferably the virus is hepatropic. By "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

"Recombinant" refers to an artificial combination of two otherwise separated segments of sequence, e.g., by chemical synthesis or by the manipulation of isolated segments of nucleic acids by genetic engineering techniques.

A transgenic mammal can also be used in order to express the protein of interest encoded by one or both of the above-described nucleic acid sequences. More specifically, once the above-described construct is created, it can be inserted into the pronucleus of an embryo. The embryo can then be implanted into a recipient female. Alternatively, a nuclear transfer method could also be utilized (Schnieke et al., 1997). Gestation and birth are then permitted to occur (see, e.g., U.S. Pat. Nos. 5,750,176 and 5,700,671), and milk, tissue or other fluid samples from the offspring should then contain the protein of interest. The mammal utilized as the host can be selected from the group consisting of, for example, a mouse, a rat, a rabbit, a pig, a goat, a sheep, a horse and a cow. However, any mammal can be used provided it has the ability to incorporate DNA encoding the protein of interest into its genome.

Therapeutic Methods

The invention further provides a method of inducing a *P. falciparum* specific immune response in a subject, vaccinating against malaria, treating and or alleviating a symptom of malaria in a subject by administering the subject a peptide or vaccine composition of the invention.

The subject has been diagnosed with malaria or is at risk of developing malaria. The subject has resistant malaria. The subject is a human, dog, cat, horse or any animal in which a *P. falciparum* specific immune response is desired. Preferably, the subject is a child under 5 years old of age. More preferably, the subject is at least about 6-8 weeks old of age.

The peptide or composition of the invention is administered in an amount sufficient to induce an immune response.

The invention provides methods of treating or prevention malaria by administering to a subject one or more peptides of the instant invention. The antigen peptide, polypeptide, nucleic acid sequences or vaccine composition of the invention can be administered alone or in combination with one or more therapeutic agents. The therapeutic agent is, for example, one, two, three, four, or more additional vaccines, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antigen peptide, polypeptide, nucleic acid sequences, or vaccine composition of the invention can be administered prior to, concurrently, or after other therapeutic agents.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. For example, doses of between 1 and 500 mg 50 µg and 1.5 mg, preferably 125 µg to 500 µg, of peptide or DNA may be given and will depend from the respective peptide or DNA. Doses of this range were successfully used in previous trials (Brunsvig P F, et al., Cancer Immunol Immunother. 2006; 55(12):1553-1564; M. Staehler, et al., ASCO meeting 2007; Abstract No 3017). Other methods of administration of the vaccine composition are known to those skilled in the art.

Pharmaceutical compositions comprising the peptide of the invention may be administered to an individual already suffering from malaria. In therapeutic applications, compositions are administered to a patient in an amount sufficient to elicit an effective immune response to the present antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition by measuring specific immune activity in the patient's blood.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. Preferably, the vaccine is administered intramuscularly. The invention provides compositions for parenteral administration which comprise a solution of the peptides and vaccine compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptide of the invention may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), USA U.S. Pat. Nos. 4,235,871, 4,501,728 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as USA U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); 5279833USA Rose U.S. Pat. Nos. 5,279,833; 9,106, 309WOAWO 91/06309; and Felgner et al., Proc. Natl. Acad. Sci. USA 84: 7413-7414 (1987).

The peptides and polypeptides of the invention can also be expressed by attenuated viral hosts, such as vaccinia or fowlpox. This approach involves the use of vaccinia virus as a vector to express nucleotide sequences that encode the peptide of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmo-* nella typhi vectors and the like, will be apparent to those skilled in the art from the description herein.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, 5, or more times, alone or in combination with 1, 2, 3, 4, or more additional vaccines in a subject, preferably a human subject.

Antibodies

"Antibody" (Ab) comprises single Abs directed against a target antigen (an anti-target antigen Ab), anti-target antigen Ab compositions with poly-epitope specificity, single chain anti-target antigen Abs, and fragments of anti-target antigen Abs. A "monoclonal antibody" (mAb) is obtained from a population of substantially homogeneous Abs, i.e., the individual Abs comprising the population are identical except for possible naturally-occurring mutations that can be present in minor amounts. Exemplary Abs include polyclonal (pAb), monoclonal (mAb), humanized, bi-specific (bsAb), and heteroconjugate Abs. The invention encompasses not only an intact monoclonal antibody, but also an immunologically-active antibody fragment, e. g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

Also provided herein are antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 6, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

Polyclonal Abs can be raised in a mammalian host by one or more injections of an immunogen and, if desired, an adjuvant. Monoclonal antibodies of the invention can be produced by any hybridoma liable to be formed according to classical methods from splenic or lymph node cells of an animal, particularly from a mouse or rat, immunized against the clone 2 polypeptides or peptides according to the invention.

The antigen and antibody of the present invention can be attached to a signal generating compound or "label". This signal generating compound or label is in itself detectable or can be reacted with one or more additional compounds to generate a detectable product. Examples of such signal generating compounds include chromogens, radioisotopes (e.g., $^{125}$I, $^{131}$I, $^{32}$P, $^{3}$H, $^{35}$S, and $^{14}$C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase,β-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Also provided herein is a method of treating P. falciparum malaria in a subject in need of by administering a therapeutically effective amount of an antibody described herewith to the subject. Preferably, the antibody is a purified monoclonal antibody, e.g., one that has been raised to and is specific for the protein of SEQ ID NO: 2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute P. falciparum malaria but has not responded to treatment with anti-malarial drugs. In this passive immunity approach, the purified humanized monoclonal antibody that binds specifically to the protein of clones of Table 1, preferably SEQ ID NO: 2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of P. falciparum malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

Kits

Kits are also included within the scope of the present invention. The present invention includes kits for determining the presence of antibodies to P. falciparum in a test sample. A kit can comprise: (a) a P. falciparum antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and (b) a conjugate comprising an antibody attached to a signal-generating compound capable of generating a detectable signal. The kit can also contain a control or calibrator which comprises a reagent which binds to the antigen. The P. falciparum antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47 preferably SEQ ID NO:2, SEQ ID NO:3, and amino acid residues 811-1083 of SEQ ID NO:3, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. Finally, the antigen can consist of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3.

The present invention also provides a pharmaceutical pack or kit comprising one or more containers filled with the vaccine in a form suitable for intramuscular administration or other routes of administration. The kits of the present invention may also contain one or more antibodies described herewith. Optionally the kit may contain disposable items, such as biodegradable items. The kit may also contain a sample collection means, including, but not limited to a needle for collecting blood, storage means for storing the collected sample, and for shipment. Alternatively, any kits of the present invention may contain an instruction for use to diagnose malaria or a receptacle for receiving subject derived bodily fluid or tissue.

The kit further comprises instructions for use or a CD, or CD-ROM with instructions on how to collect sample, ship sample, and means to interpret test results. The kit may also contain a control sample either positive or negative or a standard and/or an algorithmic device for assessing the results and additional reagents and components.

A "biological sample" is any bodily fluid or tissue sample obtained from a subject, including, but is not limited to, blood, blood serum, urine, and saliva.

The kit may further comprise one or more additional compounds to generate a detectable product. Examples of such signal generating compounds include chromogens, radioisotopes (e.g., $^{125}I$, $^{131}I$, $^{32}P$, $^{3}H$, $^{35}S$, and $^{14}C$), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, β-galactosidase, and ribonuclease).

By way of example, and not of limitation, examples of the present invention shall now be given.

Example 1: Antibodies to PfSEP-1 Block Parasite Egress from RBCs and Protect Subjects from Severe Malaria P. falciparum malaria is a leading cause of morbidity and mortality in developing countries, infecting hundreds of millions of individuals and killing over one million children in sub-Saharan Africa each year. Recent estimates indicate that even these staggering figures significantly underestimate the actual disease burden. Children suffer the greatest morbidity and mortality from malaria—yet this age group has not been targeted at the identification stage of vaccine development. Of the about 100 vaccine candidates currently under investigation, more than 60% are based on only four parasite antigens. New antigen candidates are urgently needed, but strategies to identify novel antigens are limited and many focus on rodent malarias.

Human residents of endemic areas develop protective immunity that limits parasitemia and disease, and naturally acquired human immunity provides an attractive model for vaccine antigen identification. Plasma from some chronically exposed individuals contains antibodies which limit parasite growth ex vivo and following adoptive transfer, a finding which confirms the protective efficacy of anti-parasite antibodies. One approach to identify and characterize new malarial vaccine candidate antigens is to identify malarial proteins that are uniquely recognized by antibodies in the plasma of chronically exposed, yet resistant individuals. Because of logistic difficulties in characterizing naturally acquired resistance in endemic populations, this approach has not been widely exploited.

Studies were carried out to identify vaccine candidates for pediatric falciparum malaria by identifying the parasite targets of naturally acquired protective human antibodies. A differential, whole proteome screening method using plasma and epidemiologic data from a birth cohort of children living in Tanzania was used to identify P. falciparum antigens associated with resistance in two-year old children. Schizont Egress Protein-1 (PfSEP-1), a 244-kDa parasite antigen, which localizes to the schizont/parasitophorous vacuole membrane, Maurer's clefts and the inner leaflet of the RBC membrane was identified in schizont infected RBCs. Antibodies to PfSEP-1 decrease parasite replication by 60% by arresting schizont rupture. Active vaccination with rPb-SEP-1 resulted in a 4.5 fold reduction in parasitemia after challenge with *P. berghei* ANKA parasites. Children in the cohort experienced a dramatically increased incidence of severe malaria during periods with undetectable anti-PfSEP-1 antibody levels (45 cases/23,806 child weeks) compared to periods with detectable antibody levels (0 cases/1,688 child weeks). By blocking schizont egress, PfSEP-1 synergizes with vaccines targeting hepatocyte and red cell invasion.

Identification and In Vitro Evaluation of Vaccine Candidates

Figure 6:
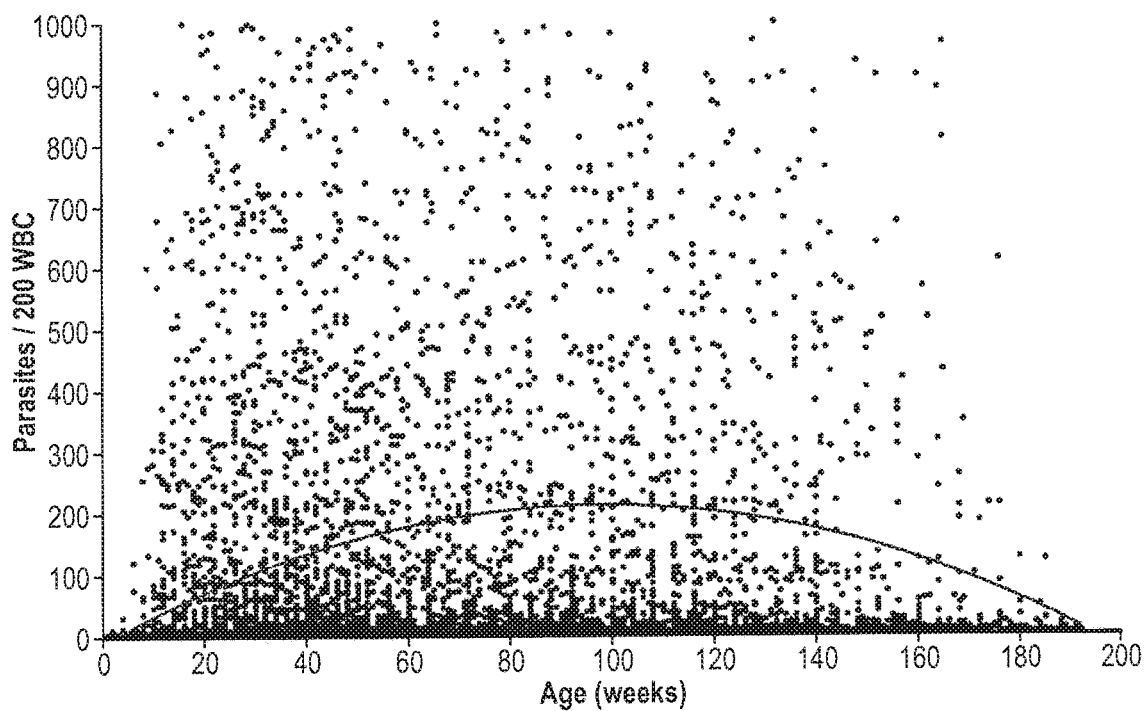
FIG. 6 is a dot plot showing the relationship between parasitemia and age for all available blood smears (n=34, 038). In multivariate regression analysis, both age (P<0.001) and age 2 (P<0.001) were related to parsitemia. Second degree (age and age 2) polynomial regression line is depicted in red. Vertical axis is truncated at 1000 parasites/200 WBC for clarity.
Figure 7:
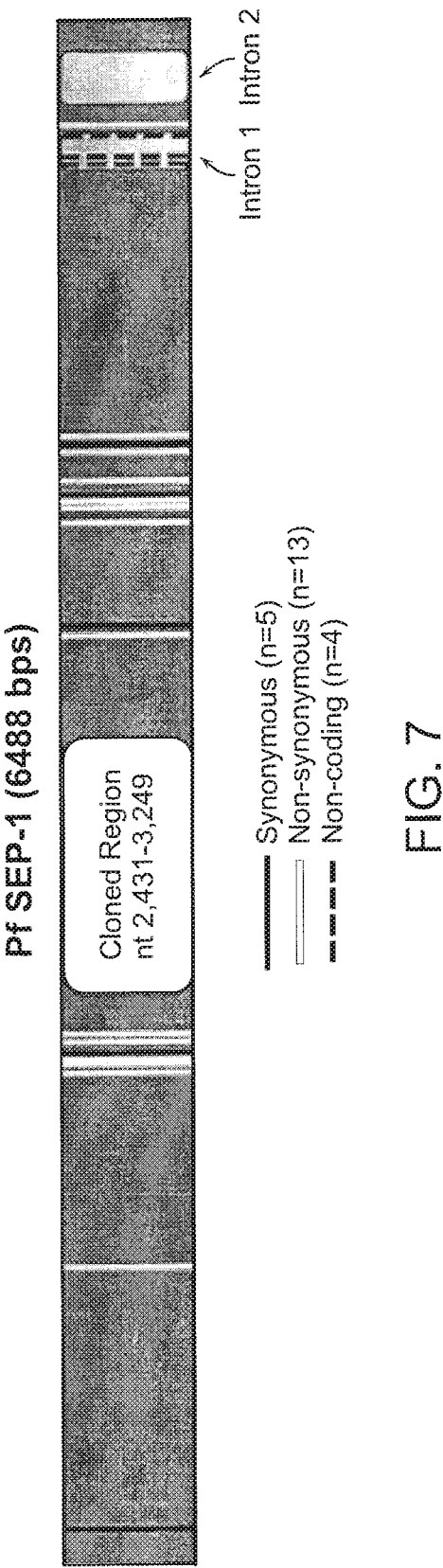
FIG. 7 is a diagram showing the location of SNPs in PfSEP-1. Data obtained from Plasmodb.org represent sequencing of fifteen lab and field isolates. No SNPs are reported in the region identified in the differential screening (nt 2,431-3,249).

Using a differential screening method, the *P. falciparum* blood stage proteome with plasma from resistant and susceptible two yr old children was interrogated to identify parasite proteins that are the targets of protective antibody responses. We focused on 2 yr old children because in our cohort, resistance to parasitemia is first detected at this age (FIG. 6). We selected twelve resistant and eleven susceptible 2 year old children with careful matching for potential non-immunologic factors, which may be related to resistance (see Table below and FIG. 16). Resistance was determined based on the geometric mean parasite density on all blood films collected between ages 2 and 3.5 yrs. We pooled plasma collected at age 2 yrs (+/−2 weeks) from the resistant individuals (RP) and susceptible individuals (SP) and performed differential screening experiments on a *P. falciparum* 3D7 strain blood stage cDNA library. We screened $1.25 \times 10^6$ clones and identified three clones that were uniquely recognized by RP, but not SP. The sequences of these clones were compared to the published *falciparum* genome (PlasmoDB.org) and found to encode nt 2,431-3,249 of PF3D7_1021800—a gene on chromosome 10, nt 3,490-5,412 of PF3D7 1134300—a gene on chromosome 11, and nt 201-1,052 of PF3D7 1335100—which encodes merozoite surface protein-7 (MSP-7)—a protein involved in RBC invasion which is currently under study as a potential vaccine candidate.

In silico analysis (PlasmoDB.org) predicts that PF3D7_1021800 contains a 6225 bp gene that encodes a 244-kDa acidic phospho-protein (SEQ ID NO:2), contains two introns near its 3' end, and has syntenic orthologs in all rodent and human malarias evaluated. Based on in vitro experiments, we designate the protein product of PF3D7_1021800 as *Plasmodium falciparum*: Schizont Egress Protein 1 (PfSEP-1). PF3D7_1021800 mRNA expression increases throughout blood stage schizogeny and the gene displays minimal sequence variation, with no SNPs in the cloned region (nt 2,431-3,249), across fifteen field and laboratory isolates (FIG. 16). A recently reported deep sequencing effort on 227 field samples identified 3 non-synonymous and 1 synonymous SNPs in the cloned region. We have sequenced nt 2,431-3,249 of PF3D7_1021800 in 6 field isolates obtained from children in our cohort and found one isolate with a six bp insertion (encoding Asp-Gly-Asp-Gly instead of the canonical Asp-Gly) as well as one synonymous SNP. These data indicate that there is little or no sequence variability among parasite strains.

Figure 8A:
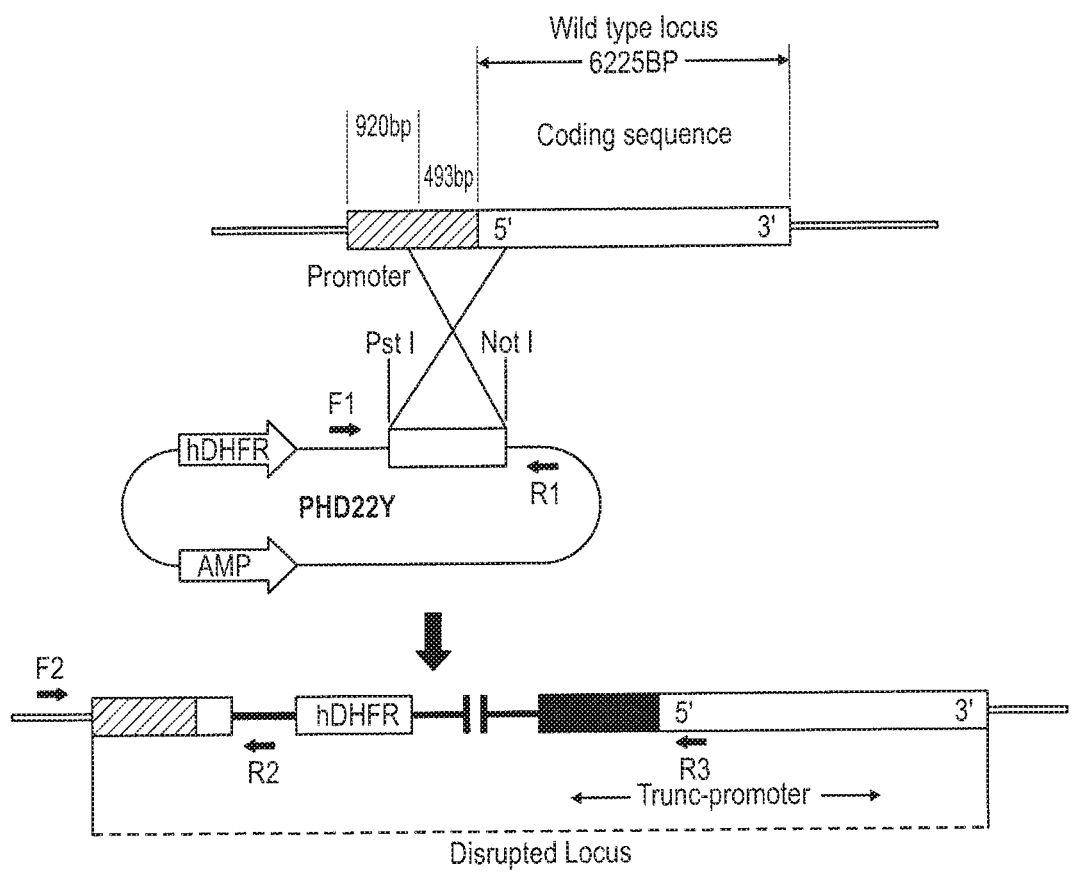
FIG. 8A-B are diagrams and FIG. 8C is a photograph of an electrophoretic gel. These figures show the knockdown and knockout strategy for PfSEP-1. A) targeting vector for knock down strategy designed to disrupt the promotor region, B) targeting vector for knock out strategy designed to disrupt protein coding region, C) Evaluation of drug resistant parasites for gene disruption. PCR amplification of drug selected parasites was carried out using: lane 1) F1 and R1 primers, lane 2) F2 and R2 primers and, lane 3) F2 and R3 primers. Only F1 and R1 primers amplified successfully indicating the presence of episomal, but not integrated vector.
Figure 8B:
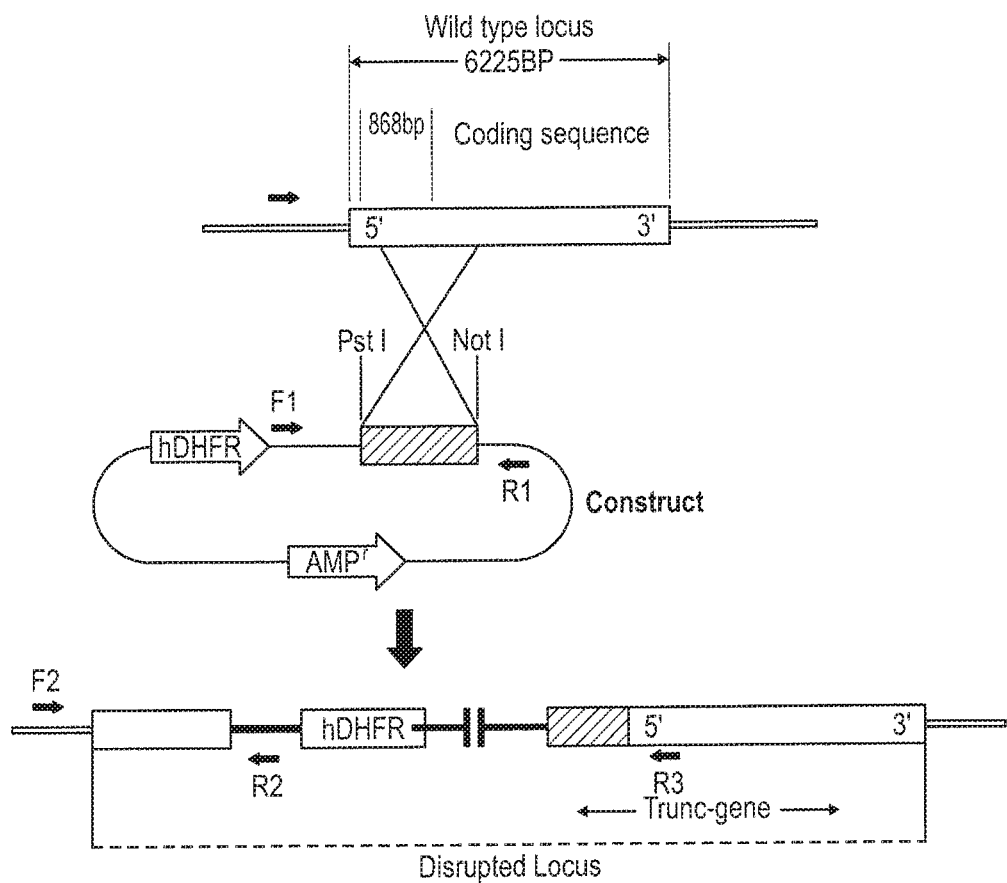
Figure 8C:
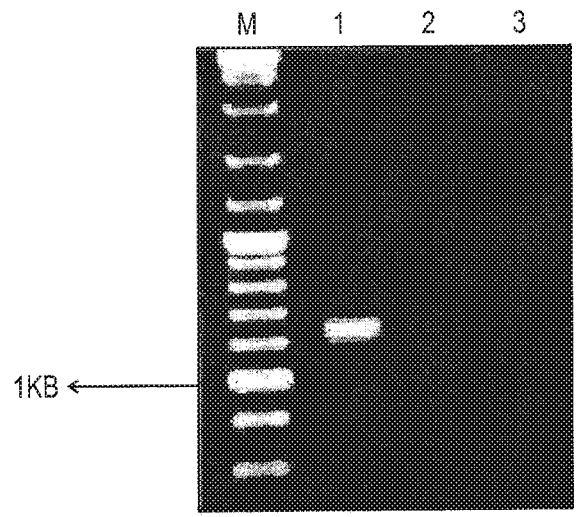

PfSEP-1 has no significant homology to proteins of known function. To explore the function of PfSEP-1, we have constructed vectors designed to disrupt the coding and promoter regions of the gene through the well described process of homologous recombination[9]. We have obtained episomal carriage of both targeting vectors, but have not recovered homologous integrants with either vector, suggesting that expression of PF3D7_1021800 is essential for blood stage replication (FIGS. 8A-C).

Figure 9:
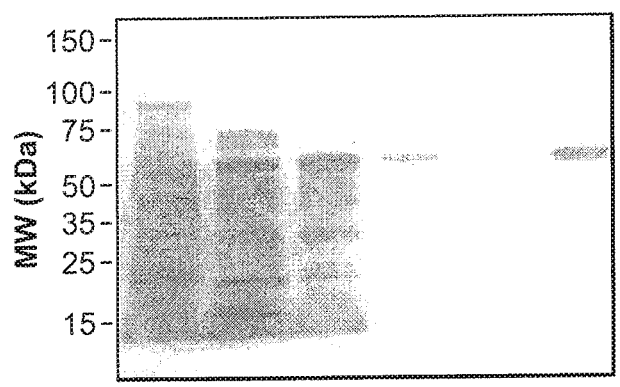
FIG. 9 is a photograph of an electrophoretic gel showing the results of chromatographic purification of rPfSEP-1A. Recombinant protein containing fractions were resolved on an 8-15% SDS PAGE-gel and stained with Gel-Code Blue. Lane 1) induced lysate, lane 2) nickel chelate chromatography of lane 1, lane 3) hydrophobic interaction chromatography of lane 2, lane 4) anion exchange chromatography of lane 3, lane 5) hydroxyappatite chromatography of lane 4, and lane 6) rPfSEP-1A post-tangential flow filtration, lyophilization and reconstitution.
Figure 10:
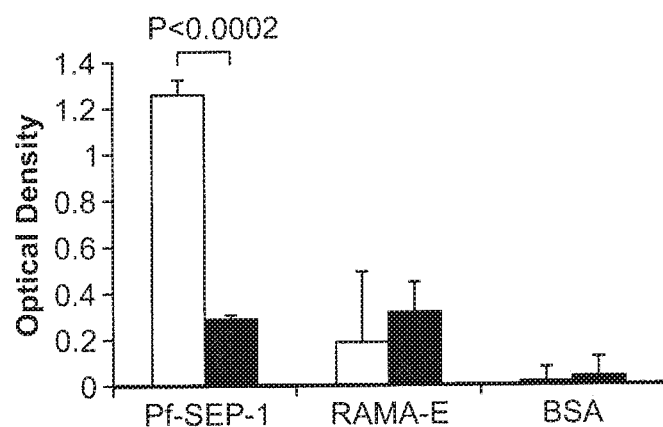
FIG. 10 is a bar graph showing differential recognition of rPfSEP-1A by IgG antibodies in plasma from resistant versus susceptible individuals. Antigen coated microtiter wells were probed with plasma pooled from resistant individuals (clear bars, n=11) or susceptible individuals (black bars, n=14, table S1) and bound antibody was detected with alkaline phosphatase conjugated goat anti-mouse IgG. RAMA-E is a P. falciparum merozoite protein, BSA is bovine serum albumin. Bars represent mean of 4 replicate wells. Error bars represent SEM. Recognition of rPfSEP-1A by antibodies in resistant plasma, as assessed by optical density, was 4.4 fold higher than by antibodies in susceptible plasma (Student's t-test, P<0.0002).

We have expressed and purified the polypeptide encoded by nt 2,431-3,249 of PF3D7_1021800 (aa 810-1083) in *E. coli* and designated this recombinant protein rPfSEP-1A (FIG. 9). Using an independent selection of resistant and susceptible individuals (see Table below), we confirmed and generalized the differential recognition of rPfSEP-1A (SEQ ID NO:2) in an ELISA based assay. IgG antibody recognition of rSEP-1A was 4.4 fold higher in RP (n=11) than in SP (n=14, P<0.0002, FIG. 10), yet did not differ for other malarial proteins or controls.

| Variable | Resistant | Susceptible | P value[a] |
| --- | --- | --- | --- |
| Number of Subjects | 12 | 11 | — |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smears from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [25.6] | 320.3 [944.1] | 0.05 |

[a]Comparisons of catagorical variables by 2 tailed Fisher's exact test.

Comparisons of continuous variables by Mann-Whitney U test

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smears from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [0] | 2106.9 [2700] | <0.001 |

Figure 11A:
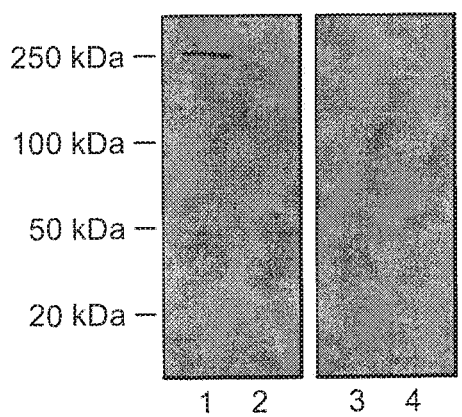
FIGS. 11A-B are photographs of electrophoretic gels showing that anti-Pf SEP-1 antibodies recognize a 244 kDa protein in *P. falciparum* extracts. Mixed stage 3D7 infected RBCs, uninfected RBCs and rPf SEP-1A were analyzed by western blot. A) lanes 1 and 3-3D7 infected RBC extracts, lanes 2 and 4-uninfected RBC extracts. Lanes 1 and 2-probed with anti-PfSEP-1 antisera (1:500), lanes 3 and 4-probed with pre-immune mouse sera (1:500). B) lanes 1 and 2-0.05 ug of rPfSEP-1A, lane 1-probed with anti-Pf SEP-1 mouse sera (1:2000), lane 2-probed with pre-immune mouse sera (1:2000).
Figure 11B:
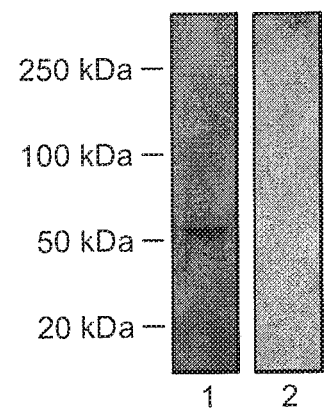
Figure 12A:
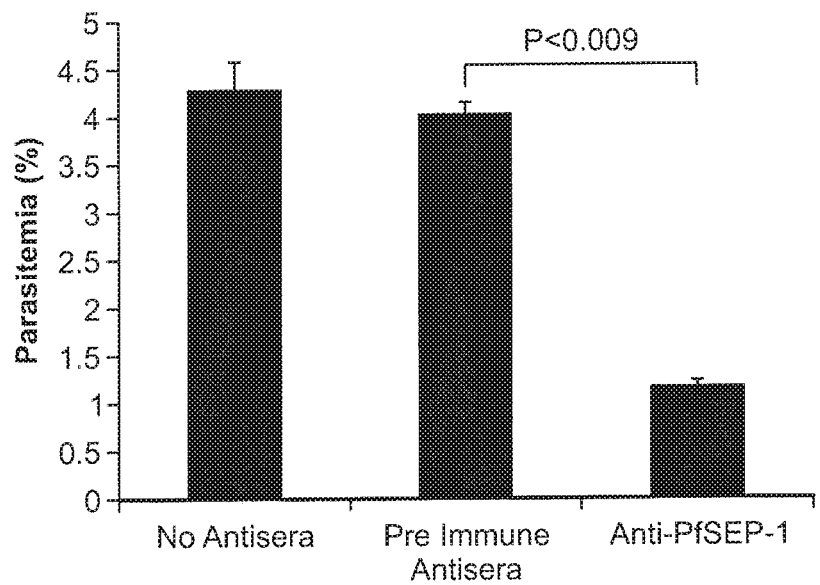
FIGS. 12A-B are bar graphs showing that anti-rPfSEP-1A antibodies generated by protein immunization inhibit parasite growth/invasion by 72-74% across 2 parasite strains in vitro. Ring stage 3D7 (A), and W2 (B) parasites were synchronized three times using sorbitol, plated at 0.3-0.4% parasitemia, and cultured to obtain mature trophozoites. Mature trophozoites were cultured in the presence of anti-rPfSEP-1A mouse sera (1:10 dilution). Negative controls included no mouse sera and pre-immune sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P<0.009 for comparison between pre and post immune mouse sera by non-parametric Mann-Whitney U test.
Figure 12B:
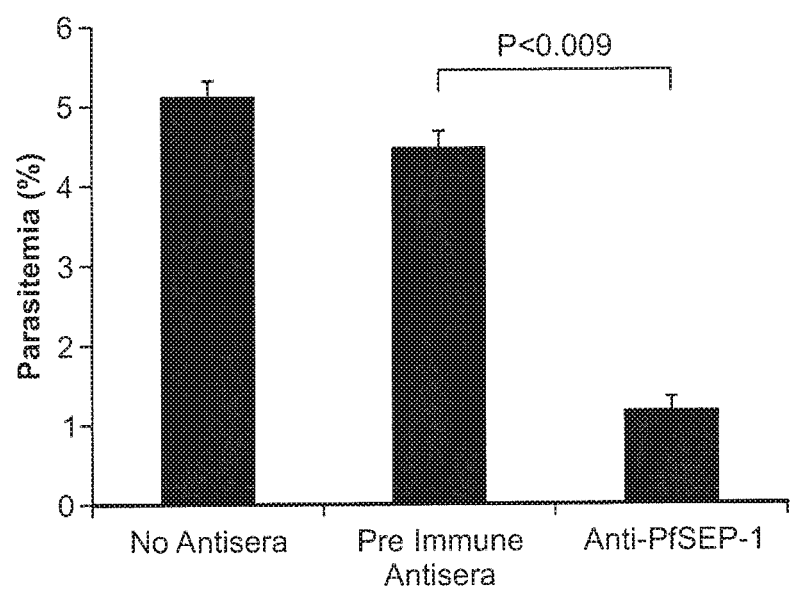

[a]Comparisons of catagorical variables by 2 tailed Fisher's exact test.
Comparisons of continuous variables by Mann-Whitney U test We have cloned this sequence into a eukaryotic expression plasmid (VR2001), immunized mice and generated anti-rPfSEP-1A anti-sera. To confirm that PF3D7_1021800 encodes a parasite protein, we probed P. falciparum 3D7 infected and uninfected RBCs with both pre-immune and post-immune sera. Anti-rPfSEP-1A recognized a 244-kDa protein in infected but not uninfected RBC (FIGS. 11A-B).

We performed growth inhibition assays using anti-rPfSEP-1A antisera prepared by both DNA vaccination and recombinant protein immunization. Parasites were synchronized to the ring stage, cultured to obtain mature trophozoites and then incubated with anti-rPfSEP-1A antisera or controls for 24 hr followed by enumeration of newly invaded ring stage parasites. Anti-rPfSEP-1A generated by both DNA plasmid and recombinant protein based immunization inhibited parasite growth by 58-75% across three parasite strains compared to controls (all P<0.009). Antisera prepared by DNA vaccination against an irrelevant falciparum protein (phosphatidylglycerophosphate synthase, PF3D7_0820200) showed no growth inhibition.

Figure 19:
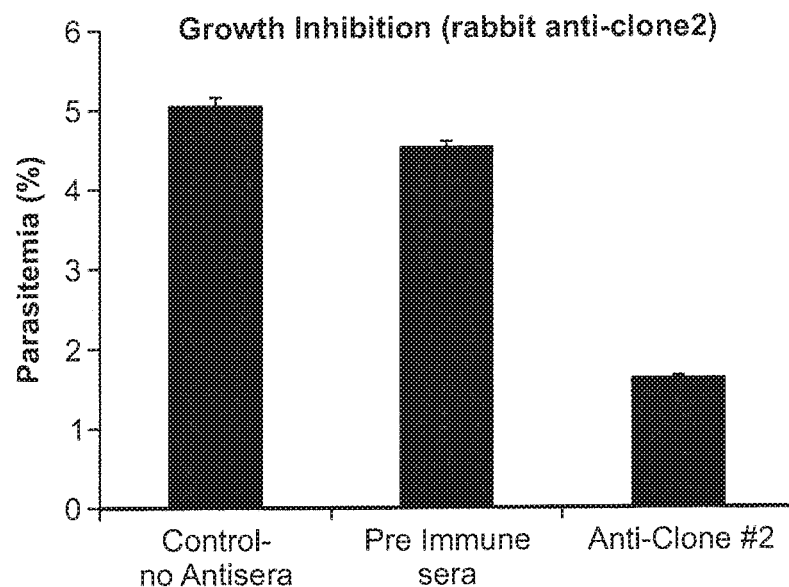
FIG. 19 is a bar graph showing growth inhibition assay. Rabbit anti-PfSEP-1 inhibits parasite growth/invasion by 68% in vitro.

As shown in FIG. 19, rabbit anti-PfSEP-1 inhibits parasite growth/invasion by 68% in vitro. Ring stage 3D7 parasites were synchronized twice using sorbitol plated at 1% parasitemia, allowed to mature to trophozoites (24 hrs), followed by addition of anti-clone 2 rabbit sera (1:10 dilution). Negative controls included no rabbit sera and pre-immune rabbit sera (1:10 dilution). Parasites were cultured for 24 hrs and ring stage parasites were enumerated by microscopic examination. Bars represent the mean of 3 independent replicates. Error bars represent SEMs. P<0.0001 for comparison between pre and post immune rabbit sera by nonparametric Mann-Whitney U test.

Figure 2A:
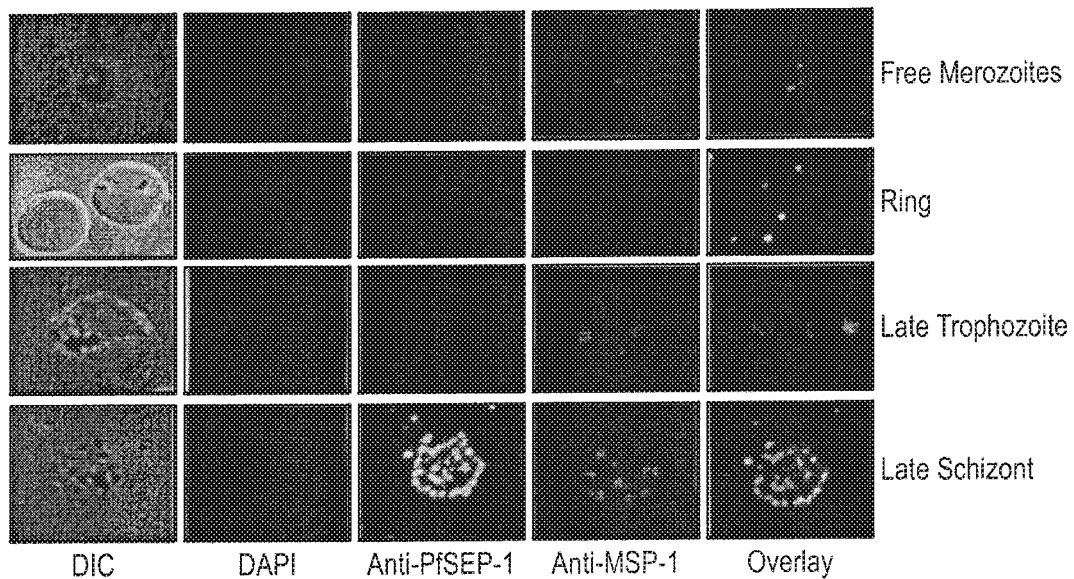
FIGS. 2A-D are photomicrographs showing immunolocalization of PfSEP-1. A) methanol fixed infected RBC were probed with mouse anti-PfSEP-1 (green) and rabbit anti-MSP-1 (red) and counterstained with DAPI to label parasite nuclei. PfSEP-1 is detected only in schizont infected RBCs, B) methanol fixed schizont infected RBCs do not label when probed with pre-immune mouse sera, C) non-permeabilized, non-fixed schizont infected RBCs were probed with mouse anti-PfSEP-1 (red) and rabbit anti-glycophorin A (green) and counterstained with DAPI to label parasite nuclei. PfSEP-1 co-localized with glycophorin A to the surface of schizont infected RBCs, D) non-permeabilized, non-fixed schizont infected RBCs were probed with mouse anti-PfSEP-1 (5 nm gold particles) and rabbit anti-glycophorin A (10 nm gold particles) and counterstained with uranyl acetate to enhance membrane contrast. PfSEP-1 localized to the schizont/parasitophorous vacuole membrane (black arrow), Maurer's clefts (yellow arrow) and the inner leaflet of the RBC membrane (grey arrow) while glycophorin A was confined to the outer leaflet of the RBC membrane (white arrow). Similar results were obtained when PfSEP-1 was detected with 18 nm gold particles.
Figure 2B:
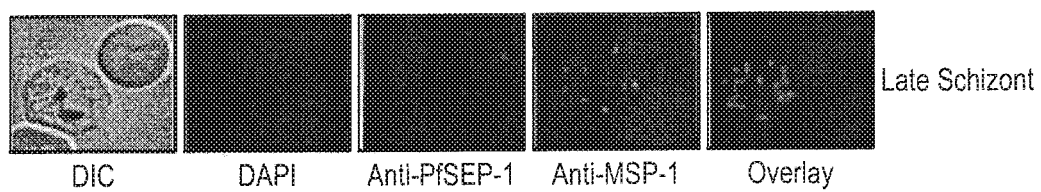
Figure 2C:
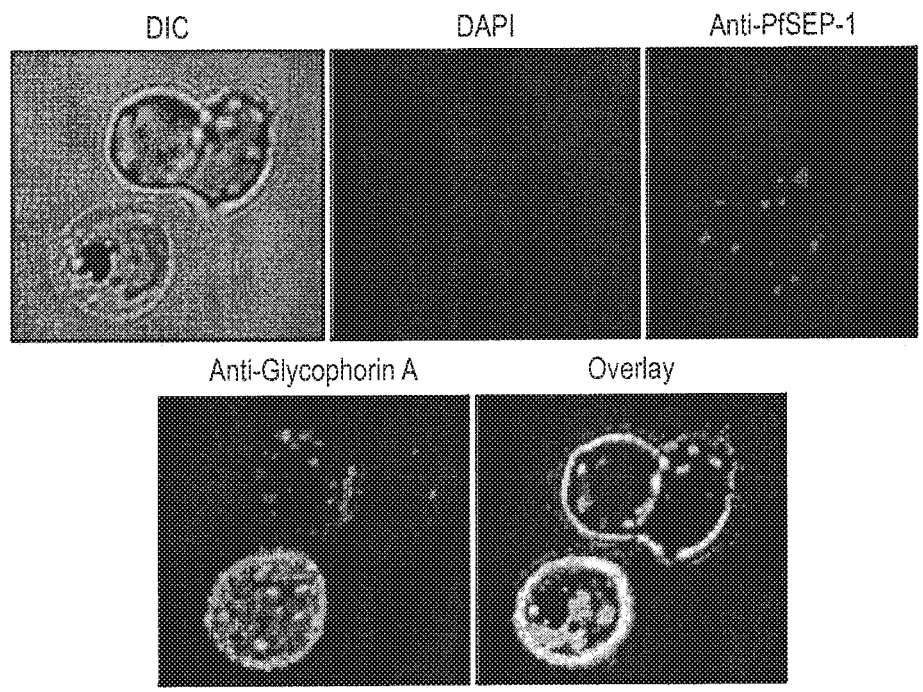
Figure 2D:
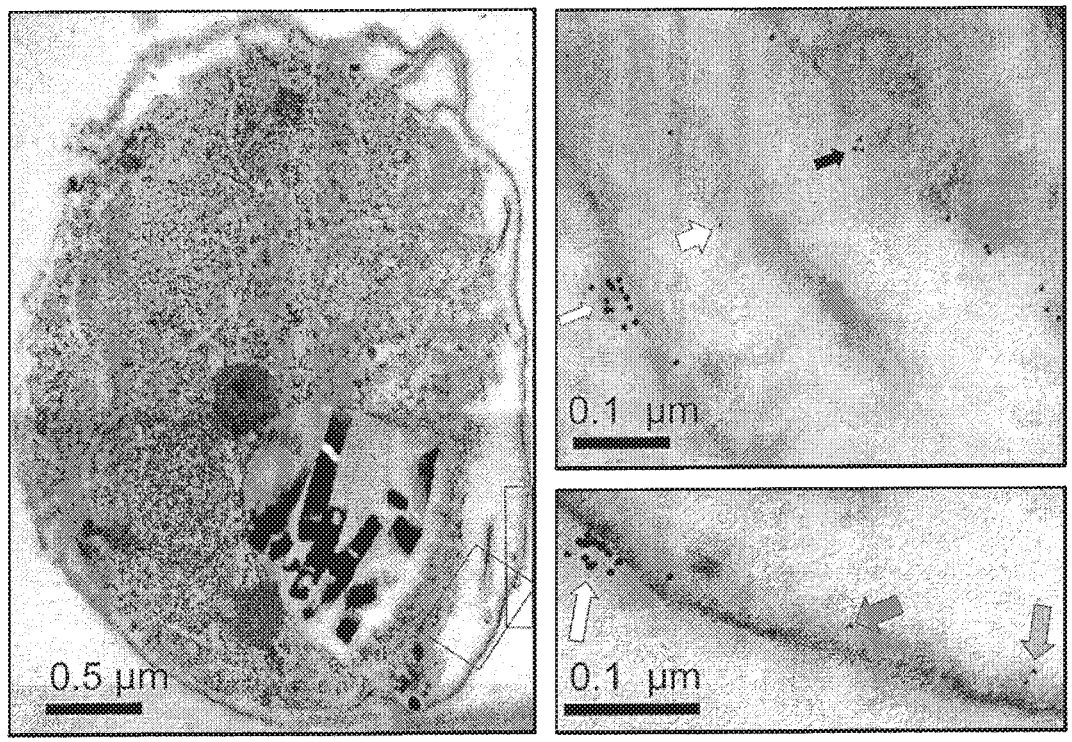

We immunolocalized PfSEP-1 by both immunofluorescence confocal microscopy and immunogold transmission electron microscopy (FIGS. 2A-C). Anti-PfSEP-1 did not bind to free merozoites, rings or late trophozoite stage parasites, but did specifically recognize an antigen expressed by late schizont infected RBC (FIGS. 2A-B). In non-permeabilized, non-fixed schizont infected RBCs, PfSEP-1 co-localized with glycophorin A (FIG. 2C). This localization was further evaluated by immunoelectron microscopy (FIG. 2D). In non-permeabilized, non-fixed schizont infected RBCs, PfSEP-1 localized to the schizont/parasitophorous vacuole membrane, Maurer's clefts and the inner leaflet of the RBC membrane while glycophorin A was confined to the outer leaflet of the RBC membrane. This pattern of staining was observed in essentially all of the late schizont infected RBCs examined. No staining for PfSEP-1 was observed in uninfected RBC or ring/trophozoite infected RBCs (FIGS. 13A-B). The close juxtaposition of these structures in late schizont infected RBCs with the RBC outer membrane explains the apparent co-localization of PfSEP-1 with glycophorin A observed by confocal microscopy. The accessibility of antibodies to PfSEP-1 in non-permeabilized, non-fixed schizont infected RBCs is consistent with the known permeability of parasitized RBCs at the later stages of schizogony.

Figure 3A:
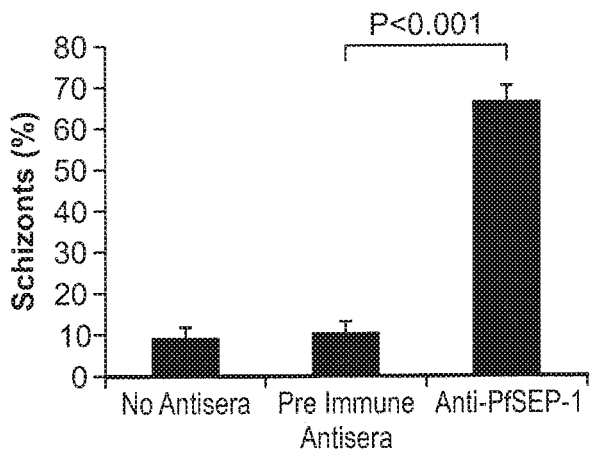
FIGS. 3A-C are bar graphs showing that anti-PfSEP-1 antibodies generated by DNA vaccination inhibit schizont egress across 3 parasite strains in vitro. Ring stage 3D7 (A), W2 (B) and D10 (C) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P<0.001 for comparison between pre and post immune mouse sera by non-parametric Mann-Whitney U test. Schizontemia was 5.3-6.8 fold higher in post versus pre-immune sera treated cultures.
Figure 3B:
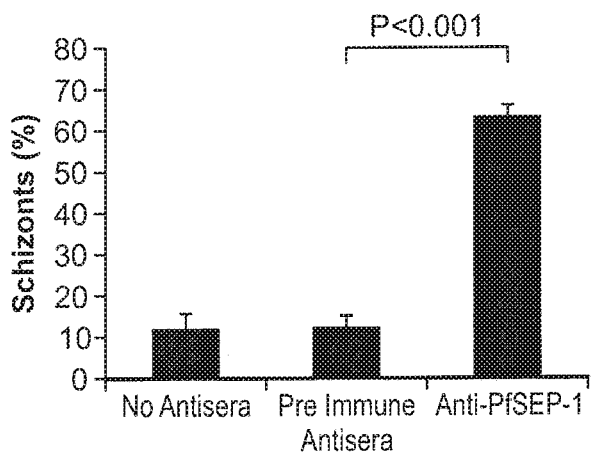
Figure 3C:
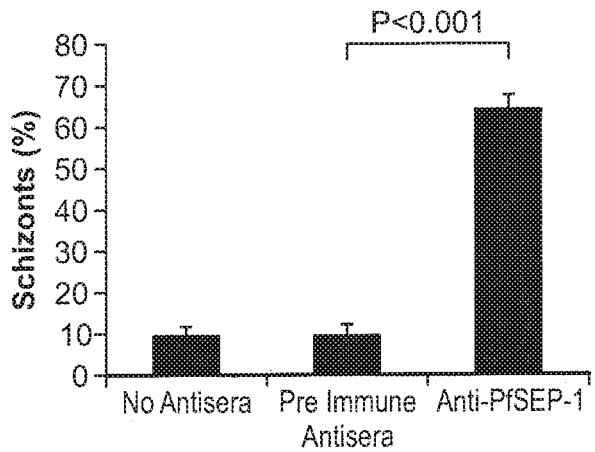
Figure 14A:
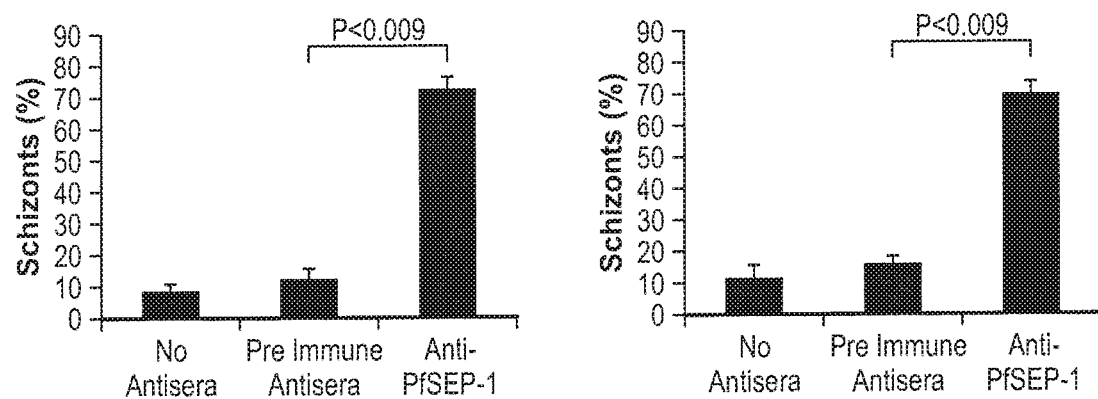
FIG. 14A is a bar graph.
Figure 14B:
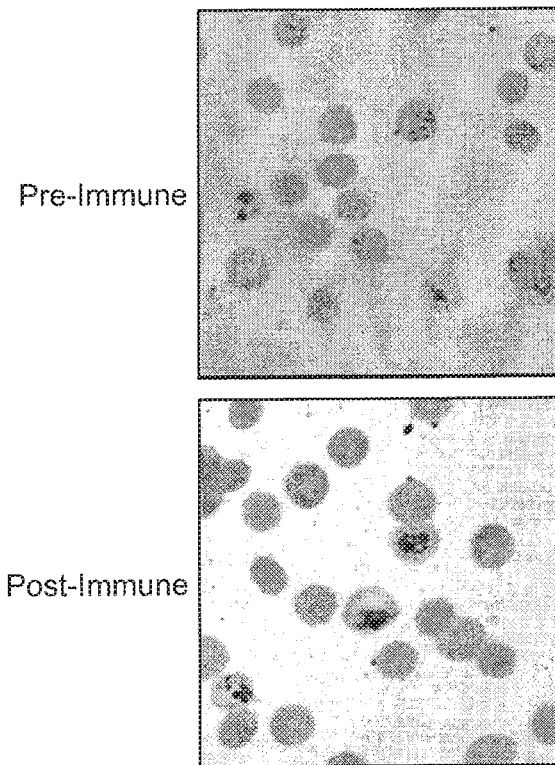
FIG. 14B is a photomicrograph showing that anti-rPfSEP-1A antibodies generated by protein immunization inhibit schizont egress across 2 parasite strains in vitro. A) Ring stage 3D7 (top panel), and W2 (bottom panel) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P<0.009 for comparison between pre and post immune mouse sera by non-parametric Mann-Whitney U test. Schizontemia was 4.3-6.0 fold higher in post versus pre-immune sera treated cultures. B) Representative micrographs of giemsa stained blood films prepared from 3D7 cultures treated with pre-immune (top panel) and post-immune (bottom panel) sera.

The localization of PfSEP-1 was not consistent with a role in RBC invasion, rather it suggested a role in parasite egress from infected RBCs. To determine the mechanism of growth inhibition we performed schizont arrest assays using anti-rPfSEP-1A antisera prepared by both DNA vaccination (FIG. 3A-C) and recombinant protein immunization (FIGS. 14A-B). Parasites were synchronized to the ring stage at high (3.5%) parasite density, cultured to obtain early schizonts and then incubated with anti-rPfSEP-1A antisera or controls for 12 hr followed by enumeration of remaining schizont stage parasites. Under these conditions, the majority of schizont infected RBCs should rupture, releasing merozoites, which would invade new RBCs and develop into ring stage parasites. Anti-rPfSEP-1A generated by both DNA plasmid and recombinant protein based immunization dramatically inhibited schizont egress resulting in 4.3-6.8 fold higher proportion of schizonts across three parasite strains compared to controls (all P<0.009).

Active Vaccination with SEP-1 Protects Mice from P. berghei Challenge

Figure 4A:
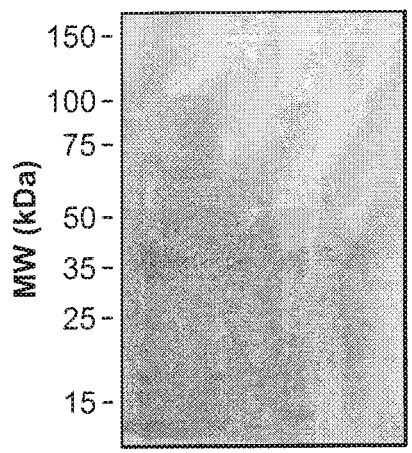
FIG. 4A is a photograph of an electrophoretic gel, FIG. 4 B is a bar graph showing antibody responses of mice vaccinated with rPbSEP-1A.
Figure 4B:
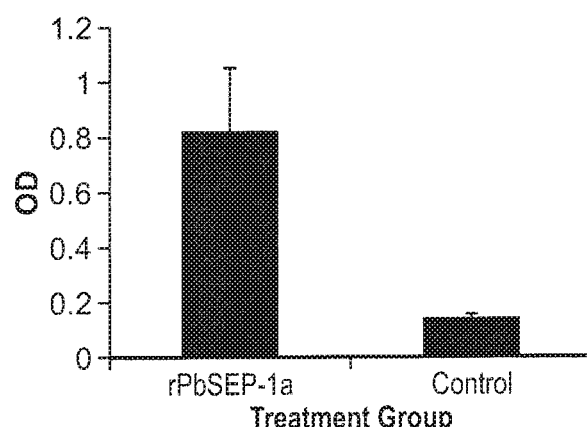
Figure 4C:
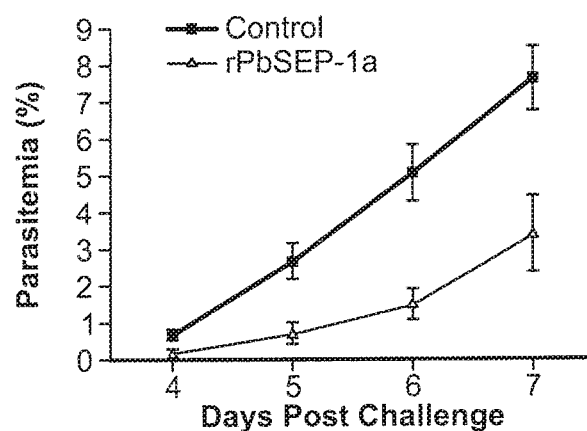
FIG. 4C is a line graph showing parasite burden.

To evaluate the protective efficacy of active vaccination with SEP-1 in vivo, we cloned the P. berghei ANKA strain ortholog of PfSEP-1 (nt 2173-3000) into the expression plasmid pET30 and expressed and purified rPbSEP-1A (aa 725-1000) from (FIG. 4A). We vaccinated Balb/C mice (n=11) with rPbSEP-1A in TiterMax Gold adjuvant or adjuvant alone (n=11), measured their antibody responses to rPbSEP-1A (FIG. 4B), and challenged them with $10^6$ P. berghei ANKA parasite infected red blood cells intraperitoneally. Mice vaccinated with rPbSEP-1A had 4.5 fold decreased parasitemia on day 7 post challenge compared to controls treated with adjuvant alone (FIG. 4C).

Human Antibody Responses to PfSEP-1

To evaluate the impact of naturally acquired anti-PfSEP-1 antibodies on clinical malaria, we measured anti-PfSEP-1 IgG antibody levels using a fluorescent, bead-based assay in our birth cohort and related these levels to subsequent malaria outcomes. We measured anti-PfSEP-1 IgG antibody levels in available plasma obtained at scheduled, non-sick visits between 2 and 3.5 yrs of life (total of 156 antibody measures on 155 children). Anti-PfSEP-1 antibodies were detectable in 3.2% of these samples and children were followed for a total of 6,350 child-weeks of observation (201 weeks with detectable anti-PfSEP-1 and 6,149 weeks with undetectable levels). We related the presence of detectable anti-PfSEP-1 antibodies to malarial outcomes, including parasite density, mild malaria, severe malaria, all cause and malaria attributed mortality. For each antibody measurement, the time interval examined for malaria outcomes extended from the time of the antibody measurement until the child had a subsequent antibody determination or completed the study.

We used generalized estimating equations (GEE) based longitudinal regression models to evaluate the relationship between time varying anti-PfSEP-1 antibody responses and dichotomous malaria endpoints. Similar GEE based linear regression models were used for the continuous endpoints of parasite density on all available blood smears and parasite density on positive blood smears. These models adjust for both potential confounders and the lack of independence (correlation) among observations taken from the same subject over time. Potential confounders included hemoglobin phenotype, age, and average prior parasitemia on all blood smears.

Figure 15A:
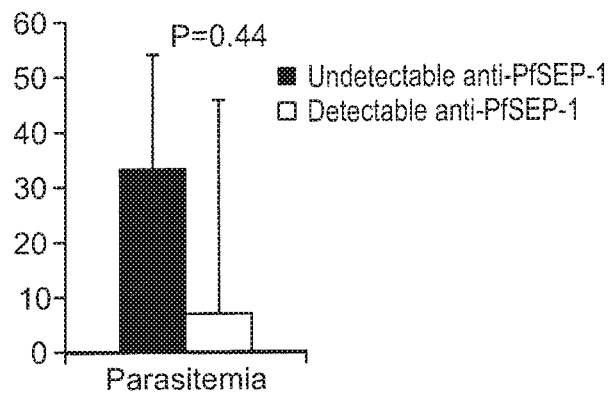
FIGS. 15A-C are bar graphs. Parasite density on A) all blood smears and B) positive blood smears in children aged 2-3.5 yrs during intervals with detectable and undetectable anti-PfSEP-1 antibodies, after adjusting for hemoglobin phenotype, age, average prior parasitemia on all blood smears, and repeated measures. Error bars represent SEM. C) Incidence of mild malaria in children aged 2-3.5 yrs of age during intervals with detectable and undetectable anti-PfSEP-1 antibodies after adjusting for hemoglobin phenotype, age, average prior parasitemia on all blood smears, and repeated measures. Error bars represent 95% CI.
Figure 15B:
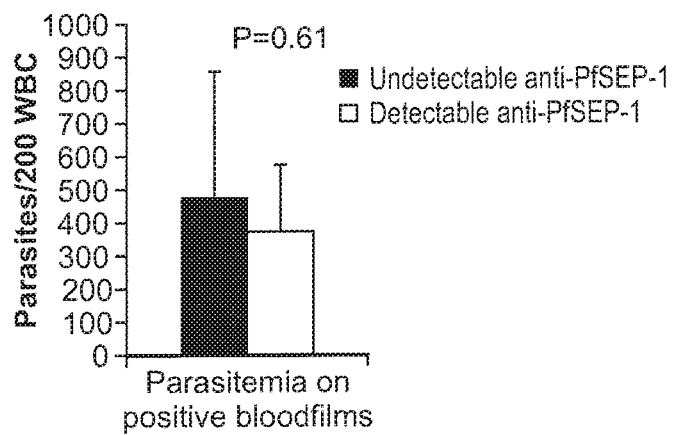
Figure 15C:
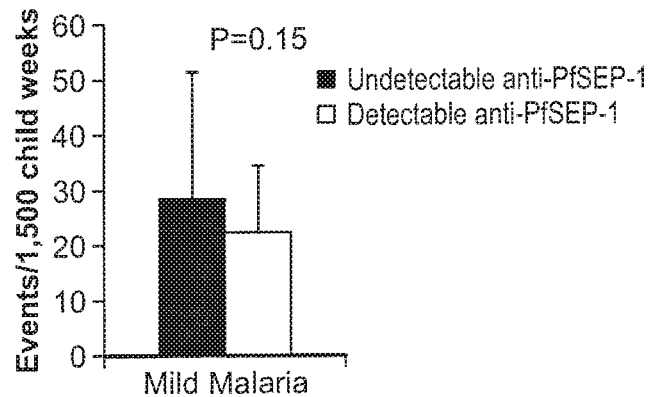

Children without detectable anti-PfSEP-1 IgG antibody had higher parasite densities on all available blood smears, higher parasite densities on positive blood smears, and increased incidence of mild malaria. (FIGS. 15A-C).

Figure 5:
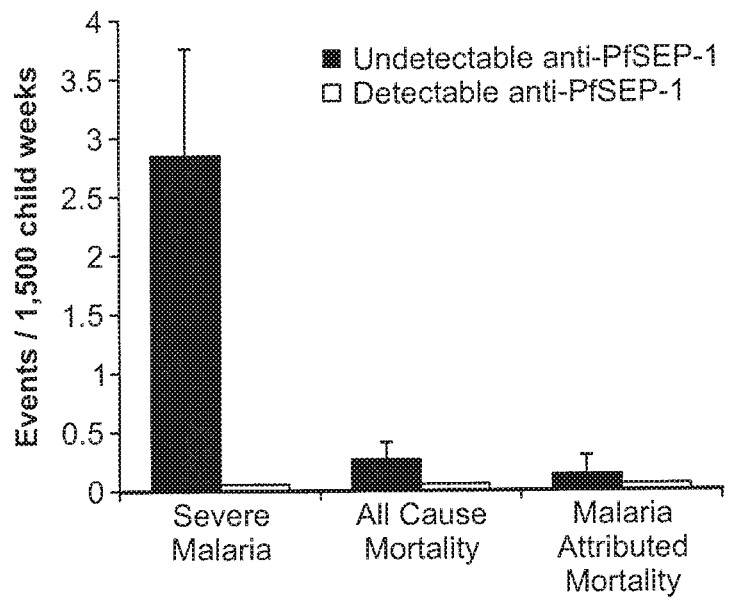
FIG. 5 is a line graph showing the incidence of severe malaria and death in children aged 1.5-3.5 yrs of age during intervals with detectable and undetectable anti-PfSEP-1 antibodies (1,688 and 23,806 weeks respectively). No cases of severe malaria or death occurred during intervals with detectable anti-PfSEP-1 antibodies. Error bars represent 95% CI adjusted for repeated measures.

Severe malaria did not occur during periods when children had detectable anti-PfSEP-1 antibody levels (0 cases/ 201 child weeks with detectable anti-PfSEP-1 antibody vs. 6 cases/6,149 child weeks with undetectable anti-PfSEP-1 antibody), however the small number of total cases precluded meaningful analysis. In our cohort, severe malaria is strongly age dependent with the majority of cases occurring before 2 yrs of age. To increase the number of severe malaria cases for analysis, we extended the age range examined to 1.5-3.5 yrs of life encompassing 687 antibody measures on 453 children. Anti-PfSEP-1 antibodies were detectable in 6.0% of these samples and children were followed for a total of 25,494 child-weeks of observation (1,688 child weeks with detectable anti-PfSEP-1 and 23,806 child weeks with undetectable levels). Strikingly, severe malaria did not occur during periods when children had detectable anti-PfSEP-1 antibody levels (0 cases/1,688 child weeks with detectable anti-PfSEP-1 antibody vs. 45 cases/23,806 child weeks with undetectable anti-PfSEP-1 antibody, FIG. 5).

Individuals without detectable anti-PfSEP-1 IgG antibody had significantly increased risk of developing severe clinical malaria (adjusted OR 4.4; Type III fixed effects P<0.01) compared to individuals with detectable anti-PfSEP-1 IgG antibody levels even after adjusting for potential confounders. There was no significant difference in the risk for all-cause mortality or malaria-associated mortality, though the event rates for mortality were low. These results represent the first demonstration that antibodies that specifically block schizont egress can protect against severe malaria in humans.

Blocking Parasite Egress Protects Against Malaria

*Falciparum* malaria remains a leading cause of childhood mortality and vaccines are urgently needed to attenuate this public health threat. We report the rational identification of vaccine candidates by identifying parasite proteins uniquely recognized by antibodies expressed by resistant, but not susceptible children. Using a differential screen, we identified two genes encoding useful vaccine antigens as well as MSP-7, a known vaccine candidate. We have extensively characterized PfSEP-1, the protein product of PF3D7 1021800. PfSEP-1 localizes to the schizont/parasitophorous vacuole membrane, Maurer's clefts and the inner leaflet of the RBC membrane in schizont infected RBCs. PfSEP-1 is accessible to antibodies during late schizogeny, and displays minimal sequence variation, particularly in the region identified by our differential screening experiments (aa 810- 1083; SEQ ID NO:2). Antibodies to PfSEP-1 significantly attenuate parasite growth via a unique mechanism; arresting schizont egress from infected RBCs without causing schizont agglutination.

Schizont egress is a complex tightly regulated process involving calcium dependent phosphorylation of parasite target proteins followed by proteolytic remodeling of parasite, as well as RBC cytoskeletal proteins. One of these proteolytic events involves SERA-5, the target of antibodies that agglutinate merozoites and schizonts and mediate schizont killing in cooperation with complement. Unlike SERA 5 and other proteins involved in schizont egress, PfSEP-1 was not identified in global profiles of proteolysis during schizont egress, and we did not observe any evidence of cleavage events within PfSEP-1 at any blood stage of development. The localization of PfSEP-1 to the inner RBC leaflet is consistent with a role in remodeling the RBC cytoskeleton prior to rupture.

In active vaccination experiments, rPbSEP-1A conferred marked protection against *P. berghei* ANKA challenge as evidenced by a 4.5 fold reduction in parasitemia seven days post-challenge. In addition, vaccination with rPbSEP-1A resulted in self-cure in one out of eleven vaccinated mice. These data constitute the first report of protection in *P. berghei* by vaccines targeting schizont egress and offer a pathway forward for advancing these vaccines toward non-human primate models.

In our longitudinal birth cohort, anti-PfSEP-1 antibodies were associated with significant protection from severe malaria, with no cases occurring while children had detectable anti-PfSEP-1 antibodies. This represents the first time that antibodies that specifically block schizont egress have been associated with protection from severe malaria. Under conditions of natural exposure, only 6% of 1.5 to 3.5 yr old children in our cohort had detectable anti-PfSEP-1 antibodies. This low natural prevalence suggests that adjuvanted vaccination with PfSEP-1 could have a marked impact on reducing severe malaria in young children.

The data validate the field-to-lab-to-field based strategy for the rational identification of vaccine candidates and indicate that PfSEP-1 is useful as a vaccine for pediatric *falciparum* malaria. By blocking schizont egress, PfSEP-1 synergizes with vaccines targeting hepatocyte and red cell invasion such as MSP-4, MSP-7, and/or RTSS.

The following materials and methods were used to generate the data described herein.

Study Population

Subjects participated in the Mother Offspring Malaria Studies (MOMS) project, which is based at Muheza Designated District Hospital (DDH), in north eastern Tanzania. Mothers presenting at Muheza DDH for delivery were enrolled and provided signed, informed consent prior to participation of themselves and their newborns in the study. Details of the MOMS study design, enrolment methods, and exclusion criteria have been described (Mutabingwa et al., PLoS Med 2, e407 (2005), and Kabyemela et al., J. Infect. Dis. 198, 163-166 (2008))

Inclusion Criteria and Clinical Monitoring

We monitored N=785 children for *P. falciparum* infection from birth up to 3.5 years of age. Children were evaluated at routine, well-child visits by a clinician every two weeks from birth to one year of age, and monthly thereafter, including blood smear analysis. Routine blood samples were collected once every 6 months from 1.5 to 3.5 years of life. Blood smears and blood samples were also collected any time the child became sick. Sick children were examined by a medical officer upon presentation to the hospital or mobile clinic. Treatment outside the study was minimized by active, weekly surveillance by our mobile clinics.

Clinical malaria was defined as asexual *P. falciparum* parasitemia by blood smear coupled with symptoms suggestive of malaria such as temperature >37.5° C., nausea or vomiting, irritability, and poor feeding. Prompt treatment was provided to sick children according to the guidelines of the Tanzanian Ministry of Health, and study participants were instructed to obtain all medications including antimalarials through the project staff.

Sample Collection and Processing

Venous blood was collected and stored at 4° C. until processing. Following centrifugation, plasma was stored at −80° C. *P. falciparum* parasitemia was determined by Giemsa-stained thick blood smears prepared from capillary or venous blood. Parasite density was expressed as the number of asexual stage parasites/200 white blood cells in the thick smear. Sickle cell trait was determined by electrophoresis (Helena Laboratories, Beaumont, TX USA). Hemograms were obtained on an impedance-based analyzer (Abbott Cell Dyne® 1200).

Case Definitions

Mild malaria was defined as a positive bloodsmear and one or more of the following: 1) anemia defined by Hgb<6 g/dL; 2) vomiting; 3) diarrheal disease or gastroenteritis; 4) lower respiratory infection; or 5) oral temperature >=38 deg C.

Severe malaria was defined as a positive bloodsmear and one or more of the following: 1) respiratory distress defined by respiratory rate of >40/min for children older than two months of age or a respiratory rate of >50/min for children less than two months of age; 2) a history of one or more convulsions in the twenty-four hours prior to or during hospitalization; 3) prostration defined by inability to sit unaided; 4) hypoglycemia defined by glucose <2.2 mmol/L; 5) severe anemia defined by Hgb<6 g/dL; or 6) oral temperature >40 deg C.

Malaria-associated mortality was defined as death with a positive blood film obtained during the terminal illness. One child who died of bacterial meningitis, but had a positive blood film was adjudicated as a non-malarial death.

Selection of Resistant and Susceptible Individuals

We excluded individuals with less than 9 of the total n=18 scheduled monthly blood smears collected between the ages of 2-3.5 yrs, individuals with less than 200 ul of plasma available from the plasma sample obtained at age 2 (+/−2 weeks), and individuals who were parasitemic at the time the 2 yrs (+/−2 weeks) plasma sample was obtained. We then rank ordered individuals based on the geometric mean parasite density on all blood films collected between ages 2 and 3.5 yrs. This mean parasite density included the scheduled monthly blood smears as well as positive blood smears obtained during sick visits. Ten individuals from the high and low extremes of this distribution were chosen to comprise the Resistant and Susceptible groups. Selections were made with matching based on village of residence, # of malaria-associated clinic visits, sex, and # of doses of anti-malarials. Potential confounders examined included: Hgb phenotype, presence of placental malaria, maternal age, birth season, use of bed nets, and # of previous pregnancies. A second, independent selection of resistant and susceptible individuals (table S2) was chosen for ELISA-based confirmatory assays.

Whole Proteome Differential Screening

We obtained a *P. falciparum* blood-stage cDNA expression library in Lambda Zap (MRA-299) from MR4. We plated this library at 25,000 clones/plate on 150 mm NZY plates in XL-1 Blue strain of *E. coli*. Duplicate IPTG-soaked nitrocellulose filters were prepared from each of 50 plates. Filters were blocked in 5% milk, TBS pH 7.4 (MTBS). Resistant plasma (RP) and susceptible plasma (SP) were diluted 1:100 in MTBS. Duplicate filters were probed with either RP or SP for 3 hr at 37 deg Celsius. Filters were washed 3×5 min in 0.05% Tween 20, TBS pH 7.4 (TTBS) and probed with alkaline phosphatase conjugated anti-human IgG diluted 1:5000 in MTBS for 1 hr at 37 deg Celsius. Filters were washed 3×5 min in TTBS. Filters were developed in BCIP/NBT. Clones which reacted with RP but not SP were cored out of their corresponding plate, eluted in SM buffer, re-plated and re-screened. Three rounds of plaque purification typically resulted in homogeneous clones which are reactive with RP but not reactive with SP. cDNA inserts uniquely reactive with RP were recovered by PCR amplification using vector specific primers and sequenced.

PfSEP-1A Expression and Purification

We subcloned the ORF encoding as 810-1083 of PfSEP-1 into pET30 (Novagen) and transformed the resulting plasmid into the expression host *E. coli* BL21(DE3) (Novagen). Transformants were grown in Terrific broth supplemented with 100 tig/mL kanamycin, at 37 deg C. in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20, 000 PSI (Microfluidics, Model 110-T). The lysate was clarified by tangential flow microfiltration (filter area 1m2, pore size 1 um, Milipore) and 8 L of clarified lysate was recovered.

Protein purification was achieved by a 4-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare)

column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]). Final purification was achieved by ceramic hydroxyapatite chromatography on a FineLine Pilot 35 (GE Healthcare) column containing 70 ml of CHT type 1 (BioRad). Recombinant proteins were eluted with a linear gradient of elution buffer (500 mmole/L potassium phosphate, and 1 mmole/L DTT, pH 7.4)

Purified rPfSEP-1A was buffer exchanged into 10 mmol/L sodium phosphate, 0.05% Tween 20, 3% sucrose and concentrated to 500 µg/ml by tangential flow ultrafiltration (filter area 50 cm2, pore size 5 kDa, Pall). rPFSEP-1A was lyophilized at 500 µg/vial and stoppered under nitrogen. Endotoxin levels were less than 2EU/mg protein as determined by an FDA cleared assay (Lonza). Typical yields are >50 mg rPfSEP-1A per 750 gr of wet cell paste.

PbSEP-1A Expression and Purification

We subcloned the ORF encoding as 725-1000 of PbSEP-1 into pET30 (Novagen) and transformed the resulting plasmid into the expression host $E.\ coli$ BL21(DE3) (Novagen). Transformants were grown in Terrific broth supplemented with 100 µg/mL kanamycin, at 37 deg C. in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20, 000 PSI (Microfluidics, Model 110-T). The lysate was clarified by tangential flow microfiltration (filter area 1m2, pore size 1 um, Milipore) and 8 L of clarified lysate was recovered.

Protein purification was achieved by a 3-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare) column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]).

Purified rPbSEP-1A was buffer exchanged into 10 mmol/L sodium phosphate, 0.05% Tween 20, 3% sucrose and concentrated to 125 µg/ml by tangential flow ultrafiltration (filter area 50 cm2, pore size 5 kDa, Pall). rPFSEP-1A was lyophilized at 125 µg/vial and stoppered under nitrogen. Endotoxin levels were less than 2EU/mg protein as determined by an FDA cleared assay (Lonza). Typical yields are >50 mg rPbSEP-1A per 750 gr of wet cell paste.

Parasite Strains and Culture $P.\ falciparum$ strains (3D7, D10, and W2) were obtained from MR4. The parasites were cultured in vitro according to the methods of Trager and Jensen with minor modifications 29. Briefly, parasites were maintained in RPMI 1640 medium containing 25 mm HEPES, 5% human 0+ erythrocytes, 0.5% Albumax II (Invitrogen) or 10% heat inactivated human AB+ serum, 24 mm sodium bicarbonate, and 10 µg/ml gentamycin at 37° C. with 5% CO2, 1% 02, and 94% N2.

$P.\ berghei$ ANKA was obtained from MR4 as a stabilite and was expanded in Balb/C mice prior to challenge studies.

Anti-PfSEP-1 Antisera Production

Mouse anti-PfSEP-1 antisera was produced by either DNA or recombinant protein immunization. For DNA immunization, we subcloned the ORF encoding as 810-1083 of PfSEP-1 into VR2001, transformed into the host $E.\ coli$ NovaBlue (Novagen), and purified endotoxin free plasmid (Endofree Giga, Qiagen). Balb/C mice were immunized with 180 µg of plasmid (50 ug intramuscular injection in each hind leg and 80 µg intradermal injection at base of tail) followed by 80 µg intradermal injections at base of tail every two weeks for a total of four doses. For protein immunization, we emulsified rPfSEP-1 in an equal volume of TiterMax adjuvant (CytRx Corporation) and injected 50 µg of rPfSEP-1 intraperitoneally at two week intervals for a total of four doses.

Western Blot

Parasite pellets were prepared by treatment of parasitized RBCs with 0.15% saponin in phosphate buffered saline (PBS), pH 7.4 on ice for 10 min followed by centrifugation (3,000×g, 5 min), and resuspension in cold PBS, and centrifugation (3,000×g, 5 min). Parasite pellets or rPfSEP-1A were dissolved in SDS sample loading buffer (Bio-Rad), heated to 95 deg C. for 10 min, and proteins were separated in 4-11% gradient SDS-PAGE gels. Separated proteins were transferred to nitrocellulose membranes which were blocked in 5% milk PBS (pH 7.4) and 0.05% Tween 20 for 1 h. Membranes were probed with polyclonal anti—PfSEP-1A or pre-immune mouse sera, detected by use of anti-mouse IgG antibody conjugated to alkaline phosphatase, and developed with 5-bromo-4-chloro-3-indolyl phosphate/nitro blue tetrazolium (Sigma).

SNP Detection in Field Isolates

We extracted DNA from filter paper containing dried blood spots obtained from six parasitemic children in our cohort (QIAmp DNA Blood Mini Kit, Qiagen). We amplified nt 2,431-3,249 of PF3D7_1021800 from extracted DNA using a nested PCR based approach. First round primers were: F1 5'-GAAGATGTTTGTCATAATAATAACGTG-GAAGACC-3' (SEQ ID NO: 49), R1 5'-TCCTACAA-CATCTATTTCTCCTGTGTAAGG-3'. (SEQ ID NO: 50) Second round primers were: F2 5'-GAATAAAAAAATG-GATGAGATGAAAG-3'(SEQ ID NO: 51), R2 5'-CTAT-TACTATCCTCATTTGCATCTGTATATTTATCC-3'(SEQ ID NO: 52). First round PCR conditions were: 10 min initial denature at 94 deg C. followed by 40 cycles of 45 sec at 94 deg C., 60 sec at 55 deg C., 90 sec at 70 deg C., extension at 70 deg C. for 10 min. Second round PCR conditions were: 10 min initial denature at 94 deg C. followed by 35 cycles of 45 sec at 94 deg C., 60 sec at 55 deg C., 60 sec at 70 deg C., extension at 70 deg C. for 10 min. DNA fragments were purified with Quickclean II PCR Kit (GenScript), cloned into pDrive (Qiagen) and sequenced.

PfSEP-1 Knock Out/Down Strategy

We constructed vectors designed to disrupt the promoter region (knockdown) and the coding region (knock-out) of the gene encoding PfSEP-1. For the knock-down construct, we amplified a 749 bp segment (−493-257 bp) from 3D7 genomic DNA using PCR forward primers 5'-GCACTGCAGAGCACTGAATAAATGAAATG-3'(SEQ ID NO: 53) and reverse primer 5'-GCAGCGGCCGCGTG-GATGCACCATCATCGAG-3' (SEQ ID NO: 54). For the knockout construct, we amplified a 868 bp segment (232-1099 bp) from 3D7 genomic DNA using PCR forward primers 5'-GCACTGCAGGAGTTATCTCGATGATGGTG-3' (SEQ ID NO: 55) and reverse primer 5'-GCAGCGGCCGCGATCCATGATATTAACATGGCTC-3'(SEQ ID NO: 56).

Amplified DNA fragments were digested with the restriction enzymes PstI and NotI and cloned into plasmid pHD22Y 30. The DNA sequences and location of all inserts were confirmed by using vector specific primers in the sequencing reaction which spanned the cloning region of the vector.

Asexual stages of W2 and 3D7 parasites were cultured as described above. The parasites were synchronized using 5% d-sorbitol, and schizont stages at 10% parasitemia were purified using a Percoll-sorbitol separation method 31. Uninfected RBCs were electroporated with 200 lag of supercoiled pHD22Y containing DNA inserts as described 9'32. Following transformation, purified schizonts were added to electroporated RBCs and were maintained in culture for 48 h before the addition of drug WR99210 (Sigma) to a final concentration of 5 nmole/L. Drug-resistant parasites appeared three to four weeks after transfection. Episomal carriage of plasmids in the drug resistant parasites was confirmed by PCR for both constructs using genomic DNA obtained from the drug resistant parasites and vector specific primers F 1 5'-CATGTTTTGTAATTTATGGGA-TAGCG-3'(SEQ ID NO: 57) and R1 5'-CGC-CAAGCTCGAAATTAACCCTCAC-3'(SEQ ID NO: 58). Six to eight weeks after transfection, we tested for chromosomal integration for both constructs by PCR using genomic DNA obtained from the drug resistant parasites and chromosomal and vector specific primers F2 5'-GCCA-CATATAATTCTTGTACTTGTC-3' (SEQ ID NO: 59) and R2 5'-CGAAATTAACCCTCACTAAAGG-3' (SEQ ID NO: 60) or R3 5'-GACAAGTACAAGAATTATATGTGGC-3' (SEQ ID NO: 61) for knockdown constructs, or F2 5'-GTAT-GATGGAAAATAAATACCCAAATG-3'(SEQ ID NO: 62) and R2 CGAAATTAACCCTCACTAAAGG-3' (SEQ ID NO: 63) or R3 5'-GACAAGTACAAGAATTATATGTGGC-3'(SEQ ID NO: 64) for knockout constructs (FIGS. 16A-C).

Anti-PfSEP-1 Antibody Assays

Initial, confirmatory antibody assays were performed with rPfSEP-1A coated ELISA plates according to known methods (FIG. 18).

To measure IgG anti-rPfSEP-1A antibody levels in the entire cohort, a bead-based assay was used. 100 lig of rPfSEP-1A or 100 ug of BSA was conjugated to 1.25×10⁷ microspheres (Luminex) and conjugated rPfSEP-1 and BSA beads were pooled and lyophilized in single use aliquots. Reconstituted beads were incubated for 30 min at 37 deg C. with human plasma samples at 1:80 dilution in Assay Buffer E (ABE, PBS pH 7.4 containing 0.1% BSA, 0.05% Tween-20, and 0.05% sodium azide) in microtiter filter bottom plates (Millipore). Beads were washed three times in ABE by vacuum filtration and incubated for 30 min at 37 deg C. with biotinylated anti-human IgG (Pharmingen) diluted 1:1000 in ABE. Beads were washed three times in ABE by vacuum filtration and incubated for 10 min at 37 deg C. with phycoerythrin conjugated streptavidin (Pharmingen) diluted 1:500 in ABE. Beads were washed three times in ABE by vacuum filtration, resuspended in ABE and analyzed on a BioPlex 200 multi-analyte analyzer. Fluorescence values for BSA beads were subtracted from rPfSEP-1A beads. The cut-off for detectable anti-PfSEP-1 antibody levels was defined as fluorescence values greater than the mean+2SD fluorescence level of 95 healthy North American children.

Growth Inhibition Assays

Growth inhibition assays (GIA) were carried out with anti-PfSEP-1 mouse sera or controls. Sera were dialyzed overnight in PBS, pH7.4, heat inactivated at 56° C. for 30 min and pre-incubated with human RBC for 1 hour before use in GIA assays. GIA assays were carried out using W2, 3D7 and D10 strains of P. falciparun. Parasites were synchronized to the ring stage by treatment with 5% sorbitol 34 for three successive replication cycles and cultured to the mature trophozoite stage. Parasites at 0.3-0.4% parasitemia and 2% hematocrit were incubated with anti-sera at a final concentration of 10% in a final volume of 100 µl in microtiter wells. Cultures were performed in triplicate with five replicates (comprising a total of 15 individual wells) prepared for each treatment condition. After 24 hr, blood films were prepared from each replicate, stained with Giemsa, ring stage parasites were enumerated, and the results from the three wells were averaged.

Schizont Arrest Assays

Schizont arrest assay (SAA) were carried out with anti-PfSEP-1 mouse sera or controls. Sera were dialyzed overnight in PBS, pH7.4, heat inactivated at 56° C. for 30 min and pre-incubated with human RBC for 1 hour before use in SAA assays. SAA assays were carried out using W2 and 3D7 strains of P. falciparum. Parasites were synchronized to the ring stage by treatment with 5% sorbitol 34 for three successive replication cycles and cultured to the early-schizont stage. Parasites at 3.5% parasitemia and 2% hematocrit, consisting mainly of early schizonts were incubated with anti-sera at a final concentration of 10% in a final volume of 100 pl in microtiter wells. Cultures were performed in triplicate with five replicates (comprising a total of 15 individual wells) prepared for each treatment condition. After 12 hr, blood films were prepared from each replicate, stained with Giemsa, schizont stage parasites were enumerated, and the results from the three wells were averaged.

Immunofluorescence Assays

Blood smears of asynchronous 3D7 strain parasite cultures were prepared, fixed in cold methanol for 15 minutes, and probed with anti-PfSEP-1 prepared by DNA vaccination, pre-immune sera, or rabbit anti-PfMSP-1 (MR4) diluted 1:200 in PBS, 5% BSA, pH 7.4. Blood smears were incubated with primary antibodies for 1 hr at 25 deg C., washed three times in PBS, 0.05% Tween-20 and incubated with goat anti-mouse IgG conjugated with Alexa fluor 488 (Molecular Probes) and goat anti-rabbit IgG conjugated with Alexa Fluor 594 (Molecular Probes). Blood smears were incubated for 10 minute in 1 lig/ml of 4',6'-diamino-2-phenylindole (DAPI, Sigma) to label nuclei and cover slipped with ProLong Gold anti-fade reagent (Invitrogen). Blood smears were imaged using a confocal microscope (Leica SP2, Leica Microsystems, Exton, PA) equipped with a 100×oil immersion objective and sequential Z-sections of the infected RBC were collected.

For localization of PfSEP-1 in late stage schizonts, we performed live cell staining and imaging. Briefly, 3D7 strain parasites were synchronized to the ring stage by treatment with 5% sorbitol 34 for three successive replication cycles and cultured to the early-schizont stage. Anti-PfSEP-1 prepared by DNA vaccination (1:200) and rabbit anti-human glycophorin A (1:200) were incubated with live schizont infected RBCs in PBS, 5% BSA pH 7.4 for one hr at 25 deg C. Samples were washed three times in PBS and incubated with goat anti-mouse IgG conjugated with Alexa Fluor 594

(Molecular Probes) and goat anti-rabbit IgG conjugated with Alexa Fluor 488 (Molecular Probes). Samples were washed 3 times with PBS and incubated for 10 minute in 1 µg/ml of 4', 6'-diamino-2-phenylindole (DAPI, Sigma) to label nuclei. Blood smears were prepared and cover slipped with ProLong Gold anti-fade reagent (Invitrogen). Blood smears were imaged using a confocal microscope (Leica SP2, Leica Microsystems, Exton, PA) equipped with a 100×oil immersion objective and sequential Z-sections of the infected RBC were collected.

Immunoelectron Microscopy

3D7 strain parasites were synchronized to the ring stage by treatment with 5% sorbitol 34 for three successive replication cycles and cultured to the early-schizont stage. Samples were blocked for 1 hour at 25 deg C. in 1×PBS containing 2% BSA. Samples were incubated with anti-PfSEP-1 prepared by DNA vaccination (diluted 1:50 in PBS) and rabbit anti-human glycophorin-A polyclonal sera (diluted 1:50 in PBS) for 3 hr at 25 deg C. Pre-immune mouse sera was used as a negative control. Samples were washed three times in 1×PBS, and incubated for 1 h at 25 deg C. with 5 or 18-nm gold-conjugated goat anti-mouse IgG (Invitrogen) and 10-nm gold-conjugated goat anti-rabbit IgG (Invitrogen). Samples were washed three times in 1×PBS, and were fixed for 30 min at 4° C. with 2% glutaraldehyde, 1% paraformaldehyde in 0.1 M sodium cacodyldate buffer. Samples were dehydrated, embedded in Epon (EMS), sectioned on an ultra-microtome, counter stained for 10 min in 5% aqueous uranyl acetate and examined on a Philips CM10 electron microscope.

PbSEP-1A Antibody and Vaccination Studies

Antibody assays were performed with rPbSEP-1A coated ELISA plates according to our published methods 14 using an HRP conjugated anti-Mouse IgG antibody (Sigma) for detection of bound anti-PbSEP-1A antibodies.

We immunized Balb/C mice (n=11) with 40 ug of rPb-SEP-1A emulsified in 100 ul of TiterMax Gold adjuvant or adjuvant alone (n=11). Mice were immunized IP on days 0, 14, 28, and 42 and SC on day 56. On day 63, mice were challenged IP with 106 $P.$ $berghei$ ANKA parasite infected red blood cells. Mice were monitored daily from day 4 post-challenge with blood films to quantify parasitemia. Mice with parasitemias greater than 20% or exhibiting signs of illness (hunching, immobility, decreased food intake, etc.) were euthanized.

Statistical Analyses

To assess the relationship between anti-PfSEP-1 antibody responses and resistance to clinical malaria outcomes, we developed repeated measures models using SAS version 9.3 (Cary, NC). Generalized estimating equations using quasi-likelihood estimation were employed for these correlated (repeated measures) binary outcome data (Zeger, S. L. & Liang, K. Y. Longitudinal data analysis for discrete and continuous outcomes. Biometrics 42, 121-130 (1986)). Proc Genmod with a binomial distribution and logit link function were specified with separate models for each of the dichotomous clinical malaria outcomes. Due to the lack of independence of the repeated measures on children over time, we utilized longitudinal (repeated measures) modeling techniques in Proc Genmod to adjust for the correlation of responses within individuals. An autoregressive correlation structure was chosen given the expectation that the correlation of responses will decline over time. The fit of the model with different correlation structures was evaluated with the Quasi-Akaike Information Criterion (QIC). Similar GEE based linear regression models were used for the continuous endpoints of parasite density on all available blood smears and parasite density on positive blood smears. For some dichotomous malaria outcomes, including severe malaria, sampling zeros (i.e. no cases of severe malaria) occurred among children with detectable anti-PfSEP-1 antibody responses. This leads to "infinite bias" whereby odds ratios are skewed far above the true odds ratio. To address this, we used the Laplace correction, adding one adverse event to the group with detectable anti-PfSEP-1 antibody levels and a proportional number of events to the group with undetectable anti-PfSEP-1 antibody levels to restore the discordant pair ratios (Greenland, S., Schwartzbaum, J. A. & Finkle, W. D. Problems due to small samples and sparse data in conditional logistic regression analysis. Am J Epidemiol 151, 531-539 (2000)).

The data from these studies indicate that resistant individuals had 4 fold higher antibody levels to recombinant Pf SEP-1 compared to susceptible individuals, anti-Pf SEP-1 detects a 244 kDa antigen in $P.$ $falciparum$ infected, but not uninfected RBCs, Pf SEP-1 localizes to the schizont/parasitophorous vacuole membrane, Mauer's clefts and the inner leaflet of the RBC membrane in schizont infected RBCs, anti-Pf SEP-1 inhibits parasite growth by 48-74%. In schizont arrest assays, anti-Pf SEP-1 inhibits schizont rupture by 4-7 fold, and PfSEP-1 is a useful vaccine antigen to target schizont rupture and thereby reduce the severity of malaria.

Example 2: Role of Phosphorylation and Protein-Protein Interaction in Schizont Egress PfSEP-1 is involved in the process of schizont egress from $P.$ $falciparum$ infected RBCs. As was described above, PfSEP-1, a 244-kDa parasite antigen, localizes to the schizont/parasitophorous vacuole membrane, Mauer's clefts and the inner leaflet of the RBC membrane in schizont infected RBCs. Antibodies to a central, highly conserved 274 aa region of PfSEP-1 (rPfSEP-1A, aa 810-1083) decrease parasite replication by 58-75% (all p<0.009) by blocking schizont rupture. Active vaccination with rPbSEP-1A results in a 2.25 fold reduction in parasitemia after in vivo challenge with $P.$ $berghei$. In human cohort studies, children experienced a dramatically increased incidence of severe malaria during periods with undetectable anti-PfSEP-1 antibody levels (45 cases/23,806 child weeks) compared to periods with detectable antibody levels (0 cases/1,688 child weeks; adjusted OR 4.4; Type III fixed effects p<0.01). These results demonstrate that PfSEP-1 is critical for parasite egress and that antibodies against this protein are protective in vivo against severe malaria.

Schizont egress is a complex and tightly regulated process that requires both calcium-signaling and activation of a protease cascade which processes both parasite and host RBC proteins. Central events include activation of PfPKG, release of PfSUB1 into the parasitophorous vacuole, and proteolytic processing/activation of PfSERA5 by PfSUB1. Conditional knockdown of the calcium dependent kinase PfCDPK5 also results in arrest of schizont egress. Vaccination with PfSERA5 reduces and blocks schizont egress as well as parasite invasion. An in vivo phosphorylation substrate(s) of PfCDPK-5 is PfSEP-1.

Figure 20:
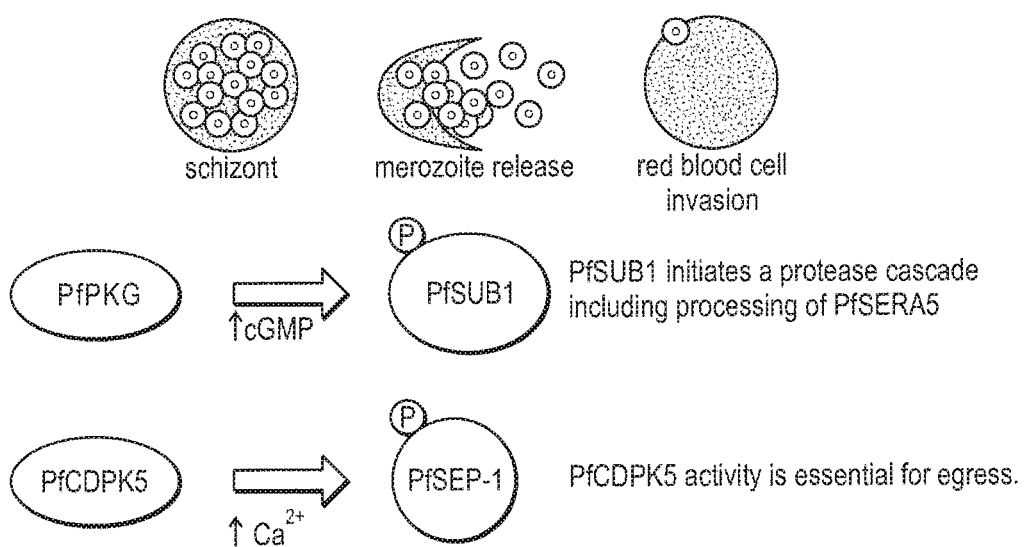
FIG. 20 is a diagram showing mechanisms of schizont egress and protein-protein interactions involved in the process.
Figures 21A, 21B:
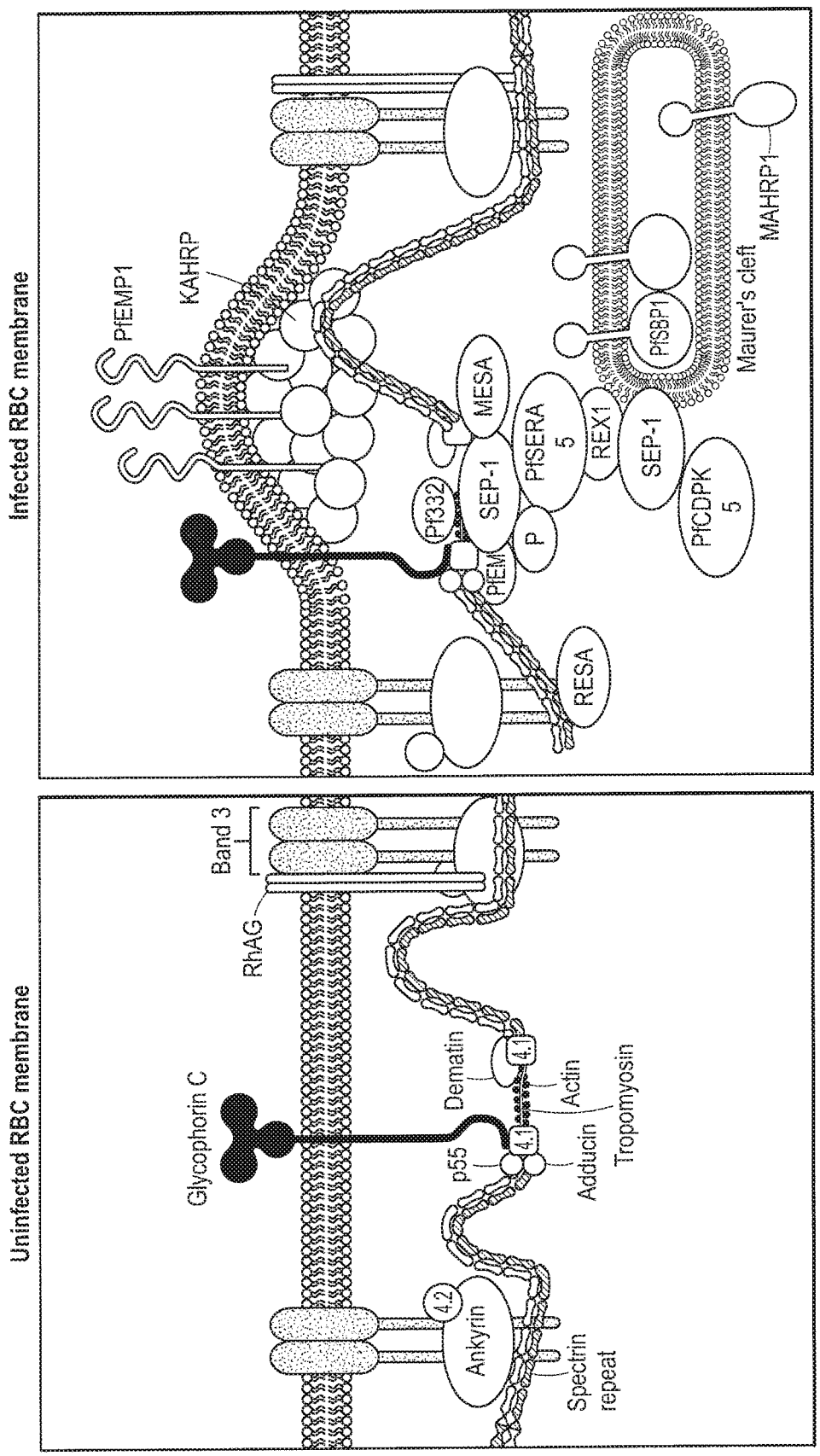
FIG. 21A-B are diagrams showing intracellular proteins and their interactions in uninfected RBCs (A) compared to parasite infected RBCs (B).

Protein-protein interactions of PfSEP-1 were studied using yeast two-hybrid (Y2H) and focusing on the rPfSEP-1A region (aa 810-1083; SEQ ID NO:2) and confirmed by immunoprecipitation of schizont extracts with anti-PfSEP-1 and sequencing (FIG. 20). PfSEP-1 was cloned into a "bait" plasmid as fusion with truncated transcription factor; malaria cDNAs were cloned into target plasmid as fusion with truncated transcription factor; screening was carried out in yeast for complementation of transcription factor via reporter gene assay; and PfSERA5 was identified as binding partner for PfSEP-1. The analysis also identified PfMESA as binding partner. These screens have identified 26 potential interacting proteins including PfSERA5, PfEMP2 (MESA), RAP-1, and RhopH3, which have also been identified as substrates for the egress critical protease PfSUB1. An immune response against SERA5 and SUB 1 sequences inhibit schizont egresss. SERA5 was identified in yeast-2-hybrid screen using PfSEP-1A as bait. rPfCDPK-5 was found to phosphorylate rPfSEP-1A (see FIGS. 20-21).

Phosphorylation-mediated regulation of PfSEP-1 and binding of this protein to both parasite and RBC proteins is essential for parasite egress. Parasite and RBC proteins which interact with, or phosphorylate PfSEP-1, are useful as vaccine antigens alone or together with PfSEP-1 (e.g., PfSEP-1A peptide) for immunization against malaria. Thus, plasmodial kinases (e.g., Pf CDPK5) and PfSEP-1-interacting proteins (e.g., PfSERA5, PfEMP2 (MESA), RAP-1, RhopH3) are used alone or as components of an PfSEP-1 based vaccine composition to generate an antibody or cellular immune response, which leads to a synergistic reduction in parasite growth, schizont egress, and (as a result) reduction in severity of malaria.

Example 3: Transmission Blocking and Reduction of Mosquito Invasion

Gametocytes, a form of blood stage parasite, are picked up by a female *Anopheles* mosquito during a blood meal. PfSEP-1 is expressed in male and female gametocytes—the sexual stage of the parasite's development that forms within host red blood cells. After being taken up by the mosquito with a blood meal, gametocytes must rupture from their encasing red blood cell in a process analogous to schizont rupture. This process takes place within the gut of the mosquito. Male and female gametocytes that fail to rupture from their red blood cell cannot join to make an ookinete and thus cannot infect the mosquito.

Several transmission blocking vaccine candidates attempt to target ookinete development in the mosquito (Kaslow et al., Infect Immun 1994; 62:5576-80; Bustamante et al., Parasite Immunol 2000; 22:373-80). Because PfSEP-1 is expressed in gametocytes (FIGS. 18 E-G), antibodies to PfSEP-1 taken up with the blood meal prevent gametocyte rupture from host red blood cells within the mosquito, thus affording a transmission blocking effect. Thus a vaccine that elicits an antibody immune response against PfSEP-1 (e.g., antibodies that specifically bind to PfSEP-1A) also leads to blocking of gametocyte egress out of RBCs. Antibodies made as a result of the vaccination regimen described herein readily gain access to the RBC, because the membrane permeability of infected RBCs. Thus, these data indicate that the vaccine is also useful to prevent or reduce invasion of mosquitos from a human blood meal.

Example 4: Vaccination of Mothers and Adolescents

Maternal transmission of anti-PfSEP-1 antibodies from a mother to a fetus, e.g., across the maternal-fetal interface via the placenta, was found to reduce malaria in infants. We have identified PfSEP-1 antibodies in the sera of pregnant women whose children were protected from severe malaria during infancy (first yr of life), but do not detect anti-PfSEP-1 antibodies in pregnant women whose children do have severe malaria during infancy. Because neonates (first 28 days of life) have poorly developed immune systems, they often do not make robust immune responses to vaccines. The vaccine described herein is therefore also useful to protect infants. Pregnant women and/or women of child bearing age are immunized with a vaccine containing PfSEP-1 peptide(s). Anti-PfSEP-1 antibodies produced as a result of the immunization cross the placenta and protect the newborn from malarial infection, morbidity and mortality. Females are immunized starting at age 9, e.g., 3 doses over 6 months. Immunization of females prior to pregnancy or early in pregnancy is useful to prevent, slow, or inhibit infection and the development of malaria in fetuses and newborns.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank, NCBI, and Plasmodb submissions indicated by accession number cited herein are hereby incorporated by reference. Plasmdb.org sequence version is the version as of Nov. 30, 2012. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for reducing the severity of malaria or immunizing against malaria in a subject, comprising the step of administering a composition to the subject;
wherein the composition comprises a polypeptide selected from the group consisting of: CDPK5 (SEQ ID NO: 47), SERA5 (SEQ ID NOS: 70, 72), PfSUB1 (SEQ ID NO: 74), and PfPKG (SEQ ID NO: 76) or a combination of polypeptides thereof;
wherein the administration of the composition including the polypeptide or combination of polypeptides elicits an immune response to the polypeptide or combination of polypeptides;
wherein the immune response inhibits schizont egress from red blood cells;
thereby reducing the severity of malaria or immunizing against malaria in the subject.

2. The method of claim 1, wherein the immune response is an antibody response.

3. The method of claim 1, wherein the immune response is a cellular immune response.

4. The method of claim 1, wherein the composition comprises the polypeptide PfSERA5.

5. The method of claim 1, wherein the composition further comprises the polypeptide PfSEP-1A.

6. The method of claim 1, wherein the subject is a human.

7. The method of claim 1, wherein the subject is an adolescent female or a female of childbearing age.

8. The method of claim 1, wherein the composition is administered intramuscularly.

* * * * *